US007141417B1

(12) United States Patent
Croce et al.

(10) Patent No.: US 7,141,417 B1
(45) Date of Patent: Nov. 28, 2006

(54) COMPOSITIONS, KITS, AND METHODS RELATING TO THE HUMAN FEZ1 GENE, A NOVEL TUMOR SUPPRESSOR GENE

(75) Inventors: Carlo M. Croce, Philadelphia, PA (US); Hideshi Ishii, Bryn Mawr, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/513,888

(22) Filed: Feb. 25, 2000

Related U.S. Application Data

(60) Provisional application No. 60/121,537, filed on Feb. 25, 1999.

(51) Int. Cl.
*C12N 15/00* (2006.01)

(52) U.S. Cl. ................. 435/320.1; 435/325; 536/24.33

(58) Field of Classification Search ............... 536/23.1, 536/23.5; 435/7.35, 91.1, 325
See application file for complete search history.

(56) References Cited

U.S. PATENT DOCUMENTS

| | | | | |
|---|---|---|---|---|
| 4,160,452 A | | 7/1979 | Theeuwes | 424/427 |
| 4,256,108 A | | 3/1981 | Theeuwes | 424/424 |
| 4,265,874 A | | 5/1981 | Bonsen et al. | 424/473 |
| 5,210,015 A | | 5/1993 | Gelfand et al. | 435/6 |
| 5,691,146 A | | 11/1997 | Mayrand | 435/6 |
| 5,804,177 A | * | 9/1998 | Humphries | |
| 5,840,686 A | * | 11/1998 | Chader et al. | |
| 6,531,456 B1 | | 3/2003 | Kurtzman et al. | |

FOREIGN PATENT DOCUMENTS

| | | | |
|---|---|---|---|
| EP | 0679716 A1 | * | 6/1995 |
| WO | WO 01 55300 A | | 8/2001 |
| WO | WO 01 55448 A | | 8/2001 |

OTHER PUBLICATIONS

Boige et al (1997) Cancer Research 57: 1986-1990.*
El-Naggar et l (1998) Oncogene 16: 2983-2987.*
Anbazhagan et al (1998) Am. J. Pathology 152: 815-819.*
Kerangueven et al (1997) Cancer Research 57: 5469-5474.*
Gustafson et al (1996) Cancer Research 56: 5238-5245.*
Database Geneseq, Accession No. T23583, 1996.*
Database GenEmbl, Accession No. G43056, Jan. 1999.*
Wang et al (1998) Science 280:1077-1082.*
Database EST, Accession No. N21184, Dec. 1995.*
Database EST, Accession No. AI042490, Feb. 1999.*
Ischii et al (1999) PNAS 96:3928-3922.*
Lockhart et al (1996) Nature Biotechnology 14: 1675-1680.*
Verma et al (1997) Nature 389:239-242.*
Palù et al (1999) J. Biotechnol. 68: 1-13.*
Luo et al (2000) Nature Biotechnology 18:33-37.*
Ishii et al (1999) Proc Natl Acad Sci 96:3928-3933.*
Database Genbank, Accession No. G43056, Wang et al.
Database Genbank, Accession No. AF123653, Ishii et al.
Database Genbank, Accession No. AF123659, Ishii et al.
Altschul, et al., 1990, J. Mol. Biol. 215:403-410.
Anbazhagan et al., 1998, Am. J. Pathol. 152:815-819.
Bec et al., 1994, J. Biol. Chem. 269:2086-2092.
Boige et al., 1997, Cancer Res. 57:1986-1990.
Bookstein et al., 1997, Br. J. Urol. 79(Suppl. 1):28-36.
Bookstein, et al., 1994, Genomics 24:317-323.
Bova et al., 1996, Genomics 35:46-54.
Brown, 1992, Nature 359:24.
Cher et al., 1994, Genes Chromosom. Cancer 11:153-162.
de Wit et al., 1998, Nucl. Acids Res. 26:676-678.
Durso and Cyr, 1994, Plant Cell 6:893-905.
El-Naggar et al., 1998, Oncogene 16:2983-2987.
Fasbender et al., 1997, J. Biol. Chem. 272:6479-89.
Fodor et al., 1993, Nature 364:555-556.
Fujiwara et al., 1995, Oncogene 10:891-895.
Gustafson et al., 1996, Cancer Res. 56:5238-5245.
Hai et al., 1989, Genes Develop. 3:2083-2090.
Heid et al., 1996, Genome Res. 6:986-994.
Ichikawa et al., 1994, Cancer Res. 54:2299-2302.
Ishii et al., 1999, Proc. Natl. Acad. Sci. USA 96:3928-3933.
Janssen et al, 1988, Eur. J. Biochem. 171:119-129.
Janssen et al., 1994, J. Biol. Chem. 269:31410-31417.
Jenkins et al., 1998, Genes Chromosom. Cancer 21:131-143.
Kagan et al., 1995, Oncogene 11:2121-2126.
Kerangueven et al., 1997, Cancer Res. 57:5469-5474.
Knudson, 1993, Proc. Natl. Acad. Sci. USA 90:10914-10921.
Komiya et al., 1997, Jpn. J. Cancer Res. 88:389-393.
Kyte and Doolittle, 1982, J. Mol. Biol. 157:105-132.
Lasko et al., 1991, Ann. Rev. Genet. 25:281-314.
Lewandoski et al., 1997, Nature Genet. 17:223-225.
Li et al., 1997, Human Gene Ther. 8:1695-1700 *.
Lockhart et al., 1996, Nature Biotechnol. 14:1675-1680.
MacGrogan et al., 1996, Genomics 35:55-65.
Macoska et al., 1995, Cancer Res. 55:5390-5395.
Marchesi and Ngo, 1993, Proc. Natl. Acad. Sci. USA 90:3028-3032.

(Continued)

*Primary Examiner*—James Ketter
(74) *Attorney, Agent, or Firm*—Hamilton, Brook, Smith & Reynolds, P.C.

(57) ABSTRACT

The invention relates to isolated polynucleotides homologous with a portion of one strand of the human tumor suppressor gene, FEZ1, and to the tumor suppressor protein encoded thereby, Fez1. The polynucleotides are useful, for example, as probes, primers, portions of expression vectors, and the like. The invention also includes diagnostic, therapeutic, cell proliferation enhancement, and screening methods which involve these polynucleotides and protein. The invention further includes kits useful for performing the methods of the invention.

43 Claims, 80 Drawing Sheets

OTHER PUBLICATIONS

Mathur et al., 1998, Cancer 82:816-821.
Mimori et al., 1995, Cancer 75:1446-1449.
Mimori et al., 1996, Gut 38:66-70.
Moore et al., 1998, Cell Motil. Cytoskel. 41:168-180.
Nagase et al., 1998, DNA Res. 5:31-39.
Nowell, 1993, Adv. Cancer Res. 62:1-16.
Ohta et al., 1996, Cell 84:587-597.
Pease et al., 1994, Proc. Natl. Acad. Sci. USA 91:5022-5026.
Plück, 1996 Intl. J. Exp. Pathol.77:269-278.
Russ et al., 1996, J. Virol. 70:4927-4932.
Sakai et al., 1995, Biochem. Biophys. Res. Comm. 217:393-401.
Sunwoo et al., 1996, Genes Chromosom. Cancer 16:164-169.
Takeuchi et al., 1995, Cancer Res. 55:5377-5382.
Wagner et al., 1997, Am. J. Pathol. 151:753-759.
Wallraff et al., 1997, Chemtech 27(2), only pp. 22 and 23 provided.
Weinberg, 1991, Science 254:1138-1145.
Wu et al., 1997, Genes Chromosom. Cancer 20:347-353.
Yaremko et al., 1995, Genes Chromosom. Cancer 13:186-191.
Yaremko et al., 1996, Genes Chromosom. Cancer 16:189-195.
Database EMBL Online, Jul. 1, 1998, "oxo62e04.x1 Soares_NhHMPu_S1 *Homo sapiens* cDNA clone IMAGE: 1660926 3," Database Accession No. AI042490 XP002266794.

* cited by examiner

```
KIAA0522 --AWERELAELRQGCSGKLQQVARRAQRAQ--QGLQLQ
Fez1     --RCRDELEGPEPKGGNKLKQASQKSQRAQ--QVLHLQ
ATF-5    ISRRRREKENPKER--NKMAAAKCRNRRRELTDTLQAE
                                           #

KIA0522  VLRLQQDKKQLQEEAARLMRQREELEDKVAACQKE
Fez1     VLQLQQEKRQLRQELESLMKEQDLLETKLRSYERE
ATF-5    TDQLEDEKSALQTEIANLLKEKEKLEFILAAH
           #    #    #    #
```

```
GCCTTTCCAA GACCCTGCCC GGCCCTGCCC CATCCTCAGC CCCGAGTCAC CATGGGCAGC 60
GTCAGTAGCC TCATCTCCGG CCACAGCTTC CACAGCAAGC ACTGCCGGGC TTCGCAGTAC 120
AAGCTGCGCA AGTCCTCCCA CCTCAAGAAG CTCAACCGGT ATTCCGACGG GCTGCTGAGG 180
TTTGGCTTCT CCCAGGACTC CGGTCACGGC AAGTCCAGCT CCAAAATGGG CAAGAGCGAA 240
GACTTCTTCT ACATCAAGGT CAGCCAGAAA GCCCGGGGCT CCCATCACCC AGATTACACG 300
GCACTGTCCA GCGGGGATTT AGGGGGCCAG GCTGGGGTGG ACTTTGACCC GTCCACACCC 360
CCCAAGCTCA TGCCCTTCTC CAATCAGCTA GAAATGGTAA GCGGGGGTCG CTGGCAAGGG 420
TAAGTGGGTT GGAAACGCAG GAGAAAGCAA AATGGGGGTG GAGAGCCTGG GGGTTCAGGG 480
GGAGTGGTGA CCTGAGCATT CAGACTCCTC AAAACCAGAG CGGCAGGGGT GCCGGCGGAA 540
GCCTGTGGCC ACACCGCAGA GATCAAACGT TTCACAAAGG AATTAGAGCA TCGCTCAGTC 600
CCCCTGAAGC AGAAGTCTTG GGTCAGGCCA TAAGCAAAGA GCACAGGGGA TATGTGAGCT 660
TTTGGAGTCC CACTGAAATG TAGCTGGATT GTCAACGTAG GATCCAGGCG TTTGCCAAGC 720
CTCGGGAAGG AGAGGGAGCC CTGTTCTCAT CTGGAAGCAC AGATGAAGAG GATGCAGGCC 780
GGGAGTTAAC CGCTTCTCTC CCCGGGAGAC TCGTGGGGGT GGGTGCGGTC TTCTCATTTG 840
CTGCCCTGGT GTGCATTAGC TCCTTGTTCA AGCTGCGCCT GGGGGCATCT TTGAATACAG 900
GCTGGAGTTT TGTCATCCAT TTACCAGAGA CTAGGGCAAA GGAGGCCCAG GCACTGAGAA 960
ATCCAGCCCT CACACCAGCT CAAGCCCTCG TGCGTCCCAC GAGTGGACAC TGAAATCAAT 1020
TTTCCTATTC AGTCCTCTGC CCCTTGCCCT GGGGAAATGA ATCCCCGGCT TTGATTTACT 1080
AGGAAAGAGC CTCTTATGTT TGCATAGAGC ATTCAGCTTT TCAAATTAAG GGGCTTGTAA 1140
ACTGTGAAGC ACTCTACCAG GGAAAATTAC AGTTTTAAAA AAGGATCGTG ATTTGGAGTG 1200
AGCCTCCCAA CCCTGTAAGG AGGCCAGGTC CGTGTCCTTG CTCCAGGCTT AATGGAAGAG 1260
GCAGTGAACA GGAAGAAGGG ATGGACCTAA AGAGGGACAG CAAGCTCGGC CAGCCTGATG 1320
CCCTAACTTG CCCCACACAG AGACCTAGAG CAGGAGCCTC AAGATGGTAT TTATCACCTC 1380
GGGAGGGCTG GGGCAAGCTG GTGGCAGGTT GCTATTTCAT AGAACAAAGT GCCCAAGTCG 1440
CCATTAGGGT TTTTCCCTCC TAAGAGAGAT GACATTCAGC TGCTTCAAAG CAACAGGCAA 1500
```

Fig. 5A-1

```
GGTCTGCTGA GACAATTGAC CAAGAGGGGT GCTGCGTGCG CTCAGAGAGC CCAGACTGGC 1560
TCAAGGTCGG CACGCGTGCC TGGGGAGGGA GGGTGCAATG CGCGCGCAGG GGAGGCATGA 1620
GTCACCGCGG TCCTTTTCCT CTACAGGGCT CCGAGAAGGG TGCAGTGAGG CCCACAGCCT 1680
TCAAGCCTGT GCTGCCACGG TCAGGAGCCA TCCTGCACTC CTCCCCGGAG AGTGCCAGCC 1740
ACCAGCTGCA CCCCGCCCCT CCAGACAAGC CCAAGGAGCA GGAGCTGAAG CCTGGCCTGT 1800
GCTCTGGGGC GCTGTCAGAC TCCGGCCGGA ACTCCATGTC CAGCCTGCCC ACACACAGCA 1860
CCAGCAGCAG CTACCAGCTG GACCCGCTGG TCACACCCGT GGGACCCACA AGCCGTTTTG 1920
GGGGCTCCGC CCACAACATC ACCCAGGGCA TCGTCCTCCA GGACAGCAAC ATGATGAGCC 1980
TGAAGGCTCT GTCCTTCTCC GACGGAGGTA GCAAGCTGGG CCACTCGAAC AAGGCAGACA 2040
AGGGCCCCTC GTGTGTCCGC TCCCCCATCT CCACGGACGA GTGCAGCATC CAGGAGCTGG 2100
AACAGAAGCT GTTGGAGAGG GAGGGCGCCC TCCAGAAGCT GCAGCGCAGC TTTGAGGAGA 2160
AGGAGCTTGC CTCCAGCCTG GCCTACGAGG AGCGGCCGCG GCGCTGCAGG GACGAGCTGG 2220
AGGGCCCGGA GCCCAAAGGC GGCAACAAGC TCAAGCAGGC CTCGCAGAAG AGCCAGCGCG 2280
CGCAGCAGGT CCTGCACCTG CAGGTACTGC AGCTTCAGCA GGAGAAGCGG CAGCTCCGGC 2340
AGGAGCTCGA GAGCCTCATG AAGGAGCAGG ACCTGCTGGA GACCAAGCTC AGGTCCTACG 2400
AGAGGGAGAA GACCAGCTTC GGCCCCGCGC TGGAGGAGAC CCAGTGGGAG GTGAGGCCAC 2460
ACAGGGCTCA TGGGTTTGGG TGGTCAGCGG TTTGGCGCCA GTACCCCCCT CTCCTTCTGG 2520
TGCTGGCCAA TAGCGTGCAA ACACAGACCG CGCAGGCAAG CGGGGCTAAT GTGCTGGCTT 2580
TATCACCCAA AGAAGGGGCT CCCTGCAAAC CATGTTGGGG GATCGACTTA CATCTGAGCT 2640
TCCTCCTGTC CCCACCATCA CCCTCATGGC TCCTAGATTT CAGTTTCCCA AGTGAGCCAT 2700
TAAATCATGA AGCCGGAAGC CAGATGACCA AGGCCCAGCC AGGCTGTGGG CTGACCTCCC 2760
TTCCATCAGC TCCCAGGAGG CTCAGAAGAA GAACAAGCCG TGCCTGAGTT CAGGCGGGGC 2820
CAGGGGCCCA AGAGAGCACA GAATGCATTT GTTGCTTTGG AGGGAGGGAC TGCACCCACT 2880
AGTAAGAGGG ACCCTATTGG TGGCAGGTTT CAGTGATGGA AGTGGCCACT CCTTGCTGAA 2940
GTGTAAGTGG AACTTCTATT TGGTGAGCTG AGATGGAAAC CTAGGAGAGG AAGTAAAGAG 3000
```

Fig. 5A-2

```
TCCCCCACTC ACACACTTAC ACACTCACAC ACACTCACTC ACCCGGTCAC ACGTGGAAAT 3060
GAGGCATCTG TACCTGACCG TGCTGGAGAA CCCCATAACC TCTGCATCTA TTAGTGGGAA 3120
AGCAGCTTTT CTCACCAGCC TGGTGGTCTG GATGACTCAT GGAGTTCAAG CCCATCGTTG 3180
AGGCTCTTTA CATGCTCGCA CCCAGCTTGG TCTGTCCACG TGCCTGCCTC ACCCCCAGTT 3240
CAGAGTCCAA ATCTCAGTCT ACACGCAAAC CCCTGGCTAT GTGCAAGTCA ACAACCAGTG 3300
GTTTAACTTG CCCACTGCTG GCAGCTGTAT CACCCCCATT TAACACCAAT GGTATTGGTT 3360
TTGGTGTCAG CCTGATTTCT GTCATCGATG TTTATGCCCA CATCCTCTGA CCTCACCCCT 3420
GCATGCACCC AGCCCTCCTC TCTCCTGTCT ACTGGAGTAA AGACTACCTC ACAAATTCAC 3480
TGCTGTACCC AGTGACTAGT ATCATGCTGG CTTGGATGCA GAGCCCAATC CACATCTGTC 3540
AAACGAGGAA TCATTTTCTT CTCCTCTTGC TCTTCTTTCT CTATTTCCCA CCCCTATCCC 3600
CCATCAAAAT TTGGCCAAGA GCAATGATGA AAACCGAAGC CACAGGTTAG ACCCATGTGT 3660
CTCTGGATCT TGGCCATCTG GGGTCATGGG AGACCAAGGC CAGTCTGGCT GAATCTTAAG 3720
AGTGAATGAA GTCCAGAGCA TGTGGCTCTA CAGAATGGAT TCTTGGAACT AGCCTGGAAG 3780
CCACCTTCAC ATTTCCTTTC ACAGTAGAAA TTTCCCCTTG CCCTCAGTGA AACACTGCAC 3840
AGTCCTGGAG AAAATCCGAC CCTACCCAGG ATGCGTGCTT GGGACCAAGA ATTTCATTCC 3900
AAGGCCAACC CTGTATTCAT GCCACGAAGG GAGTGACACA GTCATGGCTG AGGCATGGGC 3960
CTGGCTTTGA ACCTCAGCTT GACCACTTAT GATCCAGGTG ATTGTAAATA CATTAGCCAT 4020
GGTGGCAATG GGGTATAGTG ATTAAACTGT TGGGATCAAA TCTCTACTCT TATACTTTAT 4080
ATTTTATATA TATATATATA TAATATATAT ATATATTAGC CCTCAGGCTG GTCACTTCAC 4140
CAGCTGTTTG CTATCATAAC CTCTCTGTGC CTCAGTTTCA TTGATGTAAA TTGAGGACTA 4200
CTAATAGTAC CTACTTCATC GGGTTGTAAG GAATAGATGA GCAAATGTAT GGCTTGGCAC 4260
TTAATAACAC TACAAATTAT TAGTGAAAGT ATGTTTATAA TAATATACTT CTGTGTGGCT 4320
AGGCGTGGTG GCTCACGCCT GCAATCCCAG CACTTTGGGA GGCAGAGGCA GGCAGAGCAC 4380
TTGAGGTCAG GAATTCGAGA TCAGCCTGGC CAACATGAGG AAACCCCGTC TCTACTAAAA 4440
ATACAAAAAT CAGCCAGGCA TGGTGGCAGG TGTCTGTAAT CCCAGCTACT TGGGAGGCTG 4500
```

Fig. 5A-3

| | | | | | | |
|---|---|---|---|---|---|---|
| AGGCAGGAGA | ATCAGAGGGG | AGGCGGAGGT | TGCAGTGAGC | CAAGATCACG | CCACTACACC | 4560 |
| CCAGCCTAGG | TGACAAAGCG | AGACTTCTCA | AATATTAACA | ATAATAATAT | ACTATGTGTC | 4620 |
| ATTATACATG | ATGATTATTA | TTTTATCATT | TTACTATATA | GCCTAGCTCG | ATAACCTGGG | 4680 |
| ARAAAGGTCA | CAGCAATGTT | CAGCTTACTT | TCAGATTGGA | CAAAGGCTGG | AATGCCTAAC | 4740 |
| ACCGGGCCAC | CGCATCCGGA | GTGGCTTGGT | TATTTTAGGC | AGCTGAGCTG | TCACTTCCCT | 4800 |
| GGGTAAGGAC | ACTCACCTCT | TGGCACTCTG | TCTCCACCCC | ACCCTCGGCA | GGTGTGCCAG | 4860 |
| AAGTCAGGCG | AGATCTCCCT | CCTGAAGCAG | CAGCTGAAGG | AGTCCCAGAC | GGAGGTGAAC | 4920 |
| GCCAAGGCTA | GCGAGATCCT | GGGTCTCAAG | GCACAGCTGA | AGGACACGCG | GGGCAAGCTG | 4980 |
| GAGGGCCTGG | AGCTGAGGAC | CCAGGACCTG | GAGGGCGCCC | TGCGCACCAA | GGGCCTGGAG | 5040 |
| CTGGAGGTCT | GTGAGAATGA | GCTGCAGCGC | AAGAAGAACG | AGGCGGAGCT | GCTGCGGGAG | 5100 |
| AAGGTGAACC | TGCTGGAGCA | GGAGCTGCAG | GAGCTGCGGG | CCCAGGCCGC | CCTGGCCCGC | 5160 |
| GACATGGGGC | CGCCCACCTT | CCCCGAGGAC | GTCCCTGCCC | TGCAGCGGGA | GCTGGAGCGG | 5220 |
| CTGCGGGCCG | AGCTGCGGGA | GGAGCGGCAA | GGCCATGACC | AGATGTCCTC | GGGCTTCCAG | 5280 |
| CATGAGCGGC | TCGTGTGGAA | GGAGGAGAAG | GAGAAGGTGA | TTCAGTACCA | GAAACAGCTG | 5340 |
| CAGCAGAGCT | ACGTGGCCAT | GTACCAGCGG | AACCAGCGCC | TGGAGAAGGC | CCTGCAGCAG | 5400 |
| CTGGCACGTG | GGGACAGCGC | CGGGGAGCCC | TTGGAGGTTG | ACCTGGAAGG | GGCTGACATC | 5460 |
| CCCTACGAGG | ACATCATAGC | CACTGAGATC | TGAGGGGCTG | CCTGGGAAGG | CGAGTCTGGG | 5520 |
| GACCTGGCAC | TGGGAGGCAG | GGCTCTCCCG | TGCATCCCCC | CTGCTCAGCA | ATTCAGACCC | 5580 |
| CTCTGAGAGA | CGCCACTCCC | TGGGACACAG | ACCCAGGACC | CCCGAGGGGA | GGGCAGGATG | 5640 |
| GCCTTTCCTT | CCCTCTCTGA | TGTCCCAGTG | CTCACCAGCC | CTGCAGCCCA | CCAGACGTCA | 5700 |
| GGCCCTGACT | CCTCTGGCTT | TCCCAGGAGA | TGGGTCCAGG | GGTCTGTCTG | CTTTGGTTAA | 5760 |
| GGGCTCCCTA | AACTTTGGCC | TTTGTTCGAA | ATAGATATCC | TCTCCCCCTC | CTCCAGGGAA | 5820 |
| GGTGGCCACA | GCAAGAACAG | CGGCTCCCCT | CCGCTTCTCA | TCCCAACCTC | TTTTTCCTCC | 5880 |
| TGGACACATT | GGAATGCCTT | GGAAATAGAA | AGAAGCCATA | TATGACCAGA | AGCCTTGGAA | 5940 |
| CCAGCCCCAT | CAGAACCTGA | GCTATTTTCC | TCTGGCCGCA | GAGGTGTAGG | GGTGGAATGA | 6000 |

Fig. 5A-4

```
GCCGCGGGGA AGCTGGCTTT GAAACCTCAG GGCTGTCCCA GCCCCGGCAA GCCACAGGAA 6060
GGAGGGGAGA GACAGGCAGC CCAGCAGTGT GGAGACCCTG CCACAGCCAG AGGAGGGCAG 6120
AGGGAGAATC CAAGGGTTGA GAGCCAGTGG CGGGTGATGG CCAGCCCCTG GGGCCCAGCC 6180
CCTGTTTACT GGTTCTTGCA AATGGGAGCT GAGCAGCCTC TGGACAGCCA GTGACCTTTG 6240
ACCTCGGTGA CCACTCTTCT TTAAGCCATA GACCCTGAGG CCCTGGGCTG GGTGCTGGGA 6300
AGGGAGGGTT GAAACCACCG TGAACCAGAG GGTGTGGCTT TCCAGKCACC CTCAGGGAGC 6360
CTCCCCATCT GTCCAGCTGG GGCCAGAGGC TGGGAGTCCC TACCTGCTTC ACGTTGGCCG 6420
GCGGCTACTC TGGAATGTTT TTCCCTCCCC AGAATCAAGC TTTTGCTTGA TCCAGAAGAG 6480
CCCATATCAC TAAGATGGCA TATATGTGAT CTGGGCATTT TCCTCCTCTG CCTACAGCCA 6540
GGTTTAGCGG CAAACCTTTC CCCCTTAGCA CCTTCAGGGC TGAGTTCTGG GTTTCTAGAG 6600
GTCAGGACGG CTCCTCAGAG CGCCAGGAAG CCAGAGCCCC AAGCAGGACG AAAAAGAGGC 6660
ATACACACAG CAGTGTGAAT AGCCTGGCCA CCAGCCATCC TCCCTCCACC TCAAGACCCC 6720
CATTTGTCCS AGACTAAAGG ATCCAGAGAG CAGCTCCCTT TCTCAGGAGC TTGGGCAGTG 6780
CCCCAGGGAG TCCAGGGTTT CTCTGCAGAT GTGCGGAGCG GGAGGCGGTG GTAGAGAGAG 6840
ATAAAAGGTG GAGTTTCTCT GTTGTTTGGT TCAGGGATTT TATTTTTAAT TTTATGAGAC 6900
AGGGTCTTGC TCTGTCCCCC AGGCTGGAGT GCAGTGGCAT GATCATAGCT CACTGCAGCC 6960
TCATACTCCT GGGCTCAAGC AATCCTCCTG CCTCAGCCTT CCAACTAGCT GGGACTACAG 7020
GTGCGCGCCA CCGTGCCTGG CTAACTTTTC ATTTTTTTTG TAGGGACGGG GTCTCGTTTT 7080
GTTGCCAAAG CTGGTCTCAA ACTTGTGGCC TCAAGCAATC CACCTGCCTT GGCCTCCCAA 7140
AGTGCTGAGA TTGCAGATGT GAGCCACCGT GCCTGGCCAG ATTTTTCTTT TATTCTTCTT 7200
TCTTTTTCTT TTTTGCTTTC TTGTCTTTTC AGAAGCAAGC CAGACCTAGC AGGCTGTTCC 7260
ATGTTCTATT TTTGACTGTA GCCACAGCTG CTGTTCTCAG GACAGCATCC CTTCCCACAT 7320
GCCTGCGCCT GCTGCCTGCT GAGATGAGGA GGGGAGCGTC TGGGAACTTG CGAGTCCAAG 7380
GCCAGTCCCC ATTTCTGCCT CGCTCACCGC TGGCCCTTAG AGACCCCGAG GTAGGGGTGG 7440
GGAGATGCTT CTCTCCTTGC CCCCCGCCCT CATGGGTCCT AGCCCTTCCC TGAGTGCGGG 7500
```

Fig. 5A-5

```
CTGAGGCCAG AGTCACCTTT TCTGTGGCTG GCTCTACCTT CCTGTCCCTG AGGTTAAACG 7560
GTGCCCATCC TGCCATCCTC AAACGACAGA GGAGCTTTTC TGGAATTTCA AACCATTGCT 7620
CTTAGTCCCA AGCTAGGCTT AAACCTGGAA TCTACAAGCC AAAAGTCCCT CCCTGCCTGA 7680
GGGCAGTACC CTCCATTGGG CACAGTCCAG ACCCAAGTCA AAGATGCCCC ATTCCTTGCG 7740
CCTCAGCCCT CAGTTCCTTC ATTTCCACCA GGCCGTGCCT TGTTTGAGTT TTTCCTCCCA 7800
GTGAGACTGC CCCACGGAGA CAGAGGAAAG GGCTGGCTCC CCCTCCCCAG GCTGGAGACC 7860
CCCCCCAACT CCAGGAAAGA GCAGTCAGAG TCCAGTGCTC TGCCTCAGAC GTTGCCTGAG 7920
AAGAAGTGGC TGCCACACCC AGGGGAAGGC CCTGAGGCGG AGGCTGTGCT CCGCCATGGT 7980
GTCCCGGTAC CTTCCATACA CAGAGGAGTG CAGCCTTCTC CATATCTCCA TGGCCCTGTC 8040
CCAGGCCGGC CCAGATGTGT CCCCCCCAGG CCTTGTCCTA CGTCCAAGGT GGCAGATGTC 8100
TTCCCTGGGC TGCCACCAGC CCCCGCCCCA GAGTGGCCCA CCGTGGCACT AGAATGCAAG 8160
TATCCTGCGA CCTTGCAACC TCACCTTCCT GTGGGTGTTC TTTCCTGCCC TGTCCAAAAG 8220
CGCCCTCACT ATTCTTGGAC CATGCCAGAT TCTGCCTCTC TGGAAAGAGG CTCTGGACAG 8280
CAGAAGCCTC CAAGCACAGA GCCTGGCCCC AGGCCCCAGA CAGGGTGGGC TTCCTGCCCT 8340
TCCCTCTGGG CACGCCTGCT GGCCGACCCA CTGACCCACT CGGATGGACC AACCTGCTCT 8400
GTCCCCAAAG GACGCCTGCA GGAGAGAGCA GCACTCCGCA TCACCTCACC AAGGATCGGA 8460
CTCTGCCCCT GGACCTGGGA ACGACTGGAC TGTCACGGGG TTCCCTCCTA GCTCTCCCAG 8520
TGAACTCCTG CCAGGCACAC ACAGCCCCTA TAGCACTGAG CTCACATGGG ACTGGGATAT 8580
GGGGGCATCT CTTCCCCAGA GAGGCACTCA GTGAGCCTCC TGTGCCTGGC CCCAGTCTGG 8640
GCCATCTCTT AGGTGAGACA GTTGCCCGAA ACTAAGCCAG GCCTGGCTGG AGGAGCAGCA 8700
GCTTGGGGAG AGGGATTTCC CTGCAGACCT CAAGCCATCA TGCGGTGGGT GCTGCCATGA 8760
CAGAGGCTGC ACCCCTGGGC CAGCGGGGCT GCTCACCCAC CTCTTGTGCA AGGTGGCCTT 8820
TGTGCTGCGC CTGCAGGCAG AGCTGGAGCC CCCAGCAGAG GCAGGCTGGG ACGGACCAGC 8880
ATCTGGAAGA TGTACATAGT TATTTTTCTC TTTGTGGTTT CTTGTTTGGT TTGGTTTGCT 8940
TTTGACAGCT TCATTTTATT TTTGACGTCA CTTTTTGGCC ATGTAAACTA TTTGTGGCAA 9000
TTTTATGTTT TTATTTATGA ATAAAGAATG CCATTTCTCA CGCCCTCT             9048
```

Fig. 5A-6

```
TGAGGGCTTT GCTATGACCT CAGTCCCCTC ACGGAGCCAC GACTGCCCCT TGCTGCCACA 60
GCCTTTCCAA GACCCTGCCC GGCCCTGCCC CATCCTCAGC CCCGAGTCAC CATGGGCAGC 120
GTCAGTAGCC TCATCTCCGG CCACAGCTTC CACAGCAAGC ACTGCCGGGC TTCGCAGTAC 180
AAGCTGCGCA AGTCCTCCCA CCTCAAGAAG CTCAACCGGT ATTCCGACGG GCTGCTGAGG 240
TTTGGCTTCT CCCAGGACTC CGGTCACGGC AAGTCCAGCT CCAAAATGGG CAAGAGCGAA 300
GACTTCTTCT ACATCAAGGT CAGCCAGAAA GCCCGGGGCT CCCATCACCC AGATTACACG 360
GCACTGTCCA GCGGGGATTT AGGGGGCCAG GCTGGGGTGG ACTTTGACCC GTCCACACCC 420
CCCAAGCTCA TGCCCTTCTC CAATCAGCTA GAAATGGGCT CCGAGAAGGG TGCAGTGAGG 480
CCCACAGCCT TCAAGCCTGT GCTGCCACGG TCAGGAGCCA TCCTGCACTC CTCCCCGGAG 540
AGTGCCAGCC ACCAGCTGCA CCCCGCCCCT CCAGACAAGC CCAAGGAGCA GGAGCTGAAG 600
CCTGGCCTGT GCTCTGGGGC GCTGTCAGAC TCCGGCCGGA ACTCCATGTC CAGCCTGCCC 660
ACACACAGCA CCAGCAGCAG CTACCAGCTG GACCCGCTGG TCACACCCGT GGGACCCACA 720
AGCCGTTTTG GGGGCTCCGC CCACAACATC ACCCAGGGCA TCGTCCTCCA GGACAGCAAC 780
ATGATGAGCC TGAAGGCTCT GTCCTTCTCC GACGGAGGTA GCAAGCTGGG CCACTCGAAC 840
AAGGCAGACA AGGGCCCCTC GTGTGTCCGC TCCCCCATCT CCACGGACGA GTGCAGCATC 900
CAGGAGCTGG AGCAGAAGCT GTTGGAGAGG GAGGGCGCCC TCCAGAAGCT GCAGCGCAGC 960
TTTGAGGAGA AGGAGCTTGC CTCCAGCCTG GCCTACGAGG AGCGGCCGCG GCGCTGCAGG 1020
GACGAGCTGG AGGGCCCGGA GCCCAAAGGC GGCAACAAGC TCAAGCAGGC CTCGCAGAAG 1080
AGCCAGCGCG CGCAGCAGGT CCTGCACCTG CAGGTACTGC AGCTTCAGCA GGAGAAGCGG 1140
CAGCTCCGGC AGGAGCTCGA GAGCCTCATG AAGGAGCAGG ACCTGCTGGA GACCAAGCTC 1200
AGGTCCTACG AGAGGGAGAA GACCAGCTTC GGCCCCGCGC TGGAGGAGAC CCAGTGGGAG 1260
GTGTGCCAGA AGTCAGGCGA GATCTCCCTC CTGAAGCAGC AGCTGAAGGA GTCCCAGACG 1320
GAGGTGAACG CCAAGGCTAG CGAGATCCTG GGTCTCAAGG CACAGCTGAA GGACACGCGG 1380
GGCAAGCTGG AGGGCCTGGA GCTGAGGACC CAGGACCTGG AGGGCGCCCT GCGCACCAAG 1440
GGCCTGGAGC TGGAGGTCTG TGAGAATGAG CTGCAGCGCA AGAAGAACGA GGCGGAGCTG 1500
```

Fig. 5B-1

```
CTGCGGGAGA AGGTGAACCT GCTGGAGCAG GAGCTGCAGG AGCTGCGGGC CCAGGCCGCC 1560
CTGGCCCGCG ACATGGGGCC GCCCACCTTC CCCGAGGACG TCCCTGCCCT GCAGCGGGAG 1620
CTGGAGCGGC TGCGGGCCGA GCTGCGGGAG GAGCGGCAAG GCCATGACCA GATGTCCTCG 1680
GGCTTCCAGC ATGAGCGGCT CGTGTGGAAG GAGGAGAAGG AGAAGGTGAT TCAGTACCAG 1740
AAACAGCTGC AGCAGAGCTA CGTGGCCATG TACCAGCGGA ACCAGCGCCT GGAGAAGGCC 1800
CTGCAGCAGC TGGCACGTGG GGACAGCGCC GGGGAGCCCT TGGAGGTTGA CCTGGAAGGG 1860
GCTGACATCC CCTACGAGGA CATCATAGCC ACTGAGATCT GAGGGGCTGC CTGGGAAGGC 1920
GAGTCTGGGG ACCTGGCACT GGGAGGCAGG GCTCTCCCGT GCATCCCCCC TGCTCAGCAA 1980
TTCAGACCCC TCTGAGAGAC GCCACTCCCT GGGACACAGA CCCAGGACCC CCGAGGGGAG 2040
GGCAGGATGG CCTTTCCTTC CCTCTCTGAT GTCCCAGTGC TCACCAGCCC TGCAGCCCAC 2100
CAGACGTCAG GCCCTGACTC CTCTGGCTTT CCCAGGAGAT GGGTCCAGGG GTCTGTCTGC 2160
TTTGGTTAAG GGCTCCCTAA ACTTTGGCCT TTGTTCGAAA TAGATATCCT CTCCCCCTCC 2220
TCCAGGGAAG GTGGCCACAG CAAGAACAGC GGCTCCCCTC CGCTTCTCAT CCCAACCTCT 2280
TTTTCCTCCT GGACACATTG GAATGCCTTG GAAATAGAAA GAAGCCATAT ATGACCAGAA 2340
GCCTTGGAAC CAGCCCCATC AGAACCTGAG CTATTTTCCT CTGGCCGCAG AGGTGTAGGG 2400
GTGGAATGAG CCGCGGGGAA GCTGGCTTTG AAACCTCAGG GCTGTCCCAG CCCCGGCAAG 2460
CCACAGGAAG GAGGGGAGAG ACAGGCAGCC CAGCAGTGTG GAGACCCTGC CACAGCCAGA 2520
GGAGGGCAGA GGGAGAATCC AAGGGTTGAG AGCCAGTGGC GGGTGATGGC CAGCCCCTGG 2580
GGCCCAGCCC CTGTTTACTG GTTCTTGCAA ATGGGAGCTG AGCAGCCTCT GGACAGCCAG 2640
TGACCTTTGA CCTCGGTGAC CACTCTTCTT TAAGCCATAG ACCCTGAGGC CCTGGGCTGG 2700
GTGCTGGGAA GGGAGGGTTG AAACCACCGT GAACCAGAGG GTGTGGCTTT CCAGGCACCC 2760
TCAGGGAGCC TCCCCATCTG TCCAGCTGGG GCCAGAGGCT GGGAGTCCCT ACCTGCTTCA 2820
CGTTGGCCGG CGGCTACTCT GGAATGTTTT TCCCTCCCCA GAATCAAGCT TTTGCTTGAT 2880
CCAGAAGAGC CCATATCACT AAGATGGCAT ATATGTGATC TGGGCATTTT CCTCCTCTGC 2940
CTACAGCCAG GTTTAGCGGC AAACCTTTCC CCCTTAGCAC CTTCAGGGCT GAGTTCTGGG 3000
```

Fig. 5B-2

```
TTTCTAGAGG TCAGGACGGC TCCTCAGAGC GCCAGGAAGC CAGAGCCCCA AGCAGGACGA 3060
AAAAGAGGCA TACACACAGC AGTGTGAATA GCCTGGCCAC CAGCCATCCT CCCTCCACCT 3120
CAAGACCCCC ATTTGTCCCA GACTAAAGGA TCCAGAGAGC AGCTCCCTTT CTCAGGAGCT 3180
TGGGCAGTGC CCCAGGGAGT CCAGGGTTTC TCTGCAGATG TGCGGAGCGG GAGGCGGTGG 3240
TAGAGAGAGA TAAAAGGTGG AGTTTCTCTG TTGTTTGGTT CAGGGATTTT ATTTTTAATT 3300
TTATGAGACA GGGTCTTGCT CTGTCCCCCA GGCTGGAGTG CAGTGGCATG ATCATAGCTC 3360
ACTGCAGCCT CATACTCCTG GGCTCAAGCA ATCCTCCTGC CTCAGCCTTC CAACTAGCTG 3420
GGACTACAGG TGCGCGCCAC CGTGCCTGGC TAACTTTTCA TTTTTTTTGT AGGGACGGGG 3480
TCTCGTTTTG TTGCCAAAGC TGGTCTCAAA CTTGTGGCCT CAAGCAATCC ACCTGCCTTG 3540
GCCTCCCAAA GTGCTGAGAT TGCAGATGTG AGCCACCGTG CCTGGCCAGA TTTTTCTTTT 3600
ATTCTTCTTT CTTTTTCTTT TTTGCTTTCT TGTCTTTTCA GAAGCAAGCC AGACCTAGCA 3660
GGCTGTTCCA TGTTCTATTT TTGACTGTAG CCACAGCTGC TGTTCTCAGG ACAGCATCCC 3720
TTCCCACATG CCTGCGCCTG CTGCCTGCTG AGATGAGGAG GGGAGCGTCT GGGAACTTGC 3780
GAGTCCAAGG CCAGTCCCCA TTTCTGCCTC GCTCACCGCT GGCCCTTAGA GACCCCGAGG 3840
TAGGGGTGGG GAGATGCTTC TCTCCTTGCC CCCCGCCCTC ATGGGTCCTA GCCCTTCCCT 3900
GAGTGCGGGC TGAGGCCAGA GTCACCTTTT CTGTGGCTGG CTCTACCTTC CTGTCCCTGA 3960
GGTTAAACGG TGCCCATCCT GCCATCCTCA AACGACAGAG GAGCTTTTCT GGAATTTCAA 4020
ACCATTGCTC TTAGTCCCAA GCTAGGCTTA AACCTGGAAT CTACAAGCCA AAAGTCCCTC 4080
CCTGCCTGAG GGCAGTACCC TCCATTGGGC ACAGTCCAGA CCCAAGTCAA AGATGCCCCA 4140
TTCCTTGCGC CTCAGCCCTC AGTTCCTTCA TTTCCACCAG GCCGTGCCTT GTTTGAGTTT 4200
TTCCTCCCAG TGAGACTGCC CCACGGAGAC AGAGGAAAGG GCTGGCTCCC CCTCCCCAGG 4260
CTGGAGACCC CCCCCAACTC CAGGAAAGAG CAGTCAGAGT CCAGTGCTCT GCCTCAGACG 4320
TTGCCTGAGA AGAAGTGGCT GCCACACCCA GGGGAAGGCC CTGAGGCGGA GGCTGTGCTC 4380
CGCCATGGTG TCCCGGTACC TTCCATACAC AGAGGAGTGC AGCCTTCTCC ATATCTCCAT 4440
GGCCCTGTCC CAGGCCGGCC CAGATGTGTC CCCCCCAGGC CTTGTCCTAC GTCCAAGGTG 4500
```

Fig. 5B-3

```
GCAGATGTCT TCCCTGGGCT GCCACCAGCC CCCGCCCCAG AGTGGCCCAC CGTGGCACTA 4560
GAATGCAAGT ATCCTGCGAC CTTGCAACCT CACCTTCCTG TGGGTGTTCT TTCCTGCCCT 4620
GTCCAAAAGC GCCCTCACTA TTCTTGGACC ATGCCAGATT CTGCCTCTCT GGAAAGAGGC 4680
TCTGGACAGC AGAAGCCTCC AAGCACAGAG CCTGGCCCCA GGCCCCAGAC AGGGTGGGCT 4740
TCCTGCCCTT CCCTCTGGGC ACGCCTGCTG GCCGACCCAC TGACCCACTC GGATGGACCA 4800
ACCTGCTCTG TCCCCAAAGG ACGCCTGCAG GAGAGAGCAG CACTCCGCAT CACCTCACCA 4860
AGGATCGGAC TCTGCCCCTG GACCTGGGAA CGACTGGACT GTCACGGGGT TCCCTCCTAG 4920
CTCTCCCAGT GAACTCCTGC CAGGCACACA CAGCCCCTAT AGCACTGAGC TCACATGGGA 4980
CTGGGATATG GGGGCATCTC TTCCCCAGAG AGGCACTCAG TGAGCCTCCT GTGCCTGGCC 5040
CCAGTCTGGG CCATCTCTTA GGTGAGACAG TTGCCCGAAA CTAAGCCAGG CCTGGCTGGA 5100
GGAGCAGCAG CTTGGGGAGA GGGATTTCCC TGCAGACCTC AAGCCATCAT GCGGTGGGTG 5160
CTGCCATGAC AGAGGCTGCA CCCCTGGGCC AGCGGGGCTG CTCACCCACC TCTTGTGCAA 5220
GGTGGCCTTT GTGCTGCGCC TGCAGGCAGA GCTGGAGCCC CCAGCAGAGG CAGGCTGGGA 5280
CGGACCAGCA TCTGGAAGAT GTACATAGTT ATTTTTCTCT TTGTGGTTTC TTGTTTGGTT 5340
TGGTTTGCTT TTGACAGCTT CATTTTATTT TTGACGTCAC TTTTTGGCCA TGTAAACTAT 5400
TTGTGGCAAT TTTATGTTTT TATTTATGAA TAAAGAATGC CATTTCTCAC GCCCTCTAAA 5460
AAAAAAAAAA AAAAAAAAAA AAAAAAAAAA AA                               5492
```

Fig. 5B-4

```
ATGGGCAGCG TCAGTAGCCT CATCTCCGGC CACAGCTTCC ACAGCAAGCA CTGCCGGGCT 60
TCGCAGTACA AGCTGCGCAA GTCCTCCCAC CTCAAGAAGC TCAACCGGTA TTCCGACGGG 120
CTGCTGAGGT TTGGCTTCTC CCAGGACTCC GGTCACGGCA AGGCCATGAC CAGATGTCCT 180
CGGGCTTCCA GCATGAGCGG CTCGTGTGGA AGGAGGAGAA GGAGAAGGTG ATTCAGTACC 240
AGAAACAGCT GCAGCAGAGC TACGTGGCCA TGTACCAGCG GAACCAGCGC CTGGAGAAGG 300
CCCTGCAGCA GCTGGCACGT GGGGACAGCG CCGGGGAGCC CTTGGAGGTT GACCTGGAAG 360
GGGCTGACAT CCCCTACGAG GACATCATAG CCACTGAGAT CTGA                  404
```

Fig. 5C

```
ATGGGCAGCG TCAGTAGCCT CATCTCCGGC CACAGCTTCC ACAGCAAGCA CTGCCGGGCT 60
TCGCAGTACA AGCTGCGCAA GTCCTCCCAC CTCAAGAAGC TCAACCGGTA TTCCGACGGG 120
CTGCTGAGGT TTGGCTTCTC CCAGGACTCC GGTCACGGCA AGTCCAGCTC CAAAATGGGC 180
AAGAGCGAAG ACTTCTTCTA CATCAAGGTC AGCCAGAAAG CCCGGGGCTC CCATCACCCA 240
GATTACACGG CACTGTCCAG CGGGGATTTA GGGGGCCAGG CTGGGGTGGA CTTTGACCCG 300
TCCACACCCC CCAAGCTCAT GCCCTTCTCC AATCAGCTAG AAATGGGCTC CGAGAAGGGT 360
GCAGTGAGGC CCACAGCCTT CAAGCCTGTG CTGCCACGGT CAGGAGCCAT CCTGCACTCC 420
TCCCCGGAGA GTGCCAGCCA CCAGCTGCAC CCCGCCCCTC CAGACAAGCC CAAGGAGCAG 480
GAGCTGAAGC CTGGCCTGTG CTCTGGGGCG CTGTCAGACT CCGGCCGGAA CTCCATGTCC 540
AGCCTGCCCA CACACAGCGC CGGGGAGCCC TTGGAGGTTG ACCTGGAAGG GGCTGACATC 600
CCCTACGAGG ACATCATAGC CACTGAGATC TGA                             633
```

Fig. 5D

```
ATGGGCAGCG TCAGTAGCCT CATCTCCGGC CACAGCTTCC ACAGCAAGCA CTGCCGGGCT 60
TCGCAGTACA AGCTGCGCAA GTCCTCCCAC CTCAAGAAGC TCAACCGGTA TTCCGACGGG 120
CTGCTGAGGT TTGGCTTCTC CCAGGACTCC GGTCACGGCA AGTCCAGCTC CAAAATGGGC 180
AAGAGCGAAG ACTTCTTCTA CATCAAGGTC AGCCAGAAAG CCCGGGGCTC CCATCACCCA 240
GATTACACGG CACTGTCCAG CGGGGATTTA GGGGGCCAGG CTGGGGTGGA CTTTGACCCG 300
TCCACACCCC CCAAGCTCAT GCCCTTCTCC AATCAGCTAG AAATGGGCTC CGAGAAGGGT 360
GCAGTGAGGC CCACAGCCTT CAAGCCTGTG CTGCCACGGT CAGGAGCCAT CCTGCACTCC 420
TCCCCGGAGA GTGCCAGCCA CCAGCTGCAC CCCGCCCCTC CAGACAAGCC CAAGGAGCAG 480
GAGCTGAAGC CTGGCCTGTG CTCTGGGGCG CTGTCAGACT CCGGCCGGAA CTCCATGTCC 540
AGCCTGCCCA CACACAGCAC CAGCAGCAGC TACCAGCTGG ACCCGCTGGT CACACCCGTG 600
GGACCCACAA GCCGTTTTGG GGGCTCCGCC CACAACATCA CCCAGGGCAT CGTCCTCCAG 660
GACAGCAACA TGATGAGCCT GAAGGCTCTG TCCTTCTCCG ACGGAGGTAG CAAGCTGGGC 720
CACTCGAACA AGGCAGACAA GGGCCCCTCG TGTGTCCGCT CCCCCATCTC CACGGACGAG 780
TGCAGCATCC AGGAGCTGGA GCAGAAGCTG TTGGAGAGGG AGGGCGCCCT CCAGAAGCTG 840
CAGCGCAGCT TTGAGGAGAA GGAGCTTGCC TCCAGCCTGG CCTACGAGGA GCGGCCGCGG 900
CGCTGCAGGG ACGAGCTGGA GGGCCCGGAG CCCAAAGGCG GCAACAAGCT CAAGCAGGCC 960
TCGCAGAAGA GCCAGCGCGC GCAGCAGGTC CTGCACCTGC AGGTACTGCA GCTTCAGCAG 1020
GAGAAGCGGC AGCTCCGGCA GGAGCTCGAG AGCCTCATGA AGGAGCAGGA CCTGCTGGAG 1080
ACCAAGCTCA GGTCCTACGA GAGGGAGAAG ACCAGCTTCG GCCCCGCGCT GGAGGAGACC 1140
CAGTGGGAGG TGTGCCAGAA GTCAGGCGAG ATCTCCCTCC TGAAGCAGCA GCTGAAGGAG 1200
TCCCAGACGG AGGTGAACGC CAAGGCTAGC GAGATCCTGG GTCTCAAGGC ACAGCTGAAG 1260
GACACGCGGG GCAAGCTGGA GGGCCTGGAG CTGAGGACCC AGGACCTGGA GGGCGCCCTG 1320
CGCACCAAGG GCCTGGAGCT GGAGGTCTGT GAGAATGAGC TGCAGCGCAA GAAGAACGAG 1380
GCGGAGCTGC TGCGGGAGAA GCATGAGCGG CTCGTGTGGA AGGAGGAGAA GGAGAAGGTG 1440
```

Fig. 5E-1

```
ATTCAGTACC AGAAACAGCT GCAGCAGAGC TACGTGGCCA TGTACCAGCG GAACCAGCGC 1500
CTGGAGAAGG CCCTGCAGCA GCTGGCACGT GGGGACAGCG CCGGGGAGCC CTTGGAGGTT 1560
GACCTGGAAG GGGCTGACAT CCCCTACGAG GACATCATAG CCACTGAGAT CTGA
1614
```

Fig. 5E-2

```
ATGGGCAGCG TCAGTAGCCT CATCTCCGGC CACAGCTTCC ACAGCAAGCA CTGCCGGGCT 60
TCGCAGTACA AGCTGCGCAA GTCCTCCCAC CTCAAGAAGC TCAACCGGTA TTCCGACGGG 120
CTGCTGAGGT TTGGCTTCTC CCAGGACTCC GGTCACGGCA AGTCCAGCTC CAAAATGGGC 180
AAGAGCGAAG ACTTCTTCTA CATCAAGGTC AGCCAGAAAG CCCGGGGCTC CCATCACCCA 240
GATTACACGG CACTGTCCAG CGGGGATTTA GGGGGCCAGG CTGGGGTGGA CTTTGACCCG 300
TCCACACCCC CCAAGCTCAT GCCCTTCTCC AATCAGCTAG AAATGGGCTC CGAGAAGGGT 360
GCAGTGAGGC CCACAGCCTT CAAGCCTGTG CTGCCACGGT CAGGAGCCAT CCTGCACTCC 420
TCCCCGGAGA GTGCCAGCCA CCAGCTGCAC CCCGCCCCTC CAGACAAGCC CAAGGAGCAG 480
GAGCTGAAGC CTGGCCTGTG CTCTGGGGCG CTGTCAGACT CCGGCCGGAA CTCCATGTCC 540
AGCCTGCCCA CACACAGCAC CAGCAGCAGC TACCAGCTGG ACCCGCTGGT CACACCCGTG 600
GGACCCACAA GCCGTTTTGG GGGCTCCGCC CACAACATCA CCCAGGGCAT CGTCCTCCAG 660
GACAGCAACA TGATGAGCCT GAAGGCTCTG TCCTTCTCCG ACGGAGGTAG CAAGCTGGGC 720
CACTCGAACA AGGCAGACAA GGGCCCCTCG TGTGTCCGCT CCCCCATCTC CACGGACGAG 780
TGCAGCATCC AGGAGCTGGA GCAGAAGCTG TTGGAGAGGG AGGGCGCCCT CCAGAAGCTG 840
CAGCGCAGCT TTGAGGAGAA GGAGCTTGCC TCCAGCCTGG CCTACGAGGA GCGGCCGCGG 900
CGCTGCAGGG ACGAGCTGGA GGGCCCGGAG CCCAAAGGCG GCAACAAGCT CAAGCAGGCC 960
TCGCAGAAGA GCCAGCGCGC GCAGCAGGTC CTGCACCTGC AGGTACTGCA GCTTCAGCAG 1020
```

Fig. 5F-1

```
GAGAAGCGGC AGCTCCGGCA GGAGCTCGAG AGCCTCATGA AGGAGCAGGA CCTGCTGGAG 1080
ACCAAGCTCA GGTCCTACGA GAGGGAGAAG ACCAGCTTCG GCCCCGCGCT GGAGGAGACC 1140
CAGTGGGAGG TGTGCCAGAA GTCAGGCGAG ATCTCCCTCC TGAAGCAGCA GCTGAAGGAG 1200
TCCCAGACGG AGGTGAACGC CAAGGCTAGC GAGATCCTGG GTCTCAAGGC ACAGCTGAAG 1260
GACACGCGGG GCAAGCTGGA GGGCCTGGAG CTGAGGACCC AGGACCTGGA GGGCGCCCTG 1320
CGCACCAAGG GCCTGGAGCT GGAGGTCTGT GAGAATGAGC TGCAGCAGAG CTACGTGGCC 1380
ATGTACCAGC GGAACCAGCG CCTGGAGAAG GCCCTGCAGC AGCTGGCACG TGGGGACAGC 1440
GCCGGGGAGC CCTTGGAGGT TGACCTGGAA GGGGCTGACA TCCCCTACGA GGACATCATA 1500
GCCACTGAGA TC                                                   1512
```

Fig. 5F-2

```
ATGGGCAGCG TCAGTAGCCT CATCTCCGGC CACAGCTTCC ACAGCAAGCA CTGCCGGGCT 60
TCGCAGTACA AGCTGCGCAA GTCCTCCCAC CTCAAGAAGC TCAACCGGTA TTCCGACGGG 120
CTGCTGAGGT TTGGCTTCTC CCAGGACTCC GGTCACGGCA AGTCCAGCTC CAAAATGGGC 180
AAGAGCGAAG ACTTCTTCTA CATCAAGGTC AGCCAGAAAG CCCGGGGCTC CCATCACCCA 240
GATTACACGG CACTGTCCAG CGGGGATTTA GGGGGCCAGG CTGGGGTGGA CTTTGACCCG 300
TCCACACCCC CCAAGCTCAT GCCCTTCTCC AATCAGCTAG AAATGGGCTC CGAGAAGGGT 360
GCAGTGAGGC CCACAGCCTT CAAGCCTGTG CTGCCACGGT CAGGAGCCAT CCTGCACTCC 420
TCCCCGGAGA GTGCCAGCCA CCAGCTGCAC CCCGCCCCTC CAGACAAGCC CAAGGAGCAG 480
GAGCTGAAGC CTGGCCTGTG CTCTGGGGCG CTGTCAGACT CCGGCCGGAA CTCCATGTCC 540
AGCCTGCCCA CACACAGCAC CAGCAGCAGC TACCAGCTGG ACCCGCTGGT CACACCCGTG 600
GGACCCACAA GCCGTTTTGG GGGCTCCGCC CACAACATCA CCCAGGGCAT CGTCCTCCAG 660
```

Fig. 5G-1

```
GACAGCAACA TGATGAGCCT GAAGGCTCTG TCCTTCTCCG ACGGAGGTAG CAAGCTGGGC 720
CACTCGAACA AGGCAGACAA GGGCCCCTCG TGTGTCCGCT CCCCCATCTC CACGGACGAG 780
TGCAGCATCC AGGAGCTGGA GCAGAAGCTG TTGGAGAGGG AGGGCGCCCT CCAGAAGCTG 840
CAGCGCAGCT TTGAGGAGAA GGAGCTTGCC TCCAGCCTGG CCTACGAGGA GCGGCCGCGG 900
CGCTGCAGGG ACGAGCTGGA GGGCCCGGAG CCCAAAGGCG GCAACAAGCT CAAGCAGGCC 960
TCGCAGAAGA GCCAGCGCGC GCAGCAGGTC CTGCACCTGC AGGTACTGCA GCTTCAGCAG 1020
GAGAAGCGGC AGCTCCGGCA GGAGCTCGAG AGCCTCATGA AGGAGCAGGA CCTGCTGGAG 1080
ACCAAGCTCA GGTCCTACGA GAGGGAGAAG ACCAGCTTCG GCCCCGCGCT GGAGGAGACC 1140
CAGTGGGAGG TGTGCCAGAA GTCAGGCGAG ATCTCCCTCC TGAAGCAGCA GCTGAAGGAG 1200
TCCCAGACGG AGGTGAACGC CAAGGCTAGC GAGATCCTGG GTCTCAAGGC ACAGCTGAAG 1260
GACACGCGGG GCAAGCTGGA GGGCCTGGAG CTGAGGACCC AGGACCTGGA GGGCGCCCTG 1320
CGCACCAAGG GCCTGGAGCT GGAGGTCTGT GAGAATGAGC TGCAGCGCAA GAAGAACGAG 1380
GCGGAGCTGC TGCGGGAGAA GGTGAACCTG CTGGAGCGGC TGCGGGCCGA GCTGCGGGAG 1440
GAGCGGCAAG GCCATGACCA GATGTCCTCG GGCTTCCAGC ATGAGCGGCT CGTGTGGAAG 1500
GAGGAGAAGG AGAAGGTGAT TCAGTACCAG AAACAGCTGC AGCAGAGCTA CGTGGCCATG 1560
TACCAGCGGA ACCAGCGCCT GGAGAAGGCC CTGCAGCAGC TGGCACGTGG GGACAGCGCC 1620
GGGGAGCCCT TGGAGGTTGA CCTGGAAGGG GCTGACATCC CCTACGAGGA CATCATAGCC 1680
ACTGAGATCT GA                                                    1692
```

Fig. 5G-2

```
ATGGGCAGCG TCAGTAGCCT CATCTCCGGC CACAGCTTCC ACAGCAAGCA CTGCCGGGCT 60
TCGCAGTACA AGCTGCGCAA GTCCTCCCAC CTCAAGAAGC TCAACCGGTA TTCCGACGGG 120
CTGCTGAGGT TTGGCTTCTC CCAGGACTCC GGTCACGGCA AGTCCAGCTC CAAAATGGGC 180
```

Fig. 5H-1

```
AAGAGCGAAG ACTTCTTCTA CATCAAGGTC AGCCAGAAAG CCCGGGGCTC CCATCACCCA 240
GATTACACGG CACTGTCCAG CGGGGATTTA GGGGGCCAGG CTGGGGTGGA CTTTGACCCG 300
TCCACACCCC CCAAGCTCAT GCCCTTCTCC AATCAGCTAG AAATGGGCTC CGAGAAGGGT 360
GCAGTGAGGC CCACAGCCTT CAAGCCTGTG CTGCCACGGT CAGGAGCCAT CCTGCACTCC 420
TCCCCGGAGA GTGCCAGCCA CCAGCTGCAC CCCGCCCCTC CAGACAAGCC CAAGGAGCAG 480
GAGCTGAAGC CTGGCCTGTG CTCTGGGGCG CTGTCAGACT CCGGCCGGAA CTCCATGTCC 540
AGCCTGCCCA CACACAGCAC CAGCAGCAGC TACCAGCTGG ACCCGCTGGT CACACCCGTG 600
GGACCCACAA GCCGTTTTGG GGGCTCCGCC CACAACATCA CCCAGGGCAT CGTCCTCCAG 660
GACAGCAACA TGATGAGCCT GAAGGCTCTG TCCTTCTCCG ACGGAGGTAG CAAGCTGGGC 720
CACTCGAACA AGGCAGACAA GGGCCCCTCG TGTGTCCGCT CCCCCATCTC CACGGACGAG 780
TGCAGCATCC AGGAGCTGGA GCAGAAGCTG TTGGAGAGGG AGGGCGCCCT CCAGAAGCTG 840
CAGCGCAGCT TTGAGGAGAA GGAGCTTGCC TCCAGCCTGG CCTACGAGGA GCGGCCGCGG 900
CGCTGCAGGG ACGAGCTGGA GGGCCCGGAG CCCAAAGGCG GCAACAAGCT CAAGCAGGCC 960
TCGCAGAAGA GCCAGCGCGC GCAGCAGGTC CTGCACCTGC AGGTACTGCA GCTTCAGCAG 1020
GAGAAGCGGC AGCTCCGGCA GGAGCTCGAG AGCCTCATGA AGGAGCAGGA CCTGCTGGAG 1080
ACCAAGCTCA GGTCCTACGA GAGGGAGAAG ACCAGCTTCG GCCCCGCGCT GGAGGAGACC 1140
CAGTGGGAGG TGTGCCAGAA GTCAGGCGAG ATCTCCCTCC TGAAGCAGCA GCTGAAGGAG 1200
TCCCAGACGG AGGTGAACGC CAAGGCTAGC GAGATCCTGG GTCTCAAGGC ACAGCTGAAG 1260
GACACGCGGG GCAAGCTGGA GGGCCTGGAG CTGAGGACCC AGGACCTGGA GGGCGCCCTG 1320
CGCACCAAGG GCCTGGAGCT GGAGGTCTGT GAGAATGAGC TGCAGCGCAA GAAGAACGAG 1380
GCGGAGCTGC TGCGGGAGAA GGTGAACCTG CTGGAGCAGG AGCTGCAGGA GCTGCGGGCC 1440
CAGGCCGCCC TGGCCCGCGA CATGGGGCCG CCCACCTTCC CCGAGGACGT CCCTGCCCTG 1500
CAGCGGGAGC TGGAGCGGCT CGTGTGGAAG GAGGAGAAGG AGAAGGTGAT TCAGTACCAG 1560
AAACAGCTGC AGCAGAGCTA CGTGGCCATG TACCAGCGGA ACCAGCGCCT GGAGAAGGCC 1620
CTGCAGCAGC TGGCACGTGG GGACAGCGCC GGGGAGCCCT TGGAGGTTGA CCTGGAAGGG 1680
GCTGACATCC CCTACGAGGA CATCATAGCC ACTGAGATCT GA                    1722
```

Fig. 5H-2

```
ATGGGCAGCG TCAGTAGCCT CATCTCCGGC CACAGCTTCC ACAGCAAGCA CTGCCGGGCT 60
TCGCAGTACA AGCTGCGCAA GTCCTCCCAC CTCAAGAAGC TCAACCGGTA TTCCGACGGG 120
CTGCTGAGGT TTGGCTTCTC CCAGGACTCC GGTCACGGCA AGTCCAGCTC CAAAATGGGC 180
AAGAGCGAAG ACTTCTTCTA CATCAAGGTC AGCCAGAAAG CCCGGGGCTC CCATCACCCA 240
GATTACACGG CACTGTCCAG CGGGGATTTA GGGGGCCAGG CTGGGGTGGA CTTTGACCCG 300
TCCACACCCC CCAAGCTCAT GCCCTTCTCC AATCAGCTAG AAATGGGCTC CGAGAAGGGT 360
GCAGTGAGGC CCACAGCCTT CAAGCCTGTG CTGCCACGGT CAGGAGCCAT CCTGCACTCC 420
TCCCCGGAGA GTGCCAGCCA CCAGCTGCAC CCCGCCCCTC CAGACAAGCC CAAGGAGCAG 480
GAGCTGAAGC CTGGCCTGTG CTCTGGGGCG CTGTCAGACT CCGGCCGGAA CTCCATGTCC 540
AGCCTGCCCA CACACAGCAC CAGCAGCAGC TACCAGCTGG ACCCGCTGGT CACACCCGTG 600
GGACCCACAA GCCGTTTTGG GGGCTCCGCC CACAACATCA CCCAGGGCAT CGTCCTCCAG 660
GACAGCAACA TGATGAGCCT GAAGGCTCTG TCCTTCTCCG ACGGAGGTAG CAAGCTGGGC 720
CACTCGAACA AGGCAGACAA GGGCCCCTCG TGTGTCCGCT CCCCCATCTC CACGGACGAG 780
TGCAGCATCC AGGAGCTGGA GCAGAAGCTG TTGGAGAGGG AGGGCGCCCT CCAGAAGCTG 840
CAGCGCAGCT TTGAGGAGAA GGAGCTTGCC TCCAGCCTGG CCTACGAGGA GCGGCCGCGG 900
CGCTGCAGGG ACGAGCTGGA GGGCCCGGAG CCCAAAGGCG GCAACAAGCT CAAGCAGGCC 960
TCGCAGAAGA GCCAGCGCGC GCAGCAGGTC CTGCACCTGC AGGTACTGCA GCTTCAGCAG 1020
GAGAAGCGGC AGCTCCGGCA GGAGCTCGAG AGCCTCATGA AGGAGCAGGA CCTGCTGGAG 1080
ACCAAGCTCA GGTCCTACGA GAGGGAGAAG ACCAGCTTCG GCCCCGCGCT GGAGGAGACC 1140
CAGTGGGAGG TGTGCCAGAA GTCAGGCGAG ATCTCCCTCC TGAAGCAGCA GCTGAAGGAG 1200
TCCCAGACGG AGGTGAACGC CAAGGCTAGC GAGATCCTGG GTCTCAAGGC ACAGCTGAAG 1260
GACACGCGGG GCAAGCTGGA GGGCCTGGAG CTGAGGACCC AGGACCTGGA GGGCGCCCTG 1320
CGCACCAAGG GCCTGGAGCT GGAGGTCTGT GAGAATGAGC TGCAGCGCAA GAAGAACGAG 1380
GCGGAGCTGC TGCGGGAGAA GGTGAACCTG CTGGAGCAGG AGCTGCAGGA GCTGCGGGCC 1440
CAGGCCGCCC TGGCCCGCGA CATGGGGCCG CCCACCTTCC CCGAGGACGT CCCTGCCCTG 1500
```

Fig. 5I-1

```
CAGCGGGAGC TGGAGCGGCT GCGGGCCGAG CTGCGGGAGG AGCGGCAAGG CCATGACCAG 1560
ATGTCCTCGG GCTTCCAGCA TGAGCGGCTC GTGTGGAAGG AGGAGAAGGA GAAGGTGATT 1620
CAGTACCAGA AACAGCTGCA GCAGAGCTAC GTGGCCATGT ACCAGCGGAA CCAGCGCCTG 1680
GAGAAGGCCC TGCAGCAGCT GGCACGTGGG GACAGCGCCG GGGAGCCCTT GGAGGTTGAC 1740
CTGGAAGGGG CTGACATCCC CTACGAGGAC ATCATAGCCA CTGAGATCTG A          1791
```

Fig. 5I-2

```
MET GLY SER VAL SER SER LEU ILE SER GLY HIS SER PHE HIS SER LYS
 1               5                  10                  15

HIS CYS ARG ALA SER GLN TYR LYS LEU ARG LYS SER SER HIS LEU LYS
             20                  25                  30

LYS LEU ASN ARG TYR SER ASP GLY LEU LEU ARG PHE GLY PHE SER GLN
         35                  40                  45

ASP SER GLY HIS GLY LYS SER SER SER LYS MET GLY LYS SER GLU ASP
     50                  55                  60

PHE PHE TYR ILE LYS VAL SER GLN LYS ALA ARG GLY SER HIS HIS PRO
 65                  70                  75                  80

ASP TYR THR ALA LEU SER SER GLY ASP LEU GLY GLY GLN ALA GLY VAL
                 85                  90                  95

ASP PHE ASP PRO SER THR PRO PRO LYS LEU MET PRO PHE SER ASN GLN
            100                 105                 110

LEU GLU MET GLY SER GLU LYS GLY ALA VAL ARG PRO THR ALA PHE LYS
        115                 120                 125

PRO VAL LEU PRO ARG SER GLY ALA ILE LEU HIS SER SER PRO GLU SER
    130                 135                 140
```

Fig. 5J-1

```
ALA SER HIS GLN LEU HIS PRO ALA PRO PRO ASP LYS PRO LYS GLU GLN
145                 150                 155                 160

GLU LEU LYS PRO GLY LEU CYS SER GLY ALA LEU SER ASP SER GLY ARG
                165                 170                 175

ASN SER MET SER SER LEU PRO THR HIS SER THR SER SER SER TYR GLN
            180                 185                 190

LEU ASP PRO LEU VAL THR PRO VAL GLY PRO THR SER ARG PHE GLY GLY
        195                 200                 205

SER ALA HIS ASN ILE THR GLN GLY ILE VAL LEU GLN ASP SER ASN MET
    210                 215                 220

MET SER LEU LYS ALA LEU SER PHE SER ASP GLY GLY SER LYS LEU GLY
225                 230                 235                 240

HIS SER ASN LYS ALA ASP LYS GLY PRO SER CYS VAL ARG SER PRO ILE
                245                 250                 255

SER THR ASP GLU CYS SER ILE GLN GLU LEU GLU GLN LYS LEU LEU GLU
            260                 265                 270
```

Fig. 5J-2

```
ARG GLU GLY ALA LEU GLN LYS LEU GLN ARG SER PHE GLU GLU LYS GLU
        275                 280                 285

LEU ALA SER SER LEU ALA TYR GLU GLU ARG PRO ARG ARG CYS ARG ASP
    290                 295                 300

GLU LEU GLU GLY PRO GLU PRO LYS GLY GLY ASN LYS LEU LYS GLN ALA
305                 310                 315                 320

SER GLN LYS SER GLN ARG ALA GLN GLN VAL LEU HIS LEU GLN VAL LEU
                325                 330                 335

GLN LEU GLN GLN GLU LYS ARG GLN LEU ARG GLN GLU LEU GLU SER LEU
            340                 345                 350

MET LYS GLU GLN ASP LEU LEU GLU THR LYS LEU ARG SER TYR GLU ARG
        355                 360                 365

GLU LYS THR SER PHE GLY PRO ALA LEU GLU GLU THR GLN TRP GLU VAL
    370                 375                 380

CYS GLN LYS SER GLY GLU ILE SER LEU LEU LYS GLN GLN LEU LYS GLU
385                 390                 395                 400
```

Fig. 5J-3

```
SER GLN THR GLU VAL ASN ALA LYS ALA SER GLU ILE LEU GLY LEU LYS
                405                 410                 415

ALA GLN LEU LYS ASP THR ARG GLY LYS LEU GLU GLY LEU GLU LEU ARG
            420                 425                 430

THR GLN ASP LEU GLU GLY ALA LEU ARG THR LYS GLY LEU GLU LEU GLU
        435                 440                 445

VAL CYS GLU ASN GLU LEU GLN ARG LYS LYS ASN GLU ALA GLU LEU LEU
    450                 455                 460

ARG GLU LYS VAL ASN LEU LEU GLU GLN GLU LEU GLN GLU LEU ARG ALA
465                 470                 475                 480

GLN ALA ALA LEU ALA ARG ASP MET GLY PRO PRO THR PHE PRO GLU ASP
                485                 490                 495

VAL PRO ALA LEU GLN ARG GLU LEU GLU ARG LEU ARG ALA GLU LEU ARG
            500                 505                 510

GLU GLU ARG GLN GLY HIS ASP GLN MET SER SER GLY PHE GLN HIS GLU
        515                 520                 525
```

Fig. 5J-4

ARG LEU VAL TRP LYS GLU GLU LYS GLU LYS VAL ILE GLN TYR GLN LYS
530 535 540

GLN LEU GLN GLN SER TYR VAL ALA MET TYR GLN ARG ASN GLN ARG LEU
545 550 555 560

GLU LYS ALA LEU GLN GLN LEU ALA ARG GLY ASP SER ALA GLY GLU PRO
565 570 575

LEU GLU VAL ASP LEU GLU GLY ALA ASP ILE PRO TYR GLU ASP ILE ILE
580 585 590

ALA THR GLU ILE
595

Fig. 5J-5

```
MET GLY SER VAL SER SER LEU ILE SER GLY HIS SER PHE HIS SER LYS
 1              5                  10                  15
HIS CYS ARG ALA SER GLN TYR LYS LEU ARG LYS SER SER HIS LEU LYS
            20                  25                  30
LYS LEU ASN ARG TYR SER ASP GLY LEU LEU ARG PHE GLY PHE SER GLN
        35                  40                  45
ASP SER GLY HIS GLY LYS ALA MET THR ARG CYS PRO ARG ALA SER SER
    50                  55                  60
MET SER GLY SER CYS GLY ARG ARG ARG ARG ARG ARG
65                  70                  75
```

Fig. 5K

```
MET GLY SER VAL SER SER LEU ILE SER GLY HIS SER PHE HIS SER LYS
  1               5                  10                  15

HIS CYS ARG ALA SER GLN TYR LYS LEU ARG LYS SER SER HIS LEU LYS
             20                  25                  30

LYS LEU ASN ARG TYR SER ASP GLY LEU LEU ARG PHE GLY PHE SER GLN
         35                  40                  45

ASP SER GLY HIS GLY LYS SER SER SER LYS MET GLY LYS SER GLU ASP
     50                  55                  60

PHE PHE TYR ILE LYS VAL SER GLN LYS ALA ARG GLY SER HIS HIS PRO
 65                  70                  75                  80

ASP TYR THR ALA LEU SER SER GLY ASP LEU GLY GLY GLN ALA GLY VAL
                 85                  90                  95

ASP PHE ASP PRO SER THR PRO PRO LYS LEU MET PRO PHE SER ASN GLN
            100                 105                 110

LEU GLU MET GLY SER GLU LYS GLY ALA VAL ARG PRO THR ALA PHE LYS
        115                 120                 125

PRO VAL LEU PRO ARG SER GLY ALA ILE LEU HIS SER SER PRO GLU SER
    130                 135                 140
```

Fig. 5L-1

```
ALA SER HIS GLN LEU HIS PRO ALA PRO PRO ASP LYS PRO LYS GLU GLN
145                 150                 155                 160

GLU LEU LYS PRO GLY LEU CYS SER GLY ALA LEU SER ASP SER GLY ARG
                165                 170                 175

ASN SER MET SER SER LEU PRO THR HIS SER ALA GLY GLU PRO LEU GLU
            180                 185                 190

VAL ASP LEU GLU GLY ALA ASP ILE PRO TYR GLU ASP ILE ILE ALA THR
        195                 200                 205

GLU ILE
    210
```

Fig. 5L-2

```
MET GLY SER VAL SER SER LEU ILE SER GLY HIS SER PHE HIS SER LYS
 1               5                  10                  15

HIS CYS ARG ALA SER GLN TYR LYS LEU ARG LYS SER SER HIS LEU LYS
            20                  25                  30

LYS LEU ASN ARG TYR SER ASP GLY LEU LEU ARG PHE GLY PHE SER GLN
        35                  40                  45

ASP SER GLY HIS GLY LYS SER SER SER LYS MET GLY LYS SER GLU ASP
    50                  55                  60

PHE PHE TYR ILE LYS VAL SER GLN LYS ALA ARG GLY SER HIS HIS PRO
65                  70                  75                  80

ASP TYR THR ALA LEU SER SER GLY ASP LEU GLY GLY GLN ALA GLY VAL
                85                  90                  95

ASP PHE ASP PRO SER THR PRO PRO LYS LEU MET PRO PHE SER ASN GLN
            100                 105                 110

LEU GLU MET GLY SER GLU LYS GLY ALA VAL ARG PRO THR ALA PHE LYS
        115                 120                 125

PRO VAL LEU PRO ARG SER GLY ALA ILE LEU HIS SER SER PRO GLU SER
    130                 135                 140
```

Fig. 5M-1

```
ALA SER HIS GLN LEU HIS PRO ALA PRO PRO ASP LYS PRO LYS GLU GLN
145                 150                 155                 160

GLU LEU LYS PRO GLY LEU CYS SER GLY ALA LEU SER ASP SER GLY ARG
                165                 170                 175

ASN SER MET SER SER LEU PRO THR HIS SER THR SER SER SER TYR GLN
            180                 185                 190

LEU ASP PRO LEU VAL THR PRO VAL GLY PRO THR SER ARG PHE GLY GLY
        195                 200                 205

SER ALA HIS ASN ILE THR GLN GLY ILE VAL LEU GLN ASP SER ASN MET
    210                 215                 220

MET SER LEU LYS ALA LEU SER PHE SER ASP GLY GLY SER LYS LEU GLY
225                 230                 235                 240

HIS SER ASN LYS ALA ASP LYS GLY PRO SER CYS VAL ARG SER PRO ILE
                245                 250                 255

SER THR ASP GLU CYS SER ILE GLN GLU LEU GLU GLN LYS LEU LEU GLU
            260                 265                 270
```

Fig. 5M-2

```
ARG GLU GLY ALA LEU GLN LYS LEU GLN ARG SER PHE GLU GLU LYS GLU
        275                 280                 285

LEU ALA SER SER LEU ALA TYR GLU GLU ARG PRO ARG ARG CYS ARG ASP
    290                 295                 300

GLU LEU GLU GLY PRO GLU PRO LYS GLY GLY ASN LYS LEU LYS GLN ALA
305                 310                 315                 320

SER GLN LYS SER GLN ARG ALA GLN GLN VAL LEU HIS LEU GLN VAL LEU
                325                 330                 335

GLN LEU GLN GLN GLU LYS ARG GLN LEU ARG GLN GLU LEU GLU SER LEU
            340                 345                 350

MET LYS GLU GLN ASP LEU LEU GLU THR LYS LEU ARG SER TYR GLU ARG
        355                 360                 365

GLU LYS THR SER PHE GLY PRO ALA LEU GLU GLU THR GLN TRP GLU VAL
    370                 375                 380

CYS GLN LYS SER GLY GLU ILE SER LEU LEU LYS GLN GLN LEU LYS GLU
385                 390                 395                 400
```

Fig. 5M-3

```
SER GLN THR GLU VAL ASN ALA LYS ALA SER GLU ILE LEU GLY LEU LYS
                405                 410                 415

ALA GLN LEU LYS ASP THR ARG GLY LYS LEU GLU GLY LEU GLU LEU ARG
            420                 425                 430

THR GLN ASP LEU GLU GLY ALA LEU ARG THR LYS GLY LEU GLU LEU GLU
        435                 440                 445

VAL CYS GLU ASN GLU LEU GLN ARG LYS LYS ASN GLU ALA GLU LEU LEU
    450                 455                 460

ARG GLU LYS HIS GLU ARG LEU VAL TRP LYS GLU GLU LYS GLU LYS VAL
465                 470                 475                 480

ILE GLN TYR GLN LYS GLN LEU GLN GLN SER TYR VAL ALA MET TYR GLN
                485                 490                 495

ARG ASN GLN ARG LEU GLU LYS ALA LEU GLN GLN LEU ALA ARG GLY ASP
            500                 505                 510

SER ALA GLY GLU PRO LEU GLU VAL ASP LEU GLU GLY ALA ASP ILE PRO
        515                 520                 525

TYR GLU ASP ILE ILE ALA THR GLU ILE
    530                 535
```

Fig. 5M-4

```
MET GLY SER VAL SER SER LEU ILE SER GLY HIS SER PHE HIS SER LYS
  1               5                  10                  15

HIS CYS ARG ALA SER GLN TYR LYS LEU ARG LYS SER SER HIS LEU LYS
             20                  25                  30

LYS LEU ASN ARG TYR SER ASP GLY LEU LEU ARG PHE GLY PHE SER GLN
         35                  40                  45

ASP SER GLY HIS GLY LYS SER SER SER LYS MET GLY LYS SER GLU ASP
     50                  55                  60

PHE PHE TYR ILE LYS VAL SER GLN LYS ALA ARG GLY SER HIS HIS PRO
 65                  70                  75                  80

ASP TYR THR ALA LEU SER SER GLY ASP LEU GLY GLY GLN ALA GLY VAL
                 85                  90                  95

ASP PHE ASP PRO SER THR PRO PRO LYS LEU MET PRO PHE SER ASN GLN
            100                 105                 110

LEU GLU MET GLY SER GLU LYS GLY ALA VAL ARG PRO THR ALA PHE LYS
        115                 120                 125

PRO VAL LEU PRO ARG SER GLY ALA ILE LEU HIS SER SER PRO GLU SER
    130                 135                 140
```

Fig. 5N-1

```
ALA SER HIS GLN LEU HIS PRO ALA PRO PRO ASP LYS PRO LYS GLU GLN
145                 150                 155                 160

GLU LEU LYS PRO GLY LEU CYS SER GLY ALA LEU SER ASP SER GLY ARG
                165                 170                 175

ASN SER MET SER SER LEU PRO THR HIS SER THR SER SER SER TYR GLN
            180                 185                 190

LEU ASP PRO LEU VAL THR PRO VAL GLY PRO THR SER ARG PHE GLY GLY
        195                 200                 205

SER ALA HIS ASN ILE THR GLN GLY ILE VAL LEU GLN ASP SER ASN MET
    210                 215                 220

MET SER LEU LYS ALA LEU SER PHE SER ASP GLY GLY SER LYS LEU GLY
225                 230                 235                 240

HIS SER ASN LYS ALA ASP LYS GLY PRO SER CYS VAL ARG SER PRO ILE
                245                 250                 255

SER THR ASP GLU CYS SER ILE GLN GLU LEU GLU GLN LYS LEU LEU GLU
            260                 265                 270
```

Fig. 5N-2

```
ARG GLU GLY ALA LEU GLN LYS LEU GLN ARG SER PHE GLU GLU LYS GLU
        275                 280                 285

LEU ALA SER SER LEU ALA TYR GLU GLU ARG PRO ARG ARG CYS ARG ASP
    290                 295                 300

GLU LEU GLU GLY PRO GLU PRO LYS GLY GLY ASN LYS LEU LYS GLN ALA
305                 310                 315                 320

SER GLN LYS SER GLN ARG ALA GLN GLN VAL LEU HIS LEU GLN VAL LEU
                325                 330                 335

GLN LEU GLN GLN GLU LYS ARG GLN LEU ARG GLN GLU LEU GLU SER LEU
            340                 345                 350

MET LYS GLU GLN ASP LEU LEU GLU THR LYS LEU ARG SER TYR GLU ARG
        355                 360                 365

GLU LYS THR SER PHE GLY PRO ALA LEU GLU GLU THR GLN TRP GLU VAL
    370                 375                 380

CYS GLN LYS SER GLY GLU ILE SER LEU LEU LYS GLN GLN LEU LYS GLU
385                 390                 395                 400
```

Fig. 5N-3

```
SER GLN THR GLU VAL ASN ALA LYS ALA SER GLU ILE LEU GLY LEU LYS
                405                 410                 415

ALA GLN LEU LYS ASP THR ARG GLY LYS LEU GLU GLY LEU GLU LEU ARG
            420                 425                 430

THR GLN ASP LEU GLU GLY ALA LEU ARG THR LYS GLY LEU GLU LEU GLU
        435                 440                 445

VAL CYS GLU ASN GLU LEU GLN GLN SER TYR VAL ALA MET TYR GLN ARG
    450                 455                 460

ASN GLN ARG LEU GLU LYS ALA LEU GLN GLN LEU ALA ARG GLY ASP SER
465                 470                 475                 480

ALA GLY GLU PRO LEU GLU VAL ASP LEU GLU GLY ALA ASP ILE PRO TYR
                485                 490                 495

GLU ASP ILE ILE ALA THR GLU ILE
            500
```

Fig. 5N-4

```
MET GLY SER VAL SER SER LEU ILE SER GLY HIS SER PHE HIS SER LYS
 1               5                  10                  15

HIS CYS ARG ALA SER GLN TYR LYS LEU ARG LYS SER SER HIS LEU LYS
             20                  25                  30

LYS LEU ASN ARG TYR SER ASP GLY LEU LEU ARG PHE GLY PHE SER GLN
         35                  40                  45

ASP SER GLY HIS GLY LYS SER SER SER LYS MET GLY LYS SER GLU ASP
     50                  55                  60

PHE PHE TYR ILE LYS VAL SER GLN LYS ALA ARG GLY SER HIS HIS PRO
 65                  70                  75                  80

ASP TYR THR ALA LEU SER SER GLY ASP LEU GLY GLY GLN ALA GLY VAL
                 85                  90                  95

ASP PHE ASP PRO SER THR PRO PRO LYS LEU MET PRO PHE SER ASN GLN
            100                 105                 110

LEU GLU MET GLY SER GLU LYS GLY ALA VAL ARG PRO THR ALA PHE LYS
        115                 120                 125

PRO VAL LEU PRO ARG SER GLY ALA ILE LEU HIS SER SER PRO GLU SER
    130                 135                 140
```

Fig. 5O-1

```
ALA SER HIS GLN LEU HIS PRO ALA PRO PRO ASP LYS PRO LYS GLU GLN
145                 150                 155                 160

GLU LEU LYS PRO GLY LEU CYS SER GLY ALA LEU SER ASP SER GLY ARG
                165                 170                 175

ASN SER MET SER SER LEU PRO THR HIS SER THR SER SER SER TYR GLN
            180                 185                 190

LEU ASP PRO LEU VAL THR PRO VAL GLY PRO THR SER ARG PHE GLY GLY
        195                 200                 205

SER ALA HIS ASN ILE THR GLN GLY ILE VAL LEU GLN ASP SER ASN MET
    210                 215                 220

MET SER LEU LYS ALA LEU SER PHE SER ASP GLY GLY SER LYS LEU GLY
225                 230                 235                 240

HIS SER ASN LYS ALA ASP LYS GLY PRO SER CYS VAL ARG SER PRO ILE
                245                 250                 255

SER THR ASP GLU CYS SER ILE GLN GLU LEU GLU GLN LYS LEU LEU GLU
            260                 265                 270
```

Fig. 5O-2

```
ARG GLU GLY ALA LEU GLN LYS LEU GLN ARG SER PHE GLU GLU LYS GLU
        275                 280                 285

LEU ALA SER SER LEU ALA TYR GLU GLU ARG PRO ARG ARG CYS ARG ASP
    290                 295                 300

GLU LEU GLU GLY PRO GLU PRO LYS GLY GLY ASN LYS LEU LYS GLN ALA
305                 310                 315                 320

SER GLN LYS SER GLN ARG ALA GLN GLN VAL LEU HIS LEU GLN VAL LEU
                325                 330                 335

GLN LEU GLN GLN GLU LYS ARG GLN LEU ARG GLN GLU LEU GLU SER LEU
            340                 345                 350

MET LYS GLU GLN ASP LEU LEU GLU THR LYS LEU ARG SER TYR GLU ARG
        355                 360                 365

GLU LYS THR SER PHE GLY PRO ALA LEU GLU GLU THR GLN TRP GLU VAL
    370                 375                 380

CYS GLN LYS SER GLY GLU ILE SER LEU LEU LYS GLN GLN LEU LYS GLU
385                 390                 395                 400
```

Fig. 5O-3

SER GLN THR GLU VAL ASN ALA LYS ALA SER GLU ILE LEU GLY LEU LYS
405 410 415

ALA GLN LEU LYS ASP THR ARG GLY LYS LEU GLU GLY LEU GLU LEU ARG
420 425 430

THR GLN ASP LEU GLU GLY ALA LEU ARG THR LYS GLY LEU GLU LEU GLU
435 440 445

VAL CYS GLU ASN GLU LEU GLN ARG LYS LYS ASN GLU ALA GLU LEU LEU
450 455 460

ARG GLU LYS VAL ASN LEU LEU GLU ARG LEU ARG ALA GLU LEU ARG GLU
465 470 475 480

GLU ARG GLN GLY HIS ASP GLN MET SER SER GLY PHE GLN HIS GLU ARG
485 490 495

LEU VAL TRP LYS GLU GLU LYS GLU LYS VAL ILE GLN TYR GLN LYS GLN
500 505 510

LEU GLN GLN SER TYR VAL ALA MET TYR GLN ARG ASN GLN ARG LEU GLU
515 520 525

Fig. 5O-4

```
LYS ALA LEU GLN GLN LEU ALA ARG GLY ASP SER ALA GLY GLU PRO LEU
    530                 535                 540

GLU VAL ASP LEU GLU GLY ALA ASP ILE PRO TYR GLU ASP ILE ILE ALA
545                 550                 555                 560

THR GLU ILE
```

Fig. 5O-5

```
MET GLY SER VAL SER SER LEU ILE SER GLY HIS SER PHE HIS SER LYS
  1               5                  10                  15

HIS CYS ARG ALA SER GLN TYR LYS LEU ARG LYS SER SER HIS LEU LYS
              20                  25                  30

LYS LEU ASN ARG TYR SER ASP GLY LEU LEU ARG PHE GLY PHE SER GLN
         35                  40                  45

ASP SER GLY HIS GLY LYS SER SER SER LYS MET GLY LYS SER GLU ASP
     50                  55                  60
```

Fig. 5P-1

```
PHE PHE TYR ILE LYS VAL SER GLN LYS ALA ARG GLY SER HIS HIS PRO
 65                 70                  75                  80

ASP TYR THR ALA LEU SER SER GLY ASP LEU GLY GLY GLN ALA GLY VAL
                85                  90                  95

ASP PHE ASP PRO SER THR PRO PRO LYS LEU MET PRO PHE SER ASN GLN
            100                 105                 110

LEU GLU MET GLY SER GLU LYS GLY ALA VAL ARG PRO THR ALA PHE LYS
        115                 120                 125

PRO VAL LEU PRO ARG SER GLY ALA ILE LEU HIS SER SER PRO GLU SER
    130                 135                 140

ALA SER HIS GLN LEU HIS PRO ALA PRO PRO ASP LYS PRO LYS GLU GLN
145                 150                 155                 160

GLU LEU LYS PRO GLY LEU CYS SER GLY ALA LEU SER ASP SER GLY ARG
                165                 170                 175

ASN SER MET SER SER LEU PRO THR HIS SER THR SER SER SER TYR GLN
            180                 185                 190
```

Fig. 5P-2

| | | | | | | | | | | | | | | | |
|---|---|---|---|---|---|---|---|---|---|---|---|---|---|---|---|
| LEU | ASP | PRO | LEU | VAL | THR | PRO | VAL | GLY | PRO | THR | SER | ARG | PHE | GLY | GLY |
| | | 195 | | | | | 200 | | | | | 205 | | | |
| SER | ALA | HIS | ASN | ILE | THR | GLN | GLY | ILE | VAL | LEU | GLN | ASP | SER | ASN | MET |
| | 210 | | | | | 215 | | | | | 220 | | | | |
| MET | SER | LEU | LYS | ALA | LEU | SER | PHE | SER | ASP | GLY | GLY | SER | LYS | LEU | GLY |
| 225 | | | | | 230 | | | | | 235 | | | | | 240 |
| HIS | SER | ASN | LYS | ALA | ASP | LYS | GLY | PRO | SER | CYS | VAL | ARG | SER | PRO | ILE |
| | | | | 245 | | | | | 250 | | | | | 255 | |
| SER | THR | ASP | GLU | CYS | SER | ILE | GLN | GLU | LEU | GLU | GLN | LYS | LEU | LEU | GLU |
| | | | 260 | | | | | 265 | | | | | 270 | | |
| ARG | GLU | GLY | ALA | LEU | GLN | LYS | LEU | GLN | ARG | SER | PHE | GLU | GLU | LYS | GLU |
| | | 275 | | | | | 280 | | | | | 285 | | | |
| LEU | ALA | SER | SER | LEU | ALA | TYR | GLU | GLU | ARG | PRO | ARG | ARG | CYS | ARG | ASP |
| | 290 | | | | | 295 | | | | | 300 | | | | |
| GLU | LEU | GLU | GLY | PRO | GLU | PRO | LYS | GLY | GLY | ASN | LYS | LEU | LYS | GLN | ALA |
| 305 | | | | | 310 | | | | | 315 | | | | | 320 |

Fig. 5P-3

```
SER GLN LYS SER GLN ARG ALA GLN GLN VAL LEU HIS LEU GLN VAL LEU
                325                 330                 335

GLN LEU GLN GLN GLU LYS ARG GLN LEU ARG GLN GLU LEU GLU SER LEU
            340                 345                 350

MET LYS GLU GLN ASP LEU LEU GLU THR LYS LEU ARG SER TYR GLU ARG
        355                 360                 365

GLU LYS THR SER PHE GLY PRO ALA LEU GLU GLU THR GLN TRP GLU VAL
    370                 375                 380

CYS GLN LYS SER GLY GLU ILE SER LEU LEU LYS GLN GLN LEU LYS GLU
385                 390                 395                 400

SER GLN THR GLU VAL ASN ALA LYS ALA SER GLU ILE LEU GLY LEU LYS
                405                 410                 415

ALA GLN LEU LYS ASP THR ARG GLY LYS LEU GLU GLY LEU GLU LEU ARG
            420                 425                 430

THR GLN ASP LEU GLU GLY ALA LEU ARG THR LYS GLY LEU GLU LEU GLU
        435                 440                 445
```

Fig. 5P-4

```
VAL CYS GLU ASN GLU LEU GLN ARG LYS LYS ASN GLU ALA GLU LEU LEU
    450                 455                 460

ARG GLU LYS VAL ASN LEU LEU GLU GLN GLU LEU GLN GLU LEU ARG ALA
465                 470                 475                 480

GLN ALA ALA LEU ALA ARG ASP MET GLY PRO PRO THR PHE PRO GLU ASP
                485                 490                 495

VAL PRO ALA LEU GLN ARG GLU LEU GLU ARG LEU VAL TRP LYS GLU GLU
            500                 505                 510

LYS GLU LYS VAL ILE GLN TYR GLN LYS GLN LEU GLN GLN SER TYR VAL
        515                 520                 525

ALA MET TYR GLN ARG ASN GLN ARG LEU GLU LYS ALA LEU GLN GLN LEU
    530                 535                 540

ALA ARG GLY ASP SER ALA GLY GLU PRO LEU GLU VAL ASP LEU GLU GLY
545                 550                 555                 560

ALA ASP ILE PRO TYR GLU ASP ILE ILE ALA THR GLU ILE
                565                 570
```

Fig. 5P-5

```
GGACTCTGCC CCTGGACCTG GGAACGACTG GACTGTCACG GGGTTCCCTC CTAGCTCTCC 60
CAGTGAACTC CTGCCAGGCA CACACAGCCC CTATAGCACT GAGCTCACAT GGGACTGGGA 120
TATGGGGGCA TCTCTTCCCC AGAGAGGCAC TCAGTGAGCC TCCTGTGCCT GGCCCCAGTC 180
TGGGCCATCT CTTAGGTGAG ACAGTTGCCC GAAACTAAGC CAGGCCTGGC TGGAGGAGCA 240
GCAGCTTGGG GAGAGGGATT TCCCTGCAGA CCTCAAGCCA TCATGCGGTG GGTGCTGCCA 300
TGACAGAGGC TGCACCCCTG GGCCAGCGGG GCTGCTCACC CACCTCTTGT GCAAGGTGGC 360
CTTTGTGCTG CGCCTGCAGG CAGAGCTGGA GCCCCCAGCA GAGGCAGGCT GGGACGGACC 420
AGCATCTGGA AGATGTACAT AGTTATTTTT CTCTTTGTGG TTTCTTGTTT GGTTTGGTTT 480
GCTTTTGACA GCTTCATTTT ATTTTTGACG TCACTTTTTG GCCATGTAAA CTATTTGTGG 540
CAATTTTATG TTTTTATTTA TGAATAAAGA ATGCCATTTC TCACGCCCTC T          591
```

Fig. 5Q

```
   1 GAATTCGGCC GGCCATCATC AATAATATAC CTTATTTTGG ATTGAAGCCA ATATGATAAT
  61 GAGGGGGTGG AGTTTGTGAC GTGGCGCGGG GCGTGGGAAC GGGGCGGGTG ACGTAGTAGT
 121 GTGGCGGAAG TGTGATGTTG CAAGTGTGGC GGAACACATG TAAGCGACGG ATGTGGCAAA
 181 AGTGACGTTT TTGGTGTGCG CCGGTGTACA CAGGAAGTGA CAATTTTCGC GCGGTTTTAG
 241 GCGGATGTTG TAGTAAATTT GGGCGTAACC GAGTAAGATT TGGCCATTTT CGCGGGAAAA
 301 CTGAATAAGA GGAAGTGAAA TCTGAATAAT TTTGTGTTAC TCATAGCGCG TAATATTTGT
 361 CTAGGGCCGC CAGATCGATC TCCGAGGGAT CTCGACCAAA TGATTTGCCC TCCCATATGT
 421 CCTTCCGAGT GAGAGACACA AAAAATTCCA ACACACTATT GCAATGAAAA TAAATTTCCT
 481 TTATTAGCCA GAGGTCGAGG TCGGGGGATC CTCAGTTGTA CAGTTCATCC ATGCCATGTG
 541 TAATCCCAGC AGCTGTTACA AACTCAAGAA GGACCATGTG GTCTCTCTTT TCGTTGGGAT
 601 CTTTCGAAAG GGCAGATTGT GTGGACAGGT AATGGTTGTC TGGTAAAAGG ACAGGGCCAT
 661 CGCCAATTGG AGTATTTTGT TGATAATGGT CTGCTAGTTG AACGCTTCCA TCTTCAATGT
 721 TGTGGCGGGT CTTGAAGTTC ACTTTGATTC CATTCTTTTG TTTGTCTGCC ATGATGTATA
 781 CATTGTGTGA GTTATAGTTG TATTCCAATT TGTGTCCCAG AATGTTGCCA TCTTCCTTGA
 841 AGTCAATACC TTTTAACTCG ATTCTATTAA CAAGGGTATC ACCTTCAAAC TTGACTTCAG
 901 CACGTGTCTT GTAGTTGCCG TCATCTTTGA AGAAGATGGT CCTTTCCTGT ACATAACCTT
 961 CGGGCATGGC ACTCTTGAAA AAGTCATGCC GTTTCATATG ATCCGGGTAT CTTGAAAAGC
1021 ATTGAACACC ATAGCACAGA GTAGTGACTA GTGTTGGCCA TGGAACAGGC AGTTTGCCAG
1081 TAGTGCAGAT GAACTTCAGG GTAAGTTTTC CGTATGTTGC ATCACCTTCA CCCTCTCCAC
1141 TGACAGAGAA CTTGTGGCCG TTAACATCAC CATCTAATTC AACAAGAATT GGGACAACTC
1201 CAGTGAAGAG TTCTTCTCCT TTGCTAGCCA TGGCGGATCC GGCTGAACGG TCTGGTTATA
1261 GGTACATTGA GCAACTGACT GAAATGCCTC AAAATGTTCT TTACGATGCC ATTGGGATAT
1321 ATCAACGGTG GTATATCCAG TGATTTTTTT CTCCATGGTT GTGGCAAGCT TATCATCGTG
1381 TTTTTCAAAG GAAAACCACG TCCCCGTGGT TCGGGGGGCC TAGACGTTTT TTAACCTCGA
1441 CTAAACACAT GTAAAGCATG TGCACCGAGG CCCCAGATCA GATCCCATAC AATGGGGTAC
```

Fig. 10A

```
1501 CTTCTGGGCA TCCTTCAGCC CCTTGTTGAA TACGCTTGAG GAGAGCCATT TGACTCTTTC
1561 CACAACTATC CAACTCACAA CGTGGCACTG GGGTTGTGCC GCCTTTGCAG GTGTATCTTA
1621 TACACGTGGC TTTTGGCCGC AGAGGCACCT GTCGCCAGGT GGGGGGTTCC GCTGCCTGCA
1681 AAGGGTCGCT ACAGACGTTG TTTGTCTTCA AGAAGCTTCC AGAGGAACTG CTTCCTTCAC
1741 GACATTCAAC AGACCTTGCA TTCCTTTGGC GAGAGGGGAA AGACCCCTAG GAATGCTCGT
1801 CAAGAAGACA GGGCCAGGTT TCCGGGCCCT CACATTGCCA AAAGACGGCA ATATGGTGGA
1861 AAATAACATA TAGACAAACG CACACCGGCC TTATTCCAAG CGGCTTCGGC CAGTAACGTT
1921 AGGGGGGGGG GAGGGAGAGG GCGGAATTCG GAGAGGGCGG AATTCGGGGC CGCGGAGATC
1981 TTCCAAACTT GGACCTGGGA GTGGACACCT GTGGAGAGAA AGGCAAAGTG GATGTCATTG
2041 TCACTCAAGT GTATGGCCAG ATCGGGCCAG GTGAATATCA AATCCTCCTC GTTTTTGGAA
2101 ACTGACAATC TTAGCGCAGA AGTCATGCCC GCTTTTGAGA GGGAGTACTC ACCCCAACAG
2161 CTGGATCTCA AGCCTGCCAC ACCTCACCTC GACCATCCGC CGGCTCAAGA CCGCCTACTT
2221 TAATTACATC ATCAGCAGCA CCTCCGCCAG AAACAACCCC GACCGCCACC CGCTGCCGCC
2281 CGCCACGGTG CTCAGCCTAC CTTGCGACTG TGACTGGTTA GACGCCTTTC TCGAGAGGTT
2341 TTCCGATCCG GTCGATGCGG ACTGGCTCAG GTCCCTCGGT GGCGGAGTAC CGTTCGGAGG
2401 CCGACGGGTT TCCGATCCAA GAGTACTGGA AAGACCGCGA AGAGTTTGTC CTCAACCGCG
2461 AGCCCAACAG CTGGCCCTCG CAGACAGCGA TGCGGAAGAG AGTGAGGATC TGACGGTTCA
2521 CTAAACGAGC TCTGCTTATA TAGACCTCCC ACCGTACACG CCTACCGCCC ATTTGCGTCA
2581 ACGGGGCGGG GTTATTACGA CATTTTGGAA AGTCCCGTTG ATTTTGGTGC CAAAACAAAC
2641 TCCCATTGAC GTCAATGGGG TGGAGACTTG GAAATCCCCG TGAGTCAAAC CGCTATCCAC
2701 GCCCATTGGT GTACTGCCAA AACCGCATCA CCATGGTAAT AGCGATGACT AATACGTAGA
2761 TGTACTGCCA AGTAGGAAAG TCCCGTAAGG TCATGTACTG GGCATAATGC CAGGCGGGCC
2821 ATTTACCGTC ATTGACGTCA ATAGGGGGCG GACTTGGCAT ATGATACACT TGATGTACTG
2881 CCAAGTGGGC AGTTTACCGT AAATACTCCA CCCATTGACG TCAATGGAAA GTCCCTATTG
2941 GCGTTACTAT GGGAACATAC GTCATTATTG ACGTCAATGG GCGGGGGTCG TTGGGCGGTC
```

Fig. 10B

```
3001 AGCCAGGCGG GCCATTTACC GTAAGTTATG TAACGCGGAA CTCCATATAT GGGCTATGAA
3061 CTAATGACCC CGTAATTGAT TACTATTAAT AACTAGTCAA TAATCAATGT CAACATGGCG
3121 GTCATATTGG ACATGAGCCA ATATAAATGT ACATATTATG ATATAGATAC AACGTATGCA
3181 ATGGCCAATA GCCAATATTG ATTTATGCTA TATAACCAAT GACTAATATG GCTAATTGCC
3241 AATATTGATT CAATGTATAG ATCGATCTGG AAGGTGCTGA GGTACGATGA GACCCGCACC
3301 AGGTGCAGAC CCTGCGAGTG TGGCGGTAAA CATATTAGGA ACCAGCCTGT GATGCTGGAT
3361 GTGACCGAGG AGCTGAGGCC CGATCACTTG GTGCTGGCCT GCACCCGCGC TGAGTTTGGC
3421 TCTAGCGATG AAGATACAGA TTGAGGTACT GAAATGTGTG GGCGTGGCTT AAGGGTGGGA
3481 AAGAATATAT AAGGTGGGGG TCTTATGTAG TTTTGTATCT GTTTTGCAGC AGCCGCCGCC
3541 GCCATGAGCA CCAACTCGTT TGATGGAAGC ATTGTGAGCT CATATTTGAC AACGCGCATG
3601 CCCCCATGGG CCGGGGTGCG TCAGAATGTG ATGGGCTCCA GCATTGATGG TCGCCCCGTC
3661 CTGCCCGCAA ACTCTACTAC CTTGACCTAC GAGACCGTGT CTGGAACGCC GTTGGAGACT
3721 GCAGCCTCCG CCGCCGCTTC AGCCGCTGCA GCCACCGCCC GCGGGATTGT GACTGACTTT
3781 GCTTTCCTGA GCCCGCTTGC AAGCAGTGCA GCTTCCCGTT CATCCGCCCG CGATGACAAG
3841 TTGACGGCTC TTTTGGCACA ATTGGATTCT TTGACCCGGG AACTTAATGT CGTTTCTCAG
3901 CAGCTGTTGG ATCTGCGCCA GCAGGTTTCT GCCCTGAAGG CTTCCTCCCC TCCCAATGCG
3961 GTTTAAAACA TAAATAAAAA ACCAGACTCT GTTTGGATTT GGATCAAGCA AGTGTCTTGC
4021 TGTCTTTATT TAGGGGTTTT GCGCGCGCGG TAGGCCCGGG ACCAGCGGTC TCGGTCGTTG
4081 AGGGTCCTGT GTATTTTTTC CAGGACGTGG TAAAGGTGAC TCTGGATGTT CAGATACATG
4141 GGCATAAGCC CGTCTCTGGG GTGGAGGTAG CACCACTGCA GAGCTTCATG CTGCGGGGTG
4201 GTGTTGTAGA TGATCCAGTC GTAGCAGGAG CGCTGGGCGT GGTGCCTAAA AATGTCTTTC
4261 AGTAGCAAGC TGATTGCCAG GGGCAGGCCC TTGGTGTAAG TGTTTACAAA GCGGTTAAGC
4321 TGGGATGGGT GCATACGTGG GGATATGAGA TGCATCTTGG ACTGTATTTT TAGGTTGGCT
4381 ATGTTCCCAG CCATATCCCT CCGGGGATTC ATGTTGTGCA GAACCACCAG CACAGTGTAT
4441 CCGGTGCACT TGGGAAATTT GTCATGTAGC TTAGAAGGAA ATGCGTGGAA GAACTTGGAG
```

Fig. 10C

```
4501 ACGCCCTTGT GACCTCCAAG ATTTTCCATG CATTCGTCCA TAATGATGGC AATGGGCCCA
4561 CGGGCGGCGG CCTGGGCGAA GATATTTCTG GGATCACTAA CGTCATAGTT GTGTTCCAGG
4621 ATGAGATCGT CATAGGCCAT TTTTACAAAG CGCGGGCGGA GGGTGCCAGA CTGCGGTATA
4681 ATGGTTCCAT CCGGCCCAGG GGCGTAGTTA CCCTCACAGA TTTGCATTTC CCACGCTTTG
4741 AGTTCAGATG GGGGGATCAT GTCTACCTGC GGGGCGATGA AGAAAACGGT TTCCGGGGTA
4801 GGGGAGATCA GCTGGGAAGA AAGCAGGTTC CTGAGCAGCT GCGACTTACC GCAGCCGGTG
4861 GGCCCGTAAA TCACACCTAT TACCGGGTGC AACTGGTAGT TAAGAGAGCT GCAGCTGCCG
4921 TCATCCCTGA GCAGGGGGGC CACTTCGTTA AGCATGTCCC TGACTCGCAT GTTTTCCCTG
4981 ACCAAATCCG CCAGAAGGCG CTCGCCGCCC AGCGATAGCA GTTCTTGCAA GGAAGCAAAG
5041 TTTTTCAACG GTTTGAGACC GTCCGCCGTA GGCATGCTTT TGAGCGTTTG ACCAAGCAGT
5101 TCCAGGCGGT CCCACAGCTC GGTCACCTGC TCTACGGCAT CTCGATCCAG CATATCTCCT
5161 CGTTTCGCGG GTTGGGGCGG CTTTCGCTGT ACGGCAGTAG TCGGTGCTCG TCCAGACGGG
5221 CCAGGGTCAT GTCTTTCCAC GGGCGCAGGG TCCTCGTCAG CGTAGTCTGG GTCACGGTGA
5281 AGGGGTGCGC TCCGGGCTGC GCGCTGGCCA GGGTGCGCTT GAGGCTGGTC CTGCTGGTGC
5341 TGAAGCGCTG CCGGTCTTCG CCCTGCGCGT CGGCCAGGTA GCATTTGACC ATGGTGTCAT
5401 AGTCCAGCCC CTCCGCGGCG TGGCCCTTGG CGCGCAGCTT GCCCTTGGAG GAGGCGCCGC
5461 ACGAGGGGCA GTGCAGACTT TTGAGGGCGT AGAGCTTGGG CGCGAGAAAT ACCGATTCCG
5521 GGGAGTAGGC ATCCGCGCCG CAGGCCCCGC AGACGGTCTC GCATTCCACG AGCCAGGTGA
5581 GCTCTGGCCG TTCGGGGTCA AAAACCAGGT TTCCCCCATG CTTTTTGATG CGTTTCTTAC
5641 CTCTGGTTTC CATGAGCCGG TGTCCACGCT CGGTGACGAA AAGGCTGTCC GTGTCCCCGT
5701 ATACAGACTT GAGAGGCCTG TCCTCGACCG ATGCCCTTGA GAGCCTTCAA CCCAGTCAGC
5761 TCCTTCCGGT GGGCGCGGGG CATGACTATC GTCGCCGCAC TTATGACTGT CTTCTTTATC
5821 ATGCAACTCG TAGGACAGGT GCCGGCAGCG CTCTGGGTCA TTTTCGGCGA GGACCGCTTT
5881 CGCTGGAGCG CGACGATGAT CGGCCTGTCG CTTGCGGTAT TCGGAATCTT GCACGCCCTC
5941 GCTCAAGCCT TCGTCACTGG TCCCGCCACC AAACGTTTCG GCGAGAAGCA GGCCATTATC
```

Fig. 10D

```
6001 GCCGGCATGG CGGCCGACGC GCTGGGCTAC GTCTTGCTGG CGTTCGCGAC GCGAGGCTGG
6061 ATGGCCTTCC CCATTATGAT TCTTCTCGCT TCCGGCGGCA TCGGGATGCC CGCGTTGCAG
6121 GCCATGCTGT CCAGGCAGGT AGATGACGAC CATCAGGGAC AGCTTCAAGG ATCGCTCGCG
6181 GCTCTTACCA GCTGAGCAAA AGGCCAGCAA AAGGCCAGGA ACCGTAAAAA GGCCGCGTTG
6241 CTGGCGTTTT TCCATAGGCT CCGCCCCCCT GACGAGCATC ACAAAAATCG ACGCTCAAGT
6301 CAGAGGTGGC GAAACCCGAC AGGACTATAA AGATACCAGG CGTTTCCCCC TGGAAGCTCC
6361 CTCGTGCGCT CTCCTGTTCC GACCCTGCCG CTTACCGGAT ACCTGTCCGC CTTTCTCCCT
6421 TCGGGAAGCG TGGCGCTTTC TCAATGCTCA CGCTGTAGGT ATCTCAGTTC GGTGTAGGTC
6481 GTTCGCTCCA AGCTGGGCTG TGTGCACGAA CCCCCCGTTC AGCCCGACCG CTGCGCCTTA
6541 TCCGGTAACT ATCGTCTTGA GTCCAACCCG GTAAGACACG ACTTATCGCC ACTGGCAGCA
6601 GCCACTGGTA ACAGGATTAG CAGAGCGAGG TATGTAGGCG GTGCTACAGA GTTCTTGAAG
6661 TGGTGGCCTA ACTACGGCTA CACTAGAAGG ACAGTATTTG GTATCTGCGC TCTGCTGAAG
6721 CCAGTTACCT TCGGAAAAAG AGTTGGTAGC TCTTGATCCG GCAAACAAAC CACCGCTGGT
6781 AGCGGTGGTT TTTTTGTTTG CAAGCAGCAG ATTACGCGCA GAAAAAAAGG ATCTCAAGAA
6841 GATCCTTTGA TCTTTTCTAC GGGGTCTGAC GCTCAGTGGA ACGAAAACTC ACGTTAAGGG
6901 ATTTTGGTCA TGAGATTATC AAAAAGGATC TTCACCTAGA TCCTTTTAAA TTAAAAATGA
6961 AGTTTTAAAT CAATCTAAAG TATATATGAG TAAACTTGGT CTGACAGTTA CCAATGCTTA
7021 ATCAGTGAGG CACCTATCTC AGCGATCTGT CTATTTCGTT CATCCATAGT TGCCTGACTC
7081 CCCGTCGTGT AGATAACTAC GATACGGGAG GGCTTACCAT CTGGCCCCAG TGCTGCAATG
7141 ATACCGCGAG ACCCACGCTC ACCGGCTCCA GATTTATCAG CAATAAACCA GCCAGCCGGA
7201 AGGGCCGAGC GCAGAAGTGG TCCTGCAACT TTATCCGCCT CCATCCAGTC TATTAATTGT
7261 TGCCGGGAAG CTAGAGTAAG TAGTTCGCCA GTTAATAGTT TGCGCAACGT TGTTGCCATT
7321 GCTGCAGGCA TCGTGGTGTC ACGCTCGTCG TTTGGTATGG CTTCATTCAG CTCCGGTTCC
7381 CAACGATCAA GGCGAGTTAC ATGATCCCCC ATGTTGTGCA AAAAAGCGGT TAGCTCCTTC
7441 GGTCCTCCGA TCGTTGTCAG AAGTAAGTTG GCCGCAGTGT TATCACTCAT GGTTATGGCA
```

Fig. 10E

```
7501 GCACTGCATA ATTCTCTTAC TGTCATGCCA TCCGTAAGAT GCTTTTCTGT GACTGGTGAG
7561 TACTCAACCA AGTCATTCTG AGAATAGTGT ATGCGGCGAC CGAGTTGCTC TTGCCCGGCG
7621 TCAACACGGG ATAATACCGC GCCACATAGC AGAACTTTAA AAGTGCTCAT CATTGGAAAA
7681 CGTTCTTCGG GGCGAAAACT CTCAAGGATC TTACCGCTGT TGAGATCCAG TTCGATGTAA
7741 CCCACTCGTG CACCCAACTG ATCTTCAGCA TCTTTTACTT TCACCAGCGT TTCTGGGTGA
7801 GCAAAAACAG GAAGGCAAAA TGCCGCAAAA AAGGGAATAA GGGCGACACG GAAATGTTGA
7861 ATACTCATAC TCTTCCTTTT TCAATATTAT TGAAGCATTT ATCAGGGTTA TTGTCTCATG
7921 AGCGGATACA TATTTGAATG TATTTAGAAA AATAAACAAA TAGGGGTTCC GCGCACATTT
7981 CCCCGAAAAG TGCCACCTGA CGTCTAAGAA ACCATTATTA TCATGACATT AACCTATAAA
8041 AATAGGCGTA TCACGAGGCC CTTTCGTCTT CAA
```

Fig. 10F

SEQUENCE LISTING

```
<160> NUMBER OF SEQ ID NOS: 70

<210> SEQ ID NO 1
<211> LENGTH: 9048
<212> TYPE: DNA
<213> ORGANISM: Homo sapiens

<400> SEQUENCE: 1

gcctttccaa gaccctgccc ggccctgccc catcctcagc cccgagtcac catgggcagc     60

gtcagtagcc tcatctccgg ccacagcttc cacagcaagc actgccgggc ttcgcagtac    120

aagctgcgca agtcctccca cctcaagaag ctcaaccggt attccgacgg gctgctgagg    180

tttggcttct cccaggactc cggtcacggc aagtccagct ccaaaatggg caagagcgaa    240
```

-continued

```
gacttcttct acatcaaggt cagccagaaa gcccggggct cccatcaccc agattacacg    300
gcactgtcca gcggggattt agggggccag gctggggtgg actttgaccc gtccacaccc    360
cccaagctca tgcccttctc caatcagcta gaaatggtaa gcgggggtcg ctggcaaggg    420
taagtgggtt ggaaacgcag gagaaagcaa aatgggggtg gagagcctgg gggttcaggg    480
ggagtggtga cctgagcatt cagactcctc aaaaccagag cggcaggggt gccggcggaa    540
gcctgtggcc acaccgcaga gatcaaacgt ttcacaaagg aattagagca tcgctcagtc    600
cccctgaagc agaagtcttg ggtcaggcca taagcaaaga gcacagggga tatgtgagct    660
tttggagtcc cactgaaatg tagctggatt gtcaacgtag gatccaggcg tttgccaagc    720
ctcgggaagg agagggagcc ctgttctcat ctggaagcac agatgaagag gatgcaggcc    780
gggagttaac cgcttctctc cccgggagac tcgtggggggt gggtgcggtc ttctcatttg    840
ctgccctggt gtgcattagc tccttgttca agctgcgcct gggggcatct ttgaatacag    900
gctggagttt tgtcatccat ttaccagaga ctagggcaaa ggaggcccag gcactgagaa    960
atccagccct cacaccagct caagccctcg tgcgtcccac gagtggacac tgaaatcaat   1020
tttcctattc agtcctctgc cccttgccct ggggaaatga atccccggct ttgatttact   1080
aggaaagagc ctcttatgtt tgcatagagc attcagcttt tcaaattaag gggcttgtaa   1140
actgtgaagc actctaccag ggaaaattac agttttaaaa aaggatcgtg atttggagtg   1200
agcctcccaa ccctgtaagg aggccaggtc cgtgtccttg ctccaggctt aatggaagag   1260
gcagtgaaca ggaagaaggg atggacctaa agagggacag caagctcggc cagcctgatg   1320
ccctaacttg ccccacacag agacctagag caggagcctc aagatggtat ttatcacctc   1380
gggagggctg gggcaagctg gtggcaggtt gctatttcat agaacaaagt gcccaagtcg   1440
ccattagggt ttttccctcc taagagagat gacattcagc tgcttcaaag caacaggcaa   1500
ggtctgctga gacaattgac caagaggggt gctgcgtgcg ctcagagagc ccagactggc   1560
tcaaggtcgg cacgcgtgcc tggggaggga gggtgcaatg cgcgcgcagg ggaggcatga   1620
gtcaccgcgg tccttttcct ctacagggct ccgagaaggg tgcagtgagg cccacagcct   1680
tcaagcctgt gctgccacgg tcaggagcca tcctgcactc ctccccggag agtgccagcc   1740
accagctgca ccccgcccct ccagacaagc ccaaggagca ggagctgaag cctggcctgt   1800
gctctggggc gctgtcagac tccggccgga actccatgtc cagcctgccc acacacagca   1860
ccagcagcag ctaccagctg gacccgctgg tcacacccgt gggacccaca agccgttttg   1920
ggggctccgc ccacaacatc acccagggca tcgtcctcca ggacagcaac atgatgagcc   1980
tgaaggctct gtccttctcc gacggaggta gcaagctggg ccactcgaac aaggcagaca   2040
agggcccctc gtgtgtccgc tcccccatct ccacggacga gtgcagcatc caggagctgg   2100
aacagaagct gttggagagg gagggcgccc tccagaagct gcagcgcagc tttgaggaga   2160
aggagcttgc ctccagcctg gcctacgagg agcggccgcg gcgctgcagg gacgagctgg   2220
agggcccgga gcccaaaggc ggcaacaagc tcaagcaggc ctcgcagaag agccagcgcg   2280
cgcagcaggt cctgcacctg caggtactgc agcttcagca ggagaagcgg cagctccggc   2340
aggagctcga gagcctcatg aaggagcagg acctgctgga gaccaagctc aggtcctacg   2400
agagggagaa gaccagcttc ggccccgcgc tggaggagac ccagtgggag gtgaggccac   2460
acagggctca tgggtttggg tggtcagcgg tttggcgcca gtacccccct ctccttctgg   2520
tgctggccaa tagcgtgcaa acacagaccg cgcaggcaag cggggctaat gtgctggctt   2580
```

-continued

```
tatcacccaa agaaggggct ccctgcaaac catgttgggg gatcgactta catctgagct   2640
tcctcctgtc cccaccatca ccctcatggc tcctagattt cagtttccca agtgagccat   2700
taaatcatga agccggaagc cagatgacca aggcccagcc aggctgtggg ctgacctccc   2760
ttccatcagc tcccaggagg ctcagaagaa gaacaagccg tgcctgagtt caggcggggc   2820
caggggccca agagagcaca gaatgcattt gttgctttgg agggagggac tgcacccact   2880
agtaagaggg accctattgg tggcaggttt cagtgatgga agtggccact ccttgctgaa   2940
gtgtaagtgg aacttctatt tggtgagctg agatggaaac ctaggagagg aagtaaagag   3000
tcccccactc acacacttac acactcacac acactcactc acccggtcac acgtggaaat   3060
gaggcatctg tacctgaccg tgctggagaa ccccataacc tctgcatcta ttagtgggaa   3120
agcagctttt ctcaccagcc tggtggtctg gatgactcat ggagttcaag cccatcgttg   3180
aggctcttta catgctcgca cccagcttgg tctgtccacg tgcctgcctc acccccagtt   3240
cagagtccaa atctcagtct acacgcaaac ccctggctat gtgcaagtca acaaccagtg   3300
gtttaacttg cccactgctg gcagctgtat cacccccatt taacaccaat ggtattggtt   3360
ttggtgtcag cctgatttct gtcatcgatg tttatgccca catcctctga cctcacccct   3420
gcatgcaccc agccctcctc tctcctgtct actggagtaa agactacctc acaaattcac   3480
tgctgtaccc agtgactagt atcatgctgg cttggatgca gagcccaatc cacatctgtc   3540
aaacgaggaa tcattttctt ctcctcttgc tcttctttct ctatttccca cccctatccc   3600
ccatcaaaat ttggccaaga gcaatgatga aaaccgaagc cacaggttag acccatgtgt   3660
ctctggatct tggccatctg gggtcatggg agaccaaggc cagtctggct gaatcttaag   3720
agtgaatgaa gtccagagca tgtggctcta cagaatggat tcttggaact agcctggaag   3780
ccaccttcac atttcctttc acagtagaaa tttccccttg ccctcagtga aacactgcac   3840
agtcctggag aaaatccgac cctacccagg atgcgtgctt gggaccaaga atttcattcc   3900
aaggccaacc ctgtattcat gccacgaagg gagtgacaca gtcatggctg aggcatgggc   3960
ctggctttga acctcagctt gaccacttat gatccaggtg attgtaaata cattagccat   4020
ggtggcaatg gggtatagtg attaaactgt tgggatcaaa tctctactct tatactttat   4080
attttatata tatatatata taatatatat atatattagc cctcaggctg gtcacttcac   4140
cagctgtttg ctatcataac ctctctgtgc ctcagtttca ttgatgtaaa ttgaggacta   4200
ctaatagtac ctacttcatc gggttgtaag gaatagatga gcaaatgtat ggcttggcac   4260
ttaataacac tacaaattat tagtgaaagt atgtttataa taatatactt ctgtgtggct   4320
aggcgtggtg gctcacgcct gcaatcccag cactttggga ggcagaggca ggcagagcac   4380
ttgaggtcag gaattcgaga tcagcctggc caacatgagg aaaccccgtc tctactaaaa   4440
atacaaaaat cagccaggca tggtggcagg tgtctgtaat cccagctact tgggaggctg   4500
aggcaggaga atcagagggg aggcggaggt tgcagtgagc caagatcacg ccactacacc   4560
ccagcctagg tgacaaagcg agacttctca aatattaaca ataataatat actatgtgtc   4620
attatacatg atgattatta ttttatcatt ttactatata gcctagctcg ataacctggg   4680
araaaggtca cagcaatgtt cagcttactt tcagattgga caaaggctgg aatgcctaac   4740
accgggccac cgcatccgga gtggcttggt tattttaggc agctgagctg tcacttccct   4800
gggtaaggac actcacctct tggcactctg tctccacccc accctcggca ggtgtgccag   4860
aagtcaggcg agatctccct cctgaagcag cagctgaagg agtcccagac ggaggtgaac   4920
gccaaggcta gcgagatcct gggtctcaag gcacagctga aggacacgcg gggcaagctg   4980
```

-continued gagggcctgg agctgaggac ccaggacctg gagggcgccc tgcgcaccaa gggcctggag 5040
ctggaggtct gtgagaatga gctgcagcgc aagaagaacg aggcggagct gctgcgggag 5100
aaggtgaacc tgctggagca ggagctgcag gagctgcggg cccaggccgc cctggcccgc 5160
gacatggggc cgcccacctt ccccgaggac gtccctgccc tgcagcggga gctggagcgg 5220
ctgcgggccg agctgcggga ggagcggcaa ggccatgacc agatgtcctc gggcttccag 5280
catgagcggc tcgtgtggaa ggaggagaag gagaaggtga ttcagtacca gaaacagctg 5340
cagcagagct acgtggccat gtaccagcgg aaccagcgcc tggagaaggc cctgcagcag 5400
ctggcacgtg gggacagcgc cggggagccc ttggaggttg acctggaagg ggctgacatc 5460
ccctacgagg acatcatagc cactgagatc tgaggggctg cctgggaagg cgagtctggg 5520
gacctggcac tgggaggcag ggctctcccg tgcatccccc ctgctcagca attcagaccc 5580
ctctgagaga cgccactccc tgggacacag acccaggacc cccgagggga gggcaggatg 5640
gcctttcctt ccctctctga tgtcccagtg ctcaccagcc ctgcagccca ccagacgtca 5700
ggccctgact cctctggctt tcccaggaga tgggtccagg ggtctgtctg ctttggttaa 5760
gggctcccta aactttggcc tttgttcgaa atagatatcc tctccccctc ctccagggaa 5820
ggtggccaca gcaagaacag cggctcccct ccgcttctca tcccaacctc tttttcctcc 5880
tggacacatt ggaatgcctt ggaaatagaa agaagccata tatgaccaga agccttggaa 5940
ccagccccat cagaacctga gctattttcc tctggccgca gaggtgtagg ggtggaatga 6000
gccgcgggga agctggcttt gaaacctcag ggctgtccca gccccggcaa gccacaggaa 6060
ggaggggaga gacaggcagc ccagcagtgt ggagaccctg ccacagccag aggagggcag 6120
agggagaatc caagggttga gagccagtgg cgggtgatgg ccagcccctg gggcccagcc 6180
cctgtttact ggttcttgca aatgggagct gagcagcctc tggacagcca gtgacctttg 6240
acctcggtga ccactcttct ttaagccata gaccctgagg ccctgggctg ggtgctggga 6300
agggagggtt gaaaccaccg tgaaccagag ggtgtggctt tccagkcacc ctcagggagc 6360
ctccccatct gtccagctgg ggccagaggc tgggagtccc tacctgcttc acgttggccg 6420
gcggctactc tggaatgttt ttccctcccc agaatcaagc ttttgcttga tccagaagag 6480
cccatatcac taagatggca tatatgtgat ctgggcattt tcctcctctg cctacagcca 6540
ggtttagcgg caaacctttc ccccttagca ccttcagggc tgagttctgg gtttctagag 6600
gtcaggacgg ctcctcagag cgccaggaag ccagagcccc aagcaggacg aaaaagaggc 6660
atacacacag cagtgtgaat agcctggcca ccagccatcc tccctccacc tcaagacccc 6720
catttgtccs agactaaagg atccagagag cagctccctt tctcaggagc ttgggcagtg 6780
ccccagggag tccagggttt ctctgcagat gtgcggagcg ggaggcggtg gtagagagag 6840
ataaaaggtg gagtttctct gttgtttggt tcagggattt tatttttaat tttatgagac 6900
agggtcttgc tctgtccccc aggctggagt gcagtggcat gatcatagct cactgcagcc 6960
tcatactcct gggctcaagc aatcctcctg cctcagcctt ccaactagct gggactacag 7020
gtgcgcgcca ccgtgcctgg ctaacttttc attttttttg tagggacggg gtctcgtttt 7080
gttgccaaag ctggtctcaa acttgtggcc tcaagcaatc cacctgcctt ggcctcccaa 7140
agtgctgaga ttgcagatgt gagccaccgt gcctggccag atttttcttt tattcttctt 7200
tctttttctt ttttgctttc ttgtcttttc agaagcaagc cagacctagc aggctgttcc 7260
atgttctatt tttgactgta gccacagctg ctgttctcag gacagcatcc cttcccacat 7320

-continued

```
gcctgcgcct gctgcctgct gagatgagga ggggagcgtc tgggaacttg cgagtccaag   7380
gccagtcccc atttctgcct cgctcaccgc tggcccttag agaccccgag gtaggggtgg   7440
ggagatgctt ctctccttgc cccccgccct catgggtcct agcccttccc tgagtgcggg   7500
ctgaggccag agtcaccttt tctgtggctg gctctacctt cctgtccctg aggttaaacg   7560
gtgcccatcc tgccatcctc aaacgacaga ggagcttttc tggaatttca aaccattgct   7620
cttagtccca agctaggctt aaacctggaa tctacaagcc aaaagtccct ccctgcctga   7680
gggcagtacc ctccattggg cacagtccag acccaagtca aagatgcccc attccttgcg   7740
cctcagccct cagttccttc atttccacca ggccgtgcct tgtttgagtt tttcctccca   7800
gtgagactgc cccacggaga cagaggaaag ggctggctcc ccctccccag gctggagacc   7860
ccccccaact ccaggaaaga gcagtcagag tccagtgctc tgcctcagac gttgcctgag   7920
aagaagtggc tgccacaccc aggggaaggc cctgaggcgg aggctgtgct ccgccatggt   7980
gtcccggtac cttccataca cagaggagtg cagccttctc catatctcca tggccctgtc   8040
ccaggccggc ccagatgtgt ccccccccagg ccttgtccta cgtccaaggt ggcagatgtc   8100
ttccctgggc tgccaccagc ccccgcccca gagtggccca ccgtggcact agaatgcaag   8160
tatcctgcga ccttgcaacc tcaccttcct gtgggtgttc tttcctgccc tgtccaaaag   8220
cgccctcact attcttggac catgccagat tctgcctctc tggaaagagg ctctggacag   8280
cagaagcctc caagcacaga gcctggcccc aggccccaga cagggtgggc ttcctgccct   8340
tccctctggg cacgcctgct ggccgaccca ctgacccact cggatggacc aacctgctct   8400
gtccccaaag gacgcctgca ggagagagca gcactccgca tcacctcacc aaggatcgga   8460
ctctgcccct ggacctggga acgactggac tgtcacgggg ttccctccta gctctcccag   8520
tgaactcctg ccaggcacac acagccccta tagcactgag ctcacatggg actgggatat   8580
gggggcatct cttccccaga gaggcactca gtgagcctcc tgtgcctggc cccagtctgg   8640
gccatctctt aggtgagaca gttgcccgaa actaagccag gcctggctgg aggagcagca   8700
gcttggggag agggatttcc ctgcagacct caagccatca tgcggtgggt gctgccatga   8760
cagaggctgc accccctgggc cagcggggct gctcacccac ctcttgtgca aggtggcctt   8820
tgtgctgcgc ctgcaggcag agctggagcc cccagcagag gcaggctggg acggaccagc   8880
atctggaaga tgtacatagt tatttttctc tttgtggttt cttgtttggt ttggtttgct   8940
tttgacagct tcattttatt tttgacgtca ctttttggcc atgtaaacta tttgtggcaa   9000
ttttatgttt ttatttatga ataaagaatg ccatttctca cgccctct                9048
```

<210> SEQ ID NO 2
<211> LENGTH: 5492
<212> TYPE: DNA
<213> ORGANISM: Homo sapiens

<400> SEQUENCE: 2

```
tgagggcttt gctatgacct cagtcccctc acggagccac gactgcccct tgctgccaca     60
gcctttccaa gaccctgccc ggccctgccc catcctcagc cccgagtcac catgggcagc    120
gtcagtagcc tcatctccgg ccacagcttc cacagcaagc actgccgggc ttcgcagtac    180
aagctgcgca agtcctccca cctcaagaag ctcaaccggt attccgacgg gctgctgagg    240
tttggcttct cccaggactc cggtcacggc aagtccagct ccaaaatggg caagagcgaa    300
gacttcttct acatcaaggt cagccagaaa gcccggggct cccatcaccc agattacacg    360
gcactgtcca gcggggattt agggggccag gctggggtgg actttgaccc gtccacaccc    420
```

-continued

```
cccaagctca tgcccttctc caatcagcta gaaatgggct ccgagaaggg tgcagtgagg    480
cccacagcct tcaagcctgt gctgccacgg tcaggagcca tcctgcactc ctccccggag    540
agtgccagcc accagctgca ccccgcccct ccagacaagc ccaaggagca ggagctgaag    600
cctggcctgt gctctggggc gctgtcagac tccggccgga actccatgtc cagcctgccc    660
acacacagca ccagcagcag ctaccagctg gacccgctgg tcacacccgt gggacccaca    720
agccgttttg gggctccgc ccacaacatc acccagggca tcgtcctcca ggacagcaac    780
atgatgagcc tgaaggctct gtccttctcc gacggaggta gcaagctggg ccactcgaac    840
aaggcagaca agggcccctc gtgtgtccgc tcccccatct ccacggacga gtgcagcatc    900
caggagctgg agcagaagct gttggagagg gagggcgccc tccagaagct gcagcgcagc    960
tttgaggaga aggagcttgc ctccagcctg gcctacgagg agcggccgcg gcgctgcagg   1020
gacgagctgg agggcccgga gcccaaaggc ggcaacaagc tcaagcaggc ctcgcagaag   1080
agccagcgcg cgcagcaggt cctgcacctg caggtactgc agcttcagca ggagaagcgg   1140
cagctccggc aggagctcga gagcctcatg aaggagcagg acctgctgga gaccaagctc   1200
aggtcctacg agagggagaa gaccagcttc ggccccgcgc tggaggagac ccagtgggag   1260
gtgtgccaga agtcaggcga gatctccctc ctgaagcagc agctgaagga gtcccagacg   1320
gaggtgaacg ccaaggctag cgagatcctg ggtctcaagg cacagctgaa ggacacgcgg   1380
ggcaagctgg agggcctgga gctgaggacc caggacctgg agggcgccct gcgcaccaag   1440
ggcctggagc tggaggtctg tgagaatgag ctgcagcgca agaagaacga ggcggagctg   1500
ctgcgggaga aggtgaacct gctggagcag gagctgcagg agctgcgggc ccaggccgcc   1560
ctggcccgcg acatggggcc gcccaccttc cccgaggacg tccctgccct gcagcgggag   1620
ctggagcggc tgcgggccga gctgcgggag gagcggcaag gccatgacca gatgtcctcg   1680
ggcttccagc atgagcggct cgtgtggaag gaggagaagg agaaggtgat tcagtaccag   1740
aaacagctgc agcagagcta cgtggccatg taccagcgga accagcgcct ggagaaggcc   1800
ctgcagcagc tggcacgtgg ggacagcgcc ggggagccct tggaggttga cctggaaggg   1860
gctgacatcc cctacgagga catcatagcc actgagatct gaggggctgc ctgggaaggc   1920
gagtctgggg acctggcact gggaggcagg gctctcccgt gcatcccccc tgctcagcaa   1980
ttcagacccc tctgagagac gccactccct gggacacaga cccaggaccc ccgaggggag   2040
ggcaggatgg cctttccttc cctctctgat gtcccagtgc tcaccagccc tgcagcccac   2100
cagacgtcag gccctgactc ctctggcttt cccaggagat gggtccaggg gtctgtctgc   2160
tttggttaag ggctccctaa actttggcct ttgttcgaaa tagatatcct ctccccctcc   2220
tccagggaag gtggccacag caagaacagc ggctcccctc cgcttctcat cccaacctct   2280
ttttcctcct ggacacattg gaatgccttg gaaatagaaa gaagccatat atgaccagaa   2340
gccttggaac cagccccatc agaacctgag ctattttcct ctggccgcag aggtgtaggg   2400
gtggaatgag ccgcggggaa gctggctttg aaacctcagg gctgtcccag ccccggcaag   2460
ccacaggaag gaggggagag acaggcagcc cagcagtgtg gagaccctgc cacagccaga   2520
ggagggcaga gggagaatcc aagggttgag agccagtggc gggtgatggc cagcccctgg   2580
ggcccagccc ctgtttactg gttcttgcaa atgggagctg agcagcctct ggacagccag   2640
tgacctttga cctcggtgac cactcttctt taagccatag accctgaggc cctgggctgg   2700
gtgctgggaa gggagggttg aaaccaccgt gaaccagagg gtgtggcttt ccaggcaccc   2760
```

-continued tcagggagcc tccccatctg tccagctggg gccagaggct gggagtccct acctgcttca 2820
cgttggccgg cggctactct ggaatgtttt tccctcccca gaatcaagct tttgcttgat 2880
ccagaagagc ccatatcact aagatggcat atatgtgatc tgggcatttt cctcctctgc 2940
ctacagccag gtttagcggc aaacctttcc cccttagcac cttcagggct gagttctggg 3000
tttctagagg tcaggacggc tcctcagagc gccaggaagc cagagcccca agcaggacga 3060
aaaagaggca tacacacagc agtgtgaata gcctggccac cagccatcct ccctccacct 3120
caagaccccc atttgtccca gactaaagga tccagagagc agctcccttt ctcaggagct 3180
tgggcagtgc cccagggagt ccagggtttc tctgcagatg tgcggagcgg gaggcggtgg 3240
tagagagaga taaaaggtgg agtttctctg ttgtttggtt cagggatttt atttttaatt 3300
ttatgagaca gggtcttgct ctgtccccca ggctggagtg cagtggcatg atcatagctc 3360
actgcagcct catactcctg ggctcaagca atcctcctgc ctcagccttc caactagctg 3420
ggactacagg tgcgcgccac cgtgcctggc taacttttca tttttttgt agggacgggg 3480
tctcgttttg ttgccaaagc tggtctcaaa cttgtggcct caagcaatcc acctgccttg 3540
gcctcccaaa gtgctgagat tgcagatgtg agccaccgtg cctggccaga tttttctttt 3600
attcttcttt ctttttcttt tttgctttct tgtcttttca gaagcaagcc agacctagca 3660
ggctgttcca tgttctattt ttgactgtag ccacagctgc tgttctcagg acagcatccc 3720
ttcccacatg cctgcgcctg ctgcctgctg agatgaggag gggagcgtct gggaacttgc 3780
gagtccaagg ccagtcccca tttctgcctc gctcaccgct ggcccttaga gaccccgagg 3840
taggggtggg gagatgcttc tctccttgcc ccccgccctc atgggtccta gcccttccct 3900
gagtgcgggc tgaggccaga gtcacctttt ctgtggctgg ctctaccttc ctgtccctga 3960
ggttaaacgg tgcccatcct gccatcctca aacgacagag gagcttttct ggaatttcaa 4020
accattgctc ttagtcccaa gctaggctta aacctggaat ctacaagcca aaagtccctc 4080
cctgcctgag ggcagtaccc tccattgggc acagtccaga cccaagtcaa agatgcccca 4140
ttccttgcgc ctcagccctc agttccttca tttccaccag gccgtgcctt gtttgagttt 4200
ttcctcccag tgagactgcc ccacggagac agaggaaagg gctggctccc cctccccagg 4260
ctggagaccc cccccaactc caggaaagag cagtcagagt ccagtgctct gcctcagacg 4320
ttgcctgaga agaagtggct gccacaccca ggggaaggcc ctgaggcgga ggctgtgctc 4380
cgccatggtg tcccggtacc ttccatacac agaggagtgc agccttctcc atatctccat 4440
ggccctgtcc caggccggcc cagatgtgtc ccccccaggc cttgtcctac gtccaaggtg 4500
gcagatgtct tccctgggct gccaccagcc cccgccccag agtggcccac cgtggcacta 4560
gaatgcaagt atcctgcgac cttgcaacct caccttcctg tgggtgttct ttcctgccct 4620
gtccaaaagc gccctcacta ttcttggacc atgccagatt ctgcctctct ggaaagaggc 4680
tctggacagc agaagcctcc aagcacagag cctggcccca ggccccagac agggtgggct 4740
tcctgccctt ccctctgggc acgcctgctg gccgacccac tgacccactc ggatggacca 4800
acctgctctg tccccaaagg acgcctgcag gagagagcag cactccgcat cacctcacca 4860
aggatcggac tctgcccctg gacctgggaa cgactggact gtcacggggt tccctcctag 4920
ctctcccagt gaactcctgc caggcacaca cagcccctat agcactgagc tcacatggga 4980
ctgggatatg gggcatctc ttccccagag aggcactcag tgagcctcct gtgcctggcc 5040
ccagtctggg ccatctctta ggtgagacag ttgcccgaaa ctaagccagg cctggctgga 5100
ggagcagcag cttggggaga gggatttccc tgcagacctc aagccatcat gcggtgggtg 5160

```
ctgccatgac agaggctgca cccctgggcc agcggggctg ctcacccacc tcttgtgcaa   5220

ggtggccttt gtgctgcgcc tgcaggcaga gctggagccc ccagcagagg caggctggga   5280

cggaccagca tctggaagat gtacatagtt atttttctct ttgtggtttc ttgtttggtt   5340

tggtttgctt ttgacagctt cattttattt ttgacgtcac tttttggcca tgtaaactat   5400

ttgtggcaat tttatgtttt tatttatgaa taaagaatgc catttctcac gccctctaaa   5460

aaaaaaaaaa aaaaaaaaaa aaaaaaaaaa aa                                  5492
```

```
<210> SEQ ID NO 3
<211> LENGTH: 1791
<212> TYPE: DNA
<213> ORGANISM: Homo sapiens

<400> SEQUENCE: 3

atgggcagcg tcagtagcct catctccggc cacagcttcc acagcaagca ctgccgggct     60

tcgcagtaca agctgcgcaa gtcctcccac ctcaagaagc tcaaccggta ttccgacggg    120

ctgctgaggt ttggcttctc ccaggactcc ggtcacggca agtccagctc caaaatgggc    180

aagagcgaag acttcttcta catcaaggtc agccagaaag cccggggctc ccatcaccca    240

gattacacgg cactgtccag cggggattta gggggccagg ctggggtgga ctttgacccg    300

tccacacccc ccaagctcat gcccttctcc aatcagctag aaatgggctc cgagaagggt    360

gcagtgaggc ccacagcctt caagcctgtg ctgccacggt caggagccat cctgcactcc    420

tccccggaga gtgccagcca ccagctgcac cccgcccctc cagacaagcc caaggagcag    480

gagctgaagc ctggcctgtg ctctggggcg ctgtcagact ccggccggaa ctccatgtcc    540

agcctgccca cacacagcac cagcagcagc taccagctgg acccgctggt cacacccgtg    600

ggacccacaa gccgttttgg gggctccgcc cacaacatca cccagggcat cgtcctccag    660

gacagcaaca tgatgagcct gaaggctctg tccttctccg acggaggtag caagctgggc    720

cactcgaaca aggcagacaa gggcccctcg tgtgtccgct cccccatctc cacggacgag    780

tgcagcatcc aggagctgga gcagaagctg ttggagaggg agggcgccct ccagaagctg    840

cagcgcagct ttgaggagaa ggagcttgcc tccagcctgg cctacgagga gcggccgcgg    900

cgctgcaggg acgagctgga gggcccggag cccaaaggcg gcaacaagct caagcaggcc    960

tcgcagaaga gccagcgcgc gcagcaggtc ctgcacctgc aggtactgca gcttcagcag   1020

gagaagcggc agctccggca ggagctcgag agcctcatga aggagcagga cctgctggag   1080

accaagctca ggtcctacga gagggagaag accagcttcg gccccgcgct ggaggagacc   1140

cagtgggagg tgtgccagaa gtcaggcgag atctccctcc tgaagcagca gctgaaggag   1200

tcccagacgg aggtgaacgc caaggctagc gagatcctgg gtctcaaggc acagctgaag   1260

gacacgcggg gcaagctgga gggcctggag ctgaggaccc aggacctgga gggcgccctg   1320

cgcaccaagg gcctggagct ggaggtctgt gagaatgagc tgcagcgcaa gaagaacgag   1380

gcggagctgc tgcgggagaa ggtgaacctg ctggagcagg agctgcagga gctgcgggcc   1440

caggccgccc tggcccgcga catggggccg cccaccttcc ccgaggacgt ccctgccctg   1500

cagcgggagc tggagcggct gcgggccgag ctgcgggagg agcggcaagg ccatgaccag   1560

atgtcctcgg gcttccagca tgagcggctc gtgtggaagg aggagaagga gaaggtgatt   1620

cagtaccaga aacagctgca gcagagctac gtggccatgt accagcggaa ccagcgcctg   1680

gagaaggccc tgcagcagct ggcacgtggg gacagcgccg gggagccctt ggaggttgac   1740
```

-continued

```
ctggaagggg ctgacatccc ctacgaggac atcatagcca ctgagatctg a           1791


<210> SEQ ID NO 4
<211> LENGTH: 596
<212> TYPE: PRT
<213> ORGANISM: Homo sapiens

<400> SEQUENCE: 4

Met Gly Ser Val Ser Ser Leu Ile Ser Gly His Ser Phe His Ser Lys
  1               5                  10                  15

His Cys Arg Ala Ser Gln Tyr Lys Leu Arg Lys Ser Ser His Leu Lys
             20                  25                  30

Lys Leu Asn Arg Tyr Ser Asp Gly Leu Leu Arg Phe Gly Phe Ser Gln
         35                  40                  45

Asp Ser Gly His Gly Lys Ser Ser Ser Lys Met Gly Lys Ser Glu Asp
     50                  55                  60

Phe Phe Tyr Ile Lys Val Ser Gln Lys Ala Arg Gly Ser His His Pro
 65                  70                  75                  80

Asp Tyr Thr Ala Leu Ser Ser Gly Asp Leu Gly Gly Gln Ala Gly Val
                 85                  90                  95

Asp Phe Asp Pro Ser Thr Pro Pro Lys Leu Met Pro Phe Ser Asn Gln
            100                 105                 110

Leu Glu Met Gly Ser Glu Lys Gly Ala Val Arg Pro Thr Ala Phe Lys
        115                 120                 125

Pro Val Leu Pro Arg Ser Gly Ala Ile Leu His Ser Ser Pro Glu Ser
    130                 135                 140

Ala Ser His Gln Leu His Pro Ala Pro Pro Asp Lys Pro Lys Glu Gln
145                 150                 155                 160

Glu Leu Lys Pro Gly Leu Cys Ser Gly Ala Leu Ser Asp Ser Gly Arg
                165                 170                 175

Asn Ser Met Ser Ser Leu Pro Thr His Ser Thr Ser Ser Ser Tyr Gln
            180                 185                 190

Leu Asp Pro Leu Val Thr Pro Val Gly Pro Thr Ser Arg Phe Gly Gly
        195                 200                 205

Ser Ala His Asn Ile Thr Gln Gly Ile Val Leu Gln Asp Ser Asn Met
    210                 215                 220

Met Ser Leu Lys Ala Leu Ser Phe Ser Asp Gly Gly Ser Lys Leu Gly
225                 230                 235                 240

His Ser Asn Lys Ala Asp Lys Gly Pro Ser Cys Val Arg Ser Pro Ile
                245                 250                 255

Ser Thr Asp Glu Cys Ser Ile Gln Glu Leu Glu Gln Lys Leu Leu Glu
            260                 265                 270

Arg Glu Gly Ala Leu Gln Lys Leu Gln Arg Ser Phe Glu Glu Lys Glu
        275                 280                 285

Leu Ala Ser Ser Leu Ala Tyr Glu Glu Arg Pro Arg Arg Cys Arg Asp
    290                 295                 300

Glu Leu Glu Gly Pro Glu Pro Lys Gly Gly Asn Lys Leu Lys Gln Ala
305                 310                 315                 320

Ser Gln Lys Ser Gln Arg Ala Gln Gln Val Leu His Leu Gln Val Leu
                325                 330                 335

Gln Leu Gln Gln Glu Lys Arg Gln Leu Arg Gln Glu Leu Glu Ser Leu
            340                 345                 350

Met Lys Glu Gln Asp Leu Leu Glu Thr Lys Leu Arg Ser Tyr Glu Arg
        355                 360                 365
```

-continued

```
Glu Lys Thr Ser Phe Gly Pro Ala Leu Glu Glu Thr Gln Trp Glu Val
    370                 375                 380

Cys Gln Lys Ser Gly Glu Ile Ser Leu Leu Lys Gln Gln Leu Lys Glu
385                 390                 395                 400

Ser Gln Thr Glu Val Asn Ala Lys Ala Ser Glu Ile Leu Gly Leu Lys
                405                 410                 415

Ala Gln Leu Lys Asp Thr Arg Gly Lys Leu Glu Gly Leu Glu Leu Arg
            420                 425                 430

Thr Gln Asp Leu Glu Gly Ala Leu Arg Thr Lys Gly Leu Glu Leu Glu
        435                 440                 445

Val Cys Glu Asn Glu Leu Gln Arg Lys Lys Asn Glu Ala Glu Leu Leu
    450                 455                 460

Arg Glu Lys Val Asn Leu Leu Glu Gln Glu Leu Gln Glu Leu Arg Ala
465                 470                 475                 480

Gln Ala Ala Leu Ala Arg Asp Met Gly Pro Pro Thr Phe Pro Glu Asp
                485                 490                 495

Val Pro Ala Leu Gln Arg Glu Leu Glu Arg Leu Arg Ala Glu Leu Arg
            500                 505                 510

Glu Glu Arg Gln Gly His Asp Gln Met Ser Ser Gly Phe Gln His Glu
        515                 520                 525

Arg Leu Val Trp Lys Glu Glu Lys Glu Lys Val Ile Gln Tyr Gln Lys
    530                 535                 540

Gln Leu Gln Gln Ser Tyr Val Ala Met Tyr Gln Arg Asn Gln Arg Leu
545                 550                 555                 560

Glu Lys Ala Leu Gln Gln Leu Ala Arg Gly Asp Ser Ala Gly Glu Pro
                565                 570                 575

Leu Glu Val Asp Leu Glu Gly Ala Asp Ile Pro Tyr Glu Asp Ile Ile
            580                 585                 590

Ala Thr Glu Ile
        595


<210> SEQ ID NO 5
<211> LENGTH: 76
<212> TYPE: PRT
<213> ORGANISM: Homo sapiens

<400> SEQUENCE: 5

Met Gly Ser Val Ser Ser Leu Ile Ser Gly His Ser Phe His Ser Lys
  1               5                  10                  15

His Cys Arg Ala Ser Gln Tyr Lys Leu Arg Lys Ser Ser His Leu Lys
             20                  25                  30

Lys Leu Asn Arg Tyr Ser Asp Gly Leu Leu Arg Phe Gly Phe Ser Gln
         35                  40                  45

Asp Ser Gly His Gly Lys Ala Met Thr Arg Cys Pro Arg Ala Ser Ser
     50                  55                  60

Met Ser Gly Ser Cys Gly Arg Arg Arg Arg Arg Arg
 65                  70                  75


<210> SEQ ID NO 6
<211> LENGTH: 69
<212> TYPE: PRT
<213> ORGANISM: Homo sapiens

<400> SEQUENCE: 6

Arg Cys Arg Asp Glu Leu Glu Gly Pro Glu Pro Lys Gly Gly Asn Lys
  1               5                  10                  15
```

-continued

```
Leu Lys Gln Ala Ser Gln Lys Ser Gln Arg Ala Gln Gln Val Leu His
            20                  25                  30

Leu Gln Val Leu Gln Leu Gln Gln Glu Lys Arg Gln Leu Arg Gln Glu
        35                  40                  45

Leu Glu Ser Leu Met Lys Glu Gln Asp Leu Leu Glu Thr Lys Leu Arg
    50                  55                  60

Ser Tyr Glu Arg Glu
65


<210> SEQ ID NO 7
<211> LENGTH: 68
<212> TYPE: PRT
<213> ORGANISM: Homo sapiens

<400> SEQUENCE: 7

Ile Ser Arg Arg Arg Arg Glu Lys Glu Asn Pro Lys Glu Arg Asn Lys
  1               5                  10                  15

Met Ala Ala Ala Lys Cys Arg Asn Arg Arg Arg Glu Leu Thr Asp Thr
            20                  25                  30

Leu Gln Ala Glu Thr Asp Gln Leu Glu Asp Glu Lys Ser Ala Leu Gln
        35                  40                  45

Thr Glu Ile Ala Asn Leu Leu Lys Glu Lys Glu Lys Leu Glu Phe Ile
    50                  55                  60

Leu Ala Ala His
65


<210> SEQ ID NO 8
<211> LENGTH: 69
<212> TYPE: PRT
<213> ORGANISM: Homo sapiens

<400> SEQUENCE: 8

Ala Trp Glu Arg Glu Leu Ala Glu Leu Arg Gln Gly Cys Ser Gly Lys
  1               5                  10                  15

Leu Gln Gln Val Ala Arg Arg Ala Gln Arg Ala Gln Gln Gly Leu Gln
            20                  25                  30

Leu Gln Val Leu Arg Leu Gln Gln Asp Lys Lys Gln Leu Gln Glu Glu
        35                  40                  45

Ala Ala Arg Leu Met Arg Gln Arg Glu Glu Leu Glu Asp Lys Val Ala
    50                  55                  60

Ala Cys Gln Lys Glu
65


<210> SEQ ID NO 9
<211> LENGTH: 404
<212> TYPE: DNA
<213> ORGANISM: Homo sapiens

<400> SEQUENCE: 9

atgggcagcg tcagtagcct catctccggc cacagcttcc acagcaagca ctgccgggct     60

tcgcagtaca agctgcgcaa gtcctcccac ctcaagaagc tcaaccggta ttccgacggg    120

ctgctgaggt ttggcttctc ccaggactcc ggtcacggca aggccatgac cagatgtcct    180

cgggcttcca gcatgagcgg ctcgtgtgga aggaggagaa ggagaaggtg attcagtacc    240

agaaacagct gcagcagagc tacgtggcca tgtaccagcg gaaccagcgc ctggagaagg    300

ccctgcagca gctggcacgt ggggacagcg ccggggagcc cttggaggtt gacctggaag    360

gggctgacat cccctacgag gacatcatag ccactgagat ctga                     404
```

-continued

<210> SEQ ID NO 10
<211> LENGTH: 633
<212> TYPE: DNA
<213> ORGANISM: Homo sapiens

<400> SEQUENCE: 10

```
atgggcagcg tcagtagcct catctccggc cacagcttcc acagcaagca ctgccgggct     60

tcgcagtaca agctgcgcaa gtcctcccac ctcaagaagc tcaaccggta ttccgacggg    120

ctgctgaggt ttggcttctc ccaggactcc ggtcacggca agtccagctc caaaatgggc    180

aagagcgaag acttcttcta catcaaggtc agccagaaag cccggggctc ccatcaccca    240

gattacacgg cactgtccag cggggattta gggggccagg ctggggtgga ctttgacccg    300

tccacacccc ccaagctcat gcccttctcc aatcagctag aaatgggctc cgagaagggt    360

gcagtgaggc ccacagcctt caagcctgtg ctgccacggt caggagccat cctgcactcc    420

tccccggaga gtgccagcca ccagctgcac cccgcccctc cagacaagcc caaggagcag    480

gagctgaagc ctggcctgtg ctctggggcg ctgtcagact ccggccggaa ctccatgtcc    540

agcctgccca cacacagcgc cggggagccc ttggaggttg acctggaagg ggctgacatc    600

ccctacgagg acatcatagc cactgagatc tga                                 633
```

<210> SEQ ID NO 11
<211> LENGTH: 1614
<212> TYPE: DNA
<213> ORGANISM: Homo sapiens

<400> SEQUENCE: 11

```
atgggcagcg tcagtagcct catctccggc cacagcttcc acagcaagca ctgccgggct     60

tcgcagtaca agctgcgcaa gtcctcccac ctcaagaagc tcaaccggta ttccgacggg    120

ctgctgaggt ttggcttctc ccaggactcc ggtcacggca agtccagctc caaaatgggc    180

aagagcgaag acttcttcta catcaaggtc agccagaaag cccggggctc ccatcaccca    240

gattacacgg cactgtccag cggggattta gggggccagg ctggggtgga ctttgacccg    300

tccacacccc ccaagctcat gcccttctcc aatcagctag aaatgggctc cgagaagggt    360

gcagtgaggc ccacagcctt caagcctgtg ctgccacggt caggagccat cctgcactcc    420

tccccggaga gtgccagcca ccagctgcac cccgcccctc cagacaagcc caaggagcag    480

gagctgaagc ctggcctgtg ctctggggcg ctgtcagact ccggccggaa ctccatgtcc    540

agcctgccca cacacagcac cagcagcagc taccagctgg acccgctggt cacacccgtg    600

ggacccacaa gccgttttgg gggctccgcc cacaacatca cccagggcat cgtcctccag    660

gacagcaaca tgatgagcct gaaggctctg tccttctccg acggaggtag caagctgggc    720

cactcgaaca aggcagacaa gggcccctcg tgtgtccgct cccccatctc cacggacgag    780

tgcagcatcc aggagctgga gcagaagctg ttggagaggg agggcgccct ccagaagctg    840

cagcgcagct ttgaggagaa ggagcttgcc tccagcctgg cctacgagga gcggccgcgg    900

cgctgcaggg acgagctgga gggcccggag cccaaaggcg gcaacaagct caagcaggcc    960

tcgcagaaga gccagcgcgc gcagcaggtc ctgcacctgc aggtactgca gcttcagcag   1020

gagaagcggc agctccggca ggagctcgag agcctcatga aggagcagga cctgctggag   1080

accaagctca ggtcctacga gagggagaag accagcttcg gccccgcgct ggaggagacc   1140

cagtgggagg tgtgccagaa gtcaggcgag atctccctcc tgaagcagca gctgaaggag   1200
```

-continued

```
tcccagacgg aggtgaacgc caaggctagc gagatcctgg gtctcaaggc acagctgaag   1260

gacacgcggg gcaagctgga gggcctggag ctgaggaccc aggacctgga gggcgccctg   1320

cgcaccaagg gcctggagct ggaggtctgt gagaatgagc tgcagcgcaa gaagaacgag   1380

gcggagctgc tgcgggagaa gcatgagcgg ctcgtgtgga aggaggagaa ggagaaggtg   1440

attcagtacc agaaacagct gcagcagagc tacgtggcca tgtaccagcg gaaccagcgc   1500

ctggagaagg ccctgcagca gctggcacgt ggggacagcg ccggggagcc cttggaggtt   1560

gacctggaag ggctgacat ccctacgag gacatcatag ccactgagat ctga         1614
```

<210> SEQ ID NO 12
<211> LENGTH: 1512
<212> TYPE: DNA
<213> ORGANISM: Homo sapiens

<400> SEQUENCE: 12

```
atgggcagcg tcagtagcct catctccggc cacagcttcc acagcaagca ctgccgggct     60

tcgcagtaca agctgcgcaa gtcctcccac ctcaagaagc tcaaccggta ttccgacggg    120

ctgctgaggt ttggcttctc ccaggactcc ggtcacggca agtccagctc caaaatgggc    180

aagagcgaag acttcttcta catcaaggtc agccagaaag cccggggctc ccatcaccca    240

gattacacgg cactgtccag cggggattta gggggccagg ctggggtgga ctttgacccg    300

tccacacccc ccaagctcat gcccttctcc aatcagctag aaatgggctc cgagaagggt    360

gcagtgaggc ccacagcctt caagcctgtg ctgccacggt caggagccat cctgcactcc    420

tccccggaga gtgccagcca ccagctgcac cccgcccctc cagacaagcc caaggagcag    480

gagctgaagc ctggcctgtg ctctggggcg ctgtcagact ccggccggaa ctccatgtcc    540

agcctgccca cacacagcac cagcagcagc taccagctgg acccgctggt cacacccgtg    600

ggacccacaa gccgttttgg gggctccgcc cacaacatca cccagggcat cgtcctccag    660

gacagcaaca tgatgagcct gaaggctctg tccttctccg acggaggtag caagctgggc    720

cactcgaaca aggcagacaa gggcccctcg tgtgtccgct cccccatctc cacggacgag    780

tgcagcatcc aggagctgga gcagaagctg ttggagaggg agggcgccct ccagaagctg    840

cagcgcagct ttgaggagaa ggagcttgcc tccagcctgg cctacgagga gcggccgcgg    900

cgctgcaggg acgagctgga gggcccggag cccaaaggcg gcaacaagct caagcaggcc    960

tcgcagaaga gccagcgcgc gcagcaggtc ctgcacctgc aggtactgca gcttcagcag   1020

gagaagcggc agctccggca ggagctcgag agcctcatga aggagcagga cctgctggag   1080

accaagctca ggtcctacga gagggagaag accagcttcg gccccgcgct ggaggagacc   1140

cagtgggagg tgtgccagaa gtcaggcgag atctccctcc tgaagcagca gctgaaggag   1200

tcccagacgg aggtgaacgc caaggctagc gagatcctgg gtctcaaggc acagctgaag   1260

gacacgcggg gcaagctgga gggcctggag ctgaggaccc aggacctgga gggcgccctg   1320

cgcaccaagg gcctggagct ggaggtctgt gagaatgagc tgcagcagag ctacgtggcc   1380

atgtaccagc ggaaccagcg cctggagaag gccctgcagc agctggcacg tggggacagc   1440

gccggggagc ccttggaggt tgacctggaa ggggctgaca tcccctacga ggacatcata   1500

gccactgaga tc                                                       1512
```

<210> SEQ ID NO 13
<211> LENGTH: 1692
<212> TYPE: DNA
<213> ORGANISM: Homo sapiens -continued

<400> SEQUENCE: 13
atgggcagcg tcagtagcct catctccggc cacagcttcc acagcaagca ctgccgggct 60
tcgcagtaca agctgcgcaa gtcctcccac ctcaagaagc tcaaccggta ttccgacggg 120
ctgctgaggt ttggcttctc ccaggactcc ggtcacggca agtccagctc caaaatgggc 180
aagagcgaag acttcttcta catcaaggtc agccagaaag cccggggctc ccatcaccca 240
gattacacgg cactgtccag cggggattta gggggccagg ctggggtgga ctttgacccg 300
tccacacccc ccaagctcat gcccttctcc aatcagctag aaatgggctc cgagaagggt 360
gcagtgaggc ccacagcctt caagcctgtg ctgccacggt caggagccat cctgcactcc 420
tccccggaga gtgccagcca ccagctgcac cccgcccctc cagacaagcc caaggagcag 480
gagctgaagc ctggcctgtg ctctggggcg ctgtcagact ccggccggaa ctccatgtcc 540
agcctgccca cacacagcac cagcagcagc taccagctgg acccgctggt cacacccgtg 600
ggacccacaa gccgttttgg gggctccgcc cacaacatca cccagggcat cgtcctccag 660
gacagcaaca tgatgagcct gaaggctctg tccttctccg acggaggtag caagctgggc 720
cactcgaaca aggcagacaa gggcccctcg tgtgtccgct cccccatctc cacggacgag 780
tgcagcatcc aggagctgga gcagaagctg ttggagaggg agggcgccct ccagaagctg 840
cagcgcagct ttgaggagaa ggagcttgcc tccagcctgg cctacgagga gcggccgcgg 900
cgctgcaggg acgagctgga gggcccggag cccaaaggcg gcaacaagct caagcaggcc 960
tcgcagaaga gccagcgcgc gcagcaggtc ctgcacctgc aggtactgca gcttcagcag 1020
gagaagcggc agctccggca ggagctcgag agcctcatga aggagcagga cctgctggag 1080
accaagctca ggtcctacga gagggagaag accagcttcg gccccgcgct ggaggagacc 1140
cagtgggagg tgtgccagaa gtcaggcgag atctccctcc tgaagcagca gctgaaggag 1200
tcccagacgg aggtgaacgc caaggctagc gagatcctgg gtctcaaggc acagctgaag 1260
gacacgcggg gcaagctgga gggcctggag ctgaggaccc aggacctgga gggcgccctg 1320
cgcaccaagg gcctggagct ggaggtctgt gagaatgagc tgcagcgcaa gaagaacgag 1380
gcggagctgc tgcgggagaa ggtgaacctg ctggagcggc tgcgggccga gctgcgggag 1440
gagcggcaag gccatgacca gatgtcctcg ggcttccagc atgagcggct cgtgtggaag 1500
gaggagaagg agaaggtgat tcagtaccag aaacagctgc agcagagcta cgtggccatg 1560
taccagcgga accagcgcct ggagaaggcc ctgcagcagc tggcacgtgg ggacagcgcc 1620
ggggagccct tggaggttga cctggaaggg gctgacatcc cctacgagga catcatagcc 1680
actgagatct ga 1692

<210> SEQ ID NO 14
<211> LENGTH: 1722
<212> TYPE: DNA
<213> ORGANISM: Homo sapiens

<400> SEQUENCE: 14
atgggcagcg tcagtagcct catctccggc cacagcttcc acagcaagca ctgccgggct 60
tcgcagtaca agctgcgcaa gtcctcccac ctcaagaagc tcaaccggta ttccgacggg 120
ctgctgaggt ttggcttctc ccaggactcc ggtcacggca agtccagctc caaaatgggc 180
aagagcgaag acttcttcta catcaaggtc agccagaaag cccggggctc ccatcaccca 240
gattacacgg cactgtccag cggggattta gggggccagg ctggggtgga ctttgacccg 300

-continued

```
tccacacccc ccaagctcat gcccttctcc aatcagctag aaatgggctc cgagaagggt    360

gcagtgaggc ccacagcctt caagcctgtg ctgccacggt caggagccat cctgcactcc    420

tccccggaga gtgccagcca ccagctgcac cccgcccctc cagacaagcc caaggagcag    480

gagctgaagc ctggcctgtg ctctggggcg ctgtcagact ccggccggaa ctccatgtcc    540

agcctgccca cacacagcac cagcagcagc taccagctgg acccgctggt cacacccgtg    600

ggacccacaa gccgttttgg gggctccgcc cacaacatca cccagggcat cgtcctccag    660

gacagcaaca tgatgagcct gaaggctctg tccttctccg acggaggtag caagctgggc    720

cactcgaaca aggcagacaa gggcccctcg tgtgtccgct cccccatctc cacggacgag    780

tgcagcatcc aggagctgga gcagaagctg ttggagaggg agggcgccct ccagaagctg    840

cagcgcagct ttgaggagaa ggagcttgcc tccagcctgg cctacgagga gcggccgcgg    900

cgctgcaggg acgagctgga gggcccggag cccaaaggcg gcaacaagct caagcaggcc    960

tcgcagaaga gccagcgcgc gcagcaggtc ctgcacctgc aggtactgca gcttcagcag   1020

gagaagcggc agctccggca ggagctcgag agcctcatga aggagcagga cctgctggag   1080

accaagctca ggtcctacga gagggagaag accagcttcg gccccgcgct ggaggagacc   1140

cagtgggagg tgtgccagaa gtcaggcgag atctccctcc tgaagcagca gctgaaggag   1200

tcccagacgg aggtgaacgc caaggctagc gagatcctgg gtctcaaggc acagctgaag   1260

gacacgcggg gcaagctgga gggcctggag ctgaggaccc aggacctgga gggcgccctg   1320

cgcaccaagg gcctggagct ggaggtctgt gagaatgagc tgcagcgcaa gaagaacgag   1380

gcggagctgc tgcgggagaa ggtgaacctg ctggagcagg agctgcagga gctgcgggcc   1440

caggccgccc tggcccgcga catggggccg cccaccttcc ccgaggacgt ccctgccctg   1500

cagcgggagc tggagcggct cgtgtggaag gaggagaagg agaaggtgat tcagtaccag   1560

aaacagctgc agcagagcta cgtggccatg taccagcgga accagcgcct ggagaaggcc   1620

ctgcagcagc tggcacgtgg ggacagcgcc ggggagccct tggaggttga cctggaaggg   1680

gctgacatcc cctacgagga catcatagcc actgagatct ga                      1722
```

<210> SEQ ID NO 15
<211> LENGTH: 76
<212> TYPE: PRT
<213> ORGANISM: Homo sapiens

<400> SEQUENCE: 15

```
Met Gly Ser Val Ser Ser Leu Ile Ser Gly His Ser Phe His Ser Lys
  1               5                  10                  15

His Cys Arg Ala Ser Gln Tyr Lys Leu Arg Lys Ser Ser His Leu Lys
             20                  25                  30

Lys Leu Asn Arg Tyr Ser Asp Gly Leu Leu Arg Phe Gly Phe Ser Gln
         35                  40                  45

Asp Ser Gly His Gly Lys Ala Met Thr Arg Cys Pro Arg Ala Ser Ser
     50                  55                  60

Met Ser Gly Ser Cys Gly Arg Arg Arg Arg Arg Arg
 65                  70                  75
```

<210> SEQ ID NO 16
<211> LENGTH: 210
<212> TYPE: PRT
<213> ORGANISM: Homo sapiens

<400> SEQUENCE: 16

-continued

```
Met Gly Ser Val Ser Ser Leu Ile Ser Gly His Ser Phe His Ser Lys
  1               5                  10                  15

His Cys Arg Ala Ser Gln Tyr Lys Leu Arg Lys Ser Ser His Leu Lys
             20                  25                  30

Lys Leu Asn Arg Tyr Ser Asp Gly Leu Leu Arg Phe Gly Phe Ser Gln
         35                  40                  45

Asp Ser Gly His Gly Lys Ser Ser Ser Lys Met Gly Lys Ser Glu Asp
     50                  55                  60

Phe Phe Tyr Ile Lys Val Ser Gln Lys Ala Arg Gly Ser His His Pro
 65                  70                  75                  80

Asp Tyr Thr Ala Leu Ser Ser Gly Asp Leu Gly Gly Gln Ala Gly Val
                 85                  90                  95

Asp Phe Asp Pro Ser Thr Pro Pro Lys Leu Met Pro Phe Ser Asn Gln
            100                 105                 110

Leu Glu Met Gly Ser Glu Lys Gly Ala Val Arg Pro Thr Ala Phe Lys
        115                 120                 125

Pro Val Leu Pro Arg Ser Gly Ala Ile Leu His Ser Ser Pro Glu Ser
    130                 135                 140

Ala Ser His Gln Leu His Pro Ala Pro Pro Asp Lys Pro Lys Glu Gln
145                 150                 155                 160

Glu Leu Lys Pro Gly Leu Cys Ser Gly Ala Leu Ser Asp Ser Gly Arg
                165                 170                 175

Asn Ser Met Ser Ser Leu Pro Thr His Ser Ala Gly Glu Pro Leu Glu
            180                 185                 190

Val Asp Leu Glu Gly Ala Asp Ile Pro Tyr Glu Asp Ile Ile Ala Thr
        195                 200                 205

Glu Ile
    210


<210> SEQ ID NO 17
<211> LENGTH: 537
<212> TYPE: PRT
<213> ORGANISM: Homo sapiens

<400> SEQUENCE: 17

Met Gly Ser Val Ser Ser Leu Ile Ser Gly His Ser Phe His Ser Lys
  1               5                  10                  15

His Cys Arg Ala Ser Gln Tyr Lys Leu Arg Lys Ser Ser His Leu Lys
             20                  25                  30

Lys Leu Asn Arg Tyr Ser Asp Gly Leu Leu Arg Phe Gly Phe Ser Gln
         35                  40                  45

Asp Ser Gly His Gly Lys Ser Ser Ser Lys Met Gly Lys Ser Glu Asp
     50                  55                  60

Phe Phe Tyr Ile Lys Val Ser Gln Lys Ala Arg Gly Ser His His Pro
 65                  70                  75                  80

Asp Tyr Thr Ala Leu Ser Ser Gly Asp Leu Gly Gly Gln Ala Gly Val
                 85                  90                  95

Asp Phe Asp Pro Ser Thr Pro Pro Lys Leu Met Pro Phe Ser Asn Gln
            100                 105                 110

Leu Glu Met Gly Ser Glu Lys Gly Ala Val Arg Pro Thr Ala Phe Lys
        115                 120                 125

Pro Val Leu Pro Arg Ser Gly Ala Ile Leu His Ser Ser Pro Glu Ser
    130                 135                 140

Ala Ser His Gln Leu His Pro Ala Pro Pro Asp Lys Pro Lys Glu Gln
145                 150                 155                 160
```

-continued

```
Glu Leu Lys Pro Gly Leu Cys Ser Gly Ala Leu Ser Asp Ser Gly Arg
                165                 170                 175

Asn Ser Met Ser Ser Leu Pro Thr His Ser Thr Ser Ser Ser Tyr Gln
            180                 185                 190

Leu Asp Pro Leu Val Thr Pro Val Gly Pro Thr Ser Arg Phe Gly Gly
        195                 200                 205

Ser Ala His Asn Ile Thr Gln Gly Ile Val Leu Gln Asp Ser Asn Met
    210                 215                 220

Met Ser Leu Lys Ala Leu Ser Phe Ser Asp Gly Gly Ser Lys Leu Gly
225                 230                 235                 240

His Ser Asn Lys Ala Asp Lys Gly Pro Ser Cys Val Arg Ser Pro Ile
                245                 250                 255

Ser Thr Asp Glu Cys Ser Ile Gln Glu Leu Glu Gln Lys Leu Leu Glu
            260                 265                 270

Arg Glu Gly Ala Leu Gln Lys Leu Gln Arg Ser Phe Glu Glu Lys Glu
        275                 280                 285

Leu Ala Ser Ser Leu Ala Tyr Glu Glu Arg Pro Arg Arg Cys Arg Asp
    290                 295                 300

Glu Leu Glu Gly Pro Glu Pro Lys Gly Gly Asn Lys Leu Lys Gln Ala
305                 310                 315                 320

Ser Gln Lys Ser Gln Arg Ala Gln Gln Val Leu His Leu Gln Val Leu
                325                 330                 335

Gln Leu Gln Gln Glu Lys Arg Gln Leu Arg Gln Glu Leu Glu Ser Leu
            340                 345                 350

Met Lys Glu Gln Asp Leu Leu Glu Thr Lys Leu Arg Ser Tyr Glu Arg
        355                 360                 365

Glu Lys Thr Ser Phe Gly Pro Ala Leu Glu Glu Thr Gln Trp Glu Val
    370                 375                 380

Cys Gln Lys Ser Gly Glu Ile Ser Leu Leu Lys Gln Gln Leu Lys Glu
385                 390                 395                 400

Ser Gln Thr Glu Val Asn Ala Lys Ala Ser Glu Ile Leu Gly Leu Lys
                405                 410                 415

Ala Gln Leu Lys Asp Thr Arg Gly Lys Leu Glu Gly Leu Glu Leu Arg
            420                 425                 430

Thr Gln Asp Leu Glu Gly Ala Leu Arg Thr Lys Gly Leu Glu Leu Glu
        435                 440                 445

Val Cys Glu Asn Glu Leu Gln Arg Lys Lys Asn Glu Ala Glu Leu Leu
    450                 455                 460

Arg Glu Lys His Glu Arg Leu Val Trp Lys Glu Glu Lys Glu Lys Val
465                 470                 475                 480

Ile Gln Tyr Gln Lys Gln Leu Gln Gln Ser Tyr Val Ala Met Tyr Gln
                485                 490                 495

Arg Asn Gln Arg Leu Glu Lys Ala Leu Gln Gln Leu Ala Arg Gly Asp
            500                 505                 510

Ser Ala Gly Glu Pro Leu Glu Val Asp Leu Glu Gly Ala Asp Ile Pro
        515                 520                 525

Tyr Glu Asp Ile Ile Ala Thr Glu Ile
    530                 535
```

<210> SEQ ID NO 18
<211> LENGTH: 504
<212> TYPE: PRT
<213> ORGANISM: Homo sapiens -continued

<400> SEQUENCE: 18

```
Met Gly Ser Val Ser Ser Leu Ile Ser Gly His Ser Phe His Ser Lys
1               5                   10                  15

His Cys Arg Ala Ser Gln Tyr Lys Leu Arg Lys Ser Ser His Leu Lys
            20                  25                  30

Lys Leu Asn Arg Tyr Ser Asp Gly Leu Leu Arg Phe Gly Phe Ser Gln
        35                  40                  45

Asp Ser Gly His Gly Lys Ser Ser Ser Lys Met Gly Lys Ser Glu Asp
    50                  55                  60

Phe Phe Tyr Ile Lys Val Ser Gln Lys Ala Arg Gly Ser His His Pro
65                  70                  75                  80

Asp Tyr Thr Ala Leu Ser Ser Gly Asp Leu Gly Gly Gln Ala Gly Val
                85                  90                  95

Asp Phe Asp Pro Ser Thr Pro Pro Lys Leu Met Pro Phe Ser Asn Gln
            100                 105                 110

Leu Glu Met Gly Ser Glu Lys Gly Ala Val Arg Pro Thr Ala Phe Lys
        115                 120                 125

Pro Val Leu Pro Arg Ser Gly Ala Ile Leu His Ser Ser Pro Glu Ser
    130                 135                 140

Ala Ser His Gln Leu His Pro Ala Pro Pro Asp Lys Pro Lys Glu Gln
145                 150                 155                 160

Glu Leu Lys Pro Gly Leu Cys Ser Gly Ala Leu Ser Asp Ser Gly Arg
                165                 170                 175

Asn Ser Met Ser Ser Leu Pro Thr His Ser Thr Ser Ser Ser Tyr Gln
            180                 185                 190

Leu Asp Pro Leu Val Thr Pro Val Gly Pro Thr Ser Arg Phe Gly Gly
        195                 200                 205

Ser Ala His Asn Ile Thr Gln Gly Ile Val Leu Gln Asp Ser Asn Met
    210                 215                 220

Met Ser Leu Lys Ala Leu Ser Phe Ser Asp Gly Gly Ser Lys Leu Gly
225                 230                 235                 240

His Ser Asn Lys Ala Asp Lys Gly Pro Ser Cys Val Arg Ser Pro Ile
                245                 250                 255

Ser Thr Asp Glu Cys Ser Ile Gln Glu Leu Glu Gln Lys Leu Leu Glu
            260                 265                 270

Arg Glu Gly Ala Leu Gln Lys Leu Gln Arg Ser Phe Glu Glu Lys Glu
        275                 280                 285

Leu Ala Ser Ser Leu Ala Tyr Glu Glu Arg Pro Arg Arg Cys Arg Asp
    290                 295                 300

Glu Leu Glu Gly Pro Glu Pro Lys Gly Gly Asn Lys Leu Lys Gln Ala
305                 310                 315                 320

Ser Gln Lys Ser Gln Arg Ala Gln Gln Val Leu His Leu Gln Val Leu
                325                 330                 335

Gln Leu Gln Gln Glu Lys Arg Gln Leu Arg Gln Glu Leu Glu Ser Leu
            340                 345                 350

Met Lys Glu Gln Asp Leu Leu Glu Thr Lys Leu Arg Ser Tyr Glu Arg
        355                 360                 365

Glu Lys Thr Ser Phe Gly Pro Ala Leu Glu Glu Thr Gln Trp Glu Val
    370                 375                 380

Cys Gln Lys Ser Gly Glu Ile Ser Leu Leu Lys Gln Gln Leu Lys Glu
385                 390                 395                 400

Ser Gln Thr Glu Val Asn Ala Lys Ala Ser Glu Ile Leu Gly Leu Lys
                405                 410                 415
```

-continued

```
Ala Gln Leu Lys Asp Thr Arg Gly Lys Leu Glu Gly Leu Glu Leu Arg
            420                 425                 430

Thr Gln Asp Leu Glu Gly Ala Leu Arg Thr Lys Gly Leu Glu Leu Glu
        435                 440                 445

Val Cys Glu Asn Glu Leu Gln Gln Ser Tyr Val Ala Met Tyr Gln Arg
    450                 455                 460

Asn Gln Arg Leu Glu Lys Ala Leu Gln Gln Leu Ala Arg Gly Asp Ser
465                 470                 475                 480

Ala Gly Glu Pro Leu Glu Val Asp Leu Glu Gly Ala Asp Ile Pro Tyr
                485                 490                 495

Glu Asp Ile Ile Ala Thr Glu Ile
            500


<210> SEQ ID NO 19
<211> LENGTH: 563
<212> TYPE: PRT
<213> ORGANISM: Homo sapiens

<400> SEQUENCE: 19

Met Gly Ser Val Ser Ser Leu Ile Ser Gly His Ser Phe His Ser Lys
  1               5                  10                  15

His Cys Arg Ala Ser Gln Tyr Lys Leu Arg Lys Ser Ser His Leu Lys
            20                  25                  30

Lys Leu Asn Arg Tyr Ser Asp Gly Leu Leu Arg Phe Gly Phe Ser Gln
        35                  40                  45

Asp Ser Gly His Gly Lys Ser Ser Ser Lys Met Gly Lys Ser Glu Asp
     50                  55                  60

Phe Phe Tyr Ile Lys Val Ser Gln Lys Ala Arg Gly Ser His His Pro
 65                  70                  75                  80

Asp Tyr Thr Ala Leu Ser Ser Gly Asp Leu Gly Gly Gln Ala Gly Val
                85                  90                  95

Asp Phe Asp Pro Ser Thr Pro Pro Lys Leu Met Pro Phe Ser Asn Gln
            100                 105                 110

Leu Glu Met Gly Ser Glu Lys Gly Ala Val Arg Pro Thr Ala Phe Lys
        115                 120                 125

Pro Val Leu Pro Arg Ser Gly Ala Ile Leu His Ser Ser Pro Glu Ser
    130                 135                 140

Ala Ser His Gln Leu His Pro Ala Pro Pro Asp Lys Pro Lys Glu Gln
145                 150                 155                 160

Glu Leu Lys Pro Gly Leu Cys Ser Gly Ala Leu Ser Asp Ser Gly Arg
                165                 170                 175

Asn Ser Met Ser Ser Leu Pro Thr His Ser Thr Ser Ser Ser Tyr Gln
            180                 185                 190

Leu Asp Pro Leu Val Thr Pro Val Gly Pro Thr Ser Arg Phe Gly Gly
        195                 200                 205

Ser Ala His Asn Ile Thr Gln Gly Ile Val Leu Gln Asp Ser Asn Met
    210                 215                 220

Met Ser Leu Lys Ala Leu Ser Phe Ser Asp Gly Gly Ser Lys Leu Gly
225                 230                 235                 240

His Ser Asn Lys Ala Asp Lys Gly Pro Ser Cys Val Arg Ser Pro Ile
                245                 250                 255

Ser Thr Asp Glu Cys Ser Ile Gln Glu Leu Glu Gln Lys Leu Leu Glu
            260                 265                 270
```

-continued

```
Arg Glu Gly Ala Leu Gln Lys Leu Gln Arg Ser Phe Glu Glu Lys Glu
        275                 280                 285

Leu Ala Ser Ser Leu Ala Tyr Glu Glu Arg Pro Arg Arg Cys Arg Asp
    290                 295                 300

Glu Leu Glu Gly Pro Glu Pro Lys Gly Gly Asn Lys Leu Lys Gln Ala
305                 310                 315                 320

Ser Gln Lys Ser Gln Arg Ala Gln Gln Val Leu His Leu Gln Val Leu
                325                 330                 335

Gln Leu Gln Gln Glu Lys Arg Gln Leu Arg Gln Glu Leu Glu Ser Leu
            340                 345                 350

Met Lys Glu Gln Asp Leu Leu Glu Thr Lys Leu Arg Ser Tyr Glu Arg
        355                 360                 365

Glu Lys Thr Ser Phe Gly Pro Ala Leu Glu Glu Thr Gln Trp Glu Val
    370                 375                 380

Cys Gln Lys Ser Gly Glu Ile Ser Leu Leu Lys Gln Gln Leu Lys Glu
385                 390                 395                 400

Ser Gln Thr Glu Val Asn Ala Lys Ala Ser Glu Ile Leu Gly Leu Lys
                405                 410                 415

Ala Gln Leu Lys Asp Thr Arg Gly Lys Leu Glu Gly Leu Glu Leu Arg
            420                 425                 430

Thr Gln Asp Leu Glu Gly Ala Leu Arg Thr Lys Gly Leu Glu Leu Glu
        435                 440                 445

Val Cys Glu Asn Glu Leu Gln Arg Lys Lys Asn Glu Ala Glu Leu Leu
    450                 455                 460

Arg Glu Lys Val Asn Leu Leu Glu Arg Leu Arg Ala Glu Leu Arg Glu
465                 470                 475                 480

Glu Arg Gln Gly His Asp Gln Met Ser Ser Gly Phe Gln His Glu Arg
                485                 490                 495

Leu Val Trp Lys Glu Glu Lys Glu Lys Val Ile Gln Tyr Gln Lys Gln
            500                 505                 510

Leu Gln Gln Ser Tyr Val Ala Met Tyr Gln Arg Asn Gln Arg Leu Glu
        515                 520                 525

Lys Ala Leu Gln Gln Leu Ala Arg Gly Asp Ser Ala Gly Glu Pro Leu
    530                 535                 540

Glu Val Asp Leu Glu Gly Ala Asp Ile Pro Tyr Glu Asp Ile Ile Ala
545                 550                 555                 560

Thr Glu Ile


<210> SEQ ID NO 20
<211> LENGTH: 573
<212> TYPE: PRT
<213> ORGANISM: Homo sapiens

<400> SEQUENCE: 20

Met Gly Ser Val Ser Ser Leu Ile Ser Gly His Ser Phe His Ser Lys
  1               5                  10                  15

His Cys Arg Ala Ser Gln Tyr Lys Leu Arg Lys Ser Ser His Leu Lys
            20                  25                  30

Lys Leu Asn Arg Tyr Ser Asp Gly Leu Leu Arg Phe Gly Phe Ser Gln
        35                  40                  45

Asp Ser Gly His Gly Lys Ser Ser Ser Lys Met Gly Lys Ser Glu Asp
     50                  55                  60

Phe Phe Tyr Ile Lys Val Ser Gln Lys Ala Arg Gly Ser His His Pro
 65                  70                  75                  80
```

-continued

```
Asp Tyr Thr Ala Leu Ser Ser Gly Asp Leu Gly Gly Gln Ala Gly Val
                85                  90                  95

Asp Phe Asp Pro Ser Thr Pro Pro Lys Leu Met Pro Phe Ser Asn Gln
            100                 105                 110

Leu Glu Met Gly Ser Glu Lys Gly Ala Val Arg Pro Thr Ala Phe Lys
        115                 120                 125

Pro Val Leu Pro Arg Ser Gly Ala Ile Leu His Ser Ser Pro Glu Ser
    130                 135                 140

Ala Ser His Gln Leu His Pro Ala Pro Pro Asp Lys Pro Lys Glu Gln
145                 150                 155                 160

Glu Leu Lys Pro Gly Leu Cys Ser Gly Ala Leu Ser Asp Ser Gly Arg
                165                 170                 175

Asn Ser Met Ser Ser Leu Pro Thr His Ser Thr Ser Ser Ser Tyr Gln
            180                 185                 190

Leu Asp Pro Leu Val Thr Pro Val Gly Pro Thr Ser Arg Phe Gly Gly
        195                 200                 205

Ser Ala His Asn Ile Thr Gln Gly Ile Val Leu Gln Asp Ser Asn Met
    210                 215                 220

Met Ser Leu Lys Ala Leu Ser Phe Ser Asp Gly Gly Ser Lys Leu Gly
225                 230                 235                 240

His Ser Asn Lys Ala Asp Lys Gly Pro Ser Cys Val Arg Ser Pro Ile
                245                 250                 255

Ser Thr Asp Glu Cys Ser Ile Gln Glu Leu Glu Gln Lys Leu Leu Glu
            260                 265                 270

Arg Glu Gly Ala Leu Gln Lys Leu Gln Arg Ser Phe Glu Glu Lys Glu
        275                 280                 285

Leu Ala Ser Ser Leu Ala Tyr Glu Glu Arg Pro Arg Arg Cys Arg Asp
    290                 295                 300

Glu Leu Glu Gly Pro Glu Pro Lys Gly Gly Asn Lys Leu Lys Gln Ala
305                 310                 315                 320

Ser Gln Lys Ser Gln Arg Ala Gln Gln Val Leu His Leu Gln Val Leu
                325                 330                 335

Gln Leu Gln Gln Glu Lys Arg Gln Leu Arg Gln Glu Leu Glu Ser Leu
            340                 345                 350

Met Lys Glu Gln Asp Leu Leu Glu Thr Lys Leu Arg Ser Tyr Glu Arg
        355                 360                 365

Glu Lys Thr Ser Phe Gly Pro Ala Leu Glu Glu Thr Gln Trp Glu Val
    370                 375                 380

Cys Gln Lys Ser Gly Glu Ile Ser Leu Leu Lys Gln Gln Leu Lys Glu
385                 390                 395                 400

Ser Gln Thr Glu Val Asn Ala Lys Ala Ser Glu Ile Leu Gly Leu Lys
                405                 410                 415

Ala Gln Leu Lys Asp Thr Arg Gly Lys Leu Glu Gly Leu Glu Leu Arg
            420                 425                 430

Thr Gln Asp Leu Glu Gly Ala Leu Arg Thr Lys Gly Leu Glu Leu Glu
        435                 440                 445

Val Cys Glu Asn Glu Leu Gln Arg Lys Lys Asn Glu Ala Glu Leu Leu
    450                 455                 460

Arg Glu Lys Val Asn Leu Leu Glu Gln Glu Leu Gln Glu Leu Arg Ala
465                 470                 475                 480

Gln Ala Ala Leu Ala Arg Asp Met Gly Pro Pro Thr Phe Pro Glu Asp
                485                 490                 495
```

-continued

```
Val Pro Ala Leu Gln Arg Glu Leu Glu Arg Leu Val Trp Lys Glu Glu
            500                 505                 510

Lys Glu Lys Val Ile Gln Tyr Gln Lys Gln Leu Gln Gln Ser Tyr Val
        515                 520                 525

Ala Met Tyr Gln Arg Asn Gln Arg Leu Glu Lys Ala Leu Gln Gln Leu
    530                 535                 540

Ala Arg Gly Asp Ser Ala Gly Glu Pro Leu Glu Val Asp Leu Glu Gly
545                 550                 555                 560

Ala Asp Ile Pro Tyr Glu Asp Ile Ile Ala Thr Glu Ile
                565                 570


<210> SEQ ID NO 21
<211> LENGTH: 591
<212> TYPE: DNA
<213> ORGANISM: Artificial Sequence
<220> FEATURE:
<223> OTHER INFORMATION: Description of Artificial Sequence: F37 Probe

<400> SEQUENCE: 21

ggactctgcc cctggacctg ggaacgactg gactgtcacg gggttccctc ctagctctcc     60

cagtgaactc ctgccaggca cacacagccc ctatagcact gagctcacat gggactggga    120

tatgggggca tctcttcccc agagaggcac tcagtgagcc tcctgtgcct ggccccagtc    180

tgggccatct cttaggtgag acagttgccc gaaactaagc caggcctggc tggaggagca    240

gcagcttggg gagagggatt tccctgcaga cctcaagcca tcatgcggtg ggtgctgcca    300

tgacagaggc tgcacccctg ggccagcggg gctgctcacc cacctcttgt gcaaggtggc    360

ctttgtgctg cgcctgcagg cagagctgga gcccccagca gaggcaggct gggacggacc    420

agcatctgga agatgtacat agttattttt ctctttgtgg tttcttgttt ggtttggttt    480

gcttttgaca gcttcatttt atttttgacg tcactttttg gccatgtaaa ctatttgtgg    540

caattttatg tttttattta tgaataaaga atgccatttc tcacgccctc t             591


<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: FEZ1
      alterable region amplificatin primer G12

<400> SEQUENCE: 22

gctgccacag cctttccaag acc                                             23


<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: FEZ1
      alterable region amplificatin primer G13

<400> SEQUENCE: 23

taccggttga gcttcttgag gtg                                             23


<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: FEZ1
      alterable region amplification primer G14.2
```

-continued

<400> SEQUENCE: 24
acagcttcca cagcaagcac tgc 23

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: FEZ1
alterable region amplification primer G15

<400> SEQUENCE: 25
attggagaag ggcatgagct t 21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: FEZ1
alterable region amplification primer G16

<400> SEQUENCE: 26
tggactttga cccgtccaca cc 22

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: FEZ1
alterable region amplification primer IntABR

<400> SEQUENCE: 27
gtttccaacc cacttaccct tgc 23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: FEZ1
alterable region amplification primer IntABF

<400> SEQUENCE: 28
gcaggggagg catgagtcac c 21

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: FEZ1
alterable region amplification primer G17

<400> SEQUENCE: 29
ggcttcagct cctgctcctt gg 22

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: FEZ1
alterable region amplification primer G20

-continued

<400> SEQUENCE: 30
acaacatcac ccagggcatc gtc 23

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: FEZ1
alterable region amplification primer G21

<400> SEQUENCE: 31
cctccagctc gtccctgcag c 21

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: FEZ1
alterable region amplification primer G32

<400> SEQUENCE: 32
actgcagctt cagcaggaga agc 23

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: FEZ1
alterable region amplification primer IntBCR

<400> SEQUENCE: 33
ctgaccaccc aaacccatga gc 22

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: FEZ1
alterable region amplification primer IntBCF

<400> SEQUENCE: 34
tcacctcttg gcactctgtc tcc 23

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: FEZ1
alterable region amplification primer Mut6

<400> SEQUENCE: 35
caggtcctgg gtcctcagct c 21

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: FEZ1
alterable region amplification primer G1

<400> SEQUENCE: 36

-continued tgaacgccaa ggctagcgag atc 23

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: FEZ1
alterable region amplification primer G2

<400> SEQUENCE: 37
gctcctgcag ctcctgctcc ag 22

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: FEZ1
alterable region amplification primer G75

<400> SEQUENCE: 38
cccaccttcc ccgaggacgt c 21

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: FEZ1
alterable region amplification primer G82

<400> SEQUENCE: 39
agcccgagga catctggtca tgg 23

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: FEZ1
alterable region amplification primer G5

<400> SEQUENCE: 40
cctgccctgc agcgggagct ggag 24

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: FEZ1
alterable region amplification primer G6

<400> SEQUENCE: 41
agctgctgca gggccttctc cag 23

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: FEZ1
alterable region amplification primer G7

<400> SEQUENCE: 42

-continued

```
cagtaccaga aacagctgca gcagagc                                    27


<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: FEZ1
      alterable region amplification primer G8

<400> SEQUENCE: 43

ccctgcctcc cagtgccagg tc                                         22


<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: First
      strand of partially-double stranded adapter-linker

<400> SEQUENCE: 44

gatctcgacg aattcgtgag acct                                       24


<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Second
      strand of partially-double stranded adapter-linker

<400> SEQUENCE: 45

tggtctcacg aattcgtcga                                            20


<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Donor site
      sequence of truncated FEZ1 truncation region

<400> SEQUENCE: 46

tcccaggact ccggtcacgg caa                                        23


<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Acceptor
      site sequence of truncated FEZ1 truncation region

<400> SEQUENCE: 47

gagcggcaag gccatgacca g                                          21


<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Donor site
      sequence of truncated FEZ1 truncation region

<400> SEQUENCE: 48

agcctgccca cacacagcac cag                                        23
```

-continued

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Acceptor site sequence of truncated FEZ1 truncation region

<400> SEQUENCE: 49
cagcgccggg gagcccttgg a 21

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Donor site sequence of truncated FEZ1 truncation region

<400> SEQUENCE: 50
gtgagaatga gctgcagcgc aag 23

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Acceptor site sequence of truncated FEZ1 truncation region

<400> SEQUENCE: 51
cagcagagct acgtggccat gt 22

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Donor site sequence of truncated FEZ1 truncation region

<400> SEQUENCE: 52
agctgctgcg ggagaaggtg aac 23

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Acceptor site sequence of truncated FEZ1 truncation region

<400> SEQUENCE: 53
cagcatgagc ggctcgtgtg ga 22

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Donor site sequence of truncated FEZ1 truncation region

<400> SEQUENCE: 54
aggtgaacct gctggagcag gag 23

-continued

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Acceptor site sequence of truncated FEZ1 truncation region

<400> SEQUENCE: 55
gagcggctgc gggccgagct gc 22

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Donor site sequence of truncated FEZ1 truncation region

<400> SEQUENCE: 56
ctgcagcggg agctggagcg gctg 24

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Acceptor site sequence of truncated FEZ1 truncation region

<400> SEQUENCE: 57
gagcggctcg tgtggaagga g 21

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Primer for amplifying FEZ1 cDNA

<400> SEQUENCE: 58
cagatgggca gcgtcagtag cctcatc 27

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Primer for amplifying FEZ1 cDNA

<400> SEQUENCE: 59
tcagatctca gtggctatga tgtc 24

<210> SEQ ID NO 60
<211> LENGTH: 8073
<212> TYPE: DNA
<213> ORGANISM: Artificial Sequence
<220> FEATURE:
<223> OTHER INFORMATION: Description of Artificial Sequence: Nucleotide sequence of vector pQBI-AdCMV5-IRES-GFP

<400> SEQUENCE: 60
gaattcggcc ggccatcatc aataatatac cttattttgg attgaagcca atatgataat 60
gagggggtgg agtttgtgac gtggcgcggg gcgtgggaac ggggcgggtg acgtagtagt 120

-continued

```
gtggcggaag tgtgatgttg caagtgtggc ggaacacatg taagcgacgg atgtggcaaa    180
agtgacgttt ttggtgtgcg ccggtgtaca caggaagtga caattttcgc gcggttttag    240
gcggatgttg tagtaaattt gggcgtaacc gagtaagatt tggccatttt cgcgggaaaa    300
ctgaataaga ggaagtgaaa tctgaataat tttgtgttac tcatagcgcg taatatttgt    360
ctagggccgc cagatcgatc tccgagggat ctcgaccaaa tgatttgccc tcccatatgt    420
ccttccgagt gagagacaca aaaaattcca acacactatt gcaatgaaaa taaatttcct    480
ttattagcca gaggtcgagg tcgggggatc ctcagttgta cagttcatcc atgccatgtg    540
taatcccagc agctgttaca aactcaagaa ggaccatgtg gtctctcttt tcgttgggat    600
ctttcgaaag ggcagattgt gtggacaggt aatggttgtc tggtaaaagg acagggccat    660
cgccaattgg agtattttgt tgataatggt ctgctagttg aacgcttcca tcttcaatgt    720
tgtggcgggt cttgaagttc actttgattc cattcttttg tttgtctgcc atgatgtata    780
cattgtgtga gttatagttg tattccaatt tgtgtcccag aatgttgcca tcttccttga    840
agtcaatacc ttttaactcg attctattaa caagggtatc accttcaaac ttgacttcag    900
cacgtgtctt gtagttgccg tcatctttga agaagatggt cctttcctgt acataacctt    960
cgggcatggc actcttgaaa aagtcatgcc gtttcatatg atccgggtat cttgaaaagc   1020
attgaacacc atagcacaga gtagtgacta gtgttggcca tggaacaggc agtttgccag   1080
tagtgcagat gaacttcagg gtaagttttc cgtatgttgc atcaccttca ccctctccac   1140
tgacagagaa cttgtggccg ttaacatcac catctaattc aacaagaatt gggacaactc   1200
cagtgaagag ttcttctcct ttgctagcca tggcggatcc ggctgaacgg tctggttata   1260
ggtacattga gcaactgact gaaatgcctc aaaatgttct ttacgatgcc attgggatat   1320
atcaacggtg gtatatccag tgattttttt ctccatggtt gtggcaagct tatcatcgtg   1380
tttttcaaag gaaaaccacg tccccgtggt tcgggggggc tagacgtttt ttaacctcga   1440
ctaaacacat gtaaagcatg tgcaccgagg ccccagatca gatcccatac aatggggtac   1500
cttctgggca tccttcagcc ccttgttgaa tacgcttgag gagagccatt tgactctttc   1560
cacaactatc caactcacaa cgtggcactg gggttgtgcc gcctttgcag gtgtatctta   1620
tacacgtggc ttttggccgc agaggcacct gtcgccaggt ggggggttcc gctgcctgca   1680
aagggtcgct acagacgttg tttgtcttca agaagcttcc agaggaactg cttccttcac   1740
gacattcaac agaccttgca ttcctttggc gagaggggaa agacccctag gaatgctcgt   1800
caagaagaca gggccaggtt tccgggccct cacattgcca aaagacggca atatggtgga   1860
aaataacata tagacaaacg cacaccggcc ttattccaag cggcttcggc cagtaacgtt   1920
aggggggggg gagggagagg gcggaattcg gagagggcgg aattcggggc cgcggagatc   1980
ttccaaactt ggacctggga gtggacacct gtggagagaa aggcaaagtg gatgtcattg   2040
tcactcaagt gtatggccag atcgggccag gtgaatatca aatcctcctc gtttttggaa   2100
actgacaatc ttagcgcaga agtcatgccc gcttttgaga gggagtactc accccaacag   2160
ctggatctca agcctgccac acctcacctc gaccatccgc cggctcaaga ccgcctactt   2220
taattacatc atcagcagca cctccgccag aaacaacccc gaccgccacc cgctgccgcc   2280
cgccacggtg ctcagcctac cttgcgactg tgactggtta gacgcctttc tcgagaggtt   2340
ttccgatccg gtcgatgcgg actggctcag gtccctcggt ggcggagtac cgttcggagg   2400
ccgacgggtt tccgatccaa gagtactgga aagaccgcga agagtttgtc ctcaaccgcg   2460
```

-continued

```
agcccaacag ctggccctcg cagacagcga tgcggaagag agtgaggatc tgacggttca   2520
ctaaacgagc tctgcttata tagacctccc accgtacacg cctaccgccc atttgcgtca   2580
acggggcggg gttattacga cattttggaa agtcccgttg attttggtgc caaaacaaac   2640
tcccattgac gtcaatgggg tggagacttg gaaatccccg tgagtcaaac cgctatccac   2700
gcccattggt gtactgccaa aaccgcatca ccatggtaat agcgatgact aatacgtaga   2760
tgtactgcca agtaggaaag tcccgtaagg tcatgtactg ggcataatgc caggcgggcc   2820
atttaccgtc attgacgtca atagggggcg gacttggcat atgatacact tgatgtactg   2880
ccaagtgggc agtttaccgt aaatactcca cccattgacg tcaatggaaa gtccctattg   2940
gcgttactat gggaacatac gtcattattg acgtcaatgg gcgggggtcg ttgggcggtc   3000
agccaggcgg gccatttacc gtaagttatg taacgcggaa ctccatatat gggctatgaa   3060
ctaatgaccc cgtaattgat tactattaat aactagtcaa taatcaatgt caacatggcg   3120
gtcatattgg acatgagcca atataaatgt acatattatg atatagatac aacgtatgca   3180
atggccaata gccaatattg atttatgcta tataaccaat gactaatatg gctaattgcc   3240
aatattgatt caatgtatag atcgatctgg aaggtgctga ggtacgatga gacccgcacc   3300
aggtgcagac cctgcgagtg tggcggtaaa catattagga accagcctgt gatgctggat   3360
gtgaccgagg agctgaggcc cgatcacttg gtgctggcct gcacccgcgc tgagtttggc   3420
tctagcgatg aagatacaga ttgaggtact gaaatgtgtg ggcgtggctt aagggtggga   3480
aagaatatat aaggtggggg tcttatgtag ttttgtatct gttttgcagc agccgccgcc   3540
gccatgagca ccaactcgtt tgatggaagc attgtgagct catatttgac aacgcgcatg   3600
cccccatggg ccggggtgcg tcagaatgtg atgggctcca gcattgatgg tcgccccgtc   3660
ctgcccgcaa actctactac cttgacctac gagaccgtgt ctggaacgcc gttggagact   3720
gcagcctccg ccgccgcttc agccgctgca gccaccgccc gcgggattgt gactgacttt   3780
gctttcctga gcccgcttgc aagcagtgca gcttcccgtt catccgcccg cgatgacaag   3840
ttgacggctc ttttggcaca attggattct ttgacccggg aacttaatgt cgtttctcag   3900
cagctgttgg atctgcgcca gcaggtttct gccctgaagg cttcctcccc tcccaatgcg   3960
gtttaaaaca taaataaaaa accagactct gtttggattt ggatcaagca agtgtcttgc   4020
tgtctttatt taggggtttt gcgcgcgcgg taggcccggg accagcggtc tcggtcgttg   4080
agggtcctgt gtattttttc caggacgtgg taaaggtgac tctggatgtt cagatacatg   4140
ggcataagcc cgtctctggg gtggaggtag caccactgca gagcttcatg ctgcggggtg   4200
gtgttgtaga tgatccagtc gtagcaggag cgctgggcgt ggtgcctaaa aatgtctttc   4260
agtagcaagc tgattgccag gggcaggccc ttggtgtaag tgtttacaaa gcggttaagc   4320
tgggatgggt gcatacgtgg ggatatgaga tgcatcttgg actgtatttt taggttggct   4380
atgttcccag ccatatccct ccggggattc atgttgtgca gaaccaccag cacagtgtat   4440
ccggtgcact tgggaaattt gtcatgtagc ttagaaggaa atgcgtggaa gaacttggag   4500
acgcccttgt gacctccaag attttccatg cattcgtcca taatgatggc aatgggccca   4560
cgggcggcgg cctgggcgaa gatatttctg ggatcactaa cgtcatagtt gtgttccagg   4620
atgagatcgt cataggccat ttttacaaag cgcgggcgga gggtgccaga ctgcggtata   4680
atggttccat ccggcccagg ggcgtagtta ccctcacaga tttgcatttc ccacgctttg   4740
agttcagatg gggggatcat gtctacctgc ggggcgatga agaaaacggt ttccggggta   4800
ggggagatca gctgggaaga aagcaggttc ctgagcagct gcgacttacc gcagccggtg   4860
```

-continued

```
ggcccgtaaa tcacacctat taccgggtgc aactggtagt taagagagct gcagctgccg   4920
tcatccctga gcagggggc cacttcgtta agcatgtccc tgactcgcat gttttccctg   4980
accaaatccg ccagaaggcg ctcgccgccc agcgatagca gttcttgcaa ggaagcaaag   5040
tttttcaacg gtttgagacc gtccgccgta ggcatgcttt tgagcgtttg accaagcagt   5100
tccaggcggt cccacagctc ggtcacctgc tctacggcat ctcgatccag catatctcct   5160
cgtttcgcgg gttggggcgg ctttcgctgt acggcagtag tcggtgctcg tccagacggg   5220
ccagggtcat gtctttccac gggcgcaggg tcctcgtcag cgtagtctgg gtcacggtga   5280
aggggtgcgc tccgggctgc gcgctggcca gggtgcgctt gaggctggtc ctgctggtgc   5340
tgaagcgctg ccggtcttcg ccctgcgcgt cggccaggta gcatttgacc atggtgtcat   5400
agtccagccc ctccgcggcg tggcccttgg cgcgcagctt gcccttggag gaggcgccgc   5460
acgaggggca gtgcagactt ttgagggcgt agagcttggg cgcgagaaat accgattccg   5520
gggagtaggc atccgcgccg caggccccgc agacggtctc gcattccacg agccaggtga   5580
gctctggccg ttcggggtca aaaaccaggt ttcccccatg ctttttgatg cgtttcttac   5640
ctctggtttc catgagccgg tgtccacgct cggtgacgaa aaggctgtcc gtgtccccgt   5700
atacagactt gagaggcctg tcctcgaccg atgcccttga gagccttcaa cccagtcagc   5760
tccttccggt gggcgcgggg catgactatc gtcgccgcac ttatgactgt cttctttatc   5820
atgcaactcg taggacaggt gccggcagcg ctctgggtca ttttcggcga ggaccgcttt   5880
cgctggagcg cgacgatgat cggcctgtcg cttgcggtat tcggaatctt gcacgccctc   5940
gctcaagcct tcgtcactgg tcccgccacc aaacgtttcg gcgagaagca ggccattatc   6000
gccggcatgg cggccgacgc gctgggctac gtcttgctgg cgttcgcgac gcgaggctgg   6060
atggccttcc ccattatgat tcttctcgct tccggcggca tcgggatgcc cgcgttgcag   6120
gccatgctgt ccaggcaggt agatgacgac catcagggac agcttcaagg atcgctcgcg   6180
gctcttacca gctgagcaaa aggccagcaa aaggccagga accgtaaaaa ggccgcgttg   6240
ctggcgtttt tccataggct ccgcccccct gacgagcatc acaaaaatcg acgctcaagt   6300
cagaggtggc gaaacccgac aggactataa agataccagg cgtttccccc tggaagctcc   6360
ctcgtgcgct ctcctgttcc gaccctgccg cttaccggat acctgtccgc ctttctccct   6420
tcgggaagcg tggcgctttc tcaatgctca cgctgtaggt atctcagttc ggtgtaggtc   6480
gttcgctcca agctgggctg tgtgcacgaa ccccccgttc agcccgaccg ctgcgcctta   6540
tccggtaact atcgtcttga gtccaacccg gtaagacacg acttatcgcc actggcagca   6600
gccactggta acaggattag cagagcgagg tatgtaggcg gtgctacaga gttcttgaag   6660
tggtggccta actacggcta cactagaagg acagtatttg gtatctgcgc tctgctgaag   6720
ccagttacct tcggaaaaag agttggtagc tcttgatccg gcaaacaaac caccgctggt   6780
agcggtggtt tttttgtttg caagcagcag attacgcgca gaaaaaaagg atctcaagaa   6840
gatcctttga tcttttctac ggggtctgac gctcagtgga acgaaaactc acgttaaggg   6900
attttggtca tgagattatc aaaaaggatc ttcacctaga tccttttaaa ttaaaaatga   6960
agttttaaat caatctaaag tatatatgag taaacttggt ctgacagtta ccaatgctta   7020
atcagtgagg cacctatctc agcgatctgt ctatttcgtt catccatagt tgcctgactc   7080
cccgtcgtgt agataactac gatacgggag ggcttaccat ctggccccag tgctgcaatg   7140
ataccgcgag acccacgctc accggctcca gatttatcag caataaacca gccagccgga   7200
```

-continued

```
agggccgagc gcagaagtgg tcctgcaact ttatccgcct ccatccagtc tattaattgt   7260

tgccgggaag ctagagtaag tagttcgcca gttaatagtt tgcgcaacgt tgttgccatt   7320

gctgcaggca tcgtggtgtc acgctcgtcg tttggtatgg cttcattcag ctccggttcc   7380

caacgatcaa ggcgagttac atgatccccc atgttgtgca aaaaagcggt tagctccttc   7440

ggtcctccga tcgttgtcag aagtaagttg gccgcagtgt tatcactcat ggttatggca   7500

gcactgcata attctcttac tgtcatgcca tccgtaagat gcttttctgt gactggtgag   7560

tactcaacca agtcattctg agaatagtgt atgcggcgac cgagttgctc ttgcccggcg   7620

tcaacacggg ataataccgc gccacatagc agaactttaa aagtgctcat cattggaaaa   7680

cgttcttcgg ggcgaaaact ctcaaggatc ttaccgctgt tgagatccag ttcgatgtaa   7740

cccactcgtg cacccaactg atcttcagca tcttttactt tcaccagcgt ttctgggtga   7800

gcaaaaacag gaaggcaaaa tgccgcaaaa aagggaataa gggcgacacg gaaatgttga   7860

atactcatac tcttcctttt tcaatattat tgaagcattt atcagggtta ttgtctcatg   7920

agcggataca tatttgaatg tatttagaaa aataaacaaa taggggttcc gcgcacattt   7980

ccccgaaaag tgccacctga cgtctaagaa accattatta tcatgacatt aacctataaa   8040

aataggcgta tcacgaggcc ctttcgtctt caa                                8073
```

<210> SEQ ID NO 61
<211> LENGTH: 11
<212> TYPE: DNA
<213> ORGANISM: Artificial Sequence
<220> FEATURE:
<223> OTHER INFORMATION: Description of Artificial Sequence: Example

<400> SEQUENCE: 61
aaccaaaaaa a 11

<210> SEQ ID NO 62
<211> LENGTH: 11
<212> TYPE: DNA
<213> ORGANISM: Artificial Sequence
<220> FEATURE:
<223> OTHER INFORMATION: Description of Artificial Sequence: Example

<400> SEQUENCE: 62
aaccaaaaaa t 11

<210> SEQ ID NO 63
<211> LENGTH: 11
<212> TYPE: DNA
<213> ORGANISM: Artificial Sequence
<220> FEATURE:
<223> OTHER INFORMATION: Description of Artificial Sequence: Example

<400> SEQUENCE: 63
aaccaaaaaa c 11

<210> SEQ ID NO 64
<211> LENGTH: 11
<212> TYPE: DNA
<213> ORGANISM: Artificial Sequence
<220> FEATURE:
<223> OTHER INFORMATION: Description of Artificial Sequence: Example

<400> SEQUENCE: 64
aaccaaaaaa g 11

-continued

```
<210> SEQ ID NO 65
<211> LENGTH: 25
<212> TYPE: DNA
<213> ORGANISM: Homo sapiens

<400> SEQUENCE: 65

tgcgcaagtc ctcccacctc aagaa                                            25


<210> SEQ ID NO 66
<211> LENGTH: 24
<212> TYPE: DNA
<213> ORGANISM: Homo sapiens

<400> SEQUENCE: 66

gcgcaagtcc ccccacctca agaa                                             24


<210> SEQ ID NO 67
<211> LENGTH: 27
<212> TYPE: DNA
<213> ORGANISM: Homo sapiens

<400> SEQUENCE: 67

ggctccgaga agggtgcagt gaggccc                                          27


<210> SEQ ID NO 68
<211> LENGTH: 27
<212> TYPE: DNA
<213> ORGANISM: Homo sapiens

<400> SEQUENCE: 68

ggctccgagg agggtgcagt gaggccc                                          27


<210> SEQ ID NO 69
<211> LENGTH: 27
<212> TYPE: DNA
<213> ORGANISM: Homo sapiens

<400> SEQUENCE: 69

gctccagctc ccgctgcagg gcaggga                                          27


<210> SEQ ID NO 70
<211> LENGTH: 27
<212> TYPE: DNA
<213> ORGANISM: Homo sapiens

<400> SEQUENCE: 70

gctccagctc ccgctacagg gcaggga                                          27
```

COMPOSITIONS, KITS, AND METHODS RELATING TO THE HUMAN FEZ1 GENE, A NOVEL TUMOR SUPPRESSOR GENE

CROSS-REFERENCE TO RELATED APPLICATIONS

This application is entitled to priority pursuant to 35 U.S.C. § 119(e) to U.S. provisional patent application 60/121,537 which was filed on Feb. 25, 1999.

STATEMENT REGARDING FEDERALLY SUPPORTED RESEARCH AND DEVELOPMENT

This research was supported in part by U.S. Government funds (National Cancer Institute grants numbers CA39860, CA51083, and CA56336), and the U.S. Government may therefore have certain rights in the invention.

BACKGROUND OF THE INVENTION

The invention relates generally to cancer and tumor suppressor genes.

Proliferation of normal cells is thought to be regulated by growth-promoting proto-oncogenes and by growth-constraining tumor suppressor genes (Weinberg, 1991, Science 254:1138). Genetic alterations that inactivate tumor suppressor genes or that activate proto-oncogenes free cells from growth constraints imposed by the non-altered genes, thereby enabling tumor growth. Accumulation of genetic aberrations in a cell in vivo causes the cell to proceed from a normal growth or quiescent stage, potentially through a discernable pre-neoplastic stage, to a cancerous stage in which the cell replicates abnormally quickly, and potentially spreads to body locations at which the cell is not normally found (Knudson, 1993, Proc. Natl. Acad. Sci. USA 90:10914; Nowell, 1993, Adv. Cancer Res. 62:1).

The presence of a tumor suppressor gene at a particular chromosomal location is sometimes evidenced by an increased prevalence of loss of heterozygosity (LOH) at the chromosomal location in tumor tissues, relative to non-cancerous tissue (Weinberg, 1991, Science 254:1138; Lasko et al., 1991, Ann. Rev. Genet. 25:281; Knudson, 1993, Proc. Natl. Acad. Sci. USA 90:10914; Nowell, 1993, Adv. Cancer Res. 62:1). Allelotyping studies indicate that allelic loss(es) on chromosome 8p, particularly at band 21–22, are associated with various tumors, including prostate tumors, breast tumors, head and neck squamous cell carcinomas, urinary bladder carcinomas, hepatocellular carcinomas, and hematological malignancies (Kagan et al., 1995, Oncogene 11:2121; Macoska et al., 1995, Cancer Res. 55:5390; Jenkins et al., 1998, Genes Chromosom. Cancer 21:131; Yaremko et al., 1995, Genes Chromosom. Cancer 13:186; Yaremko et al., 1996, Genes Chromosom. Cancer 16:189; Kerangueven et al., 1997, Cancer Res. 57:5469; Anbazhagan et al., 1998, Am. J. Pathol. 152:815; El-Naggar et al., 1998, Oncogene 16:2983; Sunwoo et al., 1996, Genes Chromosom. Cancer 16:164; Wu et al., 1997, Genes Chromosom. Cancer 20:347; Wagner et al., 1997, Am. J. Pathol. 151:753; Boige et al., 1997, Cancer Res. 57:1986; Takeuchi et al., 1995, Cancer Res. 55:5377).

Studies in which chromosome regions were transferred into tumor cells have provided evidence that one or more tumor suppressor genes is present at human chromosome location 8p (Gustafson et al., 1996, Cancer Res. 56:5238; Ichikawa et al., 1994, Cancer Res. 54:2299; Kuramochi et al., 1997, Prostate 31:14). These observations suggest that chromosome region 8p21–22 has an important role in the development of various tumors.

Efforts by others to identify tumor suppressor gene(s) located on chromosome 8p identified two candidate tumor suppressor genes, designated N33 and PRLTS (Bookstein et al., 1997, Br. J. Urol. 79(Suppl. 1):28; Bova et al., 1996, Genomics 35:46; MacGrogan et al., 1996, Genomics 35:55; Cher et al., 1994, Genes Chromosom. Cancer 11:153; Bookstein, et al., 1994, Genomics 24:317; Fujiwara et al., 1995, Oncogene 10:891; Komiya et al., 1997, Jpn. J. Cancer Res. 88:389). Gene N33 is located at position 8p22, near the MSR gene locus, but no point mutations in N33 have been associated with tumors. Four cancer-associated point mutations have been reported in PRLTS, which is located at position 8p21.3–22. The frequency of alterations in this gene was, however, very low. Thus, it is unlikely that either the N33 gene or the PRLTS gene are tumor suppressor genes associated with common cancers.

Until the present disclosure, the tumor suppressor gene(s) located at chromosome location 8p has not been identified. The failure of others to identify this gene has delayed development of diagnostic, therapeutic, and other useful methods and compositions which involve this tumor suppressor gene. The present invention enables these methods and compositions.

BRIEF SUMMARY OF THE INVENTION

The invention relates to an isolated polynucleotide comprising a portion which anneals with high stringency with (i.e. is substantially complementary to) 20 or more, consecutive nucleotide residues of a strand of a human FEZ1 gene. An exemplary human FEZ1 gene has the nucleotide sequence SEQ ID NO: 1. The portion which anneals can be substantially homologous with the residues of the human FEZ1 gene or, preferably, it can be completely homologous with those residues. Preferably, the portion is at least substantially homologous with at least twenty residues of an exon region of the human FEZ1 gene, i.e. nucleotide residues 112–456, nucleotide residues 1707–2510, and nucleotide residues 4912–5550 of a strand of SEQ ID NO: 1.

In one embodiment, the isolated polynucleotide of the invention comprises a portion having the nucleotide sequence of a strand of SEQ ID NO: 3, and optionally further comprises a promoter. The promoter may, for example, be a constitutive promoter, an inducible promoter, or a tissue-specific promoter.

In another embodiment of the isolated polynucleotide of the invention, the isolated polynucleotide is incorporated in a nucleic acid vector or is encoded by nucleic acid which is incorporated in a nucleic acid vector. The isolated polynucleotide may, for example, have a sequence homologous with a strand of SEQ ID NO: 1, and it can be detectably labeled. Examples of detectably labeled isolated polynucleotides include immobilized polynucleotides, polynucleotides linked to a protein of a protein-ligand pair, polynucleotides linked to a ligand of a protein-ligand pair, biotinylated polynucleotides, polynucleotides linked to a fluorophore, polynucleotides linked to a chromophore, polynucleotides linked to an enzyme, and radio-labeled polynucleotides. When an immobilized polynucleotide is used, it can be immobilized on the surface of a gene chip. Preferably, the isolated polynucleotide of the invention is substantially purified.

The isolated polynucleotide of the invention need not comprise only naturally occurring bases and linkages. It may, for example, have at least two nucleotide residues linked by a non-naturally occurring linkage other than a phosphodiester linkage such as, for example, a linkage selected from the group consisting of phosphonate, phosphorothioate, phosphorodithioate, phosphoramidate methoxyethyl phosphoramidate, formacetal, thioformacetal, diisopropylsilyl, acetamidate, carbamate, dimethylene-sulfide ($—CH_2—S—CH_2—$), dimethylene-sulfoxide ($—CH_2—SO—CH_2—$), dimethylene-sulfone ($—CH_2—SO_2—CH_2—$), 2'-O-alkyl, and 2'-deoxy-2'-fluoro phosphorothioate, phosphotriester, siloxane, carbonate, carboxymethyl ester, acetamidate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate linkages, bridged sulfone linkages, and combinations of such linkages. Furthermore, an end of the isolated polynucleotide can be nucleolytically blocked.

The invention also includes an isolated polynucleotide comprising a portion which has a sequence which anneals with high stringency with at least twenty consecutive nucleotide residues of a strand of SEQ ID NO: 3.

In another aspect, the invention includes a kit for amplifying a portion of a human FEZ1 gene. The kit comprises a first isolated polynucleotide and a second isolated polynucleotide. The first isolated polynucleotide comprises a portion which anneals with high stringency with at least twenty consecutive nucleotide residues of the coding strand of SEQ ID NO: 1, and the second isolated polynucleotide comprises a portion which anneals with high stringency with at least twenty consecutive nucleotide residues of the non-coding strand of SEQ ID NO: 1.

The invention further includes a kit for amplifying a portion of a cDNA generated from a transcript of a human FEZ1 gene. The kit comprises a first isolated polynucleotide and a second isolated polynucleotide. A portion of the first isolated polynucleotide anneals with high stringency with at least twenty consecutive nucleotide residues of the coding strand of SEQ ID NO: 1, and a portion of the second isolated polynucleotide anneals with high stringency with at least twenty consecutive nucleotide residues of the non-coding strand of SEQ ID NO: 1.

Furthermore, the invention includes an animal cell comprising an exogenous DNA molecule having a portion substantially homologous with at least nucleotide residues 112–456, nucleotide residues 1707–2510, and nucleotide residues 4912–5550 of a strand of SEQ ID NO: 1. In one embodiment, the exogenous DNA molecule further comprises a promoter operably linked with the portion, and the exogenous DNA molecule is expressed in the animal cell.

The invention also includes a genetically altered animal comprising a cell into which an exogenous DNA molecule has been artificially introduced. The exogenous DNA molecule has a portion substantially homologous with at least the coding region of a strand of a human FEZ1 gene. The exogenous DNA molecule may, for example, have a portion substantially homologous with at least nucleotide residues 112–456, nucleotide residues 1707–2510, and nucleotide residues 4912–5550 of a strand of SEQ ID NO: 1, or it can comprise a portion having a sequence substantially homologous with a strand of SEQ ID NO: 2.

The invention also relates to an isolated human Fez1 protein, such as a protein having an amino acid sequence substantially, or preferably completely, homologous with SEQ ID NO: 4. In one embodiment, the protein is substantially purified.

The invention further includes an isolated antibody which binds specifically with human Fez1 protein and a hybridoma cell which produces such antibodies.

The invention still further relates to a method of determining the cancerous status of a sample tissue. This method comprises comparing FEZ1 expression in the sample tissue with FEZ1 expression in a control tissue of the same type. Decreased FEZ1 expression in the sample tissue, relative to FEZ1 expression in the control tissue, is an indication that the sample tissue is cancerous. In one embodiment, the sample tissue is a phenotypically abnormal portion of a body tissue of a human, and the control tissue is a phenotypically normal portion of the body tissue, such as an epithelial tissue. The body tissue can also, for example, be selected from the group consisting of a gastrointestinal tissue, esophagus tissue, gastric tissue, colon tissue, prostate tissue, breast tissue, a hematopoietic tissue, lung tissue, melanoma tissue, cervical tissue, and ovarian tissue. In an alternative embodiment of this method, FEZ1 expression in the sample tissue is compared with FEZ1 expression in the control tissue by comparing the relative amounts of an indicator in the sample tissue and in the control tissue. The indicator may, for example, be selected from the group consisting of a FEZ1 mRNA, a cDNA prepared using a FEZ1 mRNA, a DNA prepared by amplification of either of these, and Fez1 protein.

The invention also includes a method of determining the cancerous status of a sample tissue. This method comprises comparing the nucleotide sequence of a FEZ1-associated polynucleotide obtained from the sample tissue with the nucleotide sequence of a control FEZ1-associated polynucleotide. A difference between the nucleotide sequence of the FEZ1-associated polynucleotide obtained from the sample tissue and the nucleotide sequence of the control FEZ1-associated polynucleotide is an indication that the sample tissue is cancerous.

The invention includes another method of determining the cancerous status of a human sample tissue. This method comprises comparing the length of an FEZ1-transcript-associated polynucleotide obtained from the sample tissue with the length of a control FEZ1-transcript-associated polynucleotide. If the length of the FEZ1-transcript-associated polynucleotide obtained from the sample tissue is less than the length of the control FEZ1-transcript-associated polynucleotide, then this is an indication that the sample tissue is cancerous.

The invention includes yet another method of determining the cancerous status of a sample tissue. This method comprises assessing FEZ1 expression in the sample tissue. A substantial absence of FEZ1 expression in the sample tissue is an indication that the sample tissue is cancerous. FEZ1 expression can be assessed, for example, by assessing the presence or substantial absence of an indicator selected from the group consisting of a FEZ1 mRNA, a cDNA prepared using a FEZ1 mRNA, a DNA prepared by amplification of either of these, and Fez1 protein.

The invention includes yet another method of determining the cancerous status of a sample tissue. This method comprises detecting abnormal splicing of a FEZ1 transcript in the sample tissue. Abnormal splicing of the FEZ1 transcript is an indication that the sample tissue is cancerous. Abnormal splicing of the FEZ1 transcript can be detected, for example, by assessing the ability of an exon boundary polynucleotide probe to anneal with a FEZ1-transcript-associated polynucleotide with high stringency. The exon boundary polynucleotide probe is capable of annealing with high stringency with terminal portions of two sequential FEZ1 exons when the terminal portions are adjacent, but not when the terminal portions are not adjacent.

In another aspect, the invention relates to a method of modulating abnormal proliferation of a human cell having an altered FEZ1 gene. This method comprises providing an exogenous source of Fez1 protein to the cell. Abnormal proliferation of the cell is thereby inhibited, delayed, or prevented. The exogenous source of Fez1 protein may, for example, be a composition comprising an isolated human Fez1 protein, such as a human Fez1 protein having the amino acid sequence SEQ ID NO: 4. The exogenous source of Fez1 protein can also be an expression vector (e.g. an adenovirus vector, such as one comprising a vector nucleic acid having the nucleotide sequence SEQ ID NO: 60) comprising a polynucleotide having a coding region which encodes a functional Fez1 protein, such as a human FEZ1 gene having the nucleotide sequence of a strand of SEQ ID NO: 3. The polynucleotide can further comprise a constitutive, inducible, or tissue-specific promoter operably linked with the coding region. When the promoter is an inducible promoter, the method further comprises administering an inducer of the inducible promoter to the cell. The polynucleotide may, of course, comprise a wild-type FEZ1 promoter region.

In still another aspect, the invention relates to a method of preventing tumorigenesis in a human cell. This method comprises providing to the cell an expression vector comprising a polynucleotide having a coding region which encodes a functional Fez1 protein. Upon providing the expression vector to the cell, tumorigenesis is prevented in the cell.

The invention also includes a method of reversibly inducing proliferation of a cell. This method comprises providing an inhibitor of FEZ1 expression to the interior of the cell. Proliferation of the cell is thereby induced when the inhibitor is present in the interior of the cell, but is not induced when the inhibitor is not present in the interior of the cell. The inhibitor may, for example, be an isolated polynucleotide comprising a portion which anneals with high stringency with at least twenty consecutive nucleotide residues of a strand of a human FEZ1 gene. The isolated polynucleotide can be delivered to the interior of the cell by administering a gene vector comprising a promoter operably linked with the isolated polynucleotide to the cell. The cell can be located in the body of an animal such as a human.

In another aspect, the invention relates to a method of determining whether a test compound is an inducer of cell proliferation. This method comprises incubating a cell which comprises a functional FEZ1 gene in the presence of the test compound and assessing expression of FEZ1 in the cell. If expression of FEZ1 in the cell is decreased, relative to expression of FEZ1 in a cell of the same type incubated in the absence of the test compound, then the test compound is an inducer of cell proliferation.

The invention also includes a method of determining whether a test compound is effective to retard abnormal proliferation of a cell having an altered FEZ1 gene. This method comprises incubating the cell in the presence of the test compound and assessing expression of FEZ1 in the cell. If expression of FEZ1 in the cell is increased, relative to expression of FEZ1 in a cell of the same type incubated in the absence of the test compound, then the test compound is effective to retard abnormal proliferation of a cell.

The invention further relates to a method of determining whether Fez1 protein binds with polynucleotides having a test nucleotide sequence. This method comprises:

a) contacting Fez1 protein and a test polynucleotide having the test nucleotide sequence, and b) thereafter assessing whether a detectably labeled Fez 1-polynucleotide complex is formed. At least one of the Fez1 protein and the test polynucleotide is detectably labeled. Formation of the complex is an indication that Fez1 protein binds with polynucleotides having the test nucleotide sequence.

The invention still further relates to a method of identifying an inducer of cell proliferation. This method comprises:

a) contacting Fez1 protein and a polynucleotide with which Fez1 protein binds in the presence and absence of a test compound, and b) assessing formation of a Fez1-polynucleotide complex. Decreased formation of the complex in the presence of the test compound, relative to formation of Fez1-polynucleotide complex in the absence of the test compound is an indication that the test compound is an inducer of cell proliferation.

The invention includes a kit for selecting an anti-cancer therapeutic compound for administration to a human afflicted with a cancer. The kit comprises a plurality of candidate anti-cancer therapeutic compounds and a reagent for assessing expression of FEZ1 in a cell.

The invention also includes a method of inducing a cell to proliferate. This method comprises inhibiting expression of FEZ1 in the cell. The cell is thereby induced to proliferate. In one embodiment, the cell is a cell removed from a human. This cell can thereafter be returned to the human after inhibiting expression of FEZ1 in the cell. Alternatively, the cell can be a cell present in the body of a human. For example, expression of FEZ1 in the cell can be inhibited by providing to the interior of the cell an isolated polynucleotide comprising a portion which anneals with high stringency with at least twenty consecutive nucleotide residues of a strand of a human FEZ1 gene.

The invention further includes an enhanced human cell culture technique. This technique comprises incubating human cells according to a known human cell culture technique and inhibiting FEZ1 expression in the cells.

The invention still further includes a method of detecting FEZ1 expression in a sample tissue. This method comprises:

a) labeling an isolated antibody which binds specifically with human Fez1 protein and contacting a preparation of the isolated antibody with the sample tissue, b) thereafter rinsing the tissue sample, whereby non-specifically bound antibodies are rinsed from the tissue sample, and c) assessing the presence of labeled antibodies in the tissue sample. The presence of labeled antibodies in the tissue sample is an indication that FEZ1 is expressed in the tissue sample.

The invention includes a method of determining whether a test compound is useful for alleviating a disorder associated with aberrant tubulin polymerization. The method comprises comparing (i) tubulin polymerization in a first assay mixture which comprises tubulin, Fez1, and the test compound and (ii) tubulin polymerization in a second assay mixture which comprises tubulin and Fez1, but which does not comprise the test compound.

A difference between (e.g. the rate or extent of) tubulin polymerization in the first and second assay mixtures is an indication that the test compound is useful for alleviating the disorder. Preferably, the first and second assay mixtures are substantially identical, but for the presence or absence of the test compound. The disorder can, for example, be a tubulin hyperpolymerization disorder or a tubulin hypopolymerization disorder, such as one of a disorder associated with aberrant initiation of mitosis, a disorder associated with aberrant modulation of the rate and stage of mitosis, a disorder associated with aberrant modulation of the initiation and rate of cell proliferation, a disorder associated with aberrant modulation of the initiation and rate of cell growth, a disorder associated with aberrant modulation of cell shape, a disorder associated with aberrant modulation of cell rigidity, a disorder associated with aberrant modulation of cell motility, a disorder associated with aberrant modulation of the rate of cellular DNA replication, a disorder associated with aberrant modulation of the stage of cellular DNA replication, a disorder associated with aberrant modulation of the intracellular distribution of organelles, a disorder associated with aberrant modulating the metastatic potential of a cell, and a disorder associated with aberrant modulation of cellular transformation from a non-cancerous to a cancerous phenotype. For example, the disorder can be one of tumorigenesis, tumor survival, tumor growth, and tumor metastasis. Examples of test compounds include a fragment of Fez1, a peptidomimetic of a fragment of Fez1, a fragment of tubulin, a peptidomimetic of a fragment of tubulin, a fragment of EF1-γ, and a peptidomimetic of a fragment of EF1-γ.

The invention also includes a method of determining whether a test compound is useful for alleviating a disorder associated with aberrant phosphorylation of Fez1. This method comprises comparing (i) phosphorylation of Fez1 in a first assay mixture which comprises Fez1, at least one kinase, a phosphate source, and the test compound and (ii) phosphorylation of Fez1 in a second assay mixture which comprises Fez1, the kinase, and the phosphate source, but which does not comprise the test compound. A difference between phosphorylation of Fez1 in the first and second assay mixtures is an indication that the test compound is useful for alleviating the disorder. As with the method described in the preceding paragraph, the disorder can be one selected from the group consisting of tumorigenesis, tumor survival, tumor growth, and tumor metastasis.

The invention includes a method of determining whether a test compound is useful for alleviating a disorder associated with aberrant phosphorylation of Fez1. This method comprises comparing (i) phosphorylation of Fez1 in a first assay mixture which comprises phosphorylated Fez1, at least one phosphatase, and the test compound and (ii) phosphorylation of Fez1 in a second assay mixture which comprises phosphorylated Fez1 and the phosphatase, but which does not comprise the test compound.

A difference between phosphorylation of Fez1 in the first and second assay mixtures (e.g. a difference in the rate or extent of de-phosphorylation of phosphorylated Fez1) is an indication that the test compound is useful for alleviating the disorder.

In addition, the invention includes a method of determining whether a test compound is useful for alleviating a disorder associated with aberrant binding of Fez1 with a protein with which Fez1 normally binds. This method comprises comparing (i) binding between Fez1 and the protein in a first assay mixture which comprises Fez1, the protein, and the test compound and (ii) binding between Fez1 and the protein in a second assay mixture which comprises Fez1 and the protein, but which does not comprise the test compound, A difference between (e.g. the rate or extent of) binding of Fez1 and the protein in the first and second assay mixtures is an indication that the test compound is useful for alleviating the disorder. Examples of the protein of this method include tubulin and EF1-γ. The disorder can, for example, be any of those recited above.

The invention further includes a method of determining whether a test compound is an inhibitor of cell proliferation. This method comprises incubating a cell which comprises a functional FEZ1 gene in the presence of the test compound and assessing expression of FEZ1 in the cell. If expression of FEZ1 in the cell is increased, relative to expression of FEZ1 in a cell of the same type incubated in the absence of the test compound, then the test compound is an inhibitor of cell proliferation.

The invention still further includes a method of inhibiting tumorigenesis in a human, the method comprising administering to the human a compound selected from the group consisting of an inducer of FEZ1 gene expression, an enhancer of FEZ1 gene expression, a inhibitor of Fez1 phosphorylation, an enhancer of phosphorylated-Fez1 dephosphorylation, an agent that inhibits binding of Fez1 with EF1-γ, and an agent that inhibits binding of Fez1 with tubulin.

BRIEF DESCRIPTION OF THE DRAWINGS

FIG. 1 comprises FIGS. 1A, 1B, and 1C, and each of these figures relates to loss of heterozygosity (LOH) at human chromosome 8p in primary esophageal cancer tissue samples.

Figure 4B:
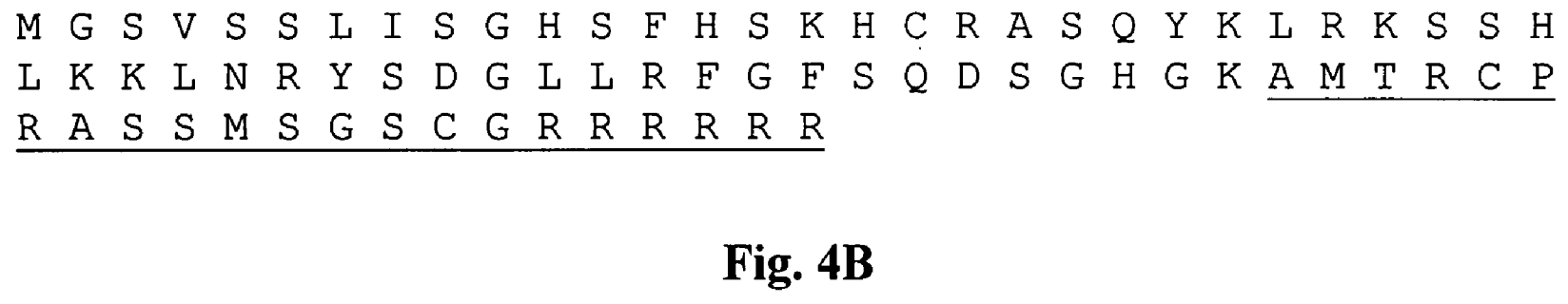

FIG. 1A, comprising FIGS. 1A-1 to 1A-8, is a series of representative LOH analysis results obtained using tissue samples obtained from two patients, designated E26 and E46. FIGS. 1A-1, 1A-3, 1A-5, and 1A-7 depict results from tissue obtained from patient E26. FIGS. 1A-2, 1A-4, 1A-6, and 1A-8 depict results from tissue obtained from patient E46. In each figure, fluorescent PCR products were generated by amplification of DNA obtained from normal (N) and tumor (T) tissue samples from the corresponding patient, and products were separated by size. For each tracing, the horizontal axis represents DNA fragment size, and the vertical axis (i.e. peak height) represents relative amount of each fragment. Several fragment sizes (in base pairs) are indicated.

FIG. 2 comprises FIGS. 2A, 2B, 2C, and 2D. The predicted Fez1 amino acid sequence (SEQ ID NO: 4) is depicted in FIG. 2A. FIG. 2A lists the predicted amino acid sequence of FEZ1 protein, as derived from the FEZ1 cDNA. Underlined amino acid residues represent a region homologous to the DNA-binding domain of ATF-5 protein. Double-underlined amino acid residues represent a leucine zipper motif, in which repeated leucine residues are indicated. Heavily-underlined amino acid residues are residues which can be phosphorylated by either a cAMP/cGMP-dependent kinase (serine residue 29) or a tyrosine kinase-dependent kinase (tyrosine residue 67). Dashed-underlined regions represent regions having related amino acid sequence motifs. Serine and threonine residues in bold or thin dotted lines represent potential casein kinase II and protein kinase C, respectively, phosphorylation sites. Triangles indicate exon boundaries. Asterisks represent missense or nonsense mutation sites.

In FIG. 2B, the predicted amino acid sequence of a region (amino acid residues 301–369; SEQ ID NO: 6) of Fez1 corresponding to the predicted DNA binding and leucine zipper regions is compared with the analogous regions (SEQ ID NOs: 7 and 8, respectively) of proteins Atf-5 and KIAA0522. Identical amino acid residues are indicated by double underlining, and similar amino acid residues are indicated by single underlining. Gaps introduced by the FASTA program are represented by "-". Closed circles are used to indicate repeated leucine residues.

FIG. 3 comprises FIGS. 3A, 3B, and 3C, and relates to alterations of the FEZ1 gene in tumor cells.

FIGS. 3B-1 to 3B-4, is a series of sequence chromatograms of FEZ1 genes obtained from three individuals having mutated FEZ1 genes, represented by SEQ ID NOs: 65 to 71. As indicated in FIGS. 3B-2 (SEQ ID NO: 66), a point mutation in FEZ1 (TCC/Ser→CCC/Pro) at codon 29 was identified in a primary esophageal cancer tissue sample obtained from patient E44. Nucleotide sequences from normal DNA from patient E44 (N) and from a BAC contig (B) are shown for comparison. A bold line overlies the altered codon. In a primary esophageal cancer tissue sample obtained from patient E50, a point mutation in FEZ1 (AAG/Lys→GAG/Glu) was detected at codon 119 was found, as indicated in FIG. 3Biv. The normal BAC sequence chromatogram is shown in FIGS. 3B-3 (SEQ ID NO: 67). A third point mutation in FEZ1 (CAG/Gln→TAG/STOP) at codon 501 was identified in prostate cancer cell line PC3, as indicated in FIGS. 3B-6 (SEQ ID NO: 70), in which the sequence chromatogram 3'- to 5'-direction. Repeated sequencing indicated the presence of a weak signal corresponding to guanine (G) within a large adenine (A) signal in the first nucleotide at codon 501, suggesting that a fraction of the cancer cells retained the normal FEZ1 allele. FIGS. 3B-1, 3B-4, and 3B-5 represent SEQ ID NOs: 65, 68, and 69, respectively.

FIG. 4 comprises FIGS. 4A and 4B.

FIG. 4B is the putative amino acid sequence (SEQ ID NO. 5) encoded by the frame-shifted FEZ1 transcript having a molecular weight of about 8.6 kilodaltons. Amino acid residues encoded by the frame-shifted portion of the transcript are underlined.

FIG. 5, comprising FIGS. 5A-1 to 5Q, is a series of nucleotide and amino acid sequences. FIG. 5A comprises FIGS. 5A-1 to 5A-6, and lists the nucleotide sequence (SEQ ID NO: 1) of a portion of the human genome comprising the FEZ1 gene. FIG. 5B comprises FIGS. 5B-1 to 5B-4, and lists the nucleotide sequence (SEQ ID NO: 2) of a cDNA which reflects the nucleotide sequence of the full-length mRNA transcript of wild type FEZ1. FIG. 5C lists the nucleotide sequence (SEQ ID NO: 9) of a cDNA which reflects the nucleotide sequence of the ORF region of a truncated (E16T8) FEZ1 mRNA transcribed by tumors cells. FIG. 5D lists the nucleotide sequence (SEQ ID NO: 10) of a cDNA which reflects the nucleotide sequence of the ORF region of a truncated (E264162) FEZ1 mRNA transcribed by tumors cells. FIG. 5E comprises FIGS. 5E-1 and 5E-2, and lists the nucleotide sequence (SEQ ID NO: 11) of a cDNA which reflects the nucleotide sequence of the ORF region of a truncated (T8D145M4) FEZ1 mRNA transcribed by tumors cells. FIG. 5F comprises FIGS. 5F-1 and 5F-2 and lists the nucleotide sequence (SEQ ID NO: 12) of a cDNA which reflects the nucleotide sequence of the ORF region of a truncated (D14) FEZ1 mRNA transcribed by tumors cells. FIG. 5G comprises FIGS. 5G-1 and 5G-2 and lists the nucleotide sequence (SEQ ID NO: 13) of a cDNA which reflects the nucleotide sequence of the ORF region of a truncated (G3611) FEZ1 mRNA transcribed by tumors cells. FIG. 5H comprises FIGS. 5H-1 and 5H-2, and lists the nucleotide sequence (SEQ ID NO: 14) of a cDNA which reflects the nucleotide sequence of the ORF region of a truncated (G3612) FEZ1 mRNA transcribed by tumors cells. FIG. 5I comprises FIGS. 5I-1 and 5I-2 and lists the nucleotide sequence (SEQ ID NO: 3) of a cDNA which reflects the nucleotide sequence of the ORF region of wild type FEZ1 mRNA. FIG. 5J comprises FIGS. 5J-1 to 5J-5 and lists the amino acid sequence (SEQ ID NO: 4) of full-length, human wild type Fez1 protein. FIG. 5K lists the amino acid sequence (SEQ ID NO: 15) of a truncated (E16T8) Fez1 protein expressed by tumors cells. FIG. 5L comprises FIGS. 5L-1 and 5L-2 and lists the amino acid sequence (SEQ ID NO: 16) of a truncated (E264162) Fez1 protein expressed by tumors cells. FIG. 5M comprises FIGS. 5M-1 to 5M-4 and lists the amino acid sequence (SEQ ID NO: 17) of a truncated (T8D145M4) Fez1 protein expressed by tumors cells. FIG. 5N comprises FIGS. 5N-1 to 5N-4 and lists the amino acid sequence (SEQ ID NO: 18) of a truncated (D14) Fez1 protein expressed by tumors cells. FIG. 5O comprises FIGS. 5O-1 to 5O-5 and lists the amino acid sequence (SEQ ID NO: 19) of a truncated (G3611) Fez1 protein expressed by tumors cells. FIG. 5P comprises FIGS. 5P-1 to 5P-5 and lists the amino acid sequence (SEQ ID NO: 20) of a truncated (G3612) Fez1 protein expressed by tumors cells. FIG. 5Q lists the nucleotide sequence (SEQ ID NO: 21) of the F37 probe described herein.

FIG. 6 is an image of an immunoblot of proteins isolated from MCF7 cell line clones which had been transfected with pTet-Off™ vector alone ("control") or with the vector having at least the coding portion of the FEZ1 gene operably linked with the promoter thereof (clones 118, 54, 18, and 15). Proteins were isolated from cells which had been maintained in the presence ("+") or absence ("−") of tetracycline.

FIG. 7, comprising FIGS. 7A (clone 15), 7B (clone 54), 7C (clone 18), and 7D (clone 118), is a quartet of graphs which indicate the time dependence of the ratio of transfected MCF7 clone cell number to control cell number for cells maintained in tetracycline-free medium containing 10% (○), 5% (●), 2.5% (□), 1% (■), or 0.5% (▲) (v/v) fetal bovine serum.

FIG. 8, comprising

FIG. 9, comprising

FIG. 10, comprising FIGS. 10A–10F, lists the nucleotide sequence (SEQ ID NO: 60) of pQBI-AdCMV5-IRES-GFP.

FIG. 11, comprising

FIG. 14, comprising

FIG. 15, comprising

FIG. 16, comprising

DETAILED DESCRIPTION

Figures 1, 1A, 2, 3, 4:
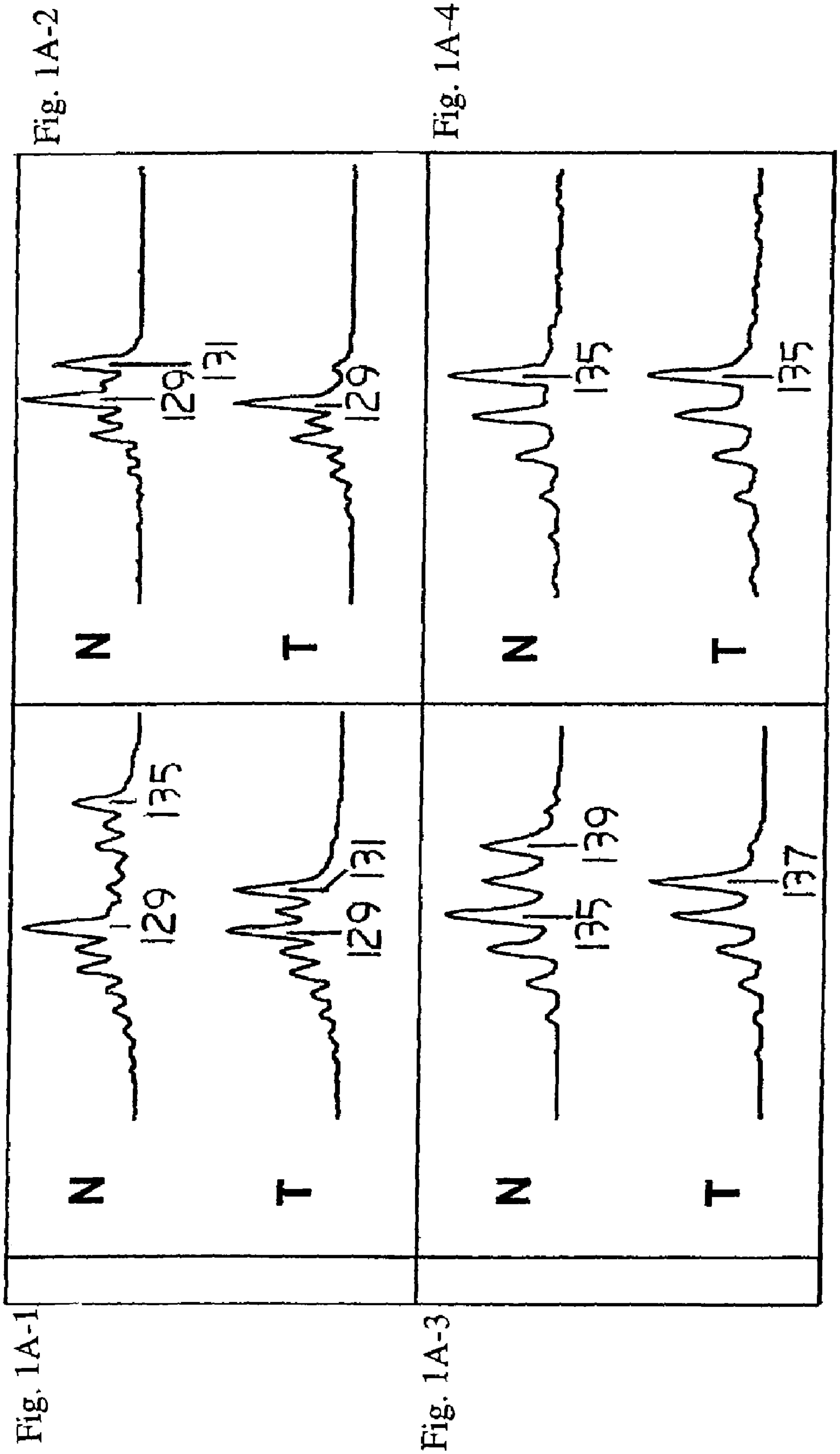

The present invention is based on the discovery, isolation, and sequencing of FEZ1, a tumor suppressor gene located at human chromosome location 8p22. It was observed that decreased, or no, expression of FEZ1 could be detected in a variety of cancer cells obtained from cancer cell lines and cancer tissue samples taken from human patients. Cancer types in which abnormal (i.e. decreased or no) expression of FEZ1 has been detected include, but are not limited to, epithelial cancers, cancers of the digestive system, esophageal cancers, gastric cancers, colon cancers, prostate cancers, breast cancers, hematopoietic cancers, lung cancers, melanomas, and cervical cancers, as described herein. It is contemplated that expression of FEZ1 will be implicated in other cancers, once those cancers are tested for altered FEZ1 expression.

Expression of FEZ1 inhibits tumor growth and proliferation, both in vitro and in vivo. The ability of Fez1 protein to interact with tubulin, with microtubules, and with protein EF1-γ indicates that expression of FEZ1 in cells modulates microtubule-associated physiological processes such as mitosis, cell proliferation, cell motility, and the like. Furthermore, post-translational phosphorylation and de-phosphorylation of Fez1 protein can modulate the effect that Fez1 protein has on these physiological processes.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element. The terms "cancerous" (e.g., cell, tissue, state, etc.) and "tumor" (cell, tissue, state, etc.) are used interchangeably herein.

A "polynucleotide" means a single strand or parallel and anti-parallel strands of a nucleic acid. Thus, a polynucleotide can be either a single-stranded or a double-stranded nucleic acid.

An "isolated" polynucleotide is one which refers to a nucleic acid segment or fragment which is separated from sequences which flank it in a naturally occurring state, e.g., a DNA fragment which is not adjacent to the sequences which are normally adjacent to the fragment, e.g., the sequences adjacent to the fragment in a genome in which it naturally occurs. The term also applies to nucleic acids which are substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

An "isolated" protein or antibody is one which is separate from one or more other components which naturally accompany it in its naturally occurring state. By way of example, an isolated protein can be prepared by separating a protein from at least one other protein which naturally accompanies it. Further by way of example, an isolated protein can be prepared by synthesizing the protein in the absence of at least one other protein which naturally accompanies it.

A "substantially purified" polynucleotide, protein, or antibody is one which is separate from at least most of the components which naturally accompany it in its naturally occurring state, and preferably from at least 75%, 80%, 90%, or even 95% of those components, as assessed on a per-weight basis or a per-mole basis.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, DNA sequences 3'-ATTGCC-5' and 3'-TATGGC-5' share 50% homology.

"Substantially homologous" means having at least 70%, 75%, 80%, 85%, 90%, 95%, 97%, 98%, or even at least 99% homology.

"Completely homologous" means having 100% homology.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is anti-parallel to the first region if the residue is thymine or uracil. Similarly, it is known that a cytosine residue of a first nucleic acid strand is capable of base pairing with a residue of a second nucleic acid strand which is anti-parallel to the first strand if the residue is guanine. A first region of a nucleic acid is complementary to a second region of the same or a different nucleic acid if, when the two regions are arranged in an anti-parallel fashion, at least one nucleotide residue of the first region is capable of base pairing with a residue of the second region. Preferably, the first region comprises a first portion and the second region comprises a second portion, whereby, when the first and second portions are arranged in an anti-parallel fashion, at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion, in which event, the two portions are described as being "completely complementary." "Substantially complementary" means having at least 70%, 75%, 80%, 85%, 90%, 95%, 97%, 98%, or even at least 99% complementarity.

A first polynucleotide "anneals" with a second polynucleotide if the nucleotide residues of at least one region of each of the two polynucleotides participate in base pairing when the two regions are arranged in an anti-parallel fashion in an appropriate solution. Such solutions are well known in the art and include, e.g. standard saline citrate (SSC) buffer.

A first polynucleotide anneals "with high stringency" with a second polynucleotide if the two polynucleotides anneal under conditions whereby only oligonucleotides which are at least about 75%, and preferably at least about 90% or at least about 95%, complementary anneal with one another. The stringency of conditions used to anneal two polynucleotides is a function of, among other factors, temperature, ionic strength of the annealing medium, the incubation period, the length of the polynucleotides, the G-C content of the polynucleotides, and the expected degree of non-homology between the two polynucleotides, if known. Methods of adjusting the stringency of annealing conditions are known (see, e.g. Sambrook et al., 1989, *Molecular Cloning: A Laboratory Manual*, Cold Spring Harbor Laboratory, New York). By way of example, high stringency hybridization conditions include hybridizing conditions that (1) employ low ionic strength and high temperature for washing, for example, 0.015 molar NaCl, 1.5 millimolar sodium citrate, and 0.1% (w/v) sodium dodecyl sulfate (SDS) at 50° C.; (2) employ during hybridization a denaturing agent such as formamide, for example, 50% (v/v) formamide, 0.1% (w/v) bovine serum albumin, 0.1% (w/v) Ficoll, 0.1% (w/v) polyvinylpyrrolidone, and 50 millimolar sodium phosphate buffer at pH 6.5 with 750 millimolar NaCl, 75 millimolar sodium citrate at 42° C.; or (3) employ 50% (v/v) formamide, 5×SSC (0.75 molar NaCl, 75 millimolar sodium pyrophosphate, 5× Denhardt's solution, sonicated salmon sperm DNA (50 micrograms per milliliter), 0.1% (w/v) SDS, and 10% (w/v) dextran sulfate at 42° C., with washes at 42° C. in 0.2×SSC and 0.1% (w/v) SDS. Under stringent hybridization conditions, only highly complementary nucleic acids hybridize.

A "functional" or "operative" protein is a protein in a form which exhibits at least one biological activity by which it is characterized in its naturally occurring state.

A "functional" or "operative" gene is a gene which, when present in an environment comprising functional gene expression proteins (e.g. the interior of a human cell or an in vitro gene expression mixture of a type described in the art), is expressed to yield the gene product encoded or specified by the gene.

A first polynucleotide is "specified" by a second polynucleotide if the first polynucleotide is either homologous with or complementary to a transcript polynucleotide generated either by transcription or by reverse transcription of at least a portion of the second polynucleotide. The first polynucleotide can be homologous with or complementary to the transcript polynucleotide either before or after the transcript polynucleotide has been acted upon by eukaryotic mRNA splicing components.

A "portion" or "region" of a polynucleotide means at least two consecutive nucleotide residues of the polynucleotide, and preferably at least 10, 11, 12, . . . , 20, 21, 22, . . . , 30, 31, 32, . . . , 40, 41, 42, . . . , or 50 or more consecutive nucleotide residues.

A first portion of a polynucleotide is "adjacent" a second portion of the same polynucleotide if the nucleotide sequences of the first and second portions are directly attached to one another, having no intervening nucleotides. By way of example, the pentanucleotide 5'-AAAAA-3' is adjacent the trinucleotide 5'-TTT-3' when the two are connected thus: 5'-AAAAATTT-3' or 5'-TTTAAAAA-3', but not when the two are connected thus: 5'-AAAAACTTT-3'.

A first portion of a polynucleotide "flanks" a second portion of the same polynucleotide if the two portions are adjacent one another or if the two portions are separated by no more than about 1000, 999, 998, . . . , 900, 899, 898, . . . , 750, 749, 748, 500, 499, 498, . . . , 250, 249, 248, . . . , and preferably no more than about 100 nucleotide residues.

By describing two polynucleotides as "operably linked", it is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked with the coding region of a gene is able to promote transcription of the coding region.

As used herein, the term "promoter" means a nucleic acid sequence which is required for expression of a gene product operably linked with the promoter sequence. In some instances, this sequence may be the core promoter sequence and in other instances, this sequence may also include an enhancer sequence and other regulatory elements which are required for expression of the gene product. The promoter sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

The "substantial absence of expression" of a gene means that the level of expression of the gene is undetectable or is at least greatly reduced (e.g. 100-fold or 1000-fold or more) relative to expression of the gene in its naturally occurring state.

An "expression vector" is a composition of matter which comprises an isolated nucleic acid and which can be used to deliver the isolated nucleic acid to the interior of a cell, such that a gene product encoded by or specified by the isolated nucleic acid is generated in the cell. Numerous expression vectors are known in the art including, but not limited to, linear polynucleotides, polynucleotides associated with ionic or amphiphilic compounds, plasmids, and viruses. Expression vectors generally either comprise a promoter operably linked with a portion of the isolated nucleic acid which encodes or specifies a gene product, or are capable of inserting the isolated nucleic acid into a cellular nucleic acid wherein the portion is operably linked with a cellular promoter.

An "exogenous" polynucleotide in an organism is one which is not present in a naturally-occurring form of the organism in the same form as the polynucleotide. By way of example, an exogenous polynucleotide can be one which comprises a nucleotide sequence which the genome of the organism does not comprise, or it can be one which comprises a portion of the organism's genome in a form (e.g. a plasmid or an artificial chromosome) which is not present in a naturally-occurring form of the organism.

An "analog" of a gene is one is substantially homologous with the gene and which encodes or specifies a gene product having a biological activity which is substantially the same as a biological activity exhibited by the gene product encoded or specified by the gene.

A "FEZ1-associated polynucleotide" means a polynucleotide which comprises a portion which is substantially homologous with or substantially complementary to at least about 20, 21, 22, . . . , 30, 31, 32, . . . , 40, 41, 42, . . . , or 50 or more consecutive nucleotide residues of either a human FEZ1 gene or a spliced mRNA specified by a human FEZ1 gene.

A "FEZ1-transcript-associated polynucleotide" means a polynucleotide which comprises a portion which is substantially homologous with or substantially complementary to at least about 20, 21, 22, . . . , 30, 31, 32, . . . , 40, 41, 42, . . . , or 50 or more consecutive nucleotide residues of either a spliced or non-spliced mRNA specified by a human FEZ1 gene.

"Contigs" of a genomic region are a collection of oligonucleotides, usually contained in a yeast, bacterial, or phage vector, which together include all or substantially all (i.e. >95%, and preferably >99%) of the sequence of the genomic region.

An "exon boundary polynucleotide probe" is a polynucleotide which is complementary to or homologous with at least five nucleotide residues of an exon of a FEZ1 gene which are adjacent to an intron of that gene.

A "protein-ligand pair" refers to a protein and another molecule, wherein the protein specifically binds with the other molecule. Examples of protein-ligand pairs include an antibody and its corresponding epitope and an avidin protein, such as streptavidin, and biotin.

A protein or polynucleotide is "detectably labeled" if the protein or polynucleotide comprises or is linked with a composition of matter which can be detected after contacting the protein or polynucleotide with another protein or polynucleotide. Innumerable methods are known in the art for detectable labeling proteins and polynucleotides including, for example, surfaces with which such compounds are linked, radionuclides incorporated into such proteins, chromophores and fluorophores which are linked with such compounds, and the like.

A "gene chip" is a manufacture comprising a surface having an ordered array of polynucleotides attached thereto, either permanently or reversibly. For example, the ordered array may comprise four sections, wherein one of four polynucleotides is attached to the surface in each section, and wherein the four polynucleotides have nucleotides sequences which are identical with the exception of one nucleotide residue (e.g. 5'-AACCAAAAAAA-3' (SEQ ID NO. 61); 5'-AACCAAAAAAT-3' (SEQ ID NO. 62); 5'-AACCAAAAAAC-3' (SEQ ID NO. 63); and 5'-AACCAAAAAAG-3' (SEQ ID NO. 64).

An "inducer of cell proliferation" is a composition of matter which, when contacted with a cell, causes the cell to grow, divide, or replicate at a rate greater than the corresponding rate in the absence of the composition.

Cell proliferation is "retarded" if the rate of cell proliferation is reduced.

The "cancerous state" of a tissue or cell refers to whether the cell or one or more cells within the tissue have accumulated enough genomic mutations that they either presently exhibit one or more characteristics of tumor cells or tissue (e.g. uncontrolled cell proliferation or metastasis) or, will, without further genomic damage, exhibit one or more characteristics of tumor cells or tissue upon incubation or maintenance of the cell.

A "phenotypically abnormal" portion of a tissue is one which comprises cells which have one or more characteristics of cancer cells of the tissue type such as, for example, abnormal morphology or abnormal growth or proliferation rate.

A "phenotypically normal" portion of a tissue is one which does not appear to be phenotypically abnormal.

A "candidate anticancer compound" is a compound which has exhibited potential anti-cancer activity in a relevant assay or a compound which has substantial structural similarity to such a compound. Methods of identifying a compound which exhibits potential anti-cancer activity and methods of designing structurally similar compounds are well known in the art.

The term "pharmaceutically acceptable carrier" means a chemical composition with which one or more active ingredients can be combined and which, following the combination, can be used to administer one or more active ingredients to a subject.

The term "physiologically acceptable" ester or salt means an ester or salt form of an active ingredient which is compatible with any other ingredients of the pharmaceutical composition and which is not deleterious to the subject to which the composition is to be administered.

An "instructional material" means a publication, a recording, a diagram, or any other medium of expression which can be used to communicate the usefulness of an isolated polynucleotide, an isolated protein, or a pharmaceutical composition of the invention for performing one or more of the methods of the invention. The instructional material may, for example, describe how to use one of these compositions to perform a diagnostic method of the invention, a therapeutic method of the invention, or a screening assay of the invention, or, for example, an appropriate dose of a pharmaceutical composition of the invention.

A "tubulin hyperpolymerization disorder" is a disorder which is associated with a greater extent or rate of tubulin polymerization in a cell or animal afflicted with the disorder than in a cell or animal which is not afflicted with the disorder.

A "tubulin hypopolymerization disorder" is a disorder which is associated with a lesser extent or rate of tubulin polymerization in a cell or animal afflicted with the disorder than in a cell or animal which is not afflicted with the disorder.

DESCRIPTION

Being a tumor suppressor gene, FEZ1 is intimately involved in control of the cancerous or non-cancerous phenotype of a cell which normally expresses it. Characteristics of tumor cells which normally express FEZ1 include abnormal cell proliferation, abnormal cell growth, and abnormal differentiation of cells.

In normal (i.e. non-cancerous) cells, expression of FEZ1 limits cell proliferation. While not wishing to be bound by any particular theory of operation, it is thought that a leucine-zipper region described herein within the putative structure of Fez1 protein is involved in binding between Fez1 and one or more regions of a physiological polynucleotide (e.g. genomic DNA), whereby expression (i.e. transcription or translation) of the polynucleotide is inhibited or prohibited. Binding between Fez1 and one or more regions on the human genome can inhibit transcription of one or more genes located nearby on the genome, and is contemplated as a potential mechanism of action for FEZ1 regulation of cell proliferation. Nonetheless, the possibility that Fez1 protein binds to and regulates translation of mRNA cannot be excluded. Regardless of the manner in which FEZ1 expression or non-expression serves to regulate cell proliferation, the compositions and methods described herein are useful for the purposes described herein.

The nucleotide sequence (SEQ ID NO: 1) of a portion of the human genome encoding wild type FEZ1 is shown in FIG. 5A. The nucleotide sequence (SEQ ID NO: 2) of cDNA generated using full-length mRNA transcribed from wild type FEZ1 is shown in FIG. 5B. The nucleotide sequence (SEQ ID NO: 3) of the open reading frame (ORF) of wild type FEZ1 is shown in FIG. 5I. The putative amino acid sequence (SEQ ID NO: 4) of wild type Fez1 protein is shown in FIG. 5J. Nucleotide sequences (SEQ ID NOs: 9–14) of cDNAs generated using truncated FEZ1 mRNA species and amino acid sequences (SEQ ID NOs: 15–20) of corresponding truncated Fez1 proteins are shown in FIGS. 5C to 5H and in FIGS. 5K to 5P, respectively.

The Isolated Polynucleotide of the Invention

The invention includes an isolated polynucleotide which anneals with high stringency with at least twenty consecutive nucleotide residues of at least one strand of the human FEZ1 gene, such as a human gene having the sequence SEQ ID NO: 1. Preferably, the isolated polynucleotide of the invention anneals with high stringency with at least 20, 21, 22, . . . , 30, 31, 32, . . . , 50, 51, 52, . . . , 75, 76, 77, . . . , or 100 consecutive nucleotide residues of at least one strand of the human FEZ1 gene, or is substantially complementary with those residues. In certain embodiments, it is preferred that the isolated polynucleotide of the invention have a length not greater than about 200, 199, 198, . . . 150, 149, 148, . . . , 100, 99, 98, . . . , 50, 49, 48, . . . , 40, 39, 38, . . . , or 35 nucleotide residues.

The isolated polynucleotide of the invention preferably has a sequence that is substantially homologous with at least 20, 21, 22, . . . , 30, 31, 32, . . . , 40, 41, 42, . . . or 50 consecutive nucleotide residues of at least one strand of the human FEZ1 gene. More preferably, the isolated polynucleotide of has a sequence completely homologous with at least 20, 21, 22, . . . , 30, 31, 32, . . . , 40, 41, 42, . . . , or 50 consecutive nucleotide residues of at least one strand of the human FEZ1 gene, and even more preferably with at least 20, 21, 22, . . . , 30, 31, 32, . . . , 40, 41, 42, . . . , or 50 consecutive nucleotide residues of at least one strand of SEQ ID NO: 1.

The isolated polynucleotide of the invention can be selected to be homologous with either the coding strand or the non-coding strand of FEZ1. Alternately, the isolated polynucleotide can comprise both a first portion that is homologous with one strand of FEZ1 and a second portion that is homologous with the other strand, such an isolated polynucleotide that is capable of forming a hairpin-type structure when the first portion thereof anneals with the second. Depending on the use to which the isolated polynucleotide of the invention is to be put, the skilled artisan will be able, in light of the present disclosure, to decide whether the isolated polynucleotide should comprise a portion homologous with the coding strand of FEZ1, a portion homologous with the non-coding strand, or both.

It is understood that, depending on the use to which the isolated polynucleotide of the invention is to be put and the length of the isolated polynucleotide, the degree of homology between the isolated polynucleotide and the at least one strand of human FEZ1 can be more or less critical in various embodiments described herein.

When the isolated polynucleotide of the invention is to be hybridized or annealed with a nucleic acid having a sequence wherein at least a portion is complementary to the isolated polynucleotide, the necessary degree of homology between the isolated polynucleotide and the at least one strand of FEZ1 is dependent on the length of the polynucleotide. As is well known, as the length of a polynucleotide increases, the degree of complementarity necessary to anneal the polynucleotide with another polynucleotide with high stringency decreases. Numerous methods, algorithms, computer programs, and the like are known whereby the skilled artisan can predict the stringency of binding between two polynucleotides (e.g. Suhai, Ed., 1992, *Computational Methods in Genome Research*, Plenum Press, New York; Swindell, Ed., 1997, *Sequence Data Analysis Guidebook*, Humana Press, New Jersey; Bishop, Ed., 1998, *Guide to Human Genome Computing*, Academic Press, New York). Any of these methods, etc., can be used by the skilled artisan, in light of the present disclosure, to design or select isolated polynucleotides of various lengths which will anneal with at least one strand of a human FEZ1 gene with high affinity. All such isolated polynucleotides are included within the invention.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264–2268), modified as in Karlin and Altschul (1993, Proc. Natl. Acad. Sci. USA 90:5873–5877). This algorithm is incorporated into the NBLAST and XBLAST programs of Altschul, et al. (1990, J. Mol. Biol. 215:403–410), and can be accessed, for example at the National Center for Biotechnology Information (NCBI) world wide web site having the universal resource locator "http://www.ncbi.nlm.nih.gov/BLAST/". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389–3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See http://www.ncbi.nlm.nih.gov.

The percent identity between two sequences can be determined using techniques similar to those described above, with or without allowing gaps. In calculating percent identity, typically exact matches are counted.

When the isolated polynucleotide of the invention is to be used to express all or a portion of a human Fez1 protein, either in vitro or in vivo, it is important that (i) the homology of the isolated polynucleotide with the human FEZ1 gene (e.g. SEQ ID NO: 1) is such that the amino acid sequence encoded by the isolated polynucleotide is identical to the corresponding region of FEZ1, (ii) the differences between the sequence of the isolated polynucleotide and the corresponding region of FEZ1 not result in differences in the encoded amino acid sequence (i.e. any sequence difference in a coding region merely substitutes a codon encoding an amino acid in place of another codon encoding the same amino acid), or (iii) any differences in the encoded amino acid sequence between the isolated polynucleotide and the corresponding region of FEZ1 results only in one or more conservative amino acid substitutions, as described in greater detail elsewhere herein. The following Human Codon Table can be used to select or identify alternate codons which encode the same amino acid.

Human Codon Table

| Amino Acid | Codons Encoding the Amino Acid |
|---|---|
| Alanine | GCA GCC GCG GCU |
| Cysteine | UGC UGU |
| Aspartic acid | GAC GAU |
| Glutamic acid | GAA GAG |
| Phenylalanine | UUC UUU |
| Glycine | GGA GGC GGG GGU |
| Histidine | CAC CAU |
| Isoleucine | AUA AUC AUU |
| Lysine | AAA AAG |
| Leucine | UUA UUG CUA CUC CUG CUU |
| Methionine | AUG |
| Asparagine | AAC AAU |
| Proline | CCA CCC CCG CCU |
| Glutamine | CAA CAG |
| Arginine | AGA AGG CGA CGC CGG CGU |

-continued

Human Codon Table

| Amino Acid | Codons Encoding the Amino Acid |
|---|---|
| Serine | AGC AGU UCA UCC UCG UCU |
| Threonine | ACA ACC ACG ACU |
| Valine | GUA GUC GUG GUU |
| Tryptophan | UGG |
| Tyrosine | UAC UAU |

In situations in which it is necessary or desirable to introduce nucleotide residue changes into a polynucleotide such as the isolated polynucleotide of the invention, or into a Fez1 protein or a portion thereof, a variety of well-known techniques can be used, such as site-specific mutagenesis. Site-specific mutagenesis, for example, allows production of mutants through the use of specific oligonucleotides which encode the sequence of the desired mutation, as well as a sufficient number of adjacent nucleotides, to provide a primer sequence of sufficient size and sequence complementarity to form a stable duplex on both sides of the nucleotide sequence to be altered (e.g. a codon). Typically, a primer of about 17 to 25 nucleotides in length is preferred, with about 5 to 10 residues on both sides of the junction of the sequence being altered. This technique typically employs a phage vector which exists in both a single stranded and double stranded form. Typical vectors useful in site-directed mutagenesis include vectors such as M13 phage. Such vectors are commercially available, and their use is well known in the art. Double stranded plasmids are also routinely employed in site-directed mutagenesis protocols, to eliminate the need to transfer the gene of interest from a plasmid to a phage vector. Site-directed mutagenesis is performed by first obtaining a single-stranded vector or dissociating the two strands of a double stranded vector which includes within its sequence a DNA sequence which comprises the desired site of mutagenesis. The oligonucleotide primer described above is annealed with the single-stranded vector, and subjected to DNA polymerization, in order to generate a mutation-bearing strand. A heteroduplex is formed between the mutation-bearing strand and either the original non-mutated strand of the double-stranded vector or an added or synthesized strand which is substantially complementary to the mutation-bearing strand. This heteroduplex is then used to transform appropriate cells, such as *E. coli* or cultured human cells, and clones are selected which comprise recombinant vectors bearing the mutated sequence arrangement. Preparation of sequence variants of the isolated polynucleotide of the invention using site-directed mutagenesis is provided merely as an example of a method of producing potentially such variants, and is not intended to be limiting, as there are other well-known methods for producing such variants. By way of example, recombinant vectors comprising or encoding the desired isolated polynucleotide can be treated with mutagenic agents, such as hydroxylamine, to obtain sequence variants.

The isolated polynucleotide of the invention can be single stranded or double-stranded, it being understood that a single-stranded form is the form referred to herein when annealing of the isolated polynucleotide of the invention with another nucleic acid is described.

The isolated polynucleotide of the invention can be substantially any nucleic acid, whether composed of deoxyribonucleosides or ribonucleosides, and whether composed of phosphodiester linkages or modified linkages such as phosphotriester, phosphoramidate, siloxane, carbonate, carboxymethyl ester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). The isolated polynucleotide of the invention is preferably in a substantially purified form.

It is not intended that the present invention be limited by the nature of the nucleic acid employed. The isolated polynucleotide of the invention can be an isolated, naturally occurring nucleic acid or it can be a synthetic nucleic acid. The isolated, naturally occurring nucleic acid can obtained be from a viral, bacterial, animal, human, or plant source. The polynucleotide can be DNA or RNA. Furthermore, the nucleic acid can be isolated, synthesized, or assembled as part of a virus or other macromolecule. See, e.g., Fasbender et al., 1996, *J. Biol. Chem.* 272:6479–89 (polylysine condensation of DNA in the form of adenovirus).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double stranded DNA, supercoiled DNA and/or triple-helical DNA; Z-DNA; and the like. The nucleic acids can be prepared by any conventional means typically used to prepare nucleic acids in large quantity. For example, DNAs and RNAs can be chemically synthesized using commercially available reagents and synthesizers by methods that are well-known in the art (see, e.g., Gait, 1985, Oligonucleotide Synthesis: A Practical Approach (IRL Press, Oxford, England)). RNAs can be produce in high yield via in vitro transcription using plasmids such as SP65 (Promega Corporation, Madison, Wis.).

In some circumstances, as where increased nuclease stability is desired, nucleic acids having modified internucleoside linkages can be preferred. Nucleic acids containing modified internucleoside linkages can also be synthesized using reagents and methods that are well known in the art. For example, methods for synthesizing nucleic acids containing phosphonate, phosphorothioate, phosphorodithioate, phosphoramidate methoxyethyl phosphoramidate, formacetal, thioformacetal, diisopropylsilyl, acetamidate, carbamate, dimethylene-sulfide ($—CH_2—S—CH_2$), dimethylene-sulfoxide ($—CH_2—SO—CH_2$), dimethylene-sulfone ($—CH_2—SO_2—CH_2$), 2'-O-alkyl, and 2'-deoxy-2'-fluoro phosphorothioate internucleoside linkages are well known in the art (Uhlmann et al., 1990, Chem. Rev. 90:543–584; Schneider et al., 1990, Tetrahedron Lett. 31:335). Stability of the isolated polynucleotide of the invention can also be enhanced by treating on or both ends of the polynucleotide (if it is linear) with at least one agent which nucleolytically blocks the end. Such agents are known in the art (e.g. agents described in *Oligonucleotides as Therapeutic Agents,* 1997, John Wiley & Sons, New York).

The isolated polynucleotide can be purified by any suitable means, such as are well known in the art. For example, the isolated polynucleotide can be purified by reverse phase or ion exchange HPLC, size exclusion chromatography, or gel electrophoresis. Of course, the skilled artisan will recognize that the method of purification will depend in part on the size and type of the nucleic acid to be purified and on the characteristics of any molecules, structure, or organisms with which it can be associated. It is furthermore contemplated that the isolated polynucleotide of the invention can comprise nucleotide residues other than the five naturally occurring bases, adenine, guanine, thymine, cytosine, and uracil.

In certain embodiments, the isolated polynucleotide of the invention is detectably labeled. Any known method of labeling a nucleic acid can be used to label the polynucleotide. By way of example, well known methods of detectably labeling a polynucleotide include incorporation of a radionuclide into the polynucleotide, linking the polynucleotide to a surface, such as a latex bead or a nylon membrane, linking a protein such as an enzyme to the polynucleotide, linking one of a protein-ligand pair (e.g. an avidin-biotin pair or an antibody-antigen pair) to the polynucleotide, linking a chromophore to the polynucleotide, and linking a fluorophore to the polynucleotide. In one embodiment useful for quantification of a nucleic acid with which the isolated polynucleotide of the invention is capable of annealing, the isolated polynucleotide is reversibly linked with both a fluorophore and a molecule capable of quenching the fluorescence of the fluorophore, whereby if either the fluorophore or the quenching molecule is dissociated from the isolated polynucleotide, then enhanced fluorescence of the fluorophore is detectable, as described (Livak et al., 1995, "Guidelines for Designing TaqMan™ Fluorogenic Probes for 5' Nuclease Assays", Perkin Elmer, Norwalk, Conn.; U.S. Pat. No. 5,210,015; U.S. Pat. No. 5,691,146; Heid et al., 1996, Genome Res. 6:986–994).

The isolated polynucleotide of the invention has numerous uses. For example, such an isolated polynucleotide can be detectably labeled and used as a probe to detect the presence of a different polynucleotide having a sequence comprising a portion to which it anneals (e.g. a genome, genomic fragment, mRNA, cDNA; DNA, or library clone encoding human FEZ1). Such a probe can be used, for example, to detect or to quantify expression of FEZ1 in a cell or tissue of a human. It is understood that numerous methods of using a polynucleotide probe for detection and quantification of nucleic acids with which the probe anneals are known in the art (e.g. Sambrook et al., 1989, *Molecular Cloning: A Laboratory Manual*, Cold Spring Harbor Laboratory, New York; Ausubel et al., 1992, *Current Protocols in Molecular Biology*, John Wiley & Sons, New York; Gerhardt et al., eds., 1994, *Methods for General and Molecular Bacteriology*, American Society for Microbiology, Washington, D.C.), and these methods are therefore not described here in detail. When the probe is used for detection or quantification of a nucleic acid encoding all or a portion of FEZ1, it is preferably detectably labeled.

The isolated polynucleotide of the invention can similarly be used to detect the presence of a non-human analog of the human FEZ1 gene in a polynucleotide obtained or derived from a non-human source (e.g. a library of genomic fragments obtained from, or a library of cDNAs derived from mRNAs of, an animal such as a mammal). It is well known that gene sequences are conserved among animals, the degree of sequence conservation being generally associated with the degree of evolutionary relatedness of the animals. Thus, it is contemplated that isolated polynucleotides which anneal with high stringency with at least 20, 21, 22, . . . , 30, 31, 32, . . . , 40, 41, 42, . . . , or 50 consecutive nucleotide residues of human FEZ1, or which are substantially complementary with those residues, are useful for identifying genomic fragments, cDNAs, mRNAs, or other polynucleotides which comprise a portion of an animal FEZ1 gene which is analogous to the portion of the human FEZ1 gene with which the isolated polynucleotide of the invention anneals. Given the fact that human FEZ1 regulates at least one important physiological function (i.e. cell proliferation), it is to be expected that the nucleotide sequence of FEZ1 will be more highly conserved among organisms than less critical genes. Thus, it is contemplated that the isolated polynucleotide of the invention is useful not only for isolation and identification of primate and other mammalian FEZ1 analogs, but also for isolating and identifying other vertebrate, other eukaryotic, and possibly any FEZ1 analog. Preferably, when a non-human analog of FEZ1 is to be isolated or identified, a plurality of isolated polynucleotides of the invention are used, each polynucleotide being complementary to a different portion of human FEZ1. Also preferably, at least one isolated polynucleotide of the invention is complementary to a portion of human FEZ1 which can be expected to be particularly conserved, such as the portion which encodes the leucine-zipper region of Fez1 protein.

Also contemplated is a manufacture comprising a plurality of isolated polynucleotide probes of the invention fixed in an ordered array on a surface. Such manufactures are colloquially known as 'gene chips.' Each of the plurality of probes anneals with high stringency with a portion of the human FEZ1 gene. By including probes which differ by a single nucleotide residue within the corresponding portion of the FEZ1 gene, nucleic acids which comprise different nucleotide residues at that position within the FEZ1 gene can be differentiated. Thus, using methods well known in the art, missense and deletion mutations in the FEZ1 sequence can be detected. Furthermore, by incorporating into the array probes which bind with high affinity with sequential portions of the wild type FEZ1 gene, wherein each sequential portion includes one nucleotide residue not included within the previous sequential portion, the nucleotide sequence of all, or any portion, of the FEZ1 gene can be determined. Preferably, the wild type human FEZ1 gene sequence which is used is SEQ ID NO: 1. An analogous ordered array can be designed to detect mRNA sequence alterations, preferably using SEQ ID NO: 2 or SEQ ID NO: 3 as the wild type human FEZ1 mRNA sequence. Manufactures of this type are analogous to the GeneChip™ devices made by Affymetrix, Inc. (Santa Clara, Calif.), which comprise pluralities of primers which bind with high stringency to, for example, portions of the human p53 gene or to portions of the HIV-1 protease or reverse transcriptase genes. Methods for making and using such manufactures have been described elsewhere, and need only be modified by the skilled artisan to include the FEZ1 gene sequences described in the present disclosure (Wallraff et al., February 1997, Chemtech 22–23; Lockhart et al., 1996, Nature Biotechnol. 14:1675–1680; Pease et al., 1994, Proc. Natl. Acad. Sci. USA 91:5022–5026; Fodor et al., 1993, Nature 364:555–556).

One or more isolated polynucleotides of the invention can also be used as primers for replication or amplification of all or a portion of a nucleic acid comprising all or part of a human FEZ1 gene or a non-human FEZ1 analog. The nucleic acid may, for example, be either strand of a human genome, a human chromosome, a fragment of a human genome, or all or a portion of a non-human genome, or it can be an mRNA generated by transcription of a human FEZ1 gene or a non-human analog thereof or either strand of a cDNA generated using such an mRNA. In light of the present disclosure, the skilled artisan can replicate or amplify substantially any nucleic acid comprising a portion homologous with or complementary to all, or a portion, of a human FEZ1 gene, such as that having the nucleotide sequence SEQ ID NO: 1. Methods of DNA transcription, RNA reverse transcription, DNA replication, polymerase chain reaction (PCR), and the like are well known and not described beyond citation to the following standard references (Sambrook et al., 1989, *Molecular Cloning: A Laboratory Manual*, Cold Spring Harbor Laboratory, New York; Ausubel et al., 1992, *Current Protocols in Molecular Biology*, John Wiley & Sons, New York; Gerhardt et al., eds., 1994, *Methods for General and Molecular Bacteriology*, American Society for Microbiology, Washington, D.C.). Methods of amplifying genomic regions which flank an already-sequenced genomic region are likewise known and are included within the scope of the invention insofar as amplification of genomic regions which flank a human FEZ1 gene or a non-human analog thereof are concerned.

When a pair of isolated polynucleotides of the invention is to be used to amplify all or a portion of a human FEZ1 gene, a transcript thereof, or a cDNA generated using such a transcript, the polynucleotides should be selected such that one polynucleotide anneals with one strand with high stringency near one end of the region to be amplified and the other polynucleotide anneals with the other strand with high stringency near the other end of the region to be amplified, as is well known in PCR methods. Of course, as is likewise well known, if the nucleic acid to be amplified is an mRNA or other RNA molecule, then a cDNA complementary to the mRNA must be made prior to performing a PCR reaction.

Substantially any region of the human FEZ1 gene, or of a non-human analog thereof, can be amplified using one or more isolated polynucleotides of the invention. In one embodiment, polynucleotides which anneal with high stringency with at least 20, 21, 22, . . . , 30, 31, 32, . . . , 40, 41, 42, . . . , or 50 nucleotide residues near opposite ends and on opposite strands of the human FEZ1 gene are used to amplify the entire human FEZ1 gene, or a non-human analog thereof, from one or more portions of a human or non-human genome.

In another embodiment, one or more pairs of isolated polynucleotide primers are selected, each of which pairs of primers comprises a first primer which anneals with high stringency with an intronic portion which flanks the 5'- or 3'-end of an exon on the coding strand of a nucleic acid encoding the exon and a second primer which anneals with high stringency with an intronic portion which flanks the 3'- or 5'-end, respectively, of the same exon on the non-coding strand of the nucleic acid. Optionally, each of the two primers of each pair is adjacent the designated end of the exon. Thus, according to this method, amplification of a nucleic acid encoding at least one exon of the human FEZ1 gene, or a non-human analog thereof, using one or more pairs of primers results in amplification of one or more exon sequences of the gene or analog, optionally not including any intronic sequence. It is understood that amplification of both an exon sequence and the intronic sequences which flank it can be more informative than amplification of exon sequences alone, since sequence alterations which appear in an intron but nonetheless affect the amino acid sequence of the encoded protein (e.g. mutations which affect mRNA splicing) can be revealed.

In another embodiment of the amplification methods of the invention, pairs of isolated polynucleotide primers of the invention are selected such that amplification of the wild type human genomic FEZ1 region (e.g. SEQ ID NO: 1), the corresponding wild type mRNA, or a cDNA generated from wild type human FEZ1 mRNA using these pairs of primers yields a mixture of amplification products having determined lengths. Fractionation of these amplification products by size (e.g. by gel electrophoresis or by chromatography) will yield a characteristic pattern for the wild type sequence. Amplification of the same nucleic acid obtained from an individual having a mutation which affects the length or presence of any of the amplification products will yield a different pattern than the wild type pattern, and the presence of the mutation in the individual can thus be identified.

In still another embodiment of the amplification methods of the invention, pairs of isolated polynucleotide primers of the invention are selected in order to amplify regions of a nucleic acid encoding human Fez1 protein, or a non-human analog thereof, which are known to be altered (i.e. wherein a deletion or missense mutation are known to occur) in tumor cells. Several such regions are described herein in Example 1, and primers useful for amplifying these regions are included in the invention. Identification of the presence of such alterations is an indication that the cell or tissue from which the nucleic acid was obtained is cancerous. Examples of primers useful in this embodiment include, for example, primer pairs G12 and G13, G14.2 and G15, and G16 and IntABR for amplifying the coding region of exon 1, primer pairs IntABF and G17, G20 and G21, and G32 and IntBCR for amplifying the coding region of exon 2, and primer pairs IntBCF and Mut6, G1 and G2, G75 and G82, G5 and G6, and G7 and G8 for amplifying the coding region of exon 3. These primers have the nucleotide sequences listed in the following table.

Primer Nucleotide Sequence Table

| Primer | Nucleotide Sequence (5'→3') | SEQ ID NO |
|---|---|---|
| G12 | GCTGCCACAGCCTTTCCAAGACC | 22 |
| G13 | TACCGGTTGAGCTTCTTGAGGTG | 23 |
| G14.2 | ACAGCTTCCACAGCAAGCACTGC | 24 |
| G15 | ATTGGAGAAGGGCATGAGCTT | 25 |
| G16 | TGGACTTTGACCCGTCCACACC | 26 |
| IntABR | GTTTCCAACCCACTTACCCTTGC | 27 |
| IntABF | GCAGGGGAGGCATGAGTCACC | 28 |
| G17 | GGCTTCAGCTCCTGCTCCTTGG | 29 |
| G20 | ACAACATCACCCAGGGCATCGTC | 30 |
| G21 | CCTCCAGCTCGTCCCTGCAGC | 31 |
| G32 | ACTGCAGCTTCAGCAGGAGAAGC | 32 |
| IntBCR | CTGACCACCCAAACCCATGAGC | 33 |
| IntBCF | TCACCTCTTGGCACTCTGTCTCC | 34 |
| Mut6 | CAGGTCCTGGGTCCTCAGCTC | 35 |
| G1 | TGAACGCCAAGGCTAGCGAGATC | 36 |
| G2 | GCTCCTGCAGCTCCTGCTCCAG | 37 |
| G75 | CCCACCTTCCCCGAGGACGTC | 38 |
| G82 | AGCCCGAGGACATCTGGTCATGG | 39 |
| G5 | CCTGCCCTGCAGCGGGAGCTGGAG | 40 |
| G6 | AGCTGCTGCAGGGCCTTCTCCAG | 41 |
| G7 | CAGTACCAGAAACAGCTGCAGCAGAGC | 42 |
| G8 | CCCTGCCTCCCAGTGCCAGGTC | 43 |

Use of isolated polynucleotide primers comprising both a fluorophore and a molecule capable of quenching fluorescence of the fluorophore for quantitative amplification of nucleic acids homologous with all or part of the human FEZ1 gene is contemplated. Use of such labeled primers has been described elsewhere (Livak et al., 1995, "Guidelines for Designing TaqMan™ Fluorogenic Probes for 5' Nuclease Assays", Perkin Elmer, Norwalk, Conn.; U.S. Pat. No. 5,210,015; U.S. Pat. No. 5,691,146; Heid et al., 1996, Genome Res. 6:986–994).

The isolated polynucleotide of the invention can also be used as an antisense oligonucleotide (ASO) to inhibit expression of a human FEZ1 gene or a non-human analog thereof. As is well known in the art, an ASO can be complementary to either the coding or non-coding strand of a gene. ASOs are used by delivering the ASO to the interior of a cell, and preferably to the interior of the nucleus of a cell, whereby the ASO is enabled to interact with one or more nucleic acids which encode a protein. When an isolated polynucleotide of the invention is used as an ASO, it binds with high stringency with at least 20, 21, 22, . . . , 30, 31, 32, . . . , 40, 41, 42, . . . , or 50 consecutive nucleotide residues of at one strand of a human FEZ1 gene, such as that having the sequence SEQ ID NO: 1, even if the ASO is used in vitro or in a non-human animal. When the recipient of the ASO is a human cell, either in vitro or in vivo, the isolated polynucleotide ASO of the invention is preferably substantially homologous, and more preferably completely homologous with at least 20, 21, 22, . . . , 30, 31, 32, . . . , 40, 41, 42, . . . , or 50 consecutive nucleotide residues of the human FEZ1 gene (SEQ ID NO: 1). Furthermore, the isolated polynucleotide ASO is preferably substantially or completely homologous with the translation start site, the transcription start site, an exon-intron boundary for splicing immature mRNA, or a coding sequence of the human FEZ1 gene. Other preferred ASO are complementary to or homologous with and approximately about as long as the FEZ1 ORF (SEQ ID NO: 3) or a significant portion (e.g. 100–500 nucleotides) thereof. ASOs can be administered either in a single-stranded or double-stranded form, although the single-stranded form is preferable. ASOs can be administered to an animal or a cell either in the form of a pharmaceutical composition comprising the ASO, as described herein.

The isolated polynucleotide of the invention can also be used as a template for expression of human Fez1 protein, either in vitro or in vivo. When in vitro expression of Fez1 protein is desired, it is preferable to use an isolated polynucleotide which does not comprise the intronic regions of FEZ1, such as an isolated polynucleotide which comprises a portion which is complementary to at least one strand of a cDNA generated using a spliced human mRNA encoding Fez1 protein (e.g. a cDNA having the nucleotide sequence SEQ ID NO: 2 or SEQ ID NO: 3). Methods and compositions useful for in vitro expression of protein from a nucleic acid are well known in the art and are described elsewhere (e.g. Sambrook et al., 1989, *Molecular Cloning: A Laboratory Manual*, Cold Spring Harbor Laboratory, New York; Ausubel et al., 1992, *Current Protocols in Molecular Biology*, John Wiley & Sons, New York).

When the isolated polynucleotide of the invention is used as a template for expression of human Fez1 protein in vivo, the isolated polynucleotide has a sequence substantially homologous with at least nucleotide residues 112–456, nucleotide residues 1707–2510, and nucleotide residues 4912–5550 of at least one strand of SEQ ID NO: 1. If the cell in which Fez1 protein is expressed is a mammalian cell, and especially if it is a human cell, it is not necessary to delete the intronic regions of FEZ1 from the isolated polynucleotide. Preferably, however, the intronic regions of FEZ1 are deleted from the isolated polynucleotide prior to providing it to the cell.

When the isolated polynucleotide of the invention is used as a template for expression of human Fez1 protein in vivo, the isolated polynucleotide is preferably provided to a cell in the form of an expression vector, wherein the region(s) encoding Fez1 protein are operably linked with a promoter region. The promoter region can be the human FEZ1 promoter region, or it can be substantially any other promoter region. In various embodiments, the promoter region of the expression vector is a constitutive promoter, an inducible promoter, or a tissue-specific promoter. Numerous constitutive promoters are known in the art and included within the scope of the invention. Exemplary constitutive promoters include, for example, a retroviral LTR promoter, the cytomegalovirus immediate early promoter, the SV40 early promoter, the herpes simplex virus thymidine kinase promoter, an adenovirus-based promoter, elongation factor 1 alpha promoter, SV40-HTLV-1 LTR fusion promoter, and the CMV-beta actin enhancer fusion promoter.

Operable linkage of an isolated polynucleotide of the invention with an inducible promoter permits controlled expression of Fez1 protein following delivery of the expression vector to a cell. Such controlled expression is modulated by providing an inducer of the promoter to, or withholding or removing such an inducer from, the cell. An example of an inducible promoter which can be operably linked to an isolated polynucleotide of the invention is a tetracycline promoter, which is well known in the art to be an inducible promoter.

Operable linkage of an isolated polynucleotide of the invention with a tissue-specific promoter permits localization of expression of Fez1 protein to a tissue of interest, thereby minimizing any side effects which can be associated with non-tissue-specific expression of Fez1 protein. The tissue-specific promoter may, for example, be selected from the group consisting of an epithelium-specific promoter, a tumor-specific promoter, a breast-specific promoter, a prostate-specific promoter, and an esophagus-specific promoter. By way of example, the prostate-specific antigen promoter can be operably linked to an isolated polynucleotide of the invention in order to achieve prostate-specific expression of Fez1 protein.

The isolated polynucleotide of the invention can be provided to a cell, either in vitro or in vivo, using a wide variety of gene delivery vectors. The identity of the vector is not critical; substantially any vector known in the art for delivering a nucleic acid to the interior of a cell can be used for this purpose. Exemplary vectors include, but are not limited to naked DNA vectors, plasmids, condensed nucleic acids, projected nucleic acid-coated micro- or nano-particles, and virus vectors.

The invention also includes an animal cell which comprises an exogenous DNA molecule having at least one portion which is substantially homologous with at least the coding regions of the human FEZ1 gene. For example, the exogenous DNA molecule can comprise one, two, three, or more regions which, individually or together are substantially homologous with nucleotide residues 112–456, nucleotide residues 1707–2510, and nucleotide residues 4912–5550 of at least one strand of SEQ ID NO: 1. Preferably, the exogenous DNA molecule comprises one region that is substantially homologous with at least one strand of SEQ ID NO: 2. More preferably, the exogenous DNA molecule is completely homologous with the coding regions of the human FEZ1 gene. Also preferably, the exogenous DNA molecule comprises a promoter operably linked with the FEZ1 coding region(s), whereby Fez1 protein is expressed in cells comprising the exogenous DNA molecule.

The cell can be a human cell, a non-human animal cell, or a non-animal cell, such as a plant cell, a yeast cell, a fungus cell, or a bacterium. The cell can likewise be a cultured cell, a cell within the body of an animal, or a cell which is removed from the body of an animal for the purpose of providing the exogenous DNA molecule prior to returning the cell to the body of the same or a different animal.

The invention further relates to an animal comprising a cell which comprises an exogenous DNA molecule having at least one portion which is substantially homologous with at least the coding regions of the human FEZ1 gene. Preferably, the animal is a human which comprises a tissue which lacks a copy of the human wild type FEZ1 gene, such as certain tumor tissues. Such animals (e.g. mice) can be made by disrupting the FEZ1 gene in the animal using known gene targeting methods. By way of example, exon 1 of FEZ1 can be replaced with a neomycin-resistance cassette. Embryonic stem cells of the animal are transfected using the targeting construct DNA vector, and cells are selected for neomycin resistance. In these cells, homologous recombination between the targeting construct DNA and one of the animal's genomic copy of the FEZ1 gene occurs. In rare instances, recombination of both FEZ1 copies can occur, but it is anticipated that most, if not all selected cells will be heterozygous for recombined FEZ1-neomycin resistance gene, and will develop as heterozygous adult animals. These heterozygous animals exhibit characteristics attributable to animals having only a single functional FEZ1 gene per cell, such as abnormal cell or tissue differentiation, abnormal cell proliferation, increased incidence of cancer and other cell proliferative disorders, and uncontrolled gene expression. Furthermore, mating of heterozygous FEZ1 animals yields animals homozygous for the recombined FEZ1-neomycin resistance gene (i.e. FEZ1 "knockout" animals). These FEZ1 knockout animals exhibit traits characteristics attributable to the lack of a functional FEZ1 gene in the cells of the animal. Such characteristics include, for example, abnormal cell or tissue differentiation, abnormal cell proliferation, increased incidence of cancer and other cell proliferative disorders, and uncontrolled gene expression.

The Isolated Fez1 Protein of the Invention

The invention also relates to an isolated Fez1 protein. The putative amino acid sequence of human Fez1 protein (SEQ ID NO: 4) is shown in FIG. 5D. Preferably, the isolated human Fez1 protein is substantially purified. The isolated human Fez1 protein can be in the form of a suspension of the native or denatured protein in a liquid such as water, a buffer, or the like, a lyophilized powder, an immunogenic composition comprising the protein and one or more adjuvants or immunogenicity enhancers such as are known in the art, or a pharmaceutical composition as described elsewhere herein.

The isolated Fez1 protein of the invention can be made by a variety of techniques. For example, the protein can be expressed in an in vitro expression mixture using an isolated polynucleotide of the invention. The isolated polynucleotide of the invention can also be operably linked with a constitutive or other promoter, and the Fez1 protein overexpressed in a human or non-human cell, and subsequently purified therefrom. Alternately, the Fez1 protein can be purified using, for example, standard chromatographic techniques from a naturally occurring source of human Fez1 protein (e.g. normal human brain or testes tissue).

The invention also includes fragments of the isolated Fez1 protein of the invention. Such fragments can be generated, for example, by expressing an isolated polynucleotide of the invention, wherein the polynucleotide encodes only a portion of human Fez1 protein, or by proteolytic degradation of human Fez1 protein.

Although it is preferred that the isolated human Fez1 protein has an amino acid sequence completely homologous with SEQ ID NO: 4, the amino acid sequence of the isolated Fez1 protein can comprise one or more conservative amino acid substitutions relative to SEQ ID NO: 4).

For example, certain amino acids of the human Fez1 protein can be substituted for other amino acids without appreciably affecting the biological activity of the protein. Preferably, the amino acid sequence of the isolated Fez1 protein of the invention is substantially homologous with SEQ ID NO: 4. The hydropathic index of naturally occurring Fez1 amino acid residues can be compared with those of potential substitute amino acid residues. The significance of amino acid hydropathic index similarity between naturally occurring and potential substitute amino acid residues, as it relates to retention of biologic function of a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each naturally occurring amino acid residue has been assigned a hydropathic index on the basis of their hydrophobicity and charge characteristics, as described (Kyte et al., 1982, J. Mol. Biol. 157:105). These hydropathic index values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). Amino acid residues can be substituted in place of other amino acid residues which having a similar hydropathic index without significantly affecting biological activity of the protein. Preferably, the substitute amino acid residue has a hydropathic index which differs from the hydropathic index of the naturally occurring amino acid residue by less than 2.0, preferably by less than 1.0, and more preferably by less than 0.5. For example, if the hydropathic index of a naturally occurring amino acid residue is 1.8, then a substitute amino acid residue should have a hydropathic index in the range from 3.8 to −0.2, preferably in the range from 2.8 to 0.8, and more preferably in the range from 2.3 to 1.3.

An alternate method can be used to predict amino acid residues which can be substituted in place of naturally occurring Fez1 amino acid residues in regions of the Fez1 protein which are predicted to interact with other molecules (e.g. the leucine zipper region of Fez1, which is thought to interact with DNA). This method has been described in the art (Hoop et al., 1981, Proc. Natl. Acad. Sci. USA 78:3824), and involves assigning the following hydrophilicity values to amino acid residues: arginine (+3.0); lysine (+3.0); aspartate (+3.0); glutamate (+3.0); serine (+0.3); asparagine (+0.2); glutamine (+0.2); glycine (0); proline (0.0); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Amino acid residues can be substituted in place of other amino acid residues having a similar hydrophilicity value without significantly affecting biological activity of the protein. Preferably, the substitute amino acid residue has a hydrophilicity value which differs from the hydrophilicity value of the naturally occurring amino acid residue by less than 2.0, preferably by less than 1.0, and more preferably by less than 0.5. For example, if the hydrophilicity value of a naturally occurring amino acid residue is 1.8, then a substitute amino acid residue should have a hydrophilicity value in the range from 3.8 to −0.2, preferably in the range from 2.8 to 0.8, and more preferably in the range from 2.3 to 1.3.

As outlined above, amino acid substitutions can be based on the relative similarity of the amino acid side-chain substituents, for example, their hydrophobicity, hydrophilicity, charge, size, and the like. For example, conservative amino acid substitutions can include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The isolated Fez1 protein of the invention, and fragments thereof, are not limited to products of any of the specific exemplary processes listed herein.

It will be appreciated, of course, that the isolated Fez1 proteins, and fragments thereof, can incorporate amino acid residues which are modified without affecting activity. For example, the termini can be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound (e.g. as an anti-proliferative agent) by sequential degradation of the compound at a terminal end thereof.

Blocking groups include protecting groups conventionally used in the art of peptide chemistry which will not adversely affect in vivo activities of the Fez1 proteins or fragments thereof. For example, suitable N-terminal blocking groups can be introduced by alkylation or acylation of the N-terminus. Examples of suitable N-terminal blocking groups include $C_1$–$C_5$ branched or non-branched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal residue. Suitable C-terminal blocking groups, in which the carboxyl group of the C-terminus is either incorporated or not, include esters, ketones, and amides. Ester or ketone-forming alkyl groups, particularly lower alkyl groups such as methyl, ethyl and propyl, and amide-forming amino groups such as primary amines ($—NH_2$), and mono- and di-alkylamino groups such as methylamino, ethylamino, dimethylamino, diethylamino, methylethylamino, and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the Fez1 proteins, or fragments thereof, to yield desamino and descarboxylated forms thereof without affect on biological activity.

Other modifications can also be incorporated without adversely affecting biological (e.g. anti-proliferative) activity and these include, but are not limited to, substitution of one or more of the amino acids in the natural L-isomeric form with amino acids in the D-isomeric form. Thus, the Fez1 proteins, or fragments thereof, can include one or more D-amino acid residues, or can comprise amino acids which are all in the D-form. Retro-inverso forms of proteins peptides in accordance with the present invention are also contemplated, for example, inverted peptides in which all amino acids are substituted with D-amino acid forms.

Acid addition salts of the Fez1 proteins, or fragments thereof, of the present invention are also contemplated as functional equivalents. Thus, a protein or peptide in accordance with the present invention can be treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tartaric, citric, benzoic, cinnamic, mandelic, methanesulfonic, ethanesulfonic, p-toluenesulfonic, or salicylic acid to provide a water soluble salt of the peptide which is suitable for use as an anti-proliferative agent.

The isolated Fez1 protein of the invention, or a fragment thereof, can be used to generate polyclonal or monoclonal antibodies using known methods. As is well known, administration of the Fez1 protein of the invention to an animal can induce a soluble immune response against the protein or fragment in the animal. Preferably, the protein or fragment is mixed with an adjuvant or other immune system enhancer. Such adjuvants include, but are not limited to, mineral gels such as aluminum hydroxide, surface active substances such as lysolecithin, pluronic polyols, and polyanions, other peptides, and oil emulsions. Antibodies which bind specifically with the Fez1 protein or fragment can be identified and isolated using well known methods (see, e.g. Harlow et al., 1988, *Antibodies: A Laboratory Manual*, Cold Spring Harbor, N.Y.). Likewise, immortal hybridomas can be generated using known methods to provide a supply of such antibodies.

Diagnostic Methods of the Invention

As described herein, reduced or no expression of the human FEZ1 gene has been demonstrated in numerous cancer cell lines and tumor samples. These data indicate that assessment of the level of FEZ1 gene expression in a cell or tissue of a human can indicate the cancerous state of the cell or tissue. Diagnostic techniques based on this relationship have the advantage that tumorigenesis can be detected in cells and tissues at an early stage, before other physiological changes associated with cancers can be detected in the same cells or tissues. Furthermore, these diagnostic techniques can be used to confirm or refute a preliminary diagnosis of tumorigenesis made by visual or cytological examination of potentially cancerous tissue.

The diagnostic methods described in this section are useful for diagnosing cancer in a body tissue of a human, particularly where the body tissue is an epithelial tissue. By way of example, the body tissue can be selected from the group consisting of a gastrointestinal tissue, esophageal tissue, gastric tissue, colon tissue, prostate tissue, breast tissue, a hematopoietic tissue, lung tissue, melanoma tissue, cervical tissue, and ovarian tissue.

The invention includes a method of determining the cancerous status of a sample tissue. This method comprises comparing FEZ1 expression in the sample tissue with FEZ1 expression in a control tissue of the same type. Decreased FEZ1 expression in the sample tissue, relative to FEZ1 expression in the control tissue, is an indication that the sample tissue is cancerous. The sample tissue can be a phenotypically abnormal tissue (e.g. a biopsy sample obtained from a potentially cancerous lesion in a human tissue such as breast or prostate), or it can be a phenotypically normal tissue. The control tissue is a non-cancerous tissue of the same type, and can be obtained from the same human from whom the sample tissue was obtained, or from one or more humans different than the one from whom the sample tissue was obtained. If a body of data exists or is created, from which a representative value for expression of FEZ1 in non-cancerous tissue of the same type as the sample tissue, then FEZ1 expression in the sample tissue can be compared with this representative value, rather than performing a separate determination of FEZ1 expression in the same or a different human.

Expression of FEZ1 in the sample tissue is compared with FEZ1 expression in a control tissue (or data set) by comparing the relative amounts of at least one indicator in the sample tissue and in the control tissue (or data set). The indicator which is used can be any indicator which can be correlated with transcription of the FEZ1 gene in the tissue or with translation of this transcript is such tissue. For example, the indicator can be selected from the group consisting of a FEZ1 mRNA, a cDNA prepared using a FEZ1 mRNA, a DNA prepared by amplification of either of these, and Fez1 protein.

The invention also includes another method of determining the cancerous status of a sample tissue. This method comprises comparing the nucleotide sequence of a FEZ1-associated polynucleotide obtained from the sample tissue with the nucleotide sequence of a control FEZ1-associated polynucleotide. A difference between the nucleotide sequence of the FEZ1-associated polynucleotide obtained from the sample tissue and the nucleotide sequence of the control FEZ1-associated polynucleotide is an indication that the sample tissue is cancerous. The FEZ1-associated polynucleotide may, for example, be one selected from the group consisting of at least a portion of a chromosome, a non-spliced mRNA, a partially spliced mRNA, a fully spliced mRNA, a cDNA prepared using a non-spliced mRNA, a cDNA prepared using a partially spliced mRNA, a cDNA prepared using a fully spliced mRNA, and a DNA prepared by amplification of any of these. By way of example, the FEZ1-associated polynucleotide can be DNA prepared by amplification of a cDNA prepared using a fully spliced mRNA obtained from a human, in which case, the control FEZ1-associated polynucleotide should be a DNA having the sequence SEQ ID NO: 3. Further by way of example, the FEZ1-associated polynucleotide can be a DNA prepared by amplification of at least a portion of chromosome 8 of a human, in which case, the control FEZ1-associated polynucleotide should be a DNA having the sequence SEQ ID NO: 1.

According to this method, the sample and control tissues can both be obtained from the same human, in which case, the sample tissue should be a phenotypically abnormal portion of a body tissue of a human or a portion of the tissue in which tumorigenesis is anticipated, and the control FEZ1-associated polynucleotide should be obtained from a phenotypically normal portion of the same body tissue or from a portion of the tissue in which tumorigenesis is not anticipated. The sample and control tissues can also be obtained from the same tissue, but from different humans, in which case the control tissue should be obtained from a human whose relevant tissue is not cancerous. Alternately, as described above, the 'control tissue' can be a body of data collected from the relevant type of tissue obtained from a plurality of humans in whom the relevant tissue was not cancerous. In this case, only the nucleotide sequence of the sample FEZ1-associated polynucleotide need be determined experimentally, and this sequence can be compared with a consensus or other sequence indicated by the body of data. For example, the FEZ1 gene sequence described herein (SEQ ID NO: 1), the FEZ1 cDNA sequence described (SEQ ID NO: 2), or the FEZ1 ORF sequence described herein (SEQ ID NO: 3) can be used as the control FEZ1-associated polynucleotide sequence.

The invention includes yet another method of determining the cancerous status of a sample tissue. As described herein, certain mutations in the human FEZ1 gene lead to production of transcripts from this gene which have lengths which are different from the length of the wild type FEZ1 gene transcript. This method correlates this transcript length difference with a cancerous state in a sample tissue. This method comprises comparing the length of an FEZ1-transcript-associated polynucleotide obtained from the sample tissue with the length of a control FEZ1-transcript-associated polynucleotide. If the length of the FEZ1-transcript-associated polynucleotide obtained from the sample tissue is less than the length of the control FEZ1-transcript-associated polynucleotide, then this is an indication that the sample tissue is cancerous. The FEZ1-transcript-associated polynucleotide may, for example, be selected from the group consisting of a fully spliced mRNA, a cDNA prepared using a fully spliced mRNA, and a DNA prepared by amplification of either of these. In one embodiment of this method, the FEZ1-transcript-associated polynucleotide is DNA prepared by amplification of a cDNA prepared using a fully spliced mRNA obtained from a human, and the control FEZ1-transcript-associated polynucleotide is DNA having the sequence SEQ ID NO: 2.

In another embodiment of this method, the FEZ1-transcript-associated polynucleotide is fully spliced mRNA obtained from a human patient, and the control FEZ1-transcript-associated polynucleotide is at least a portion of a nucleic acid which is complementary to SEQ ID NO: 2, whereby binding of the patient's mRNA and the control polynucleotide can be detected using standard RNA blot or Northern blot analytical techniques.

As in the methods described above, the sample and control FEZ1-transcript-associated polynucleotides can be obtained from the same or different humans, and the control FEZ1-transcript-associated polynucleotide can instead be a consensus or other relevant sequence described herein or formulated using FEZ1-transcript-associated polynucleotide sequences obtained from humans in whom the relevant tissue was not cancerous.

The invention includes still another method of determining the cancerous status of a sample tissue. This method comprises assessing FEZ1 expression in the sample tissue. A substantial absence of FEZ1 expression in the sample tissue is an indication that the sample tissue is cancerous. FEZ1 expression can be assessed by assessing the presence or substantial absence of at least one indicator selected from the group consisting of a FEZ1 mRNA, a cDNA prepared using a FEZ1 mRNA, a DNA prepared by amplification of either of these, and Fez1 protein.

The invention also includes another method of determining the cancerous status of a sample tissue. This method comprises detecting abnormal splicing of a FEZ1 transcript in the sample tissue. Abnormal splicing of the FEZ1 transcript is an indication that the sample tissue is cancerous. Abnormal splicing of a FEZ1 transcript may, for example, be detected by assessing the ability of at least one exon boundary polynucleotide probe to anneal with a FEZ1-transcript-associated polynucleotide with high stringency. Such an exon boundary polynucleotide probe is capable of annealing with high stringency with terminal portions of two sequential FEZ1 exons when the terminal portions are adjacent, but not when the terminal portions are not adjacent. By way of example, such an exon boundary polynucleotide probe can comprise two portions, one portion which binds with high stringency with the 3'-end of the first exon of a DNA, mRNA, or cDNA coding strand of FEZ1, and another portion which binds with high stringency with the 5'-end of the second exon of a DNA, mRNA, or cDNA coding strand of FEZ1. If the two portions of the probe are adjacent, then the probe will bind with high stringency with an mRNA, or with the coding strand of a cDNA generated using that mRNA, only if the two exons are adjacent in the mRNA or cDNA. Thus, if the mRNA has been abnormally spliced, such that the first and second exons of FEZ1 are not adjacent in the spliced mRNA (and are therefore not adjacent in the corresponding cDNA), then the probe will not bind with the mRNA, or the corresponding cDNA, with high stringency. Design of such primers is well within the level of ordinary skill in the art, in light of the present disclosure.

Immunohistological Diagnostic Methods

The invention also includes an immunohistological method for detecting expression of Fez1 protein in a cell or tissue sample obtained from a human patient. This method involves use of an antibody preparation (e.g. a monoclonal or polyclonal antibody preparation) generated using the isolated Fez1 protein of the invention (or a fragment thereof) according to standard antibody generating methods. This preparation contains one or more types of antibodies which bind specifically with human Fez1 protein. The antibody preparation is contacted with the cell or tissue sample, and the Fez1-binding antibodies are labeled, either prior to or after contact with the sample. Non-specifically bound antibody is washed from the sample, and the presence of labeled antibody in or on the sample is assessed. The presence of labeled antibody is an indication that the sample comprises human Fez1 protein. Thus, this immunohistological method can be used to detect Fez1 expression, or a decrease of such expression, which is associated with an enhanced likelihood of tumorigenesis, for example.

Therapeutic Methods of the Invention

Abnormal expression of the human FEZ1 gene is not merely a symptom of epithelial and other cancers in human tissues. It is also a contributing cause, and possibly the sole cause in some instances of tumorigenicity in those tissues. Inactivation of all genomic copies of the FEZ1 gene in one or more cells of a human tissue, especially an epithelial tissue, can lead to abnormal proliferation of those cells. Normal control of cell proliferation can be restored either by reactivating a genomic copy of the FEZ1 gene in abnormally proliferating cells or by providing at least one exogenous source of Fez1 protein to abnormally proliferating cells. The exogenous source of Fez1 protein may, for example, be a nucleic acid encoding Fez1 protein or a composition comprising Fez1 protein. The exogenous source of Fez1 protein can be provided to the cells prior to tumorigenesis (i.e. for the purpose of inhibiting, delaying, or preventing tumorigenesis) or anytime after the onset of tumorigenesis (i.e. for the purpose of inhibiting, delaying, or preventing further abnormal proliferation of tumor cells or for the purpose of reversing abnormal proliferation).

The invention thus includes a method of modulating proliferation of a human cell having an altered FEZ1 gene. This method comprises providing to the cell an exogenous source of Fez1 protein. When the protein is provided to the cell, abnormal proliferation of the cell is inhibited, delayed, or prevented.

The cell to which the exogenous source of Fez1 protein is provided can have one, two, or even more copies of an altered FEZ1 gene, and can have no normally-functioning copy of this gene. It is contemplated that, in most instances, this method will be employed in situations in which it is recognized that a tissue in a human patient comprises cells which do not express a wild type FEZ1 gene, or which express it at an abnormally low level. Expression of FEZ1 in a cell is considered to be abnormally low when less than about 50, 49, 48, . . . , 40, 39, 38, . . . , 30, . . . , 20, . . . , 10, . . . 5, . . . , or 1 percent of the level of expression of FEZ1 observed in non-cancerous cells of the same type is observed in the cell. The cell may, for example, be a cell which is recognizable as a tumor cell, a cell which is abnormally proliferating but not yet recognizable as a tumor cell, a metastatic cancer cell, a cell which is predisposed to abnormal proliferation but not yet recognizable as a tumor cell, or a cell which has an altered FEZ1 gene but is not proliferating abnormally at the time the exogenous source of Fez1 protein is provided to the cell. The cell is preferably an epithelial cell, such as a breast epithelial cell, a prostate epithelial cell, an esophageal epithelial cell, a lung epithelial cell, or an epidermal epithelial cell.

The altered FEZ1 gene may, for example, be one which is not transcribed in the cell, one which is transcribed to generate a transcript that is incorrectly spliced, one which comprises at least one mutation which reduces or abolishes the normal function of Fez1 protein, one which is transcribed but not translated, or one which has been partially or deleted from the genome of the cell.

The exogenous source of Fez1 protein may, for example, be a composition comprising an isolated human Fez1 protein of the invention, as described herein. Alternatively, the Fez1 protein can be a functional fragment or analog of Fez1 protein (i.e. a fragment of Fez1 or a peptidomimetic having structure similar to all or a portion of Fez1 protein, wherein the fragment or analog exhibits one or more of the physiological activities of Fez1 protein, such as inhibition of tubulin polymerization). The Fez1 protein is preferably a human Fez1 protein or a human Fez1 protein having one or more conservative amino acid residue substitutions. Preferably, the amino acid sequence of the Fez1 protein is completely homologous with the amino acid sequence of the Fez1 protein normally encoded by the FEZ1 gene of the cell. In one embodiment, the amino acid sequence of the Fez1 protein is SEQ ID NO: 4. The isolated Fez1 protein provided to the cell may, as described herein, be expressed in vitro, isolated from an organism which has been transformed with a FEZ1 gene, or isolated from a naturally-occurring source. For example, the Fez1 protein can be isolated from cultured cells of a patient for provision to other cells of the same patient, either in vivo or ex vivo. Further by way of example, the Fez1 protein can be isolated from cultured human or bacterial cells which have been transformed using an expression vector comprising a polynucleotide encoding at least the coding portion of a human FEZ1 gene (e.g. SEQ ID NO: 1, SEQ ID NO: 2, or SEQ ID NO: 3), and preferably at least the coding portion of a human FEZ1 gene obtained from the patient to whom the Fez1 protein is to be administered.

As described herein, the Fez1 protein can be administered to a human in numerous pharmaceutical compositions. Preferably, the composition is one which is known in the art for providing proteins to the interior of a cell (e.g. liposomes, membrane vesicles, microspheres having an aqueous core, protein-coated projected particles, etc.).

The exogenous source of Fez1 protein can also, for example, be an expression vector comprising a polynucleotide having at least one coding region which encodes a functional Fez1 protein. When the polynucleotide is expressed in the cell, Fez1 protein is provided to the cell. Preferably, the polynucleotide encodes a human Fez1 protein or a human Fez1 protein having one or more conservative amino acid residue substitutions. Preferably, the amino acid sequence of the Fez1 protein is completely homologous with the amino acid sequence of the Fez1 protein normally encoded by the FEZ1 gene of the cell. In one embodiment, the amino acid sequence of the Fez1 protein is SEQ ID NO: 4. In another embodiment, the polynucleotide comprises a portion having the nucleotide sequence SEQ ID NO: 2. Also preferably, the polynucleotide comprises a portion which is substantially homologous, and more preferably completely homologous, with the wild-type genomic sequence of the FEZ1 gene of the patient to whose cell(s) the polynucleotide is provided. For example, the polynucleotide can comprise a portion which is substantially or completely homologous with SEQ ID NO: 1. The polynucleotide may, of course, be an isolated polynucleotide of the invention, as described elsewhere herein, so long as the isolated polynucleotide encodes a functional Fez1 protein.

Nucleic acid-containing vectors, including expression vectors, are well known in the art, as are methods of targeting such vectors such that they provide the nucleic acid of the vector preferentially or exclusively to cells of certain types or to cells located primarily or only within certain tissues. Exemplary expression vectors include both non-viral vectors (e.g. plasmids, naked DNA, DNA complexed with a polycation such as polylysine, and the like) and viral vectors such as retroviral, adenoviral, and adeno-associated viral vectors. The use of all such vectors is contemplated, and the selection of an appropriate vector is within the level of ordinary skill in the art, in light of the disclosure provided herein, the size, composition, and characteristics of the nucleic acid, the symptoms and condition of the patient to whom the nucleic acid is to be provided, and the characteristics of the vector.

As described elsewhere herein, the polynucleotide can be an expression vector in which the portion(s) of the polynucleotide which encode the Fez1 protein is operably linked with a promoter. The promoter can be a constitutive promoter, an inducible promoter, a tissue-specific promoter, or substantially any other promoter, although mammalian, and particularly human, promoters are preferred. In one embodiment, the promoter of the expression vector is a normal human FEZ1 promoter region. In another embodiment, the promoter is an inducible promoter, and this therapeutic method further comprises administering an inducer of the promoter to the cell to which the polynucleotide is provided. In another embodiment, the promoter is a tissue-specific promoter which normally promotes expression of genes operably linked therewith in an epithelial tissue. In another embodiment, an expressible portion of the FEZ1 gene is contained in the expression vector and is operably linked with a genetic element which can be used to cease FEZ1 expression. Numerous genetic elements of this type are known, including, for example, those associated with the Cre-loxP system (Pluck, Intl. J. Exp. Pathol. 77:269–278; Li et al., 1997, Human Gene Ther. 8:1695–1700; Lewandoski et al., 1997, Nature Genet. 17:223–225; Russ et al., 1996, J. Virol. 70:4927–4932; Sakai et al., 1995, Biochem. Biophys. Res. Comm. 217:393–401; de Wit et al., 1998, Nucl. Acids Res. 26:676–678).

The invention also includes a method of preventing tumorigenesis in a human cell. This method comprises providing to the cell an expression vector comprising a polynucleotide having at least one coding region which encodes a functional Fez1 protein. Fez1 protein is thereby expressed in the cell, and tumorigenesis is thereby prevented in the cell. The cell may, for example, be one in which an altered FEZ1 gene has been detected, a cell of a tissue in which an altered FEZ1 gene has been detected, a normal cell in an individual predisposed to FEZ1 gene alteration (e.g. a human having a family history of FEZ1 gene alterations), or a normal cell in a normal individual. Preferably, the cell is an epithelial cell. The polynucleotide can be any of those described herein for modulating proliferation of a human cell having an altered FEZ1 gene.

The invention also relates to a method of reversibly inducing proliferation of a cell. This method comprises providing an inhibitor of FEZ1 gene expression to the interior of the cell. Proliferation of the cell is induced when the inhibitor is present in the interior of the cell, but is not induced when the inhibitor is not present in the interior of the cell. This method is useful to promote proliferation of desirable cells, either in vitro or in vivo. Examples of situations in which it would be advantageous to induce cell proliferation include, but are not limited to, when a tissue has been grafted from a location in one animal to another location in the same or a different animal (e.g. a skin allograft or a bone marrow transplant), when a mixture of desirable and undesirable cells has been treated to remove or kill undesirable cells (e.g. radiation therapy or chemotherapy of a partially cancerous tissue), or when healing of a wounded tissue is desired (e.g. healing of a skin puncture or incision).

The inhibitor used in this method can be an ASO, such as one of the isolated polynucleotides of the invention, or it can be a compound identified using one of the screening methods of the invention as an inhibitor of FEZ1 gene expression. If the inhibitor is capable of diffusing across the cell membrane, then it is not necessary to use a vector to deliver the inhibitor to the interior of the cell, otherwise, use of a vector to deliver the inhibitor to the interior of the cell. Any vector known in the art, such as any of those described herein, can be used for this purpose.

Use of an ASO is preferred for reversibly inhibiting FEZ1 gene expression. Useful ASO compositions are described elsewhere herein. According to this method, the ASO may, for example, be administered to the cell in the form a naked nucleic acid, a nucleic acid complexed with a polycationic or other condensing agent, a nucleic acid vector such as a plasmid or a virus vector, or the like. The ASO can be provided to the interior of the cell directly, or an expression vector encoding the ASO can be provided to the interior of the cell. When such an expression vector is used, it is preferred that the expression of the ASO be regulatable. By way of example, the polynucleotide encoding the ASO can be operably linked with an inducible promoter, whereby the ASO is produced only when the inducer of the promoter is provided to the cell. Alternately, the expression vector can be incapable of being replicated. Examples of such replication-deficient vectors include, but are not limited to, plasmids which lack an origin of replication and replication-deficient virus vectors (e.g. replication-deficient adenovirus vectors). The mechanism by which expression of the ASO is regulated is not critical; instead, it is important that expression of the ASO can be halted or severely limited when desired.

When an isolated polynucleotide of the invention or an isolated FEZ1 protein of the invention is administered to an animal, such as a human, for diagnostic, therapeutic, or other purposes, the polynucleotide or protein is preferably in the form of a pharmaceutical composition.

The invention includes a method of inhibiting tumorigenesis in a human. This method comprising administering to the human a compound selected from the group consisting of an inducer of FEZ1 gene expression, an enhancer of FEZ1 gene expression, a inhibitor of Fez1 phosphorylation, an enhancer of phosphorylated-Fez1 dephosphorylation, an agent that inhibits binding of Fez1 with EF1-γ, and an agent that inhibits binding of Fez1 with tubulin.

Pharmaceutical Compositions of the Invention

The invention encompasses the preparation and use of medicaments and pharmaceutical compositions comprising either Fez-1 protein, or another compound described herein as an active ingredient. The isolated polynucleotide of the invention may, as described herein, be provided in the form of a nucleic acid vector, including, but not limited to, an expression vector.

The pharmaceutical compositions of the invention can consist of one or more active ingredients alone, in a form suitable for administration to a subject, or the pharmaceutical composition can comprise one or more active ingredients and one or more pharmaceutically acceptable carriers, one or more additional ingredients, or some combination of these. Administration of one of these pharmaceutical compositions to a subject is useful for performing any of the methods of the invention, as described elsewhere in the present disclosure. The active ingredient can be present in the pharmaceutical composition in the form of a physiologically acceptable ester or salt, such as in combination with a physiologically acceptable cation or anion, as is well known in the art.

The formulations of the pharmaceutical compositions described herein can be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the invention can be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

In addition to the active ingredient, a pharmaceutical composition of the invention can further comprise one or more additional pharmaceutically active agents.

Controlled- or sustained-release formulations of a pharmaceutical composition of the invention can be made using conventional technology.

A formulation of a pharmaceutical composition of the invention suitable for oral administration can be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets can be non-coated or they can be coated using known methods to achieve delayed disintegration in the gastrointestinal tract of a subject, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin.

Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Liquid formulations of a pharmaceutical composition of the invention which are suitable for oral administration can be prepared, packaged, and sold either in liquid form or in the form of a dry product intended for reconstitution with water or another suitable vehicle prior to use.

Liquid suspensions can be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions can further comprise one or more additional ingredients including, but not limited to, suspending agents, dispersing or wetting agents, emulsifying agents, demulcents, preservatives, buffers, salts, flavorings, coloring agents, and sweetening agents. Oily suspensions can further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention can be prepared using known methods. Such formulations can be administered directly to a subject, used, for example, to form tablets, to fill capsules, or to prepare an aqueous or oily suspension or solution by addition of an aqueous or oily vehicle thereto. Each of these formulations can further comprise one or more of dispersing or wetting agent, a suspending agent, and a preservative. Additional excipients, such as fillers and sweetening, flavoring, or coloring agents, can also be included in these formulations.

A pharmaceutical composition of the invention can also be prepared, packaged, or sold in the form of oil-in-water emulsion or a water-in-oil emulsion. The oily phase can be a vegetable oil such as olive or arachis oil, a mineral oil such as liquid paraffin, or a combination of these. Such compositions can further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions can also contain additional ingredients including, for example, sweetening or flavoring agents.

A pharmaceutical composition of the invention can be prepared, packaged, or sold in a formulation suitable for rectal administration. Such a composition can be in the form of, for example, a suppository, a retention enema preparation, and a solution for rectal or colonic irrigation.

Suppository formulations can be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations can further comprise various additional ingredients including, but not limited to, antioxidants and preservatives.

Retention enema preparations or solutions for rectal or colonic irrigation can be made by combining the active ingredient with a pharmaceutically acceptable liquid carrier. As is well known in the art, enema preparations can be administered using, and can be packaged within, a delivery device adapted to the rectal anatomy of the subject. Enema preparations can further comprise various additional ingredients including, but not limited to, antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation can be made by combining the active ingredient with a pharmaceutically acceptable liquid carrier. As is well known in the art, douche preparations can be administered using, and can be packaged within, a delivery device adapted to the vaginal anatomy of the subject. Douche preparations can further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous, intraarterial, intramuscular, or intrasternal injection and intravenous, intraarterial, or kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations can further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration can further comprise one or more of the additional ingredients described herein.

A pharmaceutical composition of the invention can be prepared, packaged, or sold in a formulation suitable for pulmonary administration via the buccal cavity. Such a formulation can comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery can also provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and can further comprise one or more of the additional ingredients described herein.

A pharmaceutical composition of the invention can be prepared, packaged, or sold in a formulation suitable for buccal administration. Such formulations may, for example, be in the form of tablets or lozenges made using, conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and can further comprise one or more of the additional ingredients described herein.

A pharmaceutical composition of the invention can be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops can further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which can be included in the pharmaceutical compositions of the invention are known in the art and described, for example in Genaro, ed., 1985*, Remingon's Pharmaceutical Sciences*, Mack Publishing Co., Easton, Pa., which is incorporated herein by reference.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition can comprise between 0.1% and 100% (w/w) active ingredient. A unit dose of a pharmaceutical composition of the invention will depend upon the type of active ingredient contained therein. Generally, pharmaceutical compositions which comprise an expression vector should be administered in an amount sufficient to provide at least one expression vector to the cell(s) being treated. It is understood that the precise dosage of the vector will depend upon the efficiency with which the vector enters and transforms target cells, the number of such cells to be treated, the physical accessibility of the cells to the vector, and other factors which will be understood by the skilled in light of the present disclosure. Pharmaceutical compositions comprising an expression vector are preferably administered in an amount sufficient to provide a two-, five-, ten-, or fifty-fold excess, or more, of the minimum recommended amount of the vector to individual cells. Pharmaceutical compositions comprising an ASO should be administered in an amount sufficient to provide at least a quantity of ASO molecules equal to at least the expected or determined number of genomic copies of the ASO target or transcripts thereof. Pharmaceutical compositions comprising an ASO are preferably administered in an amount sufficient to provide a two-, ten-, one hundred-, or one thousand-fold excess, or more, of the minimum recommended amount of the ASO to the target cells.

It is understood that the ordinarily skilled physician or veterinarian will readily determine and prescribe an effective amount of the active ingredient(s) for performing the methods of the invention in a subject. In so proceeding, the physician or veterinarian may, for example, prescribe a relatively low dose at first, subsequently increasing the dose until an appropriate response is obtained. It is further understood, however, that the specific dose level for any particular subject will depend upon a variety of factors including the activity of the specific compound employed, the age, body weight, general health, gender, and diet of the subject, the time of administration, the route of administration, the rate of excretion, any drug combination, and the severity of the condition being treated.

Another aspect of the invention relates to a kit comprising a pharmaceutical composition of the invention and an instructional material. The instructional material of the kit of the invention may, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a subject. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage measuring container. The kit can further comprise an instructional material as described herein.

Screening Methods of the Invention

Identification of the human FEZ1 gene as a tumor suppressor gene, as described herein, provides a means for identifying compounds which induce cell proliferation. Also, because some altered FEZ1 genes associated with cancers in humans can prove to be capable of expression at normal, or near normal, levels in the presence of certain compounds, a method is provided for identifying such compounds, which can inhibit abnormal cell proliferation in cells having an altered FEZ1 gene, such as tumor cells and tissues.

The invention therefore includes a method of determining whether a test compound is an inducer of cell proliferation. This method comprises incubating a cell which comprises a functional FEZ1 gene in the presence of the test compound and assessing expression of FEZ1 in the cell. If expression of FEZ1 in the cell is decreased relative to expression of FEZ1 in a cell of the same type incubated in the absence of the test compound, then the test compound is an inducer of cell proliferation. Particularly contemplated test compounds include isolated polynucleotides of the invention, as described herein. This method is therefore a useful way to identify ASOs which inhibit expression of FEZ1 and which therefore induce cell proliferation.

The cell which is used in this method can be substantially any cell which expresses a FEZ1 gene, such as one which transcribes the FEZ1 gene or one which both transcribes and translates FEZ1. Preferably, the cell is a human cell, and it is more preferably an epithelial cell. When identification of a compound which induces proliferation of a certain cell type is desired, it is preferred that the cell used in this screening method be a cell of that certain type.

Expression of FEZ1 in the cell can be assessed by any known method of assessing gene expression. For example, the accumulated or steady-state amount of a transcript of FEZ1 or the rate of production of such a transcript in the cell of the screening method can be assessed using known methods. Alternately, the accumulated or steady-state amount of Fez1 protein or the rate of production of Fez1 protein can be assessed, likewise using known methods, including immunological methods involving an antibody of the invention.

The test compound can be administered to the cell in substantially any way. Preferably, the cell is incubated in a medium comprising the test compound. Where the test compound does not readily pass from the medium to the interior of the cell (e.g. the test compound is a protein or a large nucleic acid in a form which does not normally cross cell membranes) a vector can be used to deliver the test compound to the interior of the cell. However, because the screening method is intended to identify compounds which can be administered to a cell in the most convenient and physiologically acceptable form possible, it is preferred that the test compound not require a vector in order to reach the interior of the cell. Of course, it is understood that if no effective test compounds can be identified which do not require a vector in order to gain cell entry, it can be advantageous to assess the effectiveness of vector-borne test compounds.

It is not necessary that expression of FEZ1 be assessed in a cell of the same type every time a test compound is assayed. Instead, a body of data can be developed which relate to the level of FEZ1 expression in such a cell under the conditions used to assay the test compound.

The invention also relates to a method of determining whether a test compound is effective to retard proliferation of a cell having an altered FEZ1 gene. This method comprises incubating the cell having an altered FEZ1 gene in the presence of the test compound and assessing expression of FEZ1 in the cell. If expression of FEZ1 in the cell is increased, relative to expression of FEZ1 in a cell of the same type (i.e. also having the same altered FEZ1 gene) incubated in the absence of the test compound, then the test compound is effective to retard proliferation of a cell. This result furthermore indicates that the test compound is a useful cancer therapeutic compound for treating cancer in a tissue which comprises cells of the type used in this screening assay. This screening method is performed in substantially the same manner as the screening method described in the preceding paragraphs, except that the cell used in the screening method has an altered FEZ1 gene.

The presence of a leucine-zipper-like region in the putative amino acid sequence of Fez1 protein, as described herein, suggests that Fez1 protein is a nucleic acid-binding protein. This information indicates that it is possible to identify at least one nucleic acid sequence with which Fez1 protein binds by contacting Fez1 protein with a test nucleic acid sequence and assessing whether the protein and the nucleic acid form a complex. Any known method for detecting such complexes can be used, including, but not limited to, nucleic acid footprint methods, altered gel electrophoresis mobility methods, altered chromatographic mobility methods, immunological methods involving an antibody of the invention. Once such a sequence has been identified, a nucleic acid comprising that sequence can be used as an inducer of cell proliferation by delivering such a nucleic acid to a cell comprising a functional Fez1 protein. The nucleic acid binds with the Fez1 protein in the cell, preventing Fez1 from binding with its normal physiological binding partner, and thereby inducing cell proliferation. In such a method, the nucleic acid is preferably used in great excess (e.g. 10-, 100-, or 1000-fold or more excess) of the intracellular concentration of Fez1 protein.

The screening methods of the invention can be used to identify anti-cancer therapeutic compounds for administration to a human afflicted with a cancer by identifying test compounds a inducers of altered FEZ1 gene expression. Because the human FEZ1 gene can be altered in numerous ways in various cancers and in different individuals, it is advantageous to perform the screening methods of the invention using cells obtained from the patient to be treated. In order to facilitate such treatment, components used in these assay methods can be conveniently packaged in the form of a kit comprising a plurality of candidate anti-cancer therapeutic compounds and a reagent for assessing expression of FEZ1 in the patient's cells. In one embodiment, the reagent is an isolated polynucleotide which anneals with high stringency with a human FEZ1 gene, such as an isolated polynucleotide which anneals with high stringency with at least twenty consecutive nucleotide residues of at least one strand of SEQ ID NO: 1. In another embodiment, the reagent is the antibody of the invention, as described herein.

The invention includes a screening method for determining whether a test compound is useful for alleviating a disorder associated with aberrant tubulin polymerization. This method comprising comparing (i) tubulin polymerization in a first assay mixture which comprises tubulin, Fez1, and the test compound and (ii) tubulin polymerization in a second assay mixture which comprises tubulin and Fez1, but which does not comprise the test compound.

A difference (e.g. a difference between the rate of tubulin polymerization in the first and second assay mixtures or a difference between the extent of tubulin polymerization in the first and second assay mixtures between tubulin polymerization in the first and second assay mixtures) is an indication that the test compound is useful for alleviating the disorder. Preferably, the first and second assay mixtures are substantially identical, but for the presence or absence of the test compound.

Disorders which can test compounds can be tested include both tubulin hyperpolymerization disorders and tubulin hypopolymerization disorders. For example, the disorder can be one selected from the group consisting of a disorder associated with aberrant initiation of mitosis, a disorder associated with aberrant modulation of the rate and stage of mitosis, a disorder associated with aberrant modulation of the initiation and rate of cell proliferation, a disorder associated with aberrant modulation of the initiation and rate of cell growth, a disorder associated with aberrant modulation of cell shape, a disorder associated with aberrant modulation of cell rigidity, a disorder associated with aberrant modulation of cell motility, a disorder associated with aberrant modulation of the rate of cellular DNA replication, a disorder associated with aberrant modulation of the stage of cellular DNA replication, a disorder associated with aberrant modulation of the intracellular distribution of organelles, a disorder associated with aberrant modulating the metastatic potential of a cell, and a disorder associated with aberrant modulation of cellular transformation from a non-cancerous to a cancerous phenotype. Particular examples of such disorders include tumorigenesis, tumor survival, tumor growth, and tumor metastasis.

The test compound used in this screening method can be substantially any compound. Compounds which are anticipated to be particularly likely to be useful for alleviating such disorders include ones selected from the group consisting of a fragment of Fez1, a peptidomimetic of a fragment of Fez1, a fragment of tubulin, a peptidomimetic of a fragment of tubulin, a fragment of EF1-γ, and a peptidomimetic of a fragment of EF1-γ.

The invention includes another screening method for determining whether a test compound is useful for alleviating a disorder associated with aberrant phosphorylation of Fez1. This method comprises comparing (i) phosphorylation of Fez1 in a first assay mixture which comprises Fez1, at least one kinase, a phosphate source, and the test compound and (ii) phosphorylation of Fez1 in a second assay mixture which comprises Fez1, the kinase, and the phosphate source, but which does not comprise the test compound. A difference between phosphorylation of Fez1 in the first and second assay mixtures (e.g. a difference in the rate or degree of phosphorylation in the first and second assay mixtures) is an indication that the test compound is useful for alleviating the disorder. This screening method can be used to assess the utility of compounds for alleviating the same disorders referred to above.

The invention includes yet another screening method for determining whether a test compound is useful for alleviating a disorder associated with aberrant phosphorylation of Fez1. This method comprising comparing (i) phosphorylation of Fez1 in a first assay mixture which comprises phosphorylated Fez1, at least one phosphatase, and the test compound and (ii) phosphorylation of Fez1 in a second assay mixture which comprises phosphorylated Fez1 and the phosphatase, but which does not comprise the test compound.

A difference between phosphorylation of Fez1 in the first and second assay mixtures (e.g. a difference in the rate or extent of de-phosphorylation of phosphorylated Fez1) is an indication that the test compound is useful for alleviating the disorder. This screening method can be used to assess the utility of compounds for alleviating the same disorders referred to above.

The invention also includes a method of determining whether a test compound is useful for alleviating a disorder associated with aberrant binding of Fez1 with a protein with which Fez1 normally binds, the method comprising comparing (i) binding between Fez1 and the protein in a first assay mixture which comprises Fez1, the protein, and the test compound and (ii) binding between Fez1 and the protein in a second assay mixture which comprises Fez1 and the protein, but which does not comprise the test compound. A difference between (e.g. the rate or degree of) binding of Fez1 and the protein in the first and second assay mixtures is an indication that the test compound is useful for alleviating the disorder. The protein can, for example, be selected from the group consisting of tubulin and EF1-γ. This screening method is useful for assessing the utility of a test compound for alleviating a disorders such as one of tumorigenesis, tumor survival, tumor growth, and tumor metastasis.

The invention includes a method of determining whether a test compound is an inhibitor of cell proliferation. This method comprises incubating a cell which comprises a functional FEZ1 gene in the presence of the test compound and assessing expression of FEZ1 in the cell. If expression of FEZ1 in the cell is increased, relative to expression of FEZ1 in a cell of the same type incubated in the absence of the test compound, then this is an indication that the test compound is an inhibitor of cell proliferation.

Cell Proliferation Methods of the Invention

As described herein, the human FEZ1 gene has been discovered to be a tumor suppressor gene. Thus, inactivation of this gene, or inhibition of expression of this gene, leads to the enhanced rate of cell proliferation associated with cancer. In certain situations, however, enhanced cell proliferation is desirable. For example, some in vitro cell culture methods are limited by the rate of cell proliferation and by effects of cell density on this rate. Further by way of example, in certain medical procedures, such as in bone marrow transplants and skin allografts, it is desirable that cells proliferate at a greater-than-normal rate for a period and subsequently proliferate only at a normal rate. These methods would be enhanced if cell proliferation could be enhanced, especially if it could be enhanced in a reversible manner.

Providing a cell with an inhibitor of FEZ1 expression enhances the rate of proliferation of the cell, and this technique can be used to improve a variety of known methods in which the rate of cell proliferation was a limiting factor. For example, by including an inhibitor of FEZ1 expression in a cell culture medium, or by treating cells (e.g. human epithelial cells) growing on or in such medium with such an inhibitor, the in vitro rate of cell proliferation can be increased, permitting faster and denser cell growth than would otherwise be possible.

Similarly, by treating human cells, especially epithelial cells, in vivo with an inhibitor of FEZ1 expression, the rate of proliferation of those cells can be increased. This method can be used, for example to enhance graft integration into the graft site or to improve reestablishment of bone marrow in an individual who has been subjected to levels of radiation or cytotoxic chemicals that are sufficient to cause bone marrow loss. Local administration of the inhibitor to the tissue(s) or region(s) in which enhanced cell proliferation is desired minimizes undesirable cell proliferation in other tissues and at other body regions. Discontinuing administration of the inhibitor leads eventually to normal cell proliferation of treated cells, owing to degradation of the inhibitor.

Likewise, cells obtained from a human can be treated ex vivo with an inhibitor of FEZ1 expression to enhance their rate of proliferation prior to implanting those cells within the same human from which they were obtained or within a different human. The same or a different inhibitor of FEZ1 expression can be administered, locally or systemically, to the human cell recipient in order to maintain the enhanced rate of proliferation of the treated cells, or the cells can instead be permitted to retain their enhanced rate of proliferation only so long as the inhibitor delivered to them ex vivo endures. In either event, the ex vivo treated cells assume a normal rate of proliferation after the inhibitor(s) are degraded and not replaced.

In the cell proliferation enhancement methods described herein, the inhibitor of FEZ1 expression can optionally be a molecule which is capable of being replicated in a human cell, such as a virus vector encoding such an inhibitor, for example. Where it is considered desirable to be able to reversibly induce enhanced cell proliferation, the inhibitor is preferably not capable of being replicated in a human cell. Furthermore, in some embodiments, it is preferable that the inhibitor be provided to the cells in the form of a vector which comprises a polynucleotide encoding the inhibitor, and that the polynucleotide be operably linked to an inducible promoter, so that production of the inhibitor can be initiated and concluded by administration and withholding, respectively, of the inducer of the promoter.

Kits of the Invention

The invention includes various kits which comprise any two or more of the isolated polynucleotides of the invention, the isolated Fez1 proteins of the invention, pharmaceutical compositions, and instructional materials which describe use of these polynucleotides and proteins to perform the diagnostic, therapeutic, or screening methods of the invention. Although exemplary kits are described below, the contents of other useful kits will be apparent to the skilled artisan in light of the present disclosure. Each of these kits is included within the invention.

An example of a kit of the invention is a kit for amplifying at least a portion of a human FEZ1 gene. This kit comprising a first isolated polynucleotide and a second isolated polynucleotide, wherein the first isolated polynucleotide anneals with high stringency with at least twenty consecutive nucleotide residues of one strand of a human FEZ1 gene and the second isolated polynucleotide anneals with high stringency with at least twenty consecutive nucleotide residues of the other strand of the gene. For example, the first isolated polynucleotide can be one which anneals with high stringency with at least twenty consecutive nucleotide residues of the coding strand of SEQ ID NO: 1, and the second isolated polynucleotide can be one which anneals with high stringency with at least twenty consecutive nucleotide residues of the non-coding strand of SEQ ID NO: 1. This kit can further comprise other components of a reaction mixture for amplifying a region of a nucleic acid, such as a DNA polymerase (e.g. *Thermus aquaticus* DNA polymerase) or deoxyribonucleotides. Alternately, or in addition, this kit can include an instructional material which describes the polynucleotides as being useful for amplifying a portion of the gene or which describe how to perform such an amplification.

A second example of a kit of the invention is a kit for amplifying at least a portion of a cDNA generated from a transcript of a human FEZ1 gene. This kit comprises a first isolated polynucleotide and a second isolated polynucleotide. The first isolated polynucleotide anneals with high stringency with at least twenty consecutive nucleotide residues of the cDNA, and the second isolated polynucleotide anneals with high stringency with at least twenty consecutive nucleotide residues of the cDNA. In one embodiment of this kit, the first isolated polynucleotide anneals with high stringency with at least twenty consecutive nucleotide residues of the coding strand of SEQ ID NO: 1, and the second isolated polynucleotide anneals with high stringency with at least twenty consecutive nucleotide residues of the non-coding strand of SEQ ID NO: 1.

The invention is now described with reference to the following Examples. These Examples are provided for the purpose of illustration only and the invention is not limited to these Examples, but rather encompass all variations which are evident as a result of the teaching provided herein.

EXAMPLE 1

The FEZ1 Gene at Chromosome Location 8p22 Encodes a Leucine-Zipper Protein, and its Expression is Altered in Multiple Human Tumors Loss of heterozygosity (LOH) at 8p22 is a common characteristic of epithelial tumors, including breast, prostate, and esophageal carcinomas. In the experiments presented in this Example, altered expression and mutations of the FEZ1 gene at 8p22 were demonstrated in numerous cancer cell lines and tumor samples, thereby demonstrating that the FEZ1 gene is at least one of the tumor suppressor genes which had previously been hypothesized to be located near 8p21–22.

As described herein for the first time, FEZ1 encodes a leucine-zipper protein having substantial amino acid sequence similarity to the DNA-binding protein designated Atf-5. FEZ1 expression could not be detected in more than 60% of epithelial tumors and tumor cell lines of various types. Furthermore, transcript analysis of FEZ1-expressing tumor cells indicated the presence of mutations in FEZ1, as evidenced by the presence of sequence abnormalities in the FEZ1 transcript, and the presence of frame-shift mutations, as evidenced by the presence of truncated FEZ1 transcripts. Based on the results described in this Example, it is concluded that alteration or inactivation of FEZ1 is involved in development of multiple human tumors, including epithelial tumors.

The materials and methods used in the experiments presented in this Example are now described.

Esophageal cancer cell lines were cultured in RPMI 1640 medium supplemented with 10% (v/v) fetal bovine serum. Prostate cancer cell lines, breast cancer cell lines, hematological cell lines, and HeLa cells were obtained from the American Type Culture Collection and were cultured as described (Negrini, 1996). Tumor and non-tumor tissue samples were obtained from 72 patients afflicted with primary esophageal cancers, 39 patients afflicted with breast cancers, 24 patients afflicted with prostate cancers, and 8 patients afflicted with ovarian cancers.

Chromosomal DNA was isolated from 53 primary esophageal squamous cell tumors and from matched normal tissue samples obtained from the same patients. These DNA samples were analyzed for allele loss at 22 microsatellite loci on chromosome 8p.

PCR amplification of microsatellite loci using FAM- or TET-labeled primers (Research Genetics, Huntsville, Ala.) were performed as described (Niederacher et al., 1997, Genes Chromosom. Cancer 18:181), with minor modifications. Briefly, PCR was performed using AmpliTaq™ Gold (Perkin Elmer Cetus, Norwalk, Conn.), using the following reaction conditions. After heating the reaction mixture to 95° C. for 12 minutes, a total of 30 PCR cycles were performed. The first 10 cycles consisted of maintaining the reaction mixture at 94° C. for 15 seconds, at 55–58° C. for 15 seconds (to anneal DNA strands), and at 72° C. for 30 seconds. The next 20 cycles consisted of maintaining the reaction mixture at 89° C. for 15 seconds, at 55–58° C. for 15 seconds (to anneal DNA strands), and at 72° C. for 30 seconds. Following these 30 cycles, the reaction mixture was maintained at 72° C. for 30 minutes. Following heat denaturation, the amplified reaction mixtures were loaded on a 6% (w/v) polyacrylamide denaturing gel on the Applied Biosystems model 373 DNA sequencer. Data collection and fragment analysis were performed using ABI Prism™ Genescan and ABI Prism™ Genotyper Analysis Software (Perkin Elmer Cetus, Norwalk, Conn.; Applied Biosystems, Inc., Foster City, Calif.).

LOH was detected as reduction by more than 50% of an allele peak signal in DNA obtained from a tumor sample, relative to the peak signal of the same allele in corresponding normal tissue. If a tumor sample demonstrated 40–60% reduction of an allele peak signal, relative to the corresponding normal tissue, the analyses were repeated two more times, and average reductions were used as final data.

Yeast artificial chromosome (YAC) and bacterial artificial chromosome (BAC) contigs of the region of the genome near the D8S261 marker were constructed. The relative positions of the YAC and BAC contigs, relative to certain microsatellite loci, are indicated in FIG. 1C.

Human chromosome 8p BAC DNA samples were sequenced using primers T7 and SP6 (Research Genetics, Huntsville, Ala.). Southern blot hybridization and PCR analysis indicated that BAC clones overlapped, and contigs were constructed.

PCR amplification was performed using STS (sequence tagged sequences) primers in order to screen a human YAC library obtained from Research Genetics (Huntsville, Ala.). A mixture of YAC clones was embedded in an agarose gel and separated by pulse-field gel electrophoresis (PFGE), as described (Ausubel et al., 1989, In: *Current Protocols in Molecular Biology*, Wiley-Interscience, New York; Bookstein, et al., 1994, Genomics 24:317). Following PFGE, YAC DNA was transferred to a nylon membrane in the presence of 0.4 molar sodium hydroxide, and the membrane was hybridized using human genomic DNA. DNA from individual YAC clones was digested within the gel using MboI for four hours at 37° C. Digested YAC clone DNA was extracted from the gel using a Gene Clean III™ kit obtained from BIO 101, Inc. (La Jolla, Calif.), per the kit instructions.

In order to clone the genes present in YAC clone DNA, two deoxy-oligonucleotides, 5'-GATCTCGACG AATTCGTGAG ACCT-3' (SEQ ID NO: 44) and 5'-TGGTCTCACG AATTCGTCGA-3' (SEQ ID NO: 45), were annealed to form a partially-double stranded adapter-linker. This adapter-linker was ligated to the digested YAC clone DNA. Fifteen cycles of PCR amplifications were performed using 5'-biotinylated primers corresponding to the adapter-linker. PCR products were sequenced and confirmed not to be yeast genomic DNA.

cDNAs were synthesized by reverse transcription of prostate poly$(A)^+$ RNA using NotI-primer adaptor/oligo-dT primers according to the GC rich protocol (Superscript™ Plasmid system; Gibco-BRL, Grand Island, N.Y.). A Sal I adaptor (Gibco-BRL, Grand Island, N.Y.) was ligated to the cDNAs, and those cDNAs were subjected to twenty cycles of PCR amplification using adapter primers.

Blocking, hybridizing, and washing methods were adapted from described procedures (Bookstein et al., 1997, Br. J. Urol. 79(Suppl. 1):28; Bova et al., 1996, Genomics 35:46; MacGrogan et al., 1996, Genomics 35:55; Cher et al., 1994, Genes Chromosom. Cancer 11:153; Bookstein, et al., 1994, Genomics 24:317; Akiyama et al., 1997, Cancer Res. 57:3548). Repetitive sequences were blocked by hybridizing 1–2 micrograms of amplified cDNA with an equal amount (by weight) of Cot-1 DNA (Gibco-BRL, Grand Island, N.Y.) to achieve a final DNA concentration of 80 micrograms per milliliter in 120 millimolar $NaPO_4$ buffer at pH 7. Reaction mixtures were overlaid with mineral oil, heat denatured, and incubated at 60° C. for 20 hours (Cot=20). Biotin-labeled genomic DNA samples were heat-denatured, loaded into Centricon™ 100 centrifugal ultrafiltration units (Amicon, Beverly, Mass.) together with blocked cDNA (1 microgram, excluding Cot-1 DNA), concentrated by centrifugation at 1000×g for 25 minutes, and washed twice with 2 milliliters of 1 millimolar $NaPO_4$ buffer at pH 7. Samples were adjusted to achieve the following concentrations at pH 7: 120 millimolar $NaPO_4$, 1 millimolar EDTA, and about 160 micrograms per milliliter of DNA (excluding Cot-1 DNA). Reaction mixtures were overlaid with mineral oil and incubated at 60° C. for 60 hours (Cot=120).

To prevent non-specific attachment of PCR-amplifiable cDNA to the beads, 10 microliters of an avidin-coated magnetic bead suspension (Dynabeads™ M-280; Dynal, Lake Success, N.Y.) were mixed with 100 micrograms of sonicated salmon sperm DNA at room temperature for 30 minutes. The beads were pre-washed with TE buffer containing 1 molar NaCl, and were then incubated with complete hybridization reaction mixtures in 200 microliters of the same buffer at room temperature for 30 minutes. The beads were collected by using a magnetic concentrator (Dynal, Lake Success, N.Y.), and the supernatant was removed. The beads were washed twice using 0.1×SSC buffer supplemented with 0.1% (w/v) SDS for 15 minutes at room temperature, and were then washed three times using the same buffer at 65° C. Bound cDNA was eluted from beads by mixing the beads with 100 microliters of 50 millimolar NaOH for 15 minutes and then neutralizing the mixture using 100 microliters of 1 molar Tris-HC1 buffer at pH 7.5. cDNA was purified using a PCR purification column (Qiagen™, Chatsworth, Calif.), per the manufacturer's instructions. cDNA was re-amplified by PCR using the same methods and the same conditions. The resulting amplified cDNA products were purified and blocked, and a second round of cDNA selection was performed as described herein.

Amplified cDNA was digested using restriction endonucleases SalI and NotI, cloned directly into pSPORT1 vector (Gibco-BRL, Grand Island, N.Y.), and used to transform *E. coli* cells. CpG island cloning and shotgun sequencing were performed using this cDNA-containing vector. Using these methods, 87 potentially expressed clones were mapped in the YAC contig, as indicated in FIG. 1C.

In CpG island cloning experiments, BAC DNAs were digested using restriction endonucleases BssHII and SacII, which specifically cleave CpG islands. After digestion with Sau3AI, the cleavage products were ligated into a pBK-CMV vector (Stratagene, La Jolla, Calif.), as described (Elvin et al., 1992, In: *Techniques for the analysis of complex genomes: Transcribed sequences in YACs*, Anand, Ed., Academic Press, London, p. 155).

Shotgun sequencing was performed as described (Inoue et al., 1997, Proc. Natl. Acad. Sci. USA 94:14584). Six hundred clones per BAC were picked and sequenced to identify candidate cDNA sequences. cDNA selection were performed for three YAC templates, as indicated in FIG. 1C. Four hundred clones per YAC were picked up from the cDNA selected libraries, and all the clones were sequenced with vector primers. The sequences were analyzed using the BLAST computer software and the NCBI/BLAST database in order to exclude ribosomal or mitochondria-related genes. Fifty percent of clones were ribosomal or mitochondria-related genes, and the remainder were classified and were analyzed.

Two candidates CpG islands were identified from the region near marker D8S233 by CpG island cloning. The BACs were partially sequenced by the shotgun method to determine the presence of sequences matching expressed sequence tags (ESTs) in the nucleotide/EST database of NCBI/BLAST, and two ESTs from the BAC genomic region were thereby identified.

Using these approaches, a total of 123 clones 400–800 base pairs in length were selected and characterized, and 87 of those clones were mapped.

cDNA was synthesized using 2 micrograms of total RNA obtained from human brain, esophagus, or tumor cells or from 150 nanograms of poly(A)$^+$ RNA obtained from one of these cell types using the Superscript II™ plasmid system (Gibco-BRL, Grand Island, N.Y.). The cDNA and an adaptor (Catalog #K1802-1; Clontech, Inc., Palo Alto, Calif.) were ligated to generate RACE templates, and the templates were used in PCR amplification of the cDNA. The chromosomal location of the F37 gene was confirmed by identification of the presence of the F37 gene sequence at 8p22 in a radiation hybrid panel designated Gene Bridge 4™ (Research Genetics, Huntsville, Ala.).

Full-length and 3'-truncated FEZ1 cDNAs were ligated to a expression vector pcDNA3HisA (Invitrogen, Carlsbad, Calif.) and cloned by RT-PCR, using human brain cDNA as a template. The entire nucleotide sequence of the insert cDNA was verified by DNA sequencing. The truncated cDNAs (nucleotides 1–1128 in the FEZ1 ORF) lacked the portion of the ORF located 3'-with respect to the leucine zipper region.

Figure 2A:
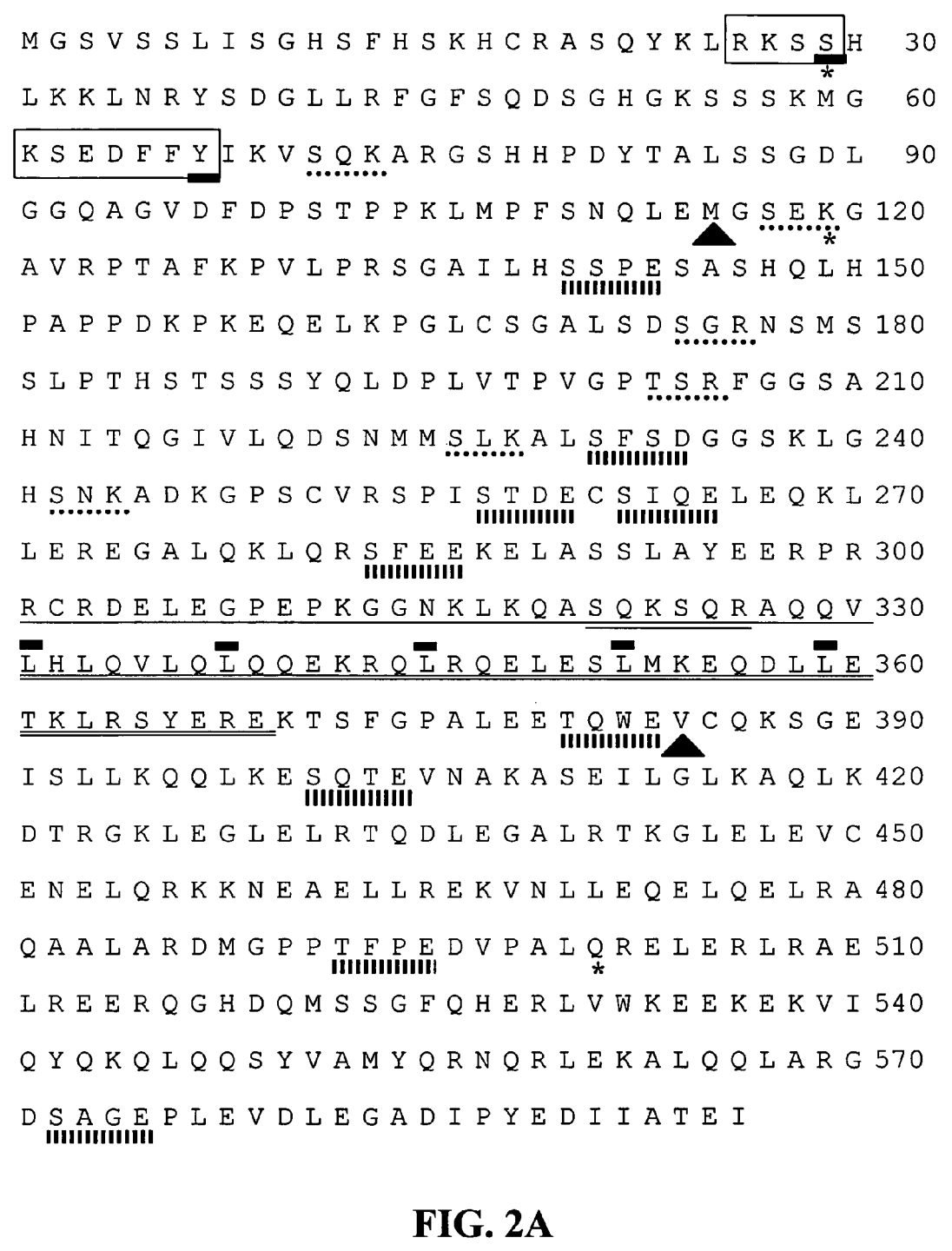
Figure 2C:
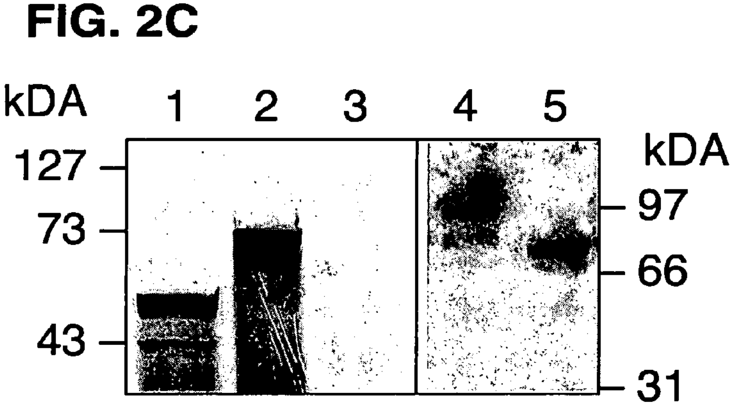
FIG. 2C is an image of SDS-PAGE results as described elsewhere herein.

In vitro transcription and translation was performed using a rabbit reticulocyte system (Quick TNT™, Pharmacia LKB Biotechnology Inc., Piscataway, N.J.), and these reactions were monitored by PAGE. Full-length and 3'-truncated FEZ1 cDNAs were ligated into a glutathione-S-transferase (GST)-fusion expression vector (pGEX; Pharmacia LKB Biotechnology Inc., Piscataway, N.J.), and the proteins encoded by those cDNAs were expressed, extracted, separated by PAGE, and visualized by Coomassie staining, as described (Ausubel et al., 1992, *Current Protocols in Molecular Biology*, John Wiley & Sons, New York). An image of the SDS-PAGE results is shown in FIG. 2C. The protein in lane 1 of that SDS-PAGE was translated from a pcDNA vector which comprised a truncated FEZ1 cDNA lacking the portion of the cDNA located 3'—with respect to the leucine zipper region. The protein in lane 2 was translated from a pcDNA vector which comprised full-length FEZ1 cDNA. The protein in lane 3 was translated from a pcDNA vector having no insert. The protein in lane 3 was translated from a pGEX vector which comprised a truncated FEZ1 cDNA lacking the portion of the cDNA located 3'—with respect to the leucine zipper region.

The nucleotide sequence of the FEZ1 gene open reading frame (ORF; exons 1–3) was analyzed in samples obtained from 194 cancer tissues, regardless of the whether or not FEZ1 was expressed in the tissue. The sampled tissues were obtained from 72 primary esophageal cancers, 18 esophageal cancer cell lines, 24 primary prostate cancers, 3 prostate cancer cell lines, 39 primary breast cancers, 25 breast cancer cell lines, 8 primary ovarian cancers, 4 leukemic cell lines, and one cervical cancer cell line. Nucleotide sequence information was obtained by PCR and sequencing. Eleven pairs of PCR primers, as described herein in the Primer Nucleotide Sequence Table, were used to amplify FEZ1 coding exons 1–3.

Genomic PCR was performed using the same conditions described herein for LOH studies, except that 4% DMSO (w/w) was added to the reaction mixture, and PCR amplifications were performed for 35 cycles, the additional 5 cycles being the same as the 20 cycles described herein. DNA sequencing was performed directly using the purified PCR amplification products. Sequencing reactions and analyses were performed by using the ABI Prism BigDye™ terminator reaction chemistry on the ABI Prism™ 377 DNA sequencing system (Applied Biosystems, Inc., Foster City, Calif.). Sequence data were confirmed by sequencing of duplicate PCR amplification products and by sequencing anti-sense strands using reverse primers.

The results of the experiments presented in this Example are now described.

Figures 1, 1A, 2, 3, 4, 5, 6, 7, 8:
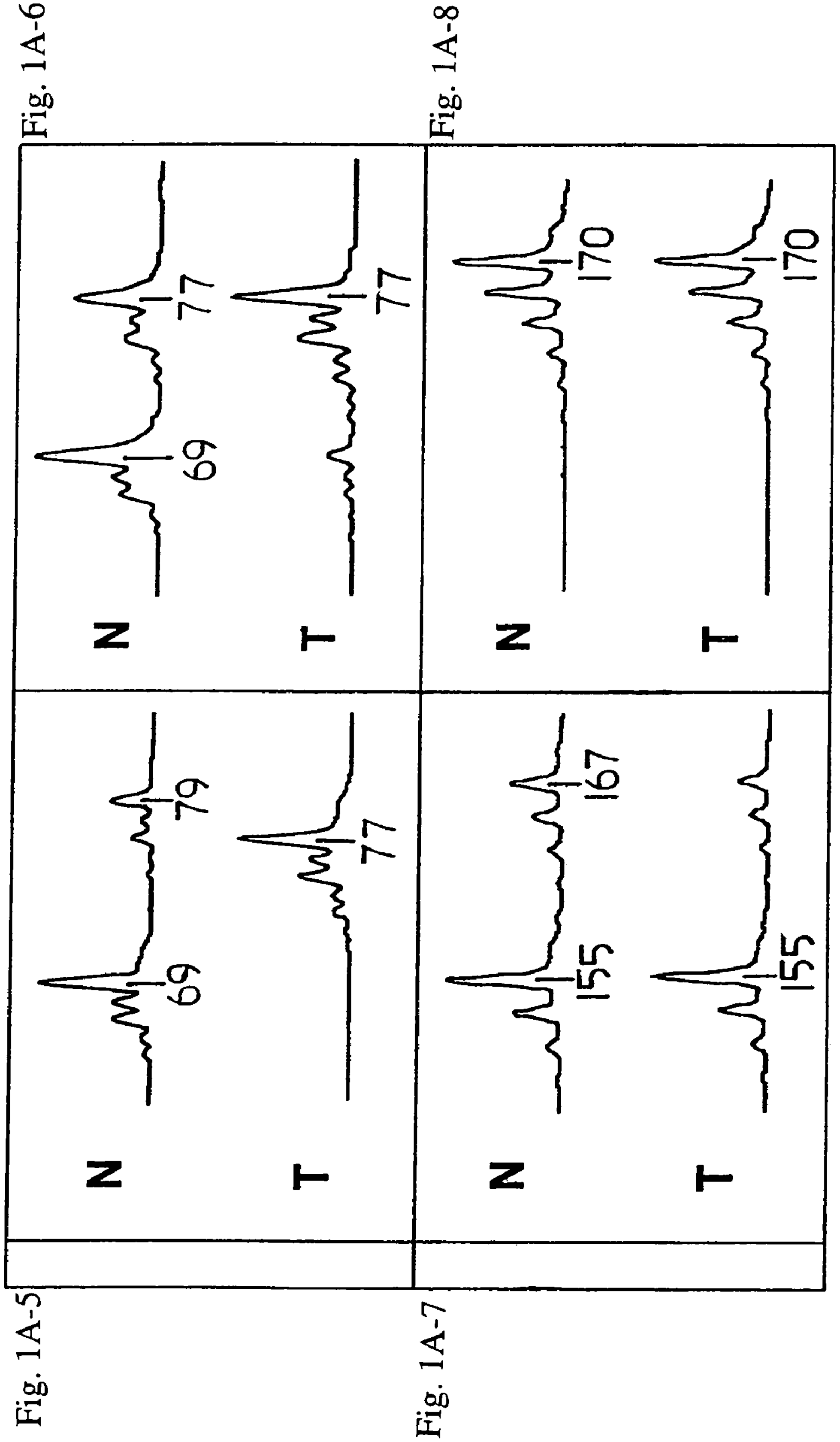
Figure 1B:
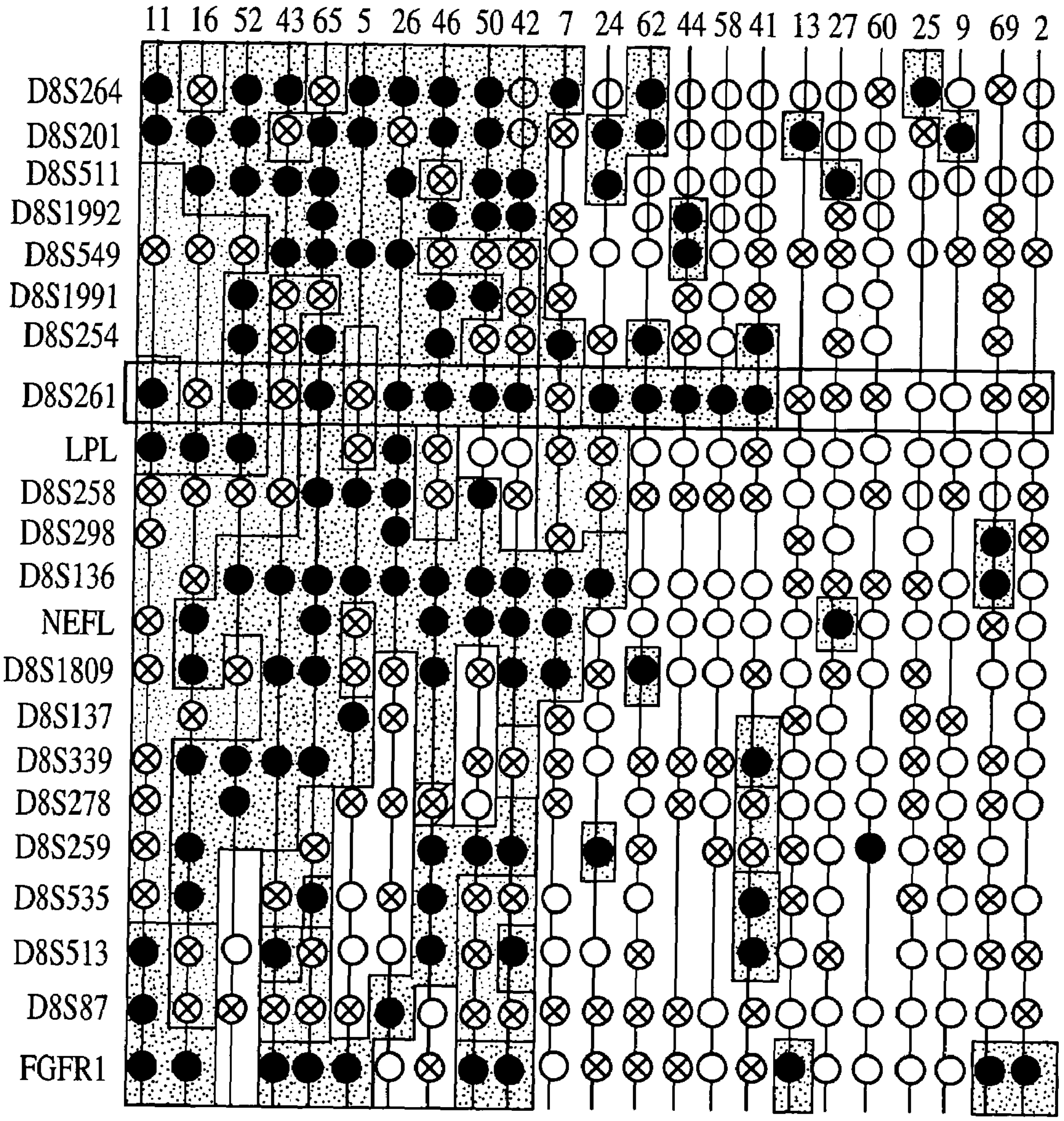
FIG. 1B is a diagram which depicts a summary of LOH analyses described herein. Results for each patient who exhibited LOH at least one locus are shown. Filled circles represent loss of an allele. Circles containing a cross represent non-information results owing to homozygosity at the corresponding locus. Open circles represent retention of both alleles. Cross-hatched areas of the diagram represent regions of allele loss. Hatched areas represent regions of non-informative results within the allele-loss area. The numbers atop each column refer to individual patients. The designation beside each row refer to polymorphic markers. The region near the marker K8S261 locus, described herein is boxed.
Figure 1C:
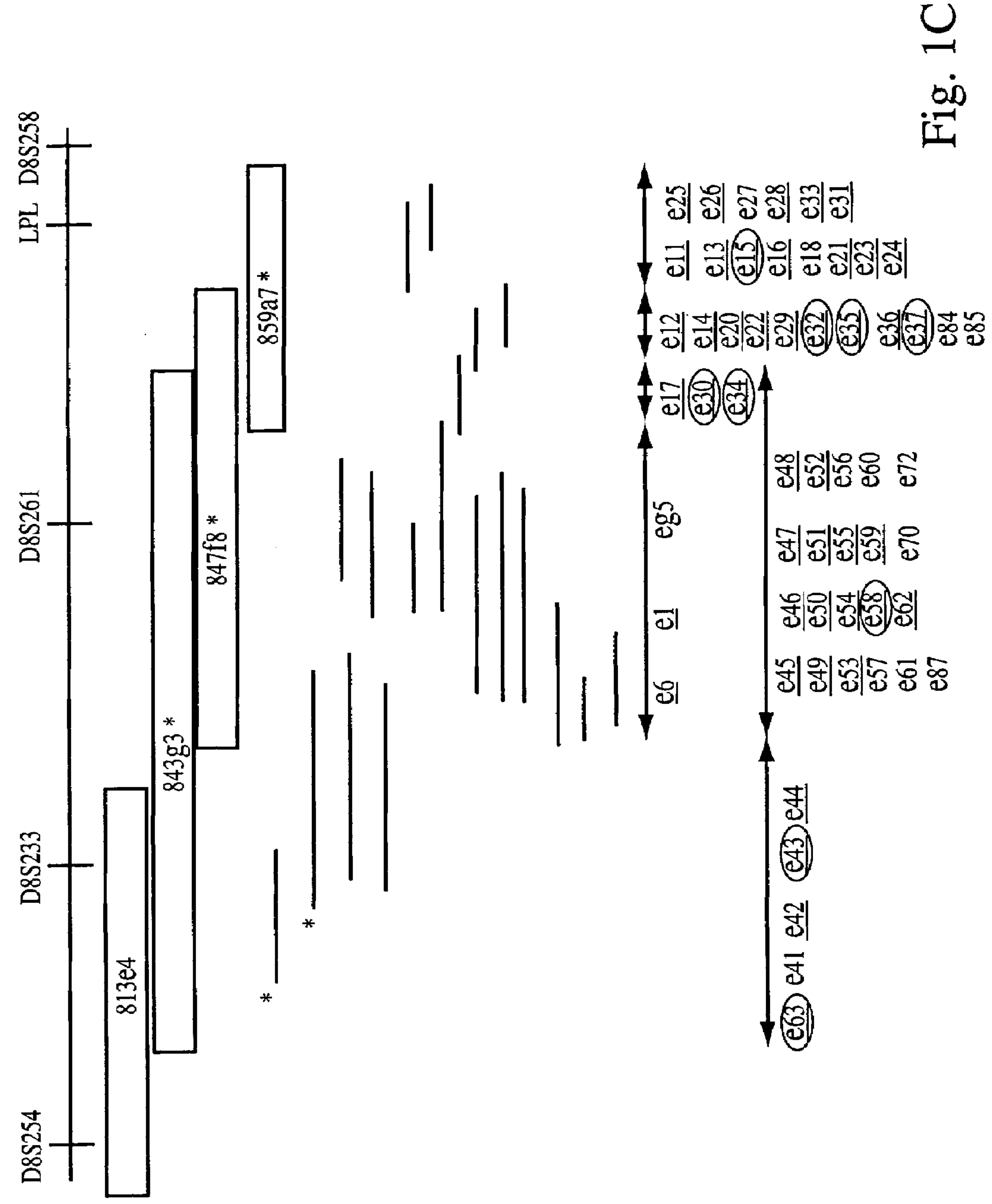
FIG. 1C is a diagram which depicts the approximate locations of genomic contigs at 8p22 which were constructed as described herein. The uppermost line depicts the location of polymorphic loci on 8p. The corresponding locations of YAC contigs (open boxes) and BAC contigs (horizontal lines) are indicated below the 8p map. cDNA selection and shotgun sequencing were performed on YACs and BACs identified by asterisks. Eighty-seven potentially expressed sequences were isolated and located within the contigs; the approximate locations of these sequences are indicated by designations below two-headed arrows. Underlined characters indicate sequences which are expressed in normal tissues. After expression analysis in tumor and normal tissues, 9 cDNAs (circled designations) were subjected to further analysis. Candidate fragment e37 corresponds to the F37 cDNA described herein.

Primary esophageal cancer tissue samples obtained from 23 of 53 patients (43%) exhibited loss of an allele at one or more loci on 8p, as indicated in FIGS. 1A and 1B. For example, tissue samples obtained from patient E26 exhibited LOH at the markers designated D8S264, LPL and D8S136, and allelic retention at the marker designated FGFR1. Tissue samples obtained from patient E46 exhibited LOH at the markers designated D8S264 and D8S136, and the markers designated LPL and FGFR1 loci were homozygous, meaning that loss of an allele from one chromosome could not be detected if it occurred.

Of the 23 tumor samples in which loss of an allele was observed, 16 (70%) exhibited a commonly lost 1.5 megabase region located near the D8S261 loci, and 14 of those 23 patients (61%) exhibited potential common LOH regions located near D8S254. These data suggest that two tumor suppressor genes are located in the chromosome region designated 8p22–23. The experiments described in this Example were focused on the more frequently affected 8p22 region around D8S261. This region is 4–6 megabases centromeric to the MSR region, and overlaps the target region in other tumors, including prostate and breast cancers (Kagan et al., 1995, Oncogene 11:2121; Macoska et al., 1995, Cancer Res. 55:5390; Jenkins et al., 1998, Genes Chromosom. Cancer 21:131; Yaremko et al., 1995, Genes Chromosom. Cancer 13:186; Yaremko et al., 1996, Genes Chromosom. Cancer 16:189; Kerangueven et al., 1997, Cancer Res. 57:5469; Anbazhagan et al., 1998, Am. J. Pathol. 152:815; El-Naggar et al., 1998, Oncogene 16:2983; Sunwoo et al., 1996, Genes Chromosom. Cancer 16:164; Wu et al., 1997, Genes Chromosom. Cancer 20:347).

In order to clone the genes present in this region, cDNA selection, CpG island cloning, and shotgun sequencing were performed. Using these procedures, 87 potentially expressed clones were mapped in the YAC contig, as illustrated in FIG. 1C. RT-PCR amplification was used to select clones which exhibited reduced expression in tumor cells, and indicated that 43 of the 87 clones were expressed in normal adult tissues, including prostate. Nine clones showed reduced or no expression in cancer cells. Rapid amplification of cDNA ends (RACE) was performed, and the sequences of 6 of the 9 clones were extended successfully. Northern blot analyses indicated that expression of 5 clones was not remarkable in cancer cells. In contrast, RACE analysis using an F37 clone, obtained by hybrid selection, indicated that a 6.5 kilobase transcript was expressed in non-cancerous tissues, but that the expression of F37 could not be detected in the LNCaP prostate cancer cell line.

About $6\times10^6$ clones from a human testes cDNA library obtained from Clontech (Palo Alto, Calif.) were screened using probes specific for F37, and the nucleotide sequence of the 5'-end of the cDNA was obtained by the RACE procedures. The F37 probe which was used had the sequence listed in FIG. 5Q. The chromosomal location of the F37 gene was confirmed by presence of the F37 gene sequence at 8p22 in a radiation hybrid panel designated Gene Bridge 4 (Research Genetics, Huntsville, Ala.). These result indicated that the F37 gene is located within 3.36 cR (centirads) of the genetic marker designated WI-5962. F37 cDNA comprises a 1791 base pair open reading frame (ORF) which encodes a 597 amino acid residue protein having a molecular weight of approximately 67 kilodaltons. Homology searching of protein sequence databases indicated the amino acid sequence of F37 comprises a leucine-zipper motif, and that this region has 32% identity (68% similarity) to the DNA-binding domain of a cAMP-responsive activating-transcription factor designated Atf-5 (Hai et al., 1989, Genes Develop. 3:2083). The homology search also indicated that the F37 protein has 38% identity to the protein designated KIAA0552, which consists of 673 amino acids (Nagase et al., 1998, DNA Res. 5:31–39).

Motif analysis software (Searching Protein and Nucleic Acid Sequence Motifs in Genome Net) predicted a cAMP-dependent phosphorylation site, located at Ser 29 of F37, and a predicted tyrosine-kinase phosphorylation site, located at Tyr 67 of F37. The ORF comprised three coding exons. The F37 gene was designated FEZ1 (F37/Esophageal cancer gene encoding leucine-zipper motif). The putative amino acid sequence of Fez1, the protein encoded by FEZ1 is listed in FIG. 2A. Nucleotide residues around the first methionine codon in FEZ1 cDNA were matched using the Kozak recognition rule (Kozak, 1989, J. Cell. Biol. 108:229–241). a 5' in-frame stop codon was identified in the cDNA, located at −111 to −109 from the first methionine codon.

Figure 2D:
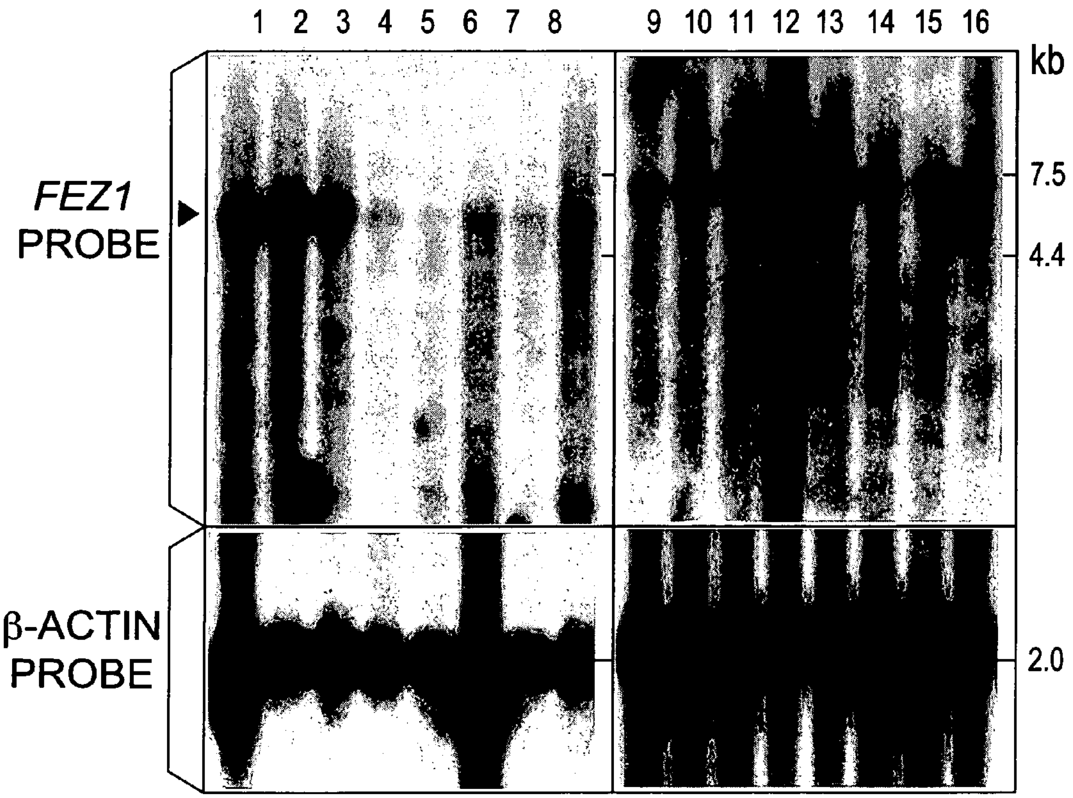
FIG. 2D is an image of Northern blot analysis results which indicate FEZ1 gene expression in normal tissues. In the upper panel, a FEZ1 ORF probe (SEQ ID NO: 3) was used to detect expression of FEZ1. In the lower panel, a beta-actin probe was used, as a control, to detect expression of the beta-actin gene. The arrowhead on the left of the top panel indicates the approximate position of the 6.8 kilobase FEZ1 transcript. Poly(A)$^+$ RNAs (5 micrograms) were obtained from normal (i.e. non-cancerous) tissues, and loaded as follows: lane 1, heart; lane 2, brain; lane 3, placenta; lane 4, lung; lane 5, liver; lane 6, skeletal muscle; lane 7, kidney; lane 8, pancreas; lane 9, spleen; lane 10, thymus; lane 11, prostate; lane 12, testes; lane 13, ovary; lane 14, small intestine; lane 15, colon; and lane 16, peripheral blood lymphocyte.
Figure 3A:
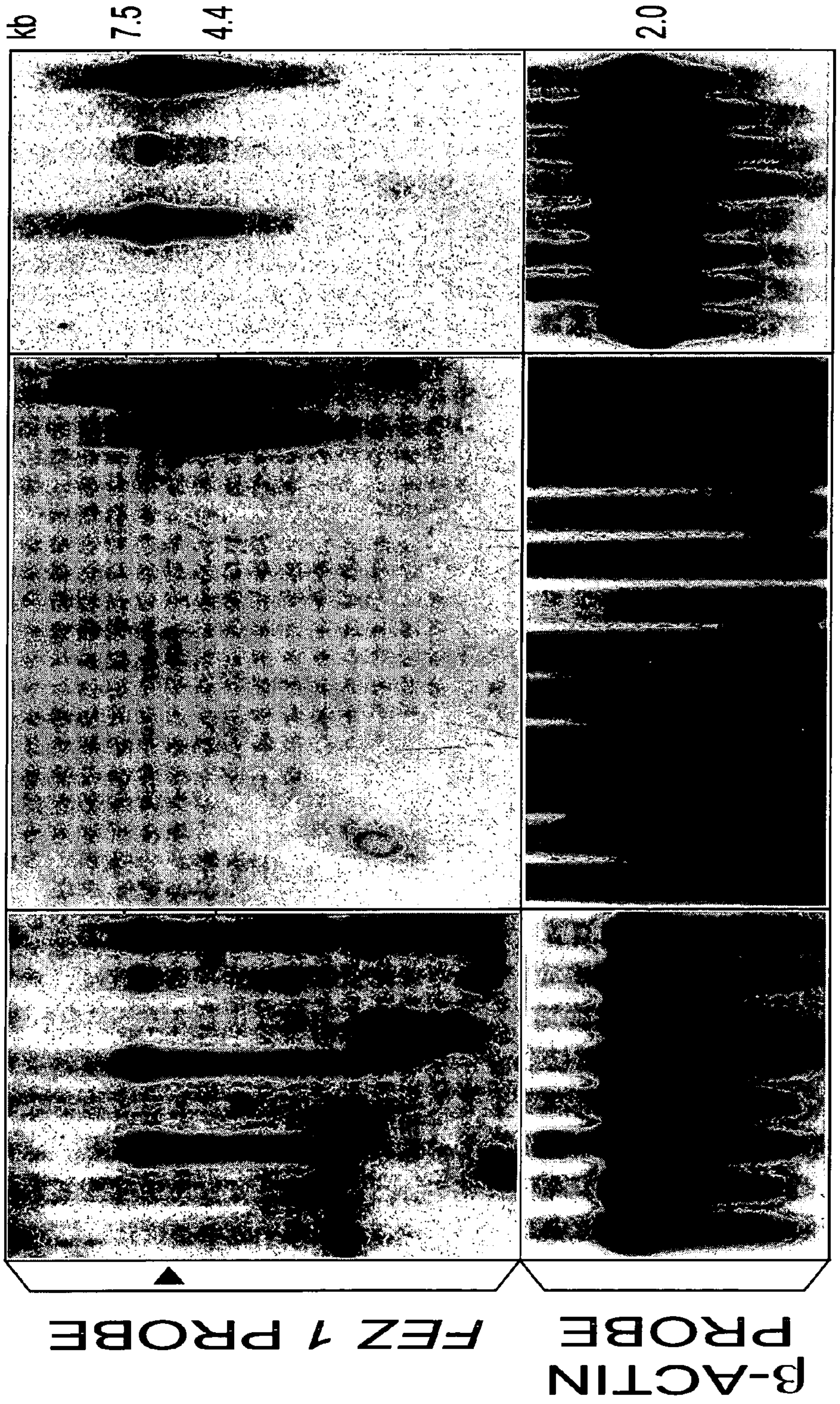
FIG. 3A is an image which depicts results of Northern blot analysis of FEZ1 gene expression in cancer cells. A FEZ1 cDNA probe (upper panel) and a beta-actin probe (lower panel) were used to detect expression of the corresponding genes. The arrowhead on the left side of the upper panel indicates the approximate position of the 6.8-kilobase transcript of FEZ1. Poly(A)$^+$ RNAs (5 micrograms) were obtained from tumor cell lines, and loaded as follows: esophageal cancer cell lines KYSE170 (lane 1), TE12 (lane 2), TE8 (lane 3) and TE3 (lane 4); prostate cancer cell lines DU145 (lane 5), LNCaP (lane 6), PC3 (lane 7); normal prostate (lane 8); breast cancer cell lines MB231 (lane 9), SKBr3 (lane 10), BT549 (lane 11), HBL100 (lane 12), MB436S (lane 13), BT20 (lane 14), MB543 (lane 15), MB175 (lane 16), MCF7 (lane 17) and T47B (lane 18); normal breast (lane 19); total RNA of normal breast (lane 20); cervical cancer cell line HeLa S3 (lane 22); chronic myelogenous leukemia cell line K562 (lane 23); lymphoblastic leukemia cell line MOLT4 (lane 24); Burkitt's lymphoma cell line Raji (lane 25); colorectal adenocarcinoma cell line SW480 (lane 26); lung cancer cell line A549 (lane 27); and melanoma cell line G361 (lane 28). Total RNA (5 micrograms) was obtained from promyelocytic leukemia cell line HL60 and loaded on lane 21.

Northern blot analysis revealed that FEZ1 gene expression was almost ubiquitous in normal tissues. FEZ1 expression was most prominent in testes, as indicated in FIG. 2D. FEZ1 gene expression was analyzed by Northern blotting and by RT-PCR amplifications in human tumor tissue samples, including 41 cancer-derived cell lines and 25 primary tumors, as indicated in FIG. 3A and summarized in Table 1. FEZ1 expression was undetectable in 31 cancer cell lines (76%) and 16 primary tumor samples (64%). FEZ1 expression was not detected in any of the 15 breast cancer cell lines studied or in any of the 10 primary breast tumor samples studied. However, FEZ1 was expressed in normal tissues.

TABLE 1

| Origin of Tumor Samples | Number of Cases Analyzed | Cases Expressing FEZ1 mRNAs[1] | Cases with Aberrant Size Transcripts: Number of Cases | Cases with Aberrant Size Transcripts: Case Names[2] |
|---|---|---|---|---|
| Esophagus | | | | |
| Cell Lines | 4 | 1 | 1 | TE8 |
| Primary Tumors | 12 | 9* | 4 | E16, E26, E41, E62 |

TABLE 1-continued

| Origin of Tumor Samples | Number of Cases Analyzed | Cases Expressing FEZ1 mRNAs[1] | Cases with Aberrant Size Transcripts: Number of Cases | Case Names[2] |
|---|---|---|---|---|
| Gastric | | | | |
| Cell Lines | 8 | 3* | Not Done | |
| Colon | | | | |
| Cell Lines | 3 | 2 | 1 | SW480 |
| Prostate | | | | |
| Cell Lines | 3 | 2 | 1 | DU145 |
| Primary Tumors | 3 | 0* | — | |
| Breast | | | | |
| Cell Lines | 15 | 0 | — | |
| Primary Tumors | 10 | 0* | — | |
| Hematopoietic | | | | |
| Cell Lines | 5 | 1 | 1 | MOLT4 |
| Lung | | | | |
| Cell Lines | 1 | 0 | — | |
| Melanoma | | | | |
| Cell Lines | 1 | 1 | 1 | G361 |
| Cervical | | | | |
| Cell Lines | 1 | 0 | — | |

[1]FEZ1 Expression was detected by Northern blot or RT-PCR (indicated by *).

In E16, E26 and E41, normal tissues from a single patients' organs were analyzed, and did not exhibit alterations in the coding region sequences. In addition, the coding sequences from normal prostate as well as the other four samples from normal esophagus were analyzed, and no alterations were found except that one of twelve sequenced clones from testis cDNA showed a deletion of nucleotide.

In order to exclude the possibility that normal stromal cells, but not normal epithelial cells, might express FEZ1, FEZ1 expression was assessed in normal breast epithelial cells and fibroblasts and in normal prostate epithelial cells (these three types of cells were obtained from Clonetics, San Diego, Calif.). RT-PCR amplification indicated that FEZ1 was expressed in these three types of normal cells. No FEZ1 expression could be detected in breast and prostate (LNCaP) cancer cells.

To exclude the possibility that the apparent differences in FEZ1 expression observed among cell types might be attributable to alternative splicing of the FEZ1 transcript, Northern blot analysis was performed using three different probes. The three probes were constructed to be complementary to a region of the ORF of the FEZ1 transcript, complementary to a 3'-noncoding region just downstream from the ORF of the FEZ1 transcript, or complementary to the 3'-noncoding terminal region of the FEZ1 transcript. No difference was observed among Northern blots made using these three probes, suggesting that FEZ1 expression was absent in the cell lines and tumors which were examined.

Figure 3B:
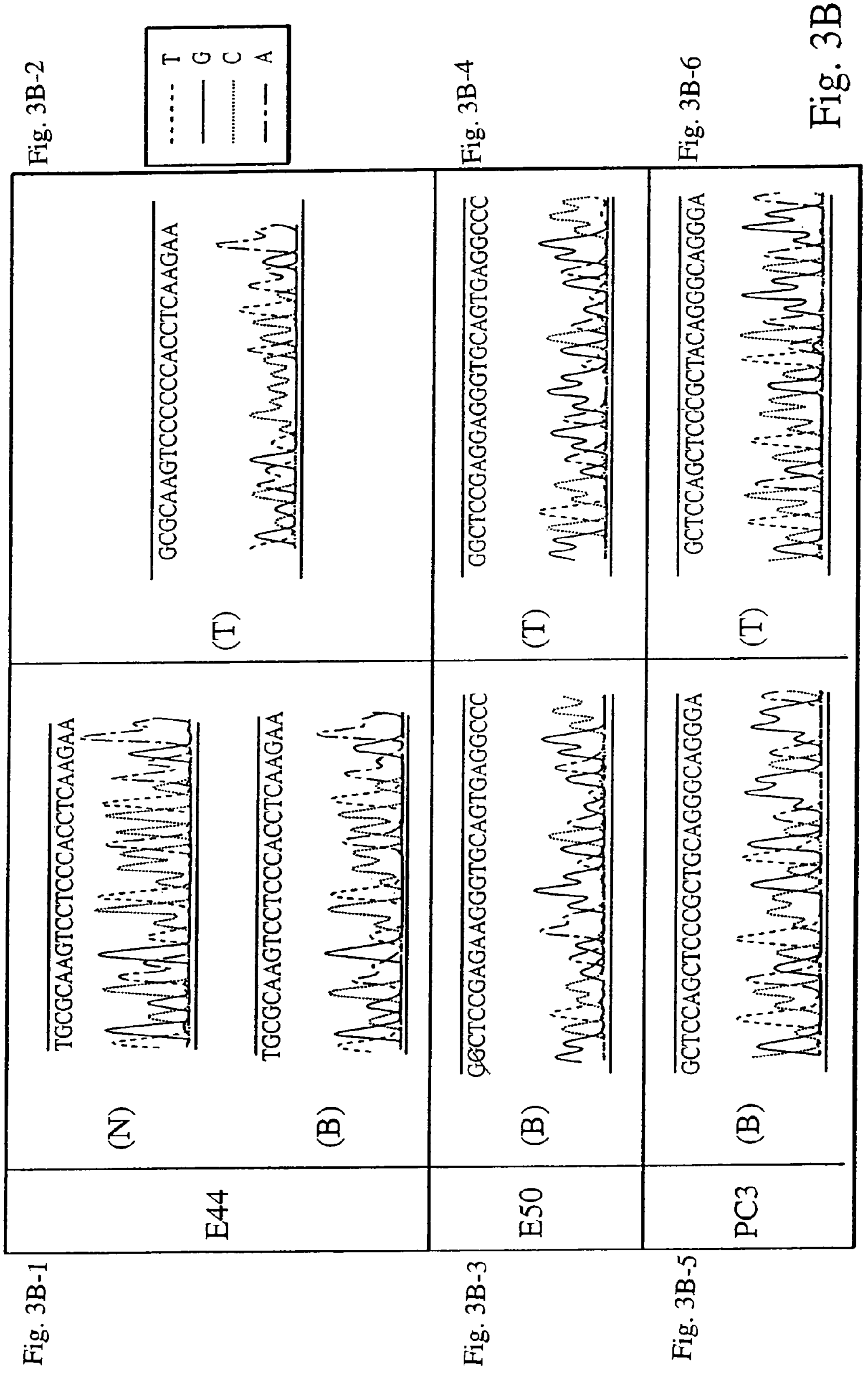
FIG. 3B, comprising

The nucleotide sequence of the FEZ1 gene ORF was analyzed in a total of 194 cancer tissue samples, regardless of whether FEZ1 was expressed in the tissue. These tissue samples included 72 primary esophageal cancer tissue samples, 18 esophageal cancer cell lines, 24 primary prostate cancer tissue samples, 3 prostate cancer cell lines, 39 primary breast cancer tissue samples, 25 breast cancer cell lines, 8 primary ovarian cancer tissue samples, 4 leukemic cell lines, and one cervical cancer cell line. Three point mutations were identified, two in two primary esophageal cancer tissue samples, and one in a prostate cancer cell line, as indicated in FIG. 3B. These point mutations are summarized in Table 2.

TABLE 2

| Tumor | Codon | Mutation | LOH at 8p22[1] | FEZ1 Gene Expression[2] |
|---|---|---|---|---|
| E44 | 29 | TCC (Ser) → CCC (Pro) | + | Yes |
| E50 | 119 | AAG (Lys) → GAG (Glu) | + | Yes |
| PC3 | 501 | CAG (Glu) → TAG (STOP) | − | Yes |

[1]+ means that locus D8S261 is observed; − means that a normal FEZ1 allele was retained in at least a fraction of cells, as suggested by the results presented in FIG. 3B.
[2]Expression of FEZ1 was analyzed by RT-PCR in the two primary tumors or by Northern blot in the cell line.

In a primary esophageal tumor tissue sample designated E44, a point mutation resulted in an amino acid substitution of serine (normal) to proline (mutant) at amino acid residue 29. Amino acid residue 29 is, as described herein, a predicted cAMP-dependent kinase phosphorylation site. In another primary esophageal cancer tissue sample designated E50, a second point mutation resulted in a different amino acid substitution, namely lysine (normal) to glutamate (mutant) at amino acid residue 119. The LOH study described herein indicated that the two patients from whom samples E44 and E50 were obtained each exhibited allelic loss at the D8S261 marker. Thus, tumor cells obtained from these two patients retained the mutated FEZ1 allele and lost the normal FEZ1 allele.

The third point mutation which was detected was a change of a codon encoding a glutamine residue in the normal FEZ1 transcript to a stop codon at codon 501 in a prostate cancer cell line designated PC3. This mutation resulted in a FEZ1 transcript which encoded a putative 166 amino acid residue protein lacking the normal carboxyl terminal region of wild type FEZ1 protein. Northern blotting, RT-PCR, and nucleotide sequencing revealed that these three mutated DNA sequences were expressed in the patients and cells in which they were identified. These data suggest that FEZ1 encodes a tumor suppressor protein, and that inactivation of FEZ1 is involved in development of several common cancers.

The nucleotide sequences of cDNAs generated from mRNA expressed from FEZ1 in several of the tumors were determined. Several internally-truncated transcripts were identified, as indicated in Table 3, Table 4, and FIG. 3B. With one exception, FEZ1 ORF sequences did not differ from wild type sequences in samples obtained from normal brain and prostate tissues (obtained from Clontech, Inc., Palo Alto, Calif.), from normal esophagus tissue samples obtained from seven individuals, or from matched normal cDNA obtained from patients E16, E26, and E41. One of twelve clones derived from testes cDNA samples (obtained from ClonTech Inc., Palo Alto, Calif.) exhibited a deletion at nucleotides 1441–1527 in the ORF. The cDNAs obtained from two esophageal cancer tissue samples exhibited a frame shift, with the result that the cDNA encoded a 76 amino acid residue protein.

TABLE 3

| Tumor | Deletion[1] | Results[3] | Affected Exons | Putative Protein Coded in Frame[2] |
|---|---|---|---|---|
| E16 | 156–1542 | FS | 1, 2, 3 | Zip(−) |
| E26 | 558–1715 | IF | 2, 3 | Zip(−) |
| E41 | 558–1715 | IF | 2, 3 | Zip(−) |
| E62 | 558–1715 | IF | 2, 3 | Zip(−) |
| TE8 | | | | |
| a | 156–1542 | FS | 1, 2, 3 | Zip(−) |
| b | 1402–1578 | IF | 3 | Zip(+) |
| DU145 | | | | |
| a | 1366–1641 | IF | 3 | Zip(+) |
| b | 1402–1578 | IF | 3 | Zip(+) |
| MOLT4 | | | | |
| a | 1402–1578 | IF | 3 | Zip(+) |
| G361 | | | | |
| a | 1417–1515 | IF | 3 | Zip(+) |
| b | 1516–1584 | IF | 3 | Zip(+) |

[1]The positions of the first and last nucleotides of deletions are shown according to the nucleotide number counted from first coding codon.
[2]Zip(+) means a protein comprising a leucine-zipper region; Zip(−) means a protein not comprising a leucine-zipper region.
[3]IF means that an in-frame region; FS means that a frame shift mutation was detected.

TABLE 4

| | Deletion[1] | Donor Site[2] | Acceptor Site[2] |
|---|---|---|---|
| a | 156–1542 | TCCCAGGACTCCGGTCA(cggcaa (SEQ ID NO: 46) | . . . gag)CGGCAAGGCCATGACCAG (SEQ ID NO: 47) |
| b | 558–1715 | AGCCTGCCCACACACAG(caccag (SEQ ID NO: 48) | . . . cag)CGCCGGGGAGCCCTTGGA (SEQ ID NO: 49) |
| c | 1366–1641 | GTGAGAATGAGCTGCAG(cgcaag (SEQ ID NO: 50) | . . . cag)CAGAGCTACGTGGCCATGT (SEQ ID NO: 51) |
| d | 1402–1578 | AGCTGCTGCGGGAGAAG(gtgaac (SEQ ID NO: 52) | . . . cag)CATGAGCGGCTCGTGTGGA (SEQ ID NO: 53) |
| e | 1417–1515 | AGGTGAACCTGCTGGAG(caggag (SEQ ID NO: 54) | . . . gag)CGGCTGCGGGCCGAGCTGC (SEQ ID NO: 55) |
| f | 1417–1515 | CTGCAGCGGGAGCTGGAG(cggctg (SEQ ID NO: 56) | . . . gag)CGGCTCGTGTGGAAGGAG (SEQ ID NO: 57) |

[1]Nucleotide residues are numbered relative to the position of the first nucleotide residue of the first codon of FEZ1 (i.e. residue 1).
[2]Nucleotide sequences flanking cDNAs deletion endpoints of are indicated. Upper case letters indicate nucleotide residues which are present in truncated cDNAs. Lower case letters in parenthesis indicate nucleotide residuess not present in truncated cDNAs. Underlined characters indicate conserved nucleotide residues at donor/acceptor sites. The deletion in a results in a frame-shift which encodes a protein having a putative molecular weight of 8.6 kilodaltons.

The nucleotide sequences flanking deleted regions of FEZ1 cDNAs indicated that the intronic AG sequence was present at the 3'-boundary of the deleted region in the cDNA, suggesting that the deleted FEZ1 transcripts in tumors can be attributable to physiologically inappropriate splicing events. The allelic expression status of FEZ1 was analyzed using a polymorphic site in the 3'-noncoding cDNA region, namely the 2134th nucleotide residue of FEZ1 cDNA, numbered from the first nucleotide residue of the first codon. In four informative normal primary tissues, the FEZ1 gene was transcribed from both alleles, i.e. it was not imprinted. In contrast, expression of FEZ1 in FEZ1-expressing cancer cells was, in each sample studied, from a single allele, probably attributable to allelic loss.

Figure 3C:
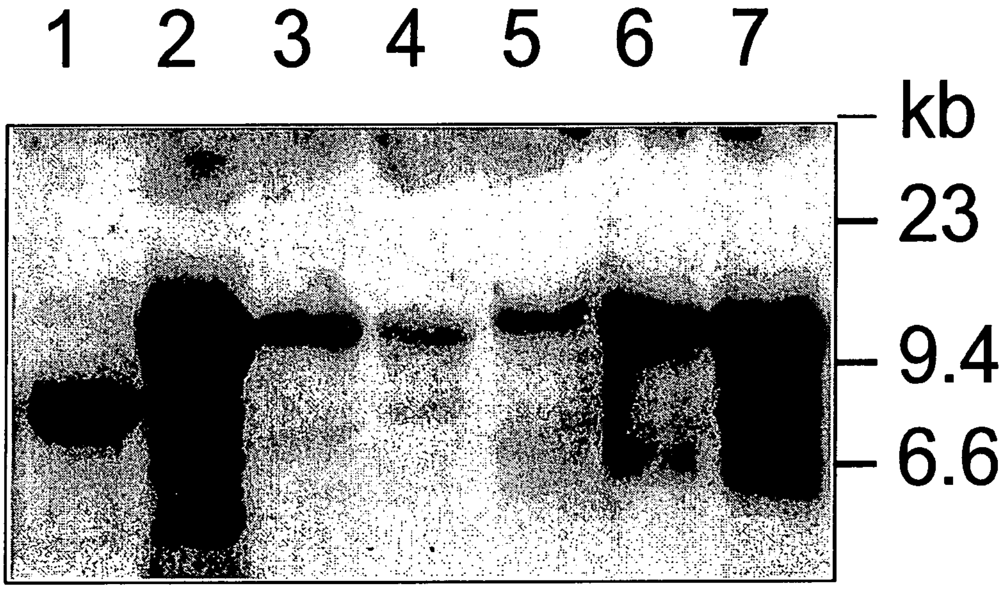
FIG. 3C is an image which depicts Southern blot analysis results using the FEZ1 gene locus. High-molecular weight DNAs from cancer cells were cleaved using restriction endonuclease EcoRI, separated electrophoretically, transferred to nylon membrane, and probed with the 1.7 kilobase FEZ1 ORF probe (SEQ ID NO: 3). The DNAs applied to each lane (10 micrograms per lane) were obtained from the following cells: lane 1, cell line MB436S; lane 2, normal placental cells obtained from a first healthy individual; lane 3, cell line MB231; lane 4, cell line MB361; lane 5, cell line TE8; and lane 6, cell line TE3. The DNA applied to lane 7 was isolated from normal placental cells obtained from a second healthy individual.
Figure 4A:
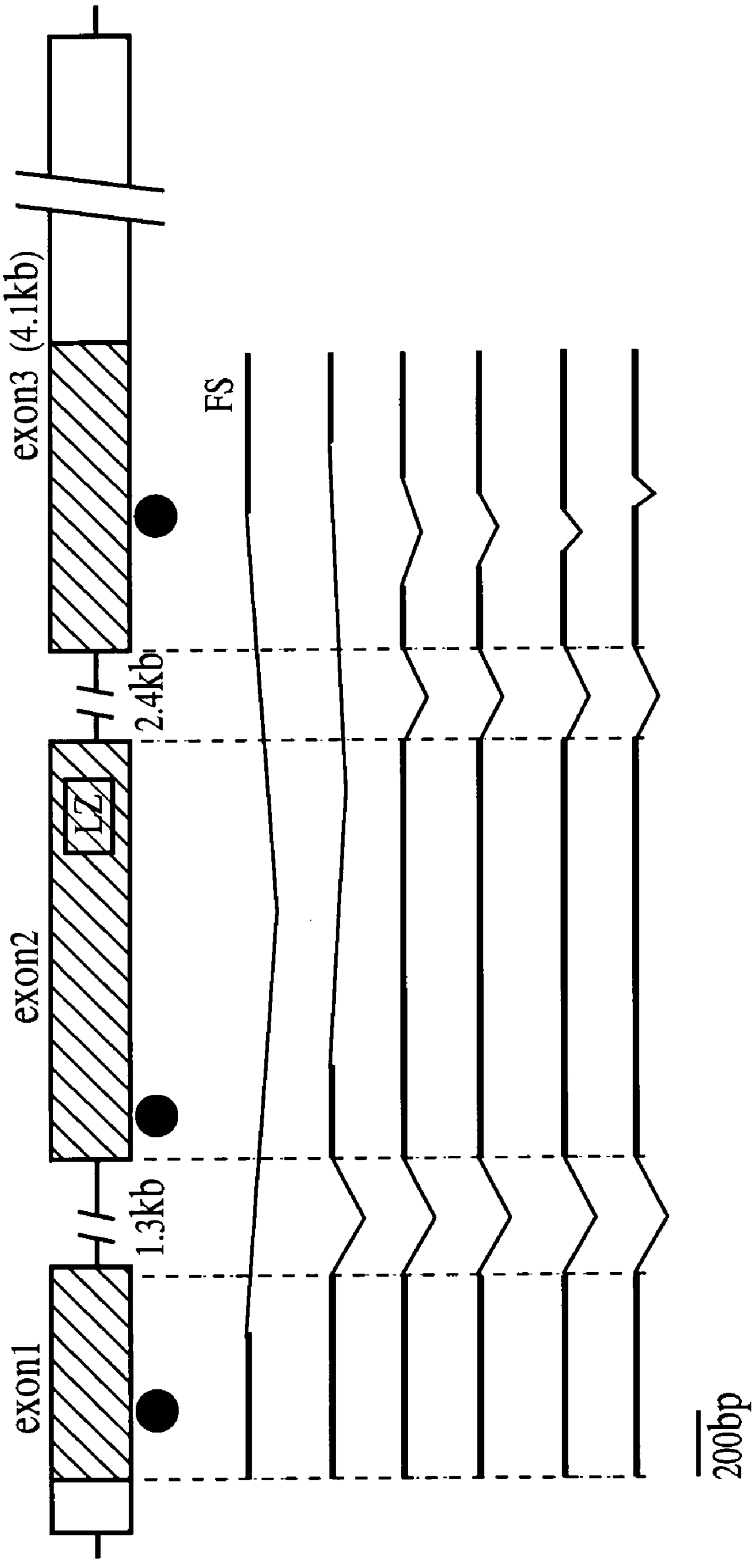
FIG. 4A is a diagram which depicts truncated FEZ1 transcripts observed in cancer cells, as described herein. The normal exon/intron structure is indicated on the top line of the diagram, and was determined by sequencing of normal (i.e. non-cancerous) brain, prostate and esophagus cDNAs and by sequencing FEZ1 gene in BAC. Boxes represent exons; the hatched areas represent the open reading frame (1788 base pairs; SEQ ID NO: 3). Horizontal lines represent introns, and closed circles represent point mutations which were observed, as described herein. The boxed notation "LZ" represents the approximate location of the leucine-zipper motif described herein. "FS" represents the approximate position of a frame-shift described herein. Aberrant transcripts observed in tumors are depicted by bold lines on the lines below the top line in the diagram.
Figure 6:
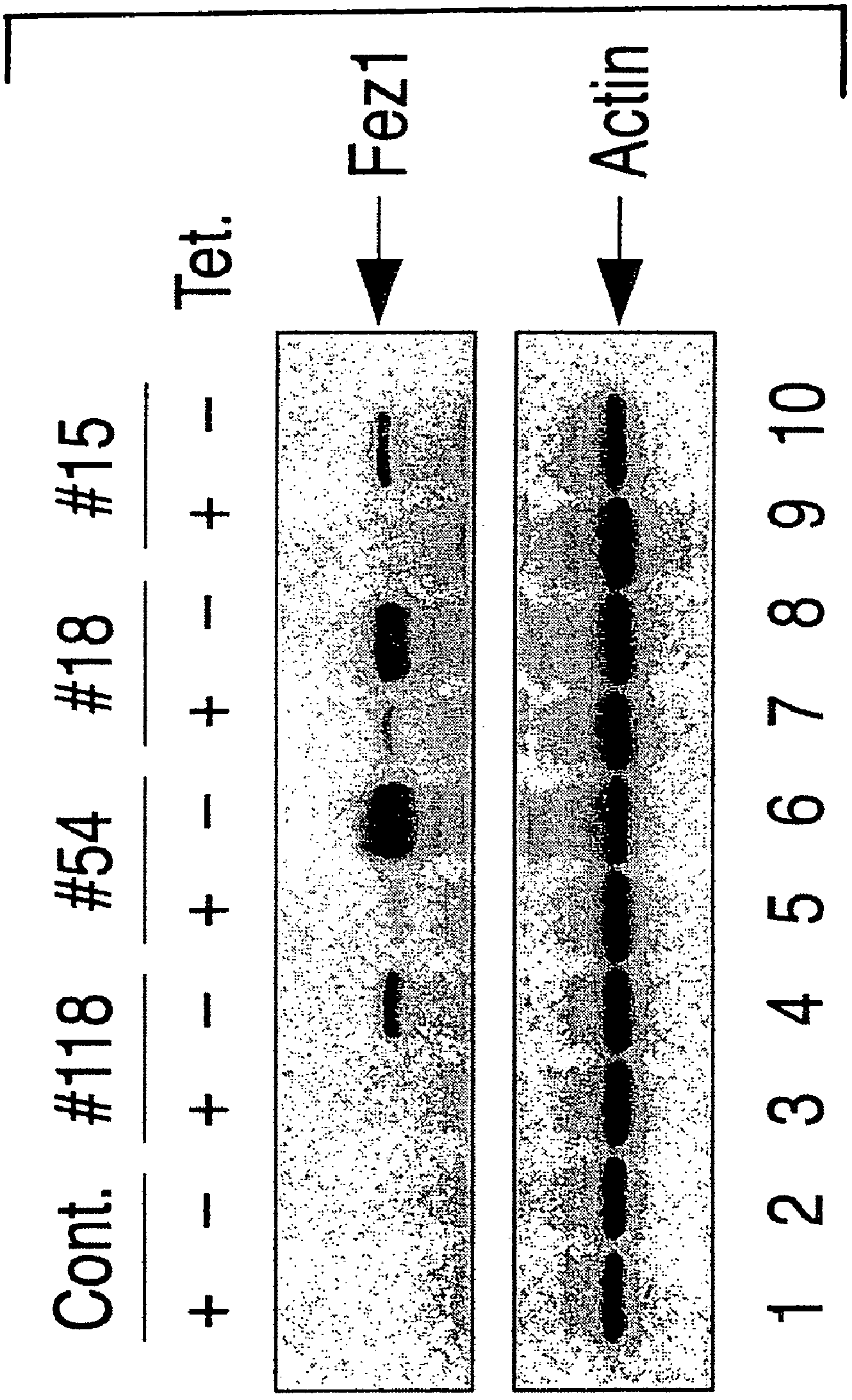
Figure 7A:
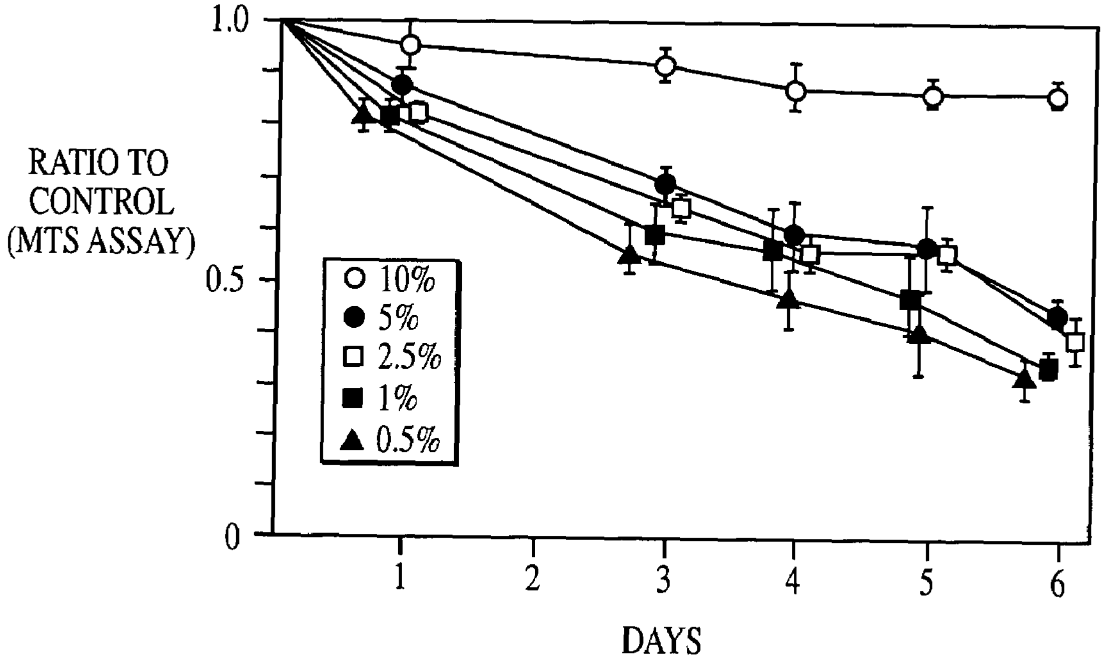
Figure 7B:
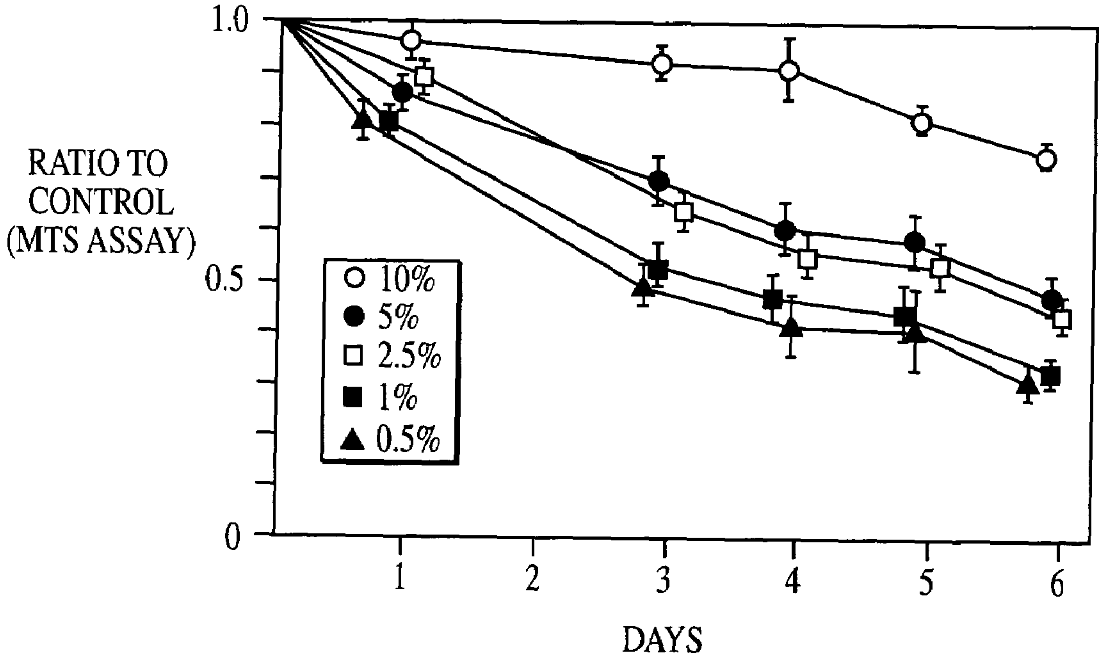
Figure 7C:
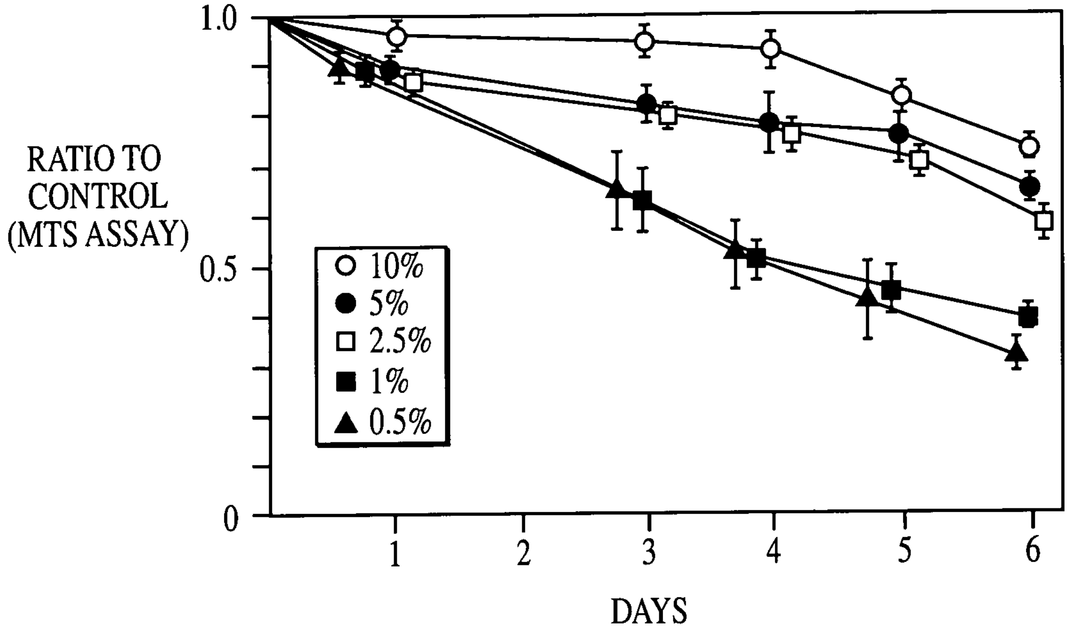
Figure 7D:
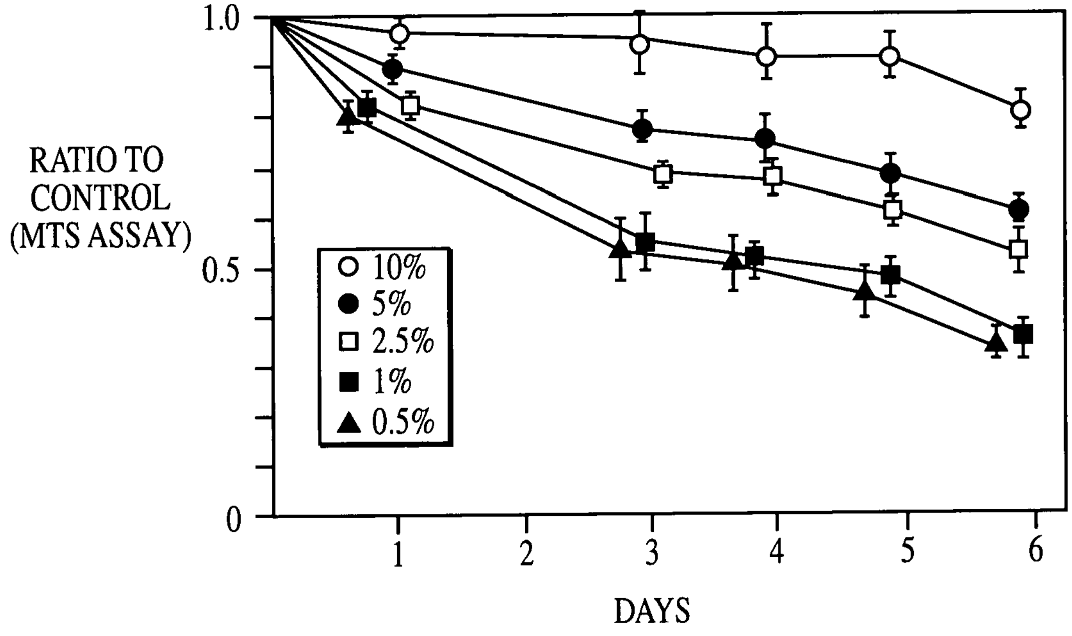

Southern blot analysis of the FEZ1 gene locus using an FEZ1 ORF probe in 18 cancer cell lines indicated that one breast cancer cell line had a single rearranged FEZ1 band and did not express the normal allele, as indicated in FIG. 3C. No homozygous deletions were detected in the other 17 cell lines examined. Several tumor suppressor genes are associated with frequent allelic loss, and some are involved in homozygous deletions (Weinberg, 1991, Science 254: 1138; Lasko et al., 1991, Ann. Rev. Genet. 25:281; Knudson, 1993, Proc. Natl. Acad. Sci. USA 90:10914; Nowell, 1993, Adv. Cancer Res. 62:1; Bookstein et al., 1997, Br. J. Urol. 79(Suppl. 1):28; Bova et al., 1996, Genomics 35:46; Mac-Grogan et al., 1996, Genomics 35:55; Cher et al., 1994, Genes Chromosom. Cancer 11:153; Bookstein, et al., 1994, Genomics 24:317; Ohta et al., 1996, Cell 84:587). These data suggest that, although LOH in the genomic region around the D8S261 locus, as well as at the FEZ1 gene locus, is a frequent abnormality, homozygous deletions of this gene are infrequent in tumors. Thus, the major mechanism of FEZ1 inactivation appears to be attributable to "two-hit" events such as allelic loss and point mutations and, possibly, allele loss in combination with shut-down (i.e. null) transcription of the remaining allele.

The experiments presented in this Example demonstrate that loss of FEZ1 function enhances tumorigenesis at least in prostate, breast, and esophagus cancers, and likely in other malignancies associated with chromosomal alteration at 8p22.

EXAMPLE 2

Effect of Fez1 Expression on Growth of Cells of Breast Cancer Cell Line MCF7

The Experiments described in this Example involve cells of the breast cancer line designated MCF7 (available from American Type Culture Collection, Gaithersburg, Md.; accession number HTB-22) which were transfected with a vector which induces expression of FEZ1 in the absence of tetracycline and represses FEZ1 expression in the presence of tetracycline. Induction of FEZ1 expression inhibited cell growth in vitro and in vivo.

MCF7 cells were stably transfected using a pTet-Off™ plasmid vector (ClonTech, Palo Alto Calif.; GenBank Accession number U89929) in which at least the coding portion of the FEZ1 gene was operably linked with the tetracycline-responsive element and promoter of the vector. Cells were maintained in DMEM medium supplemented with 2 micrograms per milliliter doxycycline (Sigma Chemical Co., St. Louis, Mo., catalog number D-9891) and 10% (v/v) certified fetal bovine serum (FBS; ClonTech). About $1\times10^5$ cells were grown in 3.5 centimeter diameter culture dish, and were transfected with about 4 nanograms of plasmid DNA using the GenePORTER™ reagent according to the supplier's instructions (Gene Therapy Systems, San Diego, Calif.), according to the instruction manuals.

Stable transfectants were made by maintaining transfected cells for about 2 weeks in medium containing hygromycin (Gibco, Grand Island, N.Y.) at a concentration of about 200 micrograms per milliliter, beginning 36 hours after transfection. Four well-isolated transfectant clones were selected and designated clones 15, 18, 54 and 118. These clones were cultured in tetracycline-free medium comprising 10% (v/v) serum medium for 72 hours in order to induce expression of FEZ1. In the experiments described in this application, tetracycline and doxycycline were used interchangeably, because the tetracycline-responsive elements are substantially equally responsive to tetracycline and doxycycline.

Cellular proteins were extracted before and after induction of FEZ1 expression, and separated by SDS-PAGE. Separated proteins were transferred to a nitrocellulose membrane, and immunoblot analysis was used to determine the presence of Fez1 protein or actin (as a control). A polyclonal antibody which binds specifically with Fez1 was used. The results of this immunoblot procedure are shown in FIG. 6, and demonstrate that Fez1 protein was produced by each of the four selected clones when they were maintained in the absence of tetracycline. Fez1 protein was not produced by cells transfected with vector alone, indicating that there was no endogenous FEZ1 expression in MCF7 cells.

The effect of FEZ1 expression in vitro cell growth of MCF7 cells was analyzed using the CellTiter 96™ Aqueous non-radioactive cell proliferation assay obtained from Promega Corporation (Madison, Wis.) per the supplier's instructions. The absorbance of the MTS compound of the assay system at 490 nanometers exhibited a linear correlation between the number of MCF7 cells in a range between 102 and 104 cells, as confirmed by cell counting in which dead cells were excluded by tryptan blue staining. Cells of clones 15, 18, 54, and 118 were selected in wells of 96-well plates containing tetracycline-free medium supplemented with 10, 5, 2.5, 1, or 0.5% (v/v) FBS. Culture medium was exchanged daily with the corresponding fresh medium. Absorption at 490 nanometers was assessed in order to estimate the number of cells present in each well at selected times. The results of these experiments are presented in FIG. 7, in which data are shown as a ration of the number of transfected cells to the number of control mock MCF7 transfectants (i.e. transfected with vector alone) cultured in the corresponding medium. Data were calculated as an average of four independent experiments, and bars in FIG. 7 indicate the standard deviations.

Figure 8A:
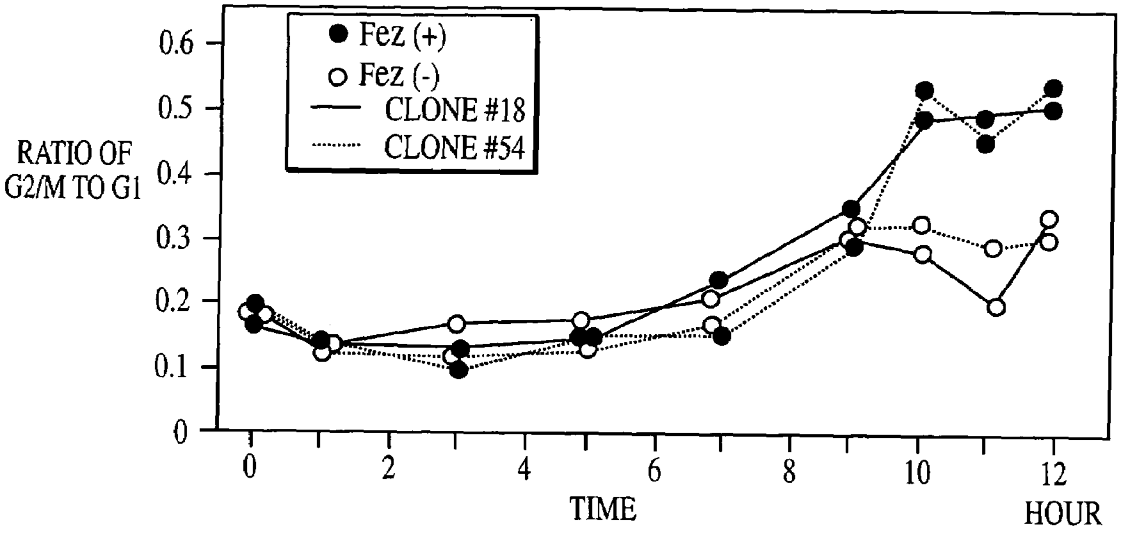
FIGS. 8A and 8B, is a pair of graphs which indicate the ratios of the number of transfected MCF7 clone cells which were in the G2 cell cycle stage, relative to the number in the M stage (FIG. 8A; i.e., G2/M) or the ratio of the number of cells in the S phase, relative to the number in the G1 stage (FIG. 8B; i.e., S/G1). In these figures, solid lines correspond to clone 18, and broken lines correspond to clone 54. Filled circles correspond to ratios in the of presence tetracycline (i.e. non-expression of FEZ1), and open circles correspond to ratios in the absence of tetracycline (i.e. expression of FEZ1).
Figure 8B:
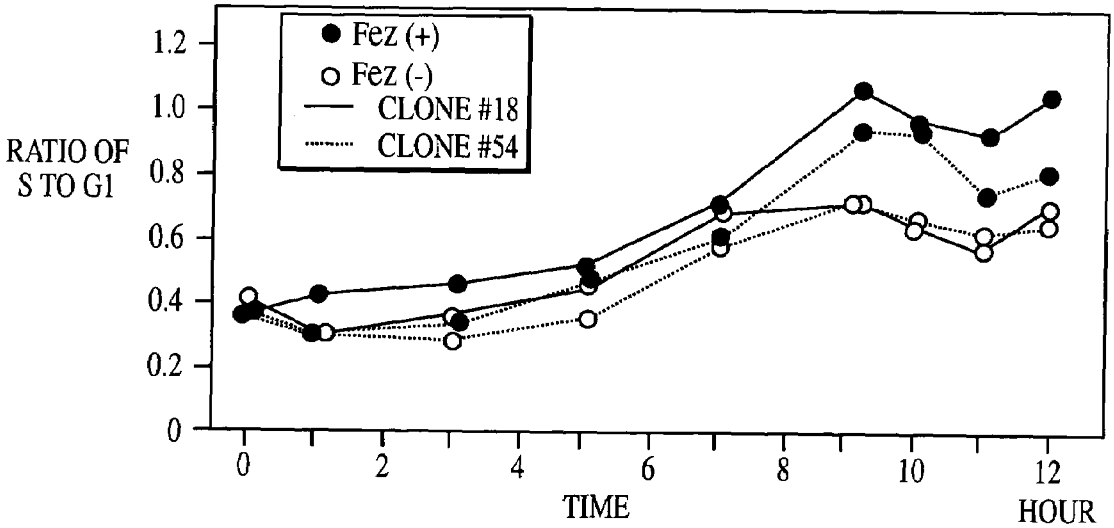

FIG. 8 shows the results of a cell cycle analysis of synchronized transfected MCF7 cells. MCF7 transfectants were cultured in growth medium supplemented with 1.5% (v/v) FBS for 3 days in the presence or absence of tetracycline (i.e. in order to induce expression of FEZ1 in cells maintained in the absence of tetracycline). Thereafter, the cells were maintained in medium comprising thymidine in order to induce accumulation of cells at the G1/S stage of the cell cycle. The thymidine-containing medium was replaced with the same growth medium, and cells were fixed at selected times thereafter. The cells were fixed in 70% ethanol and treated with propidium iodide and RNase A prior to flow-cytometry analysis. Ratios were calculated as a ratio of the number of cells in the G2/M stage of the cell cycle to the number of cells in the G1 stage of the cell cycle (FIG. 8A), or as a ratio of the number of cells in the S stage of the cell cycle to the number of cells in the G1 stage of the cell cycle (FIG. 8B). The results of this analysis indicate that expression of FEZ1 appears to inhibit MCF7 cell proliferation in vitro by causing accumulation of cells in the late S or G2/M stages of the cell cycle.

Figure 9A:
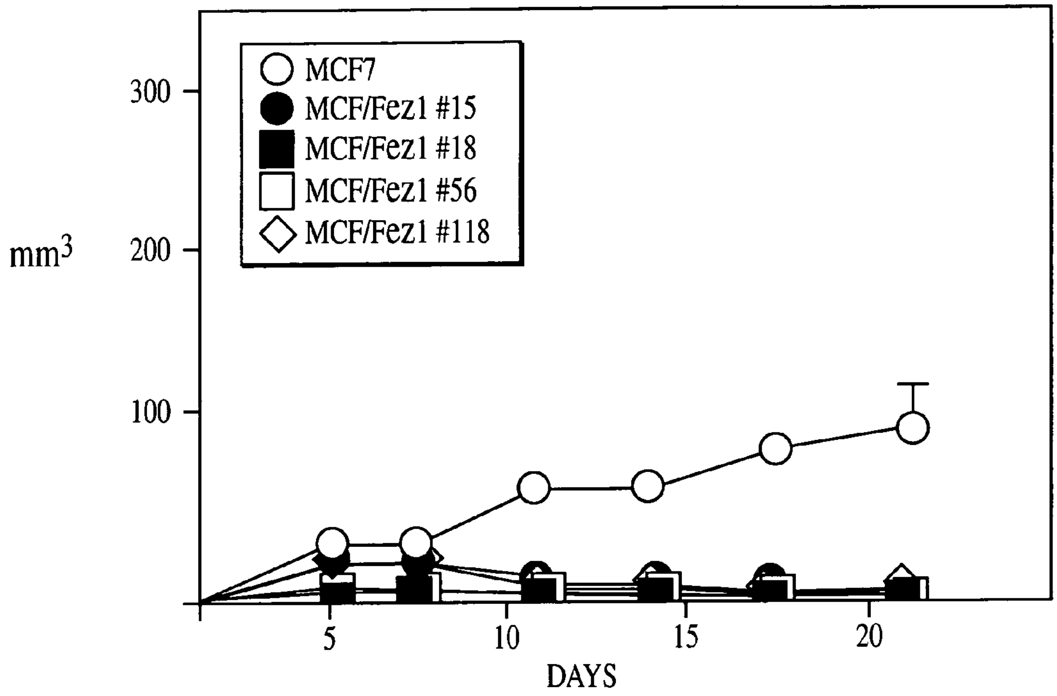
FIGS. 9A and 9B, is a pair of graphs which indicate the temporal dependence of tumor volume in nude mice into which about $5\times10^6$ (FIG. 9A) or about $2\times10^7$ (FIG. 9B) MCF7 cells transfected with vector alone (○), transfected MCF7 clone 15 cells (●), transfected MCF7 clone 18 cells (■), transfected MCF7 clone 56 cells (□), or transfected MCF7 clone 118 cells (◇) were implanted.
Figure 9B:
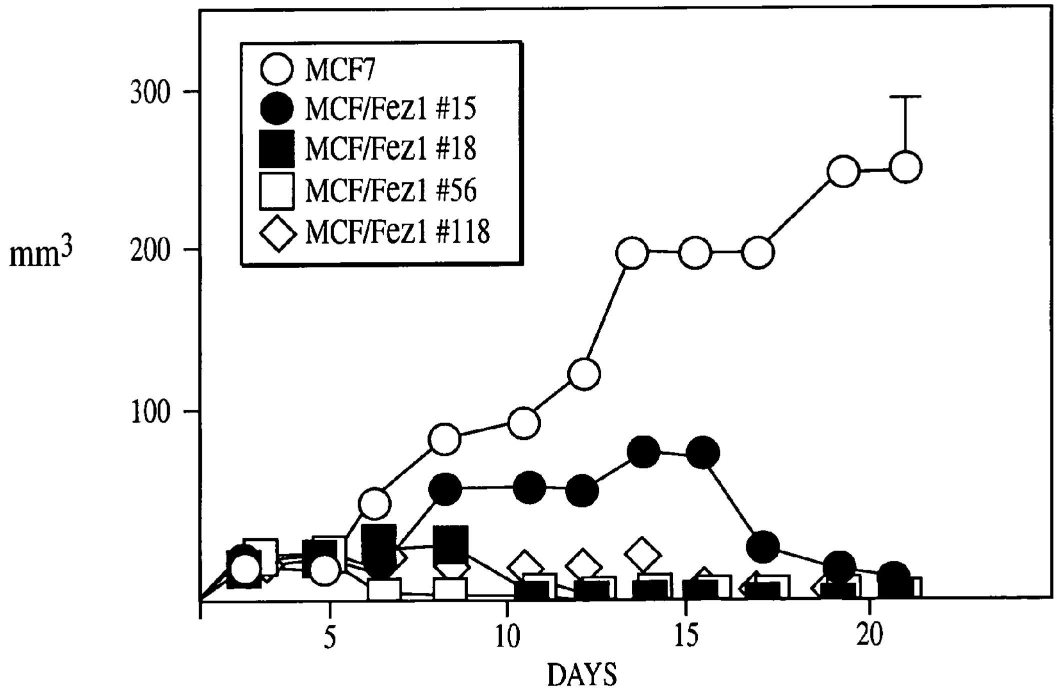

About $5\times10^6$ or about $2\times10^7$ cells (MCF7 cells transfected with the pTet-Off™ vector alone or MCF7 transfectant clone 15, 18, 56, or 118 clone cells) were subcutaneously inoculated into the left dorsal subclavicular region of 6 week-old female Balb/nude mice. Four mice were used for each experimental group. Tumor volume was estimated for each mouse by measuring in two directions using Vernier calipers, and was calculated as tumor volume=length×(width) $^2/2$. These results indicate that expression of FEZ1 inhibited proliferation of MCF7 cells in vivo, and indicate that FEZ1 expression inhibits (or even reverses) proliferation of epithelial tumor cells in animals. The results of these experiments are presented in FIG. 9.

EXAMPLE 3

Construction of an Adenovirus Vector Having an Isolated Nucleic Acid Encoding at Least an Operative Portion of Fez1 Protein Incorporated Therein Isolation of FEZ1 cDNA To construct an adenoviral expression vector, full-length FEZ1 cDNA is isolated from human normal placental poly (A)+ RNA by reverse transcription polymerase-chain-reaction (RT-PCR) amplification using a pair of promoters, such as promoters having the nucleotide sequences, 5'-CAG ATG GGC AGC GTC AGT AGC CTC ATC-3' (SEQ ID NO: 58) and 5'-TCA GAT CTC AGT GGC TAT GAT GTC-3' (SEQ ID NO: 59).

Of course, any other pair of primers can be used to isolate Fez1 cDNA, or the cDNA can be made synthetically, since the sequence is now available (FIG. 5B; SEQ ID NO: 2; GenBank accession number AF123659). When the cDNA is isolated by RT-PCR, reverse transcription can be performed using the commercially-available SuperScript-II™ system (Gibco-BRL, catalog no. 18064–022, Rockville, Md.) according to the supplier's instructions. PCR can be performed, for example, using Advantage Taq (Clontech, catalog no. K1905-y) according to the supplier's instructions). For example, reverse-transcribed cDNA can be subjected to PCR amplification by maintaining a standard PCR reaction mixture at 94° C. for 30 seconds, and then performing 35 cycles comprising maintaining the reaction mixture at 94° C. for 10 seconds, at 58° C. for 10 seconds, and at 72° C. for 60 seconds, and thereafter maintaining the reaction mixture at 72° C. for 60 seconds.

The amplified product can be separated by electrophoresis in a 1.5% (w/v) agarose gel (Gibco-BRL, catalog no. 15510-019) as described in the Current Protocols in Molecular Biology, ed. Frederick M Ausubel et al., John Wiley & Sons, Inc 1987).

Poly (A)+ RNA can, for example, be purchased from Clontech (catalog no. 6518-1) and used to make cDNA. The Clontech poly (A)+ RNA material was extracted and purified from normal placenta tissue of Caucasian humans (ages 22–31) by a standard method described in Current Protocols in Molecular Biology (John Wiley & Sons, Inc. 1987).

Adenoviral shuttle vector DNA can, for example, be obtained from Quantum company (Montreal, Quebec, Canada; e.g., pAdCMV-IRES-GFP, catalog no. AES050M).

Amplified FEZ1 cDNA is isolated from an agarose gel and purified using, for example, a Qiagen™ PCR purification column (Stanford Valencia, Calif.; catalog no. 28104) according to the supplier's instructions. Adenovirus shuttle vector DNA is digested using restriction endonuclease BglII (Boehringer Mannheim-Roche; Indianapolis, Ind.). After the ends of the DNA are blunted using, for example, T4 DNA polymerase (Promega, Madison, Wis.), 10 nanograms of cDNA is ligated with 100 nanograms of vector DNA. The resulting construct is used to transform an electrocompetent *Escherichia coli* strain, such as strain DH5a (Gibco), and the transformed cells are transferred to a culture plate containing LB agarose medium supplemented with ampicillin (e.g., as described in Current Protocol in Molecular Biology, John Wiley & Sons, Inc. 1987).

Clones which contain FEZ1 cDNA are selected, e.g. using a colony hybridization technique employing full-length FEZ1 cDNA as a DNA probe (e.g., as described in Current Protocol in Molecular Biology, John Wiley & Sons, Inc. 1987). These 'positive' clones are grown overnight in 5 ml of LB medium, and plasmid DNA is extracted from the positive clones, e.g. using a Qiagen miniprep column. The sequence of the extracted plasmid DNA can be analyzed at this point to confirm recovery of the anticipated construct. For example, sequencing reactions and analysis can be performed using the Applied Biosystems Prism™ BigDye™ terminator reaction chemistry and a Perkin-Elmer Gene Amp™ PCR system 9600 and the Applied Biosystems Prism™ 377 DNA sequencing system (Norwalk Conn.). After confirming the orientation of the cDNA strand within the vector DNA, the plasmid can be amplified in *E. coli.*

Confirming Transient Expression Using FEZ1 Adenoviral Shuttle Vectors

Promoter activity and adequacy of the plasmid vector can be checked by assessing transient expression of FEZ1 in HeLaS3 cells (ATCC) maintained in F12/MEM medium supplemented with 10% FBS. For instance, about $5\times10^5$ cells per cubic centimeter are grown in 6-well plate overnight. Three micrograms of plasmid is used to transfect the cells in each well, for example using a lipofection method (e.g. the GenePORTER™ Reagent, Gene Therapy System Inc.). After maintaining the cells under culturing conditions (e.g. for about 48 hours), the cells are harvested and FEZ1 expression is assessed, e.g. by immunoblot analysis using an anti-Fez1 antibody, as described in Current Protocol in Molecular Biology (John Wiley & Sons, Inc. 1987).

The nucleotide sequence (SEQ ID NO: 60) of an adenovirus vector (designated pQBI-AdCMV5-IRES-GFP) into which an isolated nucleic acid encoding at least an operative portion of Fez1 protein can be incorporated is listed in FIG. 10 and an isolated nucleic acid encoding at least a fluorescent portion of GFP.

Production of Recombinant Adenoviral Vector

Adenoviral vectors can be constructed in fetal kidney 293 cells (Microbix Biosystems Inc., Toronto, Ontario, Canada) by transfecting the cells with the adenoviral shuttle vector described above and adenovirus DNA (e.g. obtained from Quantum), as described (Miyake et al., 1996, Proc. Natl. Acad. Sci. USA 93:1320; Kanegae et al., 1994, Jpn. J. Med. Sci. Biol. 17:157). 293 cells obtained from Microbix Biosystems Inc. are low passages and would be adequate to obtain favorable homologous recombination efficiency. Transfected 293 cells are seeded in 96-well plate, and well-isolated plaques are selected.

293 cells can be transfected using the shuttle plasmid by the calcium phosphate precipitation method and grown in 100 millimeter diameter dishes. Twenty-four hours following transfection, the transfectants are seeded into individual wells of a 96-well plate (containing about 200 microliters of medium per well). The cells in the well are diluted with from about 10 to 100 times the number of non-transfected 293 cells. After 2 to 3 weeks of incubation, plaque formed cells are harvested and virus particles are extracted, e.g. by multiple freeze-and-thaw cycles. The number of plaque-forming wells is estimated to about 10–50 wells per 96-well plate.

The virus-containing supernatant obtained from plaque-forming wells is subjected to sequential infection of 293 cells in soft agar. For example about $5\times10^5$ 293 cells are infected with 100 microliters of virus-containing supernatant, and the cells are seeded in 1.25% (w/v) low-melting temperature gel (Gibco) in a 60 millimeter diameter culture dish. After 10 days, plaques formed within the soft agar are isolated under microscopic observation. For example, in a vector encoding green fluorescent protein (GFP), GFP can observed by fluorescence microscopy. Virus titers are propagated, for example by sequential infection of 293 cells grown in 75 to 175 milliliters of liquid culture medium in a flask.

Analysis of Expression of FEZ1 in Cells Transfected Using the Adenovirus Vector

Expression of FEZ1 in cells transfected using an adenovirus vector containing an isolated nucleic acid which encodes at least an operative portion of Fez1 protein can be detected by immunoblot analysis of proteins extracted from the cell, e.g. using a rabbit anti-Fez1 polyclonal antibody. For example, infectivity of the virus vector can be assessed by incubating HeLaS3 cells (ATCC) with an adenovirus vector-containing supernatant at a volumetric ratio of 1/40–1/10 (v/v), extracting protein from the cells, and assessing whether Fez1 protein can be detected by immunoblot analysis. Alternatively, if the adenovirus vector also encodes a detectable protein such as GFP, infectivity of the virus vector preparation can be assessed by assessing expression of the detectable protein in the cells incubated with the virus-containing supernatant. By way of example, if the adenovirus vector encodes GFP, infectivity of the virus vector can be assessed by detecting fluorescence in the cells at an excitation/emission wavelength pair that is characteristic of GFP.

EXAMPLE 4

Identification of Fez1 Binding Partner Proteins

Yeast Two Hybrid Screening

Yeast two hybrid screening was performed in yeast strain Y190 using the MATCHMAKER™ system 2 (Clontech) according to supplier's instructions. We screened numerous clones of a human testes cDNA expression library individually fused with a GAL4 protein transcription activation domain-fusion pACT2 vector using a fusion protein comprising the GAL4 protein DNA binding domain fused with full length Fez1 protein. After first screening using a β-galactosidase assay, DNA was extracted from positive clones and sequencing using vector primers in order to identify the cDNA clones.

In vitro Transcription/Translation, GST-Fusion Protein and in vitro Binding Assay In vitro transcription and translation was performed using a commercially-available, rabbit reticulocyte-based system, (TNT™ T7 Quick Coupled Transcription/Translation System, Promega) by labeling with $^{35}$S-methionine, according to supplier's instructions. GST-fusion proteins were isolated using a glutathione-agarose column (Pharmacia). Proteins were incubated in two binding buffers: buffer A (comprising 100 millimolar NaCl, 0.5% NP-40, 0.75 milligrams per milliliter bovine serum albumin (BSA), 20 millimolar Tris-HCl pH 8.0, and 1 millimolar EDTA) and buffer B (comprising 150 millimolar NaCl, 0.1% (v/v) Tween 20, 0.75 milligrams per milliliter BSA, 50 millimolar Tris-HCl pH 8.0, 5 millimolar EDTA, 10% (v/v) glycerol). After the glutathione-agarose beads had been pre-incubated in a 10% (w/v) BSA suspension, the beads were mixed with protein samples and washed 5 times, each wash comprising mixing the beads with 10 volumes of the binding buffer. After the beads had been washed, the bead-containing liquid was centrifuged to recover binding proteins. The samples were boiled for 3 minutes and then the proteins in the samples were separated by SDS-PAGE. The gel was dried and exposed to film for 4–24 hours at −80° C.

About 100 clones which encoded proteins that exhibited binding with Fez1 protein were identified. When the DNA corresponding to these clones was extracted sequenced, it was found that many positive clones were redundant. Several independent clones were identified, including clones encoding peptide elongation factor 1-γ (EF1-γ; cDNA sequence deposited by others as EMBL accession number X68142). EF1-γ is a member of microtubule-associated protein family. To confirm the result, β-galactosidase assay was performed, and EF1-γ exhibited strong interaction with Fez1. The reaction time was <15 minutes, compared with a positive control reaction time of 15–20 minutes and a negative control reaction time of no reaction at >48 hours.

Figures 11A, 11B, 11C:
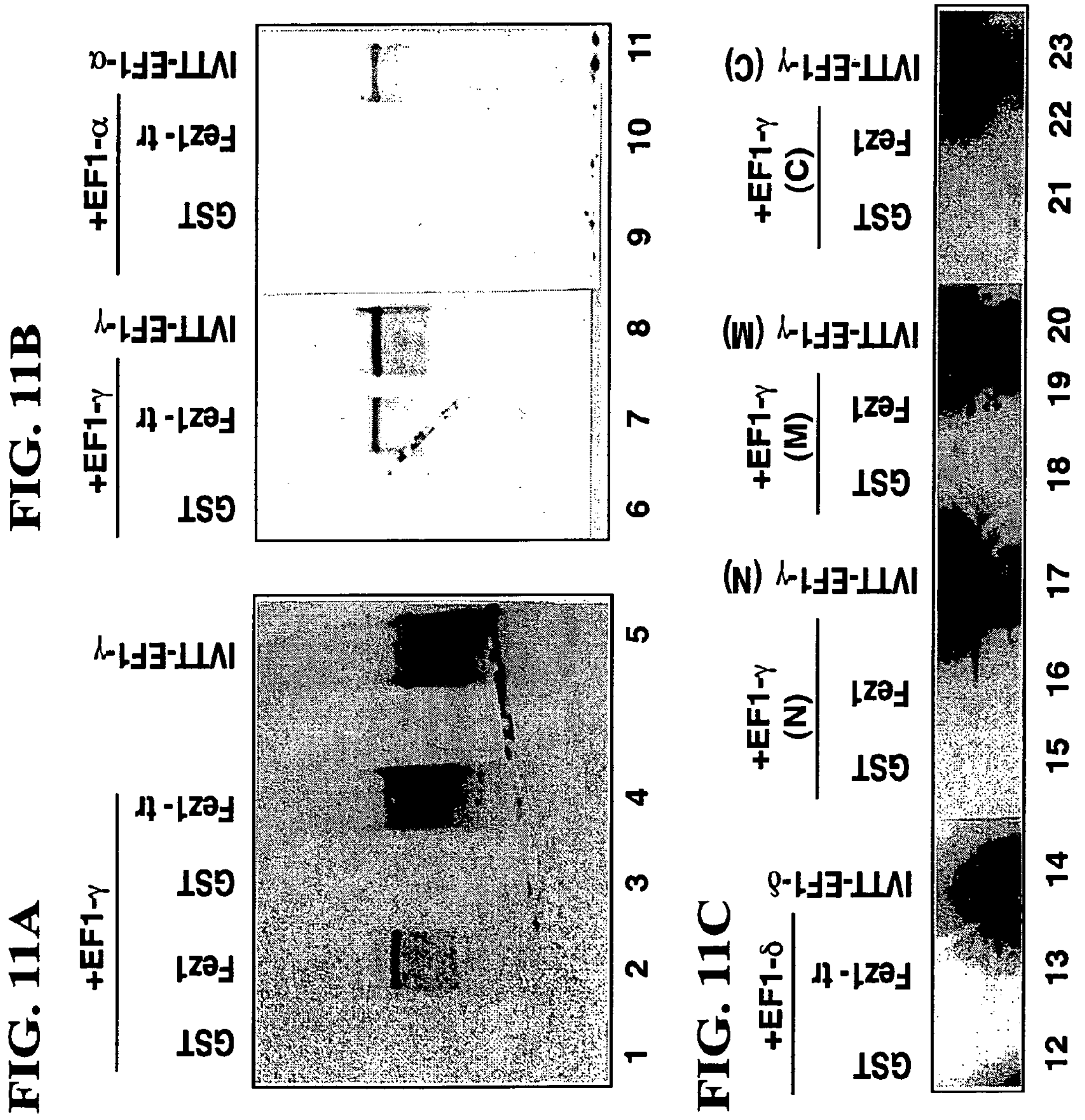
FIGS. 11A, 11B, and 11C, is a trio of images of the results of an in vitro binding assay demonstrating binding between $^{35}$S-methionine-labeled EF1-γ and Fez1 protein.

The results of an in vitro binding assay demonstrating binding between $^{35}$S-methionine-labeled EF1-γ and Fez1 protein are shown in FIGS. 11A, 11B, and 11C. In vitro binding assay mixtures corresponding to lanes 1–8 contained in vitro translated EF1-γ protein. The mixture corresponding to lane 2 contained glutathione S-transferase (GST) fused with full-length (67 kilodalton) Fez1 protein, and the mixtures corresponding to lanes 4 and 7 contained GST fused with truncated (40 kilodalton) Fez1 protein. Mixtures corresponding to lanes 1, 3 and 6 contained GST protein (as a negative control). Mixtures corresponding to lanes 5 and 8 contained in vitro translated EF1-γ protein alone. The reproducibility of binding was confirmed by performing the binding assay in two different buffers, buffer A (lanes 1–5) and buffer B (lanes 6–8). The results of this experiment demonstrate that Fez1 protein and EF1-γ bind with one another.

Others have reported that the peptide elongation factors form a protein family, which is composed of at least EF-1α, EF-1β, EF-1γand EF-1δ (J. Biol. Chem. 269:31410–31417, 1994; J. Biol. Chem. 269:2086–2092, 1994). We analyzed the binding of $^{35}$S-methionine-labeled in vitro translated EFs to the GST-fused Fez1 protein (lanes 9–14 in FIG. 11). No binding could be detected between Fez1 and either EF1-α or EF-16. An assay performed to detect binding of EF1-β with Fez1 was not informative, because EF1-βbinds with GST.

Three $^{35}$S-methionine-labeled deletion mutants of in vitro translated EF1-γ protein were made: a mutant designated EF1-γ(N) in which all but the amino-terminal 153 amino acid residues of EF1-γ were deleted, a mutant designated EF1-γ(C) in which all but the carboxyl-terminal 126 amino acid residues of EF1-γ were deleted, and a mutant designated EF1-γ(M) in which all but 149 amino acid residues in the central portion of the EF-1γ were deleted (i.e. EF1-γ(M) consisted of residues 154–302, measured from the amino terminus of EF1-γ). The amino acid sequence of EF1-γ can be found at GenBank accession number X68142. In vitro binding of these deletion mutants with GST-fused Fez1 was analyzed. EF1-γ(N) bound with Fez1, but neither EF1-γ(C) nor EF1-γ(M) bound with Fez1.

In Vitro Binding Assay of Fez1 Proteins to the Amino-Terminal Portion of EF1-γ Protein.

Figure 12:
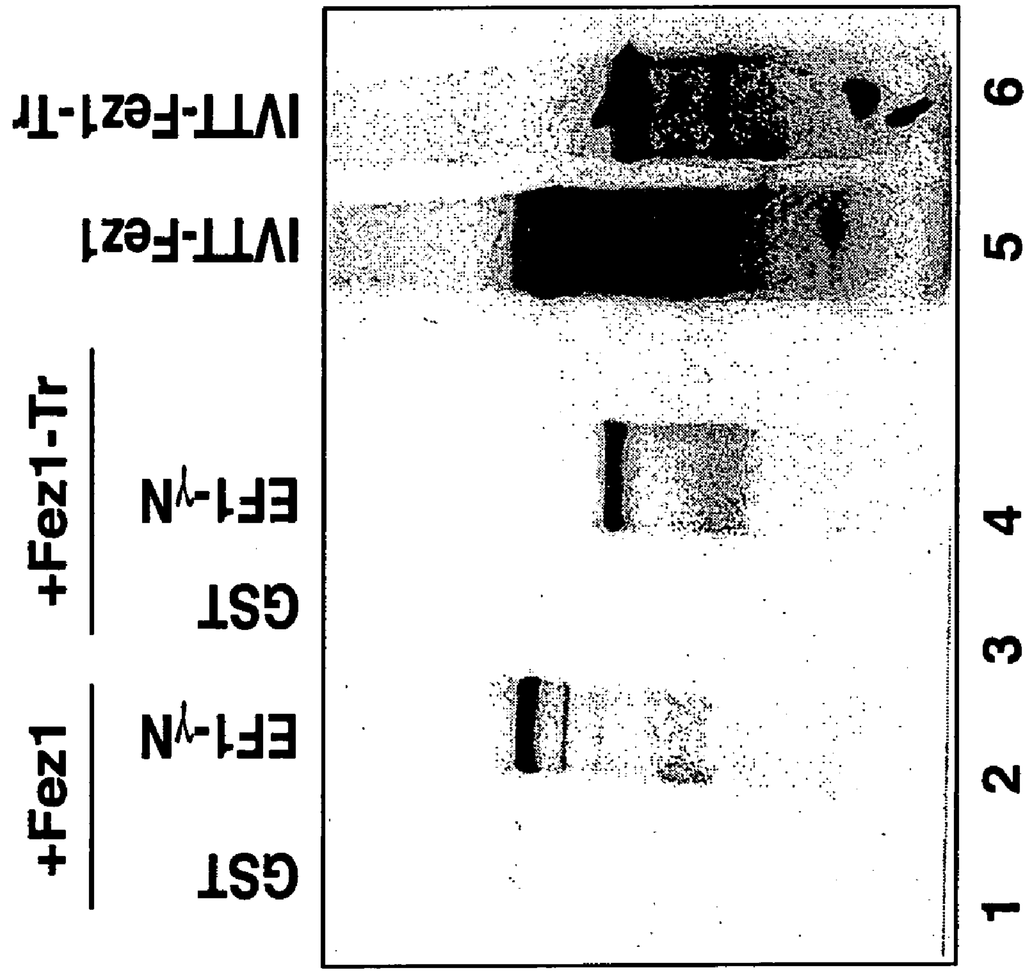
FIG. 12 is an image of the results of an in vitro binding assay demonstrating binding between $^{35}$S-methionine-labeled EF1-γ(N) and Fez1 protein and between EF1-γ(N) and a truncated Fez1 protein.

The complementary binding assay was performed in buffer B using $^{35}$S-methionine-labeled in vitro translated full-length 67 kDa Fez1 (lanes 1 and 2 in FIG. 12) or truncated 40 kDa Fez1 protein (lanes 3 and 4 in FIG. 12). The assay mixtures corresponding to lanes 2 and 4 of FIG. 12 contained GST fused with EF1-γ(N), and the mixtures corresponding to lanes 1 and 3 of FIG. 12 contained GST protein (as a negative control). In vitro translated full-length 67 kDa Fez1 protein (lane 5) or truncated 40 kDa Fez1 protein (lane 6) were loaded alone as controls. These results indicate that the amino-terminal ⅔ portion of Fez1 protein (40 kDa) binds with all or part of the 153 amino-terminal amino acid residues of EF1-γ in vitro.

Dimerization of Fez1 Protein in vitro

Figure 13:
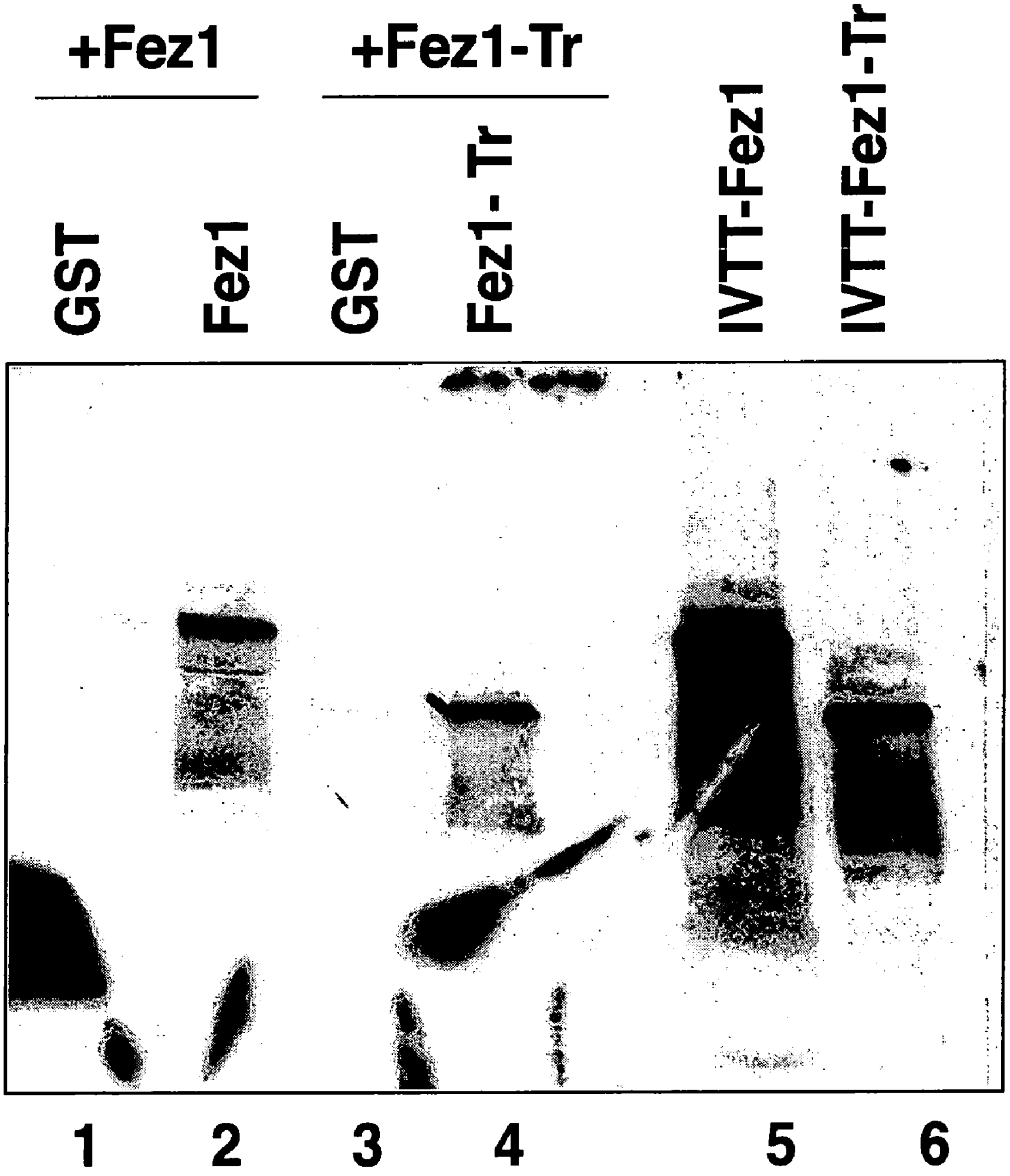
FIG. 13 is an image of the results of an in vitro binding assay demonstrating dimerization of Fez1 protein and dimerization of truncated Fez1 protein.
Figure 14A:
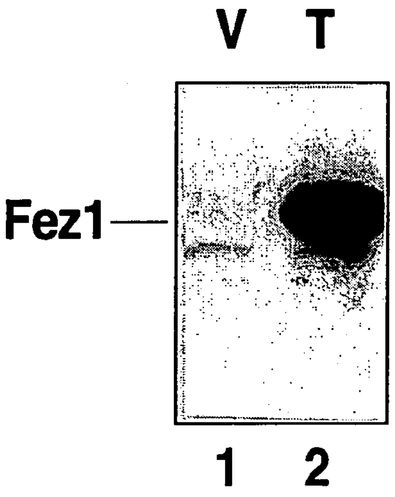
FIGS. 14A, 14B, 14C, and 14D, is a series of four images which depict the results of immunoblotting experiments involving HeLaS3 cells which were co-transfected with a vector encoding a V5/Fez1 fusion protein and a vector encoding an EXP/EF1-γ fusion protein.
Figure 14B:
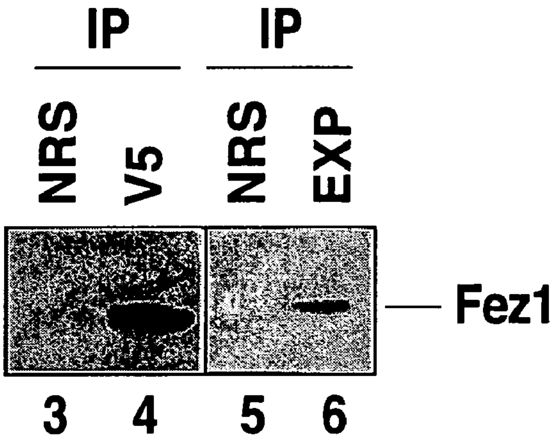
Figure 14C:
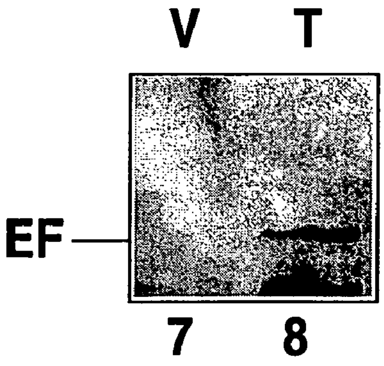
Figure 14D:
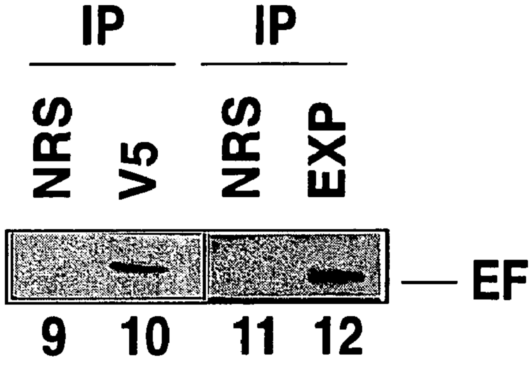
Figure 15B:
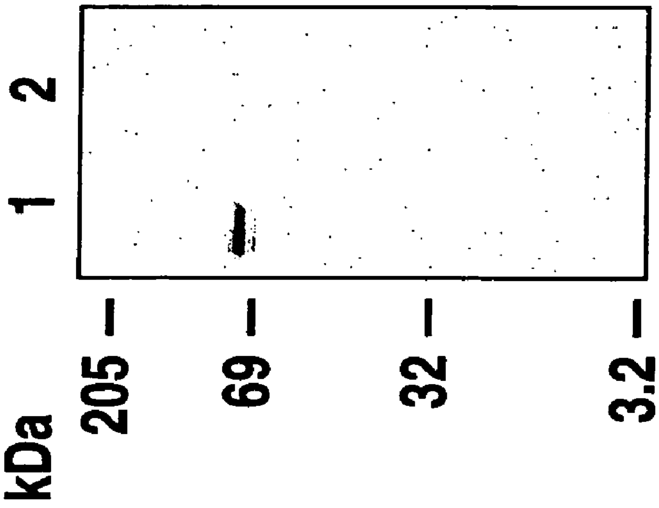
FIGS. 15A and 15B, is a pair of images of the results of immunoblotting experiments.
Figure 15A:
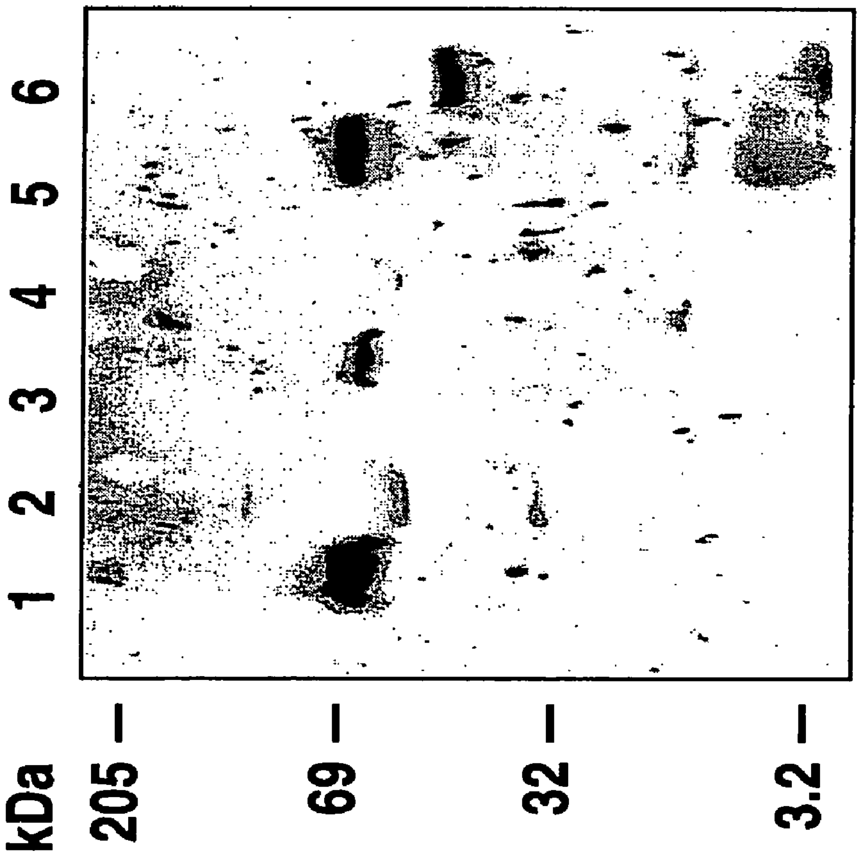

The amino acid sequence of Fez1 comprises a leucine-zipper-like region. Leucine zipper regions are known to be involved in the protein—protein and/or protein-nucleotide interactions in other proteins (Proc. Natl. Acad. Sci. USA 96:3928–3933, 1999). An in vitro binding assay was performed in buffer B, wherein the assay mixtures contained either $^{35}$S-methionine-labeled in vitro translated full-length (67 kDa) Fez1 proteins (lanes 1, 2, and 5 of FIG. 13) or $^{35}$S-methionine-labeled in vitro translated truncated 40 kDa Fez1 protein (lanes 3, 4, and 6). The assay mixtures also contained either GST-fused full-length 67 kDa Fez1 (lane 2), GST-fused truncated 40 kDa Fez1 (lane 4), or GST protein (lanes 1 and 3; negative control). The results of these assays indicate that the 67-kDa Fez1 and truncated 40-kDa Fez1 proteins can dimerize.

Interaction of Fez1 with EF1-γ in Transfected Cells

Full-length FEZ1 cDNA was ligated with pcDNAV5 vector (Invitrogen, Carlsbad, Calif.) in order to express V5 tag-fused Fez1 protein in cells transfected with the vector. Full-length EF1-γ cDNA was ligated with pcDNAHis vector (Invitrogen) in order to express EXP tag-fused EF1-γ protein in cells transfected with the vector.

HeLaS3 cells were co-transfected with these two vectors using the lipofection method in order to analyze in vivo interaction between Fez1 and EF1-γ. Immunoblot analysis using anti-tag antibodies demonstrated that the transfected cells expressed V5/Fez1 fusion protein (lane 2 in FIG. 14) and 50-kDa EXP/EF1-γ fusion protein (lane 8). Lanes 1 and 7 in FIG. 14 represent vector control transfectant lysates, in which neither tag could be detected. A series of immunoprecipitation experiments (IP; lanes 3–6 and 9–12 in FIG. 14) using anti-tag antibodies or control normal serum (NRS) was performed using the co-transfected cell lysate. Interaction of Fez1 and EF1-γ was indicated by precipitation of an apparently common band by anti-Fez1, anti-EF1-γ, and anti-V5 antibodies, as shown in lanes 4, 6, 10, and 12 of FIG. 14.

EXAMPLE 5

Making Antibodies Which Bind Specifically with Fez1 Protein

A rabbit polyclonal antibody which binds specifically with human Fez1 has been developed. Specificity of binding of the polyclonal antibody for Fez1 protein was demonstrated as follows. FEZ1 cDNA was ligated with a GST-fusion expression vector (pGEX, Pharmacia), and the protein was expressed in *E. coli* cells and purified. The Fez1-GST fusion protein was inoculated into rabbits to raise the anti-Fez1 antibody, which was harvested according to standard methods.

FIG. 13A shows the results of an immunoblot analysis performed using the polyclonal anti-Fez1 antibody. About 100 (lanes 1–3) or 50(lanes 4–6) micrograms of protein obtained from human brain (lanes 1 and 4), testis (lanes 2 and 5), and spleen (lanes 3 and 6) were blotted onto a surface. Longer exposure of the film showed faint expression of Fez1 in testis and spleen. Lane 7 contained in vitro translated full-length Fez1 protein, and lane 8 contained in vitro translated truncated Fez1 protein (i.e. lacking the C-terminal portion).

FIG. 13B shows the results of an immunoprecipitation assay performed using the polyclonal anti-Fez1 antibody. HeLaS3 cells, which do not express FEZ1, were transfected with FEZ1 cDNA ligated into expression vector pcDNA (Invitrogen) in frame with a V5 tag sequence. The cells were lysed, and the lysate was immunoprecipitated with polyclonal anti-Fez1 antibody (lane 1) or with the pre-immune normal rabbit serum (lane2). The precipitates were blotted and probed using the anti-V5 tag antibody.

Standard methods can be used to construct one or more monoclonal antibodies which bind specifically with Fez1 protein.

EXAMPLE 6

Post-Translational Modification of Fez1 Protein

Cells of MCF7 clone 54 were cultured in tetracycline-free medium containing aphidicolin and either 10% (v/v) FBS or no FBS in order to synchronize cell cycles. At a selected time, the medium was replaced with aphidicolin-free medium with 10% serum, and the cells were incubated for the periods indicated in FIGS. 16A and 16B. Following the incubation, cell lysates were obtained, and the lysates were subjected to immunoblot analysis using the rabbit anti-Fez1 polyclonal antibody or with an anti-actin monoclonal antibody. The results of this experiment demonstrated that cellular Fez1 protein is post-translationally modified in a cell cycle progression-dependent manner.

Figure 17:
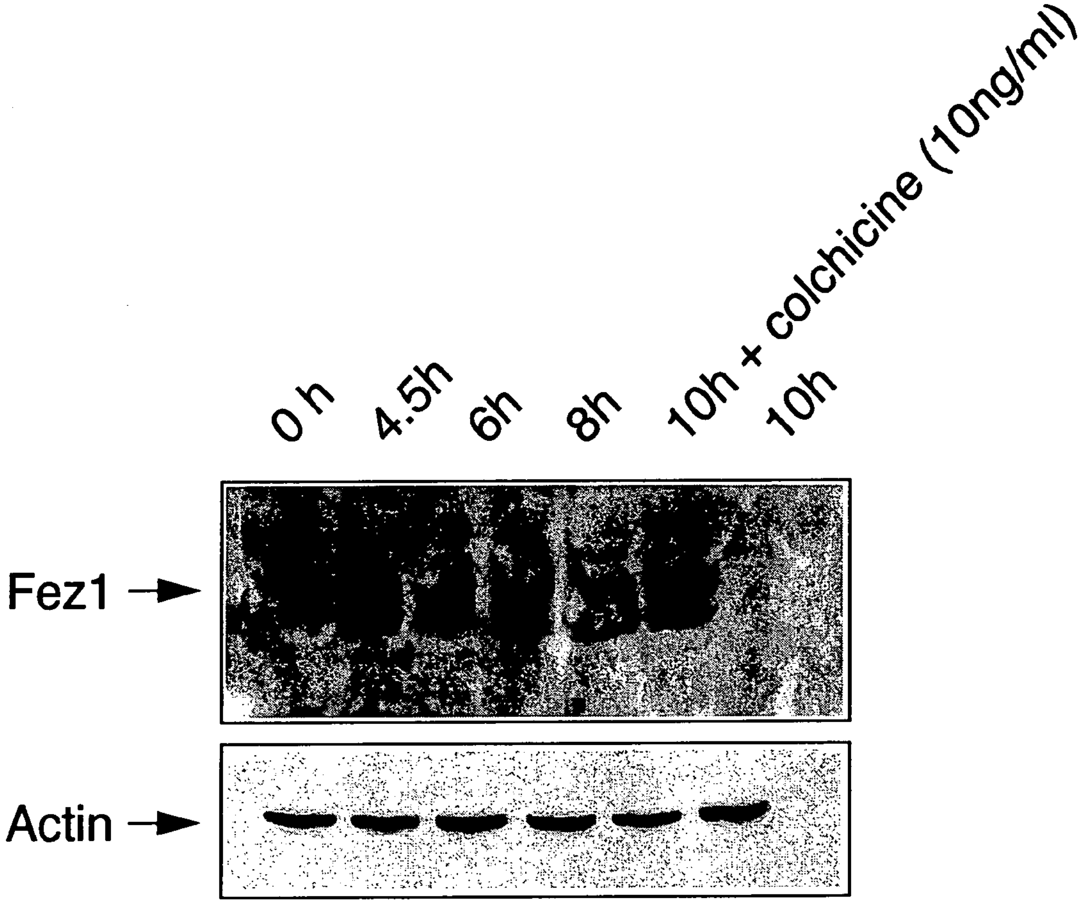
FIG. 17 is an image of the results of an immunoblotting experiment involving proteins extracted from cell cycle-synchronized fetal kidney 293 cells.
Figure 18:
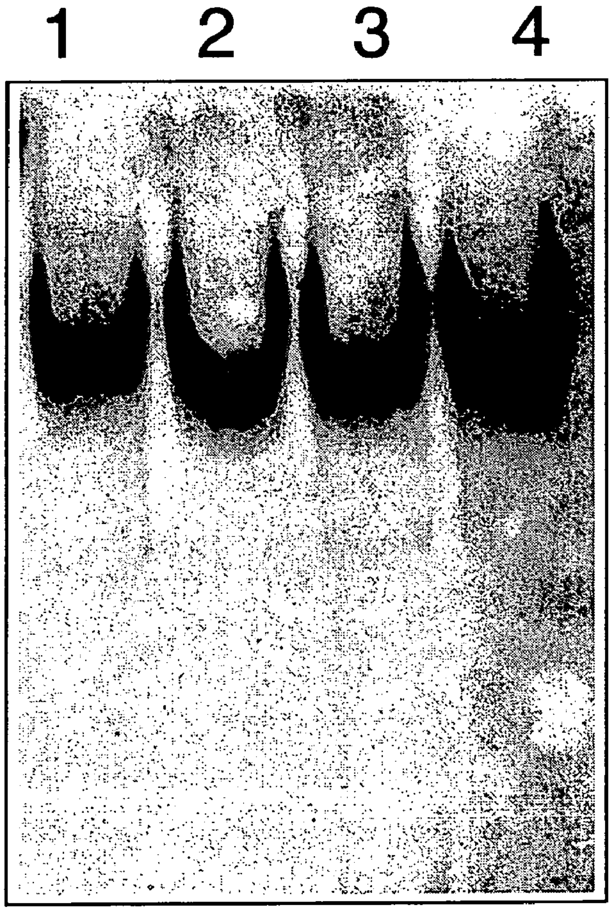
FIG. 18 is an image of the results of an SDS-PAGE separation of the proteins obtained from the cells corresponding to FIG. 16A. The cells corresponding to lanes 1, 2, 3, and 4 in FIG. 18 correspond to lanes designated 0, 1.5, 5, and 9 in FIG. 16A.
Figure 19:
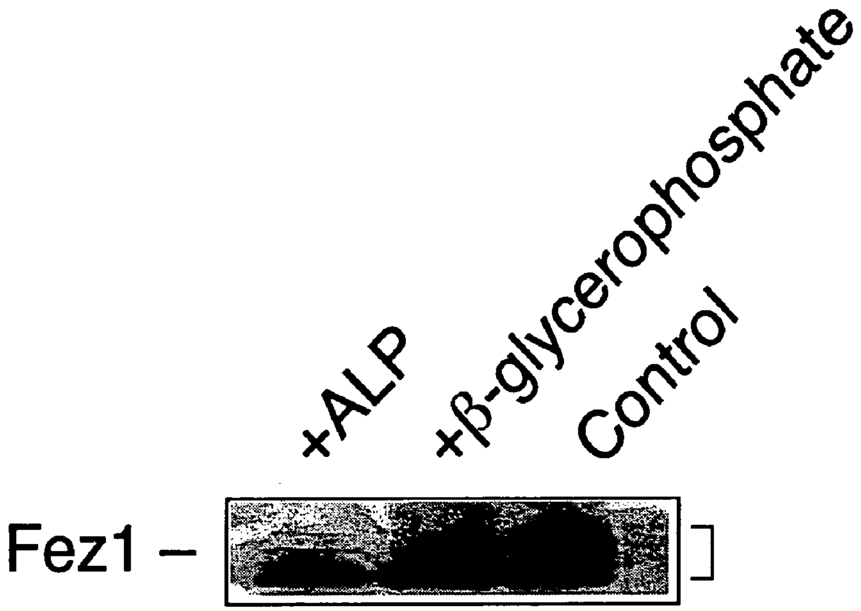
FIG. 19 is an image of the results of an immunoblotting experiment in which the cell lysates used in the experiments corresponding to FIG. 16A were contacted with alkaline phosphatase (lane 1), β-glycerophosphate (lane 2), or a control.

Fetal kidney 293 cells (which express FEZ1) were maintained in serum-free medium containing aphidicolin in order to synchronize cell cycles. At a selected time, the medium was replaced with aphidicolin-free medium containing 10% (v/v) FBS, and the cells were incubated for the times indicated in FIG. 17, after which incubation cellular proteins were extracted. The extracted proteins were subjected to immunoblot analysis using rabbit anti-Fez1 polyclonal antibody or with an anti-actin monoclonal antibody. The results of this experiment are depicted in FIG. 17.

Figure 16A:
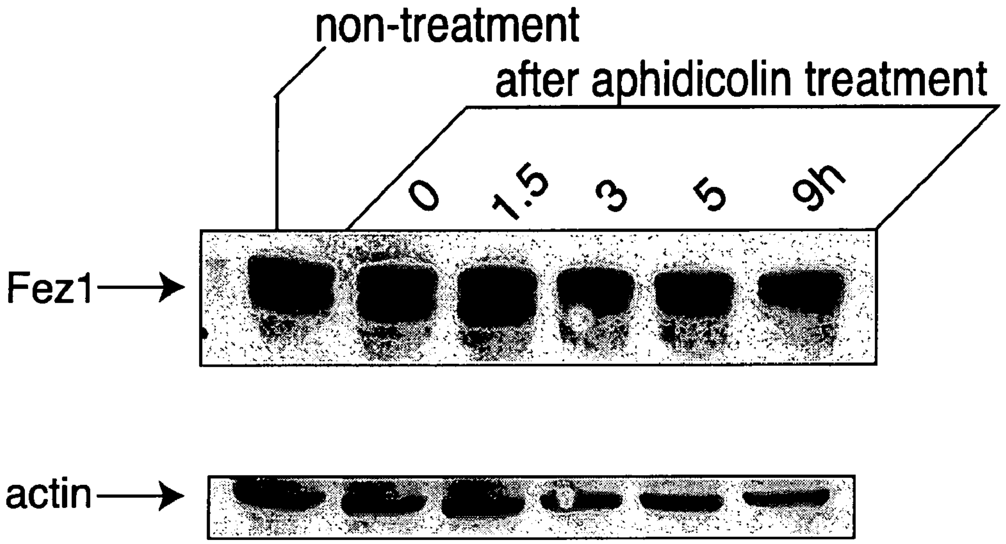
FIGS. 16A and 16B, is a pair of images of the results of immunoblotting experiments in synchronized, transfected MCF7 cells, using an antibody which binds specifically with Fez1 ("Fez1") and an antibody which binds specifically with actin ("actin"). Numbers above the columns indicate the elapsed time following aphidicolin treatment. The proteins immunoblotted in the experiments corresponding to FIG. 16A were obtained from transfected MCF7 cells which were maintained in the presence of 10% (v/v) FBS, and the proteins immunoblotted in the experiments corresponding to FIG. 16B were obtained from transfected MCF7 cells which were maintained in the absence of FBS.
Figure 16B:
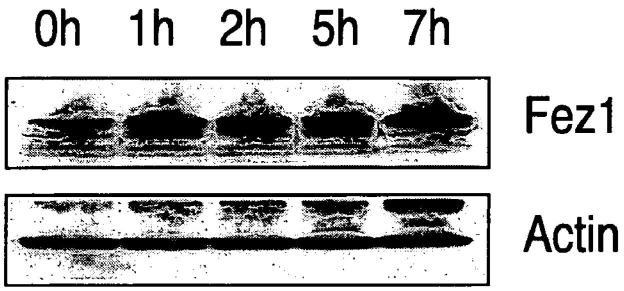

The MCF7/Fez1 transfectant lysate which were used in the experiments for which results are depicted in FIG. 16A were separated by SDS-PAGE in the presence of 6 molar urea. Under these separation conditions, only a single band corresponding to Fez1 protein was observed. Treatment of the same lysates with alkaline phosphatase (AP) resulted in formation of only a single band corresponding to FEZ1 upon SDS-PAGE separation. Treatment of the lysates with an AP inhibitor, β-glycerophosphate or a control did not lead to formation of a single band.

Cell Cycle Progression-Dependent in vivo Phosphorylation of Fez1

Figure 20:
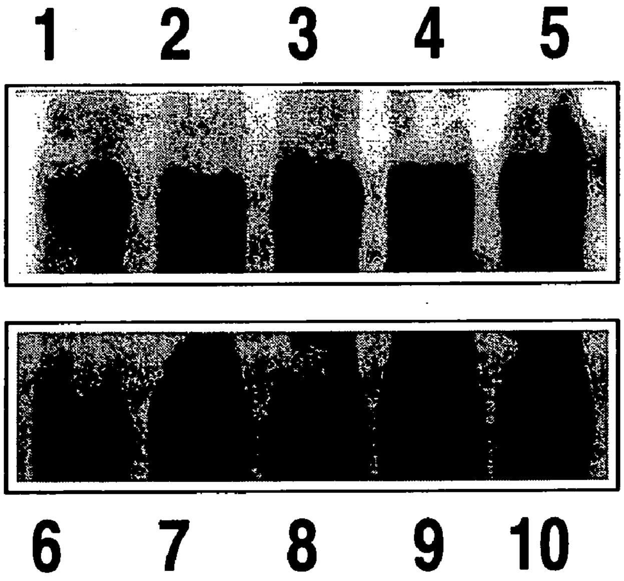
FIG. 20 is an image of SDS-PAGE separated Fez1 proteins obtained from synchronized, transfected MCF7 cells and immunoblotted with either an anti-Fez1 polyclonal antibody (lanes 6–10) or an anti-phosphoserine antibody (lanes 1–5) at increasing times from 0 (lanes 1 and 6) to 8 hours (lanes 5 and 10) following cessation of cell cycle inhibition.

Cells of MCF7 clone 54 were cultured in medium which contained 2% FBS and aphidicolin for 2 days in order to synchronize cell cycle at G1/S. At a selected time, the medium was replaced with aphidicolin-free medium which comprised 10% FBS. Cells were harvested at selected times from 0 to 8 hours following replacement of the medium, and the cells were lysed to extract protein therefrom. The proteins were immunoprecipitated using rabbit anti-Fez1 polyclonal antibody, and the precipitated proteins were separated by SDS-PAGE. The separated proteins were blotted onto a surface and bound with either labeled anti-phosphoserine antibody (Sigma Chemical Co., St. Louis, Mo.; lanes 1–5 in FIG. 20) or labeled rabbit anti-Fez1 polyclonal antibody (lanes 6–10 in FIG. 20). The results of this experiment demonstrate cell-cycle dependence of Fez1 phosphorylation.

EXAMPLE 7

Intracellular Localization of Fez1 Protein

Cytoplasmic and nuclear protein samples were prepared as the followings. Cytoplasmic and nuclear protein were isolated as described (DNA 7:47–55, 1998) with minor modifications. Briefly, about $10^7$ 293 cells were harvested and washed with PBS (10 millimolar $NaPO_4$ pH 7.4, 150 millimolar NaCl). After sedimenting the cells, the packed cell volume (PCV) was measured and the cells were re-suspended in 3 PCVs of freshly prepared hypotonic buffer (10 millimolar HEPES pH 7.9, 0.75 millimolar spermidine, 0.15 millimolar spermine, 0.1 millimolar EDTA, 0.1 millimolar EGTA, 1 millimolar DTT, 10 millimolar KCl). The cells were allowed to swell for 10 minutes at about 0° C., and were centrifuged at 300×g for 10 min at 4° C. The supernatant was collected as cytoplasmic extract I (C1).

The pellet was re-suspended with 2.9 PCVs of hypotonic buffer. The cells were broken by ten strokes using a Dounce homogenizer (Kontes Glass Co.). One volume of Sucrose restore buffer (prepared by adding 9 volumes of 75% sucrose to 1 volume of 10×salts) was added and was homogenized with 10 additional strokes of the homogenizer. The composition of 10×salts was as follows: 500 millimolar HEPES pH 7.9, 7.5 millimolar spermidine, 1.5 millimolar spermine, 100 millimolar KCl, 2 millimolar EDTA, 10 millimolar DTT. The homogenate was centrifuged for 30 seconds at 10,000 rotations per minute in a Sorvall HB-4 rotor (16,000×g) at 4° C. The supernatant was collected as cytoplasmic extract II (C2).

The pellet was re-suspended in nuclear re-suspension buffer, using about 3 milliliters per $10^9$ cells. Nuclear re-suspension buffer comprises 9 volumes of 20 millimolar HEPES pH 7.9, 0.75 millimolar spermidine, 0.15 millimolar spermine, 0.2 millimolar EDTA, 2 millimolar EGTA, 2 millimolar DTT, 25% (v/v) glycerol and 1 volume of a (4°

C.) saturated solution of ammonium sulfate. The re-suspended pellet was incubated for about 30 minutes at 4° C. with occasional rocking. The extract was sedimented by centrifugation at 4° C. for 120 minutes at 150,000×g. The supernatant was removed, solid ammonium sulfate (0.33 grams per milliliter of supernatant) was added, and the sample was incubated for 20 minutes with occasionally rocking following dissolution of the ammonium sulfate. The sample was centrifuged at 85,000×g for 20 minutes at 4° C. The pellet was dissolved in nuclear dialysis buffer, using 1 milliliter per $10^9$ cells, and dialyzed overnight. Nuclear dialysis buffer comprises 20 millimolar HEPES pH 7.9, 20% (v/v) glycerol, 100 millimolar KCl, 0.2 millimolar EDTA, 0.2 millimolar EGTA, 2 millimolar DTT). The nuclear extract (N) was stored at −80° C.

Figure 21:
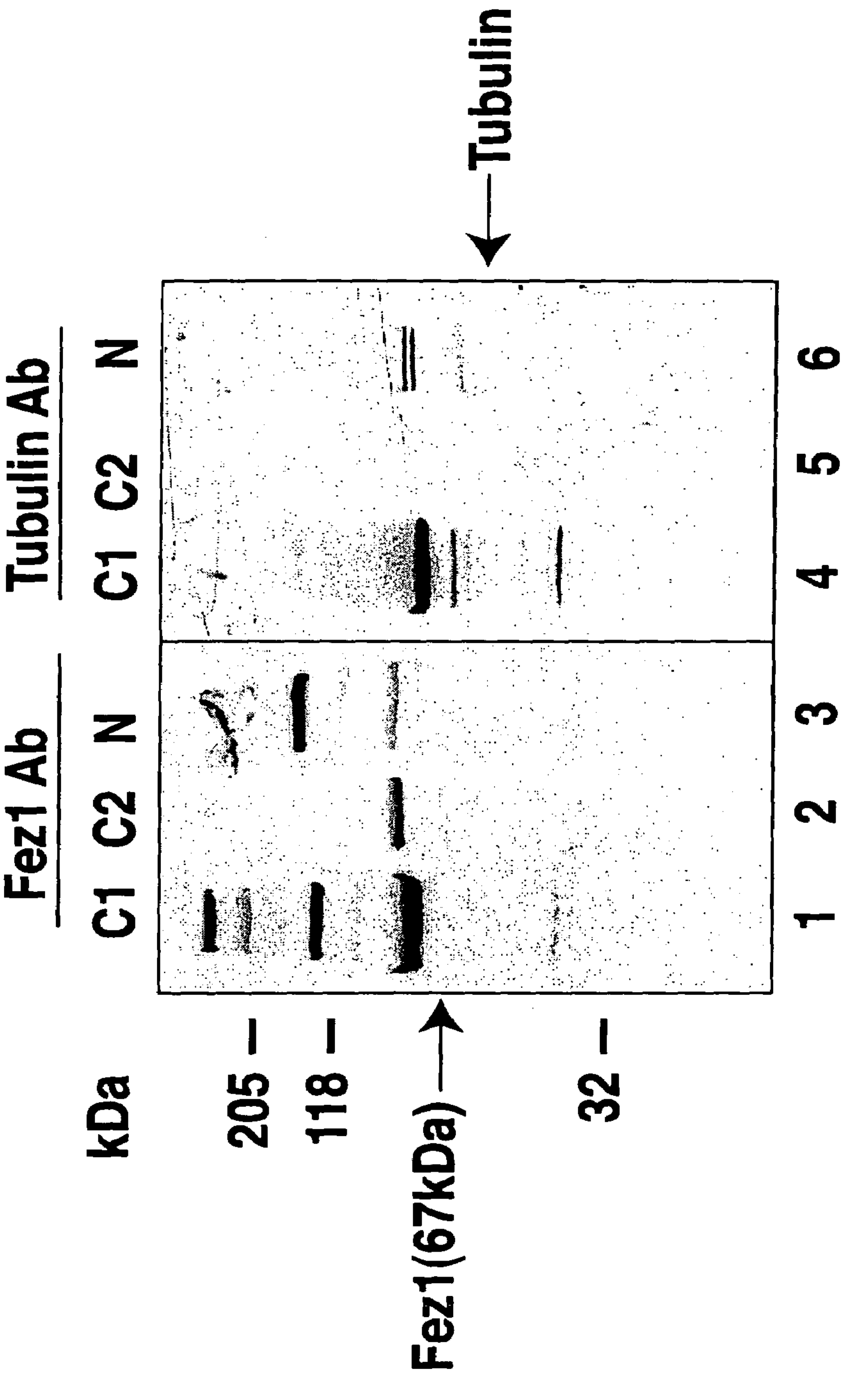
FIG. 21 is an image of the results of an experiment in which cytoplasmic ("C1" and "C2") and nuclear ("N") protein extracts obtained from 293 cells were immunoblotted using a polyclonal anti-Fez1 antibody ("Fez1") or an anti-tubulin antibody ("tubulin").

Forty micrograms of each of protein extracts C1, C2, and N by each method was separated by SDS-PAGE, transferred to a membrane, probed using either the rabbit polyclonal anti-Fez1 antibody (lanes 1–3 of FIG. 21) or with an anti-tubulin antibody (Santa Cruz Biotechnology, Santa Cruz, Calif.; lanes 4–6 of FIG. 21). The results of these experiments demonstrate that Fez1 protein is localized predominantly in the cytoplasm, although a fraction of Fez1 protein appears to be present in the nucleus.

EXAMPLE 8

Interaction of Fez1 with Microtubules

Figure 22:
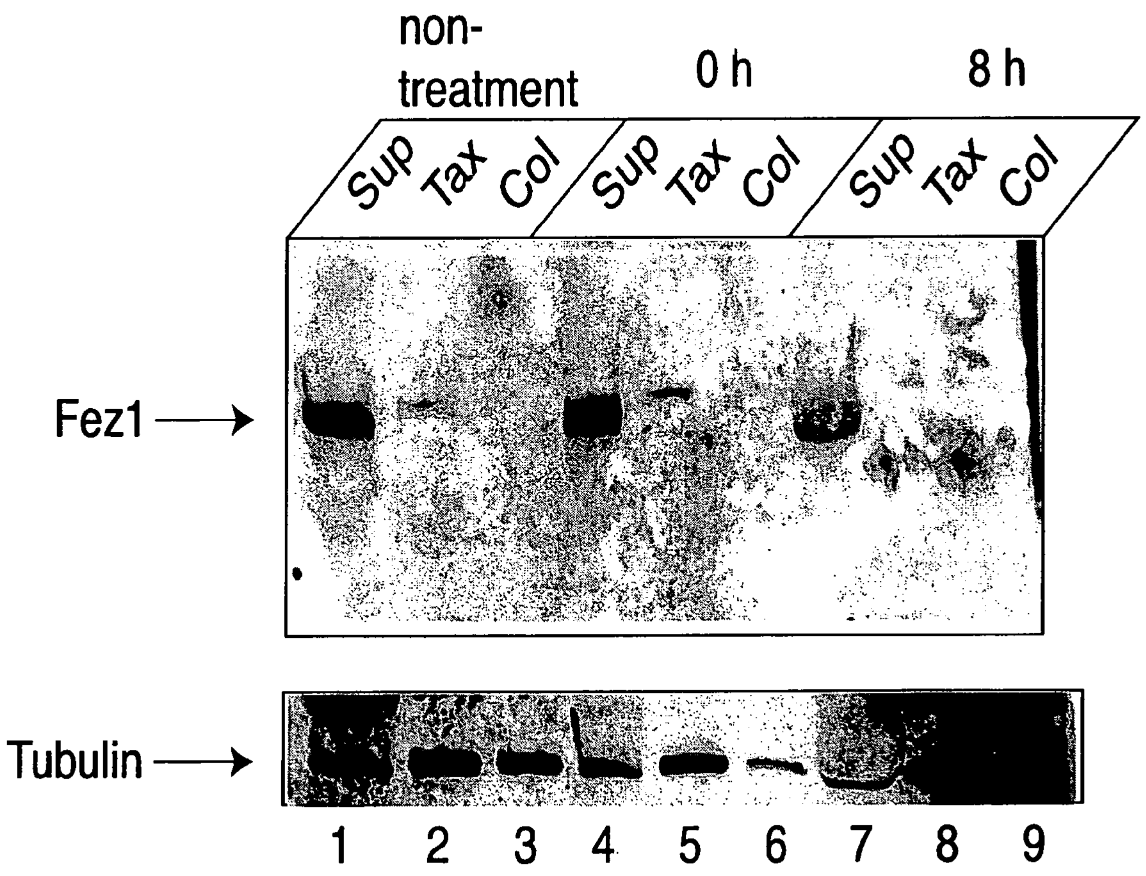
FIG. 22 is an image of the results of an experiment in which Fez1 protein which Fez1 protein "Fez1" was detected using a polyclonal antibody in extracts obtained from centrifugation-sedimented cell structures in synchronized cells which had been incubated with paclitaxel ("Tax") or with colchicine ("Col").
Figure 23:
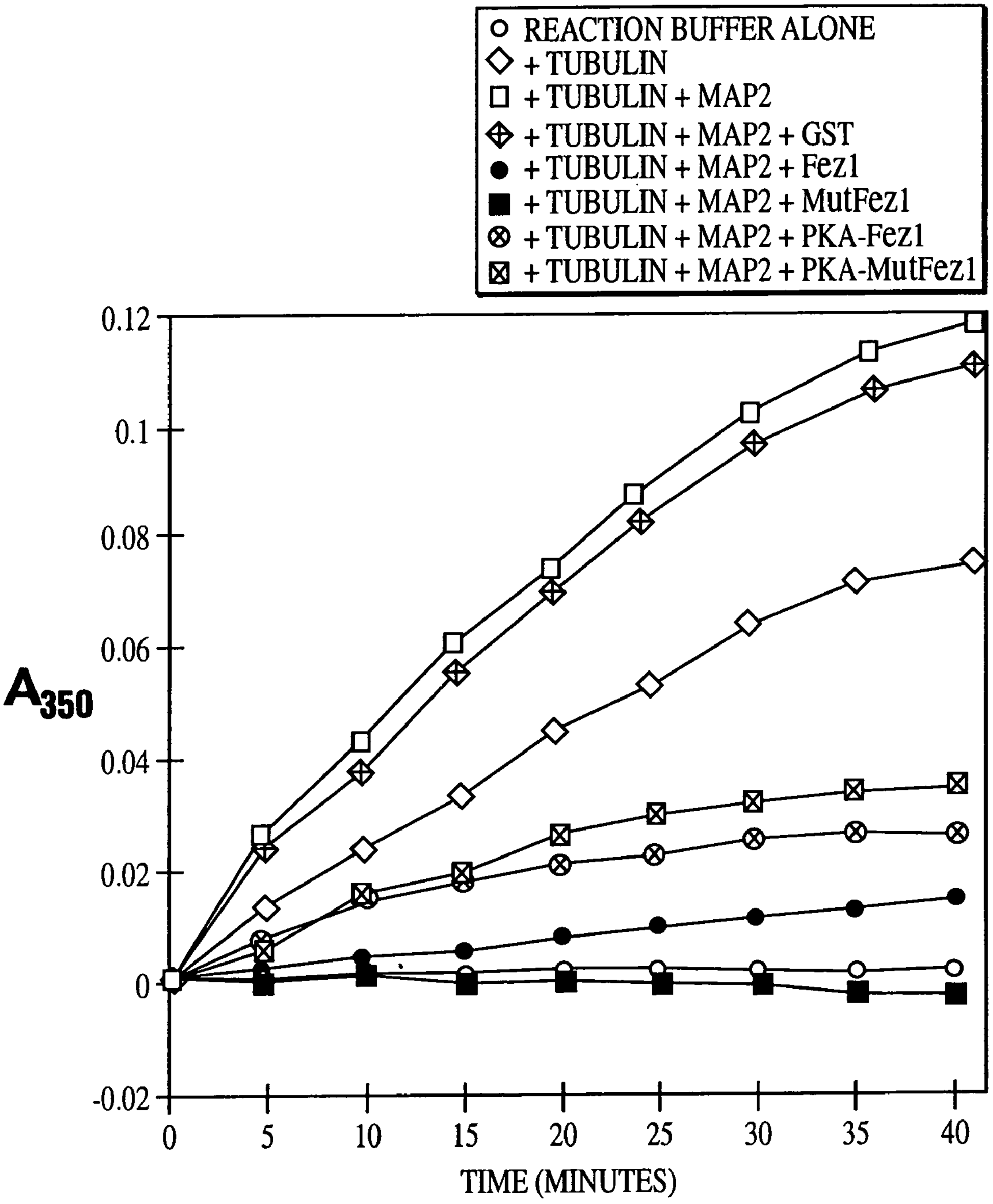
FIG. 23 is a graph which indicates the effect of Fez1 protein on inhibition of tubulin polymerization in the presence of MAP2 protein. Reaction mixtures contained, in addition to reaction buffer: nothing (open circle); tubulin (open diamond); tubulin and MAP2 (open square); tubulin, MAP2, and GST (diamond enclosing cross); tubulin, MAP2, and GST-fused Fez1 (filled circle); tubulin, MAP2, GST-fused mutated (29 Ser Pro) Fez1 (filled square); tubulin, MAP2, and PKA-phosphorylated GST-fused Fez1 (circle enclosing cross); and tubulin, MAP2, and PKA-phosphorylated GST-fused mutated (29 Ser Pro) Fez1 (square enclosing cross). "PKA" is protein kinase A, a 3':5'-monophosphate-dependent protein kinase.

Cytoplasmic protein fractions were obtained from Fez1-expressing 293 cells ("Tax" in FIG. 22) which had been incubated with paclitaxel in order to polymerize tubulin and from Fez1-expressing 293 cells ("Col" in FIG. 22) which had been incubated with colchicine for non-polymerization (i.e. as a control). The 293 cells were selected from three groups: non-synchronized cells ("non-treatment" in FIG. 22), G1/S-synchronized cells ("0 h" in FIG. 22), and S-to-G2/M-synchronized cells ("8 h" in FIG. 22). The protein fractions were subjected to centrifugation in the presence of a sucrose cushion, as described (J. Cell Biol. 131:1015–1024, 1995). Pelleted proteins were subjected to immunoblot analysis using the rabbit polyclonal anti-Fez1 antibody. Protein remaining in the supernatant ("Sup" in FIG. 22) were immunoblotted as well. The lower portion of FIG. 22 demonstrates the presence of tubulin in all samples tested. The results of these experiments demonstrate interaction of Fez1 with microtubules in vivo and involvement of Fez1 with tubulin polymerization.

Involvement of GST-Fused Fez1 Protein with Tubulin Polymerization in vitro

Purified tubulin and microtubule-associated protein MAP2 were incubated at 37° C. for 0–40 minutes with one of:

GST,

GST-fused Fez1

GST-fused mutated (29 Ser→Pro) Fez1

PKA-phosphorylated GST-fused Fez1 and

PKA-phosphorylated GST-fused mutated (29 Ser→Pro) Fez1.

Polymerization of tubulin was assessed by spectrophotometric measurement of the increase in absorbance at 350 nanometers known to accompany polymerization. The results of this experiment demonstrate that Fez1 protein is able to inhibit polymerization of tubulin. The inhibitory effect of Fez1 protein on tubulin polymerization is modulated by the phosphorylation state of Fez1, as indicated by the effect of PKA-mediated phosphorylation of Fez1 on tubulin polymerization in vitro.

EXAMPLE 9

A Proposed Biological Function for Fez1 Protein

It is recognized that the characteristics described herein for Fez1 proteins and nucleic acids which encode them do not depend on the accuracy or reliability of any theories presented in this Example with regard to the physiological function of Fez1 protein. Thus, without being bound by any particular theory of operation, the inventors propose the following biological functions for Fez1 protein.

Immunoblot analysis of extracts obtained from cells which express FEZ1 demonstrates that Fez1 protein is predominantly localized in the cytoplasm, but is also found in the nucleus. Yeast two-hybrid screening demonstrates that at least one peptide elongation factor (EF1-γ) is a likely binding partner of Fez1 protein. Others have discovered that the EF family of proteins not only function as a peptide chain elongation factors, but are involved in interactions between microtubules and in the process of tubulin polymerization (see, e.g., Eur. J. Biochem. 171:119, 1988; Proc. Natl. Acad. Sci. USA 90:3028, 1993; Plant Cell 6:893, 1994; Cell Motil. Cytoskel. 41:168, 1998). Other investigators have shown that EF proteins can determine susceptibility of cells to transformation (see, e.g., Nature 359:24, 1992). Overexpression of EF proteins has been observed in stomach, esophageal, and colon cancers (e.g., Cancer 75:1446, 1995; Gut, 38:66, 1996; Cancer 82:816, 1998). The results of experiments presented in this application demonstrate interaction between Fez1 protein and microtubules and their substituent proteins. For example, when cellular extract from Fez1-expressing cells was incubated with paclitaxel in order to induce tubulin polymerization, Fez1 was determined to be associated with tubulin precipitates. However, Fez1 was determined not to be associated with depolymerized microtubule precipitates in the presence of the tubulin polymerization inhibitor colchicine.

The data presented in this application indicate that Fez1 protein serves to modulate polymerization and stability of microtubules, and possibly other cytoskeletal features, in vivo. Thus, Fez1 protein can be expected to be involved in cellular processes which are modulated by cytoskeletal stability and changes. Examples of such cellular processes include initiation of mitosis, modulation of the rate and stage of mitosis, modulation of the initiation and rate of cell proliferation and growth, modulation of cell shape and rigidity, modulation of cell motility, modulation of the rate and stage of cellular DNA replication, modulation of the intracellular distribution of organelles (e.g. mitochondria, endoplasmic reticulum, Golgi apparatus, chloroplasts, and the like), modulating the metastatic potential of a cell, and modulation of cellular transformation from a non-cancerous to a cancerous phenotype.

For example, cell division of higher eukaryotes is known to be initiated and be regulated according to a dynamic process, which involves the so-called mitotic apparatus (an organized complex of proteins) that distribute the duplicated chromosome to daughter cells (see, e.g., Nurse, 1990, Nature 344:503–508). The extended microtubular cytoskeleton of an interphase cell is disassembled into tubulin subunits, and, when an appropriate point in cell cycle occurs, the tubulin subunits are re-assembled into two sets of polarized spindle tubes, that function as a central part of the mitotic apparatus. Once nucleation of spindle tubes occurs, the growing tubules attached at an end of a condensed chromosome. At the other end, the tubules meet or attach at a collection of proteins designated the centrosome or microtubule organellar center. The centrosome complex has been isolated by others (see, e.g., Telzer, 1979, J. Cell Biol. 81:484–497; Mitchison, 1984, Nature 312:232–237), and previous reports characterized soluble protein precursors of the centrosome. The centrosome comprises α-, β- and γ-tubulin, heat shock protein 70, and an elongation factor protein (Eur. J. Biochem. 171:119, 1988; Proc. Natl. Acad. Sci. USA 90:3028, 1993; Plant Cell 6:893, 1994; Cell Motil. Cytoskel. 41:168, 1998).

As a normal cycle of cell division progresses, both disassembly and re-assembly of microtubules occurs. Thus, some gene product or reagent, which targets microtubules or their subunits, can be used to modulate progression through the cell cycle. Tubulin is a target for known anti-cancer drugs, such as paclitaxel (which can induce tubulin polymerization) and vinca alkaloids (which can inhibit polymerization process; Med. Res. Rev. 18:259–296, 1998). Other known tumor suppressor genes have been shown to be involved in the dynamics of microtubule assembly and disassembly. For example, APC can promote microtubules assembly (Eur. J. Biochem. 253:591, 1998; Cancer Res. 54:3672, 1994). Fhit can induce microtubule assembly (J. Biol. Chem. 274:34, 1999). As demonstrated herein, Fez1 can inhibit tubulin polymerization. Because, as demonstrated herein, Fez1 binds with at least one EF protein, and because these proteins have been identified as a soluble protein component from the centrosome, it can be expected that Fez1 has an role in the late events of the cell division process or centrosomal dynamics. This is in keeping with the finding herein that Fez1 protein induces accumulation of cells in the late S to G2/M stage(s) of the cell cycle. In these stages the centrosome is undergoing assembly in daughter cells.

The experiments described herein demonstrate at least two ways in which the activity of Fez1 can be affected, namely by phosphorylation of Fez1 protein and by binding a polypeptide or polypeptide-like molecule with Fez1 protein. The results presented herein demonstrate that phosphorylation of Fez1 by PKA can diminish the ability of Fez1 to inhibit tubulin polymerization.

Agents which directly phosphorylate Fez1 or which induce its phosphorylation or inhibit its dephosphorylation by other proteins are useful for diminishing the ability of Fez1 to inhibit tubulin polymerization and corresponding growth/shrinkage and maintenance of cytoskeletal features (e.g. microtubules) which contain tubulin or tubulin-like proteins. Agents which directly dephosphorylate Fez1 or which induce its dephosphorylation or inhibit its phosphorylation by other proteins are useful for enhancing the ability of Fez1 to inhibit polymerization and corresponding growth/shrinkage and maintenance of cytoskeletal features which contain tubulin or tubulin-like proteins.

Agents which are able to bind specifically with Fez1 protein can also modulate its physiological activity. Examples of such agents are antibodies which are raised against Fez1 protein, tubulin, and EF1-γ. Fragments of such proteins (e.g. Fc portions of antibodies or the EF1-γ(N) fragment described herein) can exhibit effects on Fez1 protein that are similar to the effects of the whole protein on Fez1 protein. Similarly, peptide or peptidomimetic compounds which mimic the structure of the portion of a protein that binds specifically with Fez1 protein can exhibit effects on Fez1 protein that are similar to the effects of the corresponding whole protein on Fez1 protein. The inventors recognize that numerous methods known in the art can be used to construct and screen libraries of compounds which are structurally similar to proteins that bind specifically with Fez1 protein (e.g. peptide or peptidomimetic compounds which are structurally similar to one or more portions of tubulin, EF1-γ, or an antibody that binds specifically with Fez1). In addition, the observation herein that Fez1 protein appears to form dimers or multimers indicates that compounds which are identical to or which mimic the structure of a portion of Fez1 involved in dimerization or multimerization can also be used to modulate the physiological activity of Fez1. Thus, methods of constructing and screening libraries of compounds which are identical to or structurally similar to a dimerization/multimerization domain (e.g. a library including random fragments of Fez1 protein) can be used to identify compounds which modulate the physiological activity of Fez1.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A kit for amplifying a portion of a human FEZ1 gene, the kit comprising a first isolated polynucleotide and a second isolated polynucleotide, wherein the first isolated polynucleotide comprises a portion which anneals with high stringency with at least twenty consecutive nucleotide residues of the coding strand of SEQ ID NO: 1, and wherein the second isolated polynucleotide comprises a portion which anneals with high stringency with at least twenty consecutive nucleotide residues of the non-coding strand of SEQ ID NO:1.

2. A kit for amplifying a portion of a cDNA generated from a transcript of a human FEZ1 gene, the kit comprising a first isolated polynucleotide and a second isolated polynucleotide, wherein a portion of the first isolated polynucleotide anneals with high stringency with at least twenty consecutive nucleotide residues of the coding strand of SEQ ID NO: 1, and wherein a portion of the second isolated polynucleotide anneals with high stringency with at least twenty consecutive nucleotide residues of the non-coding strand of SEQ ID NO: 1.

3. An isolated polynucleotide comprising a sequence that anneals under conditions of high stringency to a nucleic acid having the sequence of:

i) SEQ ID NO: 1;

ii) the complement of SEQ ID NO: 1;

iii) SEQ ID NO: 2;

iv) the complement of SEQ ID NO: 2;

v) SEQ ID NO: 3; and/or vi) the complement of SEQ ID NO: 3;

wherein said conditions of high stringency comprise hybridizing said isolated polynucleotide in 0.015 M NaCl, 1.5 mM sodium citrate, and 0.1% (w/v) SDS at 50° C., with washes at 42° C. in 0.2×SSC and 0.1% (w/v) SDS; and wherein said isolated polynucleotide encodes a protein that binds to a compound selected from the group consisting of an amino-terminal 40 KDa fragment of Fez1, tubulin, EF1-γ, and an amino terminal 153-amino acid fragment of EF1-γ.

4. The isolated polynucleotide of claim 3, wherein said isolated polynucleotide anneals under conditions of high stringency to a nucleic acid having the sequence of SEQ ID NO: 1.

5. The isolated polynucleotide of claim 3, wherein said isolated polynucleotide anneals under conditions of high stringency to a nucleic acid having the sequence of the complement of SEQ ID NO: 1.

6. The isolated polynucleotide of claim 3, wherein said isolated polynucleotide anneals under conditions of high stringency to a nucleic acid having the sequence of SEQ ID NO: 2.

7. The isolated polynucleotide of claim 3, wherein said isolated polynucleotide anneals under conditions of high stringency to a nucleic acid having the sequence of the complement of SEQ ID NO: 2.

8. The isolated polynucleotide of claim 3, wherein said isolated polynucleotide anneals under conditions of high stringency to a nucleic acid having the sequence of SEQ ID NO: 3.

9. The isolated polynucleotide of claim 3, wherein said isolated polynucleotide anneals under conditions of high stringency to a nucleic acid having the sequence of the complement of SEQ ID NO: 3.

10. The isolated polynucleotide of claim 3 further comprising a promoter operably linked to said sequence.

11. The isolated polynucleotide of claim 10, wherein said promoter is selected from the group consisting of a constitutive promoter, an inducible promoter and a tissue specific promoter.

12. The isolated polynucleotide of claim 3, wherein said protein inhibits tubulin polymerization.

13. The isolated polynucleotide of claim 3, wherein said protein inhibits cellular proliferation.

14. The isolated polynucleotide of claim 3, wherein said protein inhibits tumorigenesis.

15. A nucleic acid vector comprising the isolated polynucleotide of claim 3.

16. The nucleic acid vector of claim 15 selected from the group consisting of a plasmid, an expression vector and a viral vector.

17. An isolated cell comprising the nucleic acid vector of claim 15.

18. An isolated polynucleotide comprising a sequence that anneals under conditions of high stringency to a nucleic acid having the sequence of i) SEQ ID NO: 1;

ii) the complement of SEQ ID NO: 1;

iii) SEQ ID NO: 2;

iv) the complement of SEQ ID NO: 2;

v) SEQ ID NO: 3; and/or vi) the complement of SEQ ID NO: 3;

wherein said conditions of high stringency comprise hybridizing said isolated polynucleotide in wherein said conditions of high stringency comprise hybridizing said isolated polynucleotide in 0.015 M NaCl, 1.5 mM sodium citrate, and 0.1% (w/v) SDS at 50° C., with washes at 42° C. in 0.2×SSC and 0.1% (w/v) SDS; and wherein said isolated polynucleotide encodes a protein that has an activity selected from the group consisting of inhibiting cellular proliferation and tumor suppression.

19. The isolated polynucleotide of claim 18, wherein said isolated polynucleotide anneals under conditions of high stringency to a nucleic acid having the sequence of SEQ ID NO: 1.

20. The isolated polynucleotide of claim 18, wherein said isolated polynucleotide anneals under conditions of high stringency to a nucleic acid having the sequence of the complement of SEQ ID NO: 1.

21. The isolated polynucleotide of claim 18, wherein said isolated polynucleotide anneals under conditions of high stringency to a nucleic acid having the sequence of SEQ ID NO: 2.

22. The isolated polynucleotide of claim 18, wherein said isolated polynucleotide anneals under conditions of high stringency to a nucleic acid having the sequence of the complement of SEQ ID NO: 2.

23. The isolated polynucleotide of claim 18, wherein said isolated polynucleotide anneals under conditions of high stringency to a nucleic acid having the sequence of SEQ ID NO: 3.

24. The isolated polynucleotide of claim 18, wherein said isolated polynucleotide anneals under conditions of high stringency to a nucleic acid having the sequence of the complement of SEQ ID NO: 3.

25. The isolated polynucleotide of claim 18 further comprising a promoter operably linked to said sequence.

26. The isolated polynucleotide of claim 25, wherein said promoter is selected from the group consisting of a constitutive promoter, an inducible promoter and a tissue specific promoter.

27. A nucleic acid vector comprising the isolated polynucleotide of claim 18.

28. The nucleic acid vector of claim 27 selected from the group consisting of a plasmid, an expression vector and a viral vector.

29. An isolated cell comprising the nucleic acid vector of claim 27.

30. An isolated polynucleotide comprising a nucleotide sequence that encodes a protein comprising the amino acid sequence of SEQ ID NO: 4.

31. The isolated polynucleotide of claim 30 wherein the isolated polynucleotide encodes the polypeptide of SEQ ID NO: 4.

32. The isolated polynucleotide of claim 30 further comprising a promoter operably linked to said sequence.

33. The isolated polynucleotide of claim 32, wherein said promoter is selected from the group consisting of a constitutive promoter, an inducible promoter and a tissue specific promoter.

34. A nucleic acid vector comprising the isolated polynucleotide of claim 30.

35. The nucleic acid vector of claim 34 selected from the group consisting of a plasmid, an expression vector and a viral vector.

36. An isolated cell comprising the nucleic acid vector of claim 34.

37. An isolated polynucleotide comprising a nucleotide sequence that encodes a protein comprising an amino terminal 40 KDa fragment of the sequence of SEQ ID NO: 4.

38. The isolated polynucleotide of claim 37 wherein the isolated polynucleotide encodes the amino terminal 40 KDa fragment of the sequence of SEQ ID NO: 4.

39. The isolated polynucleotide of claim 37 further comprising a promoter operably linked to said sequence.

40. The isolated polynucleotide of claim 39, wherein said promoter is selected from the group consisting of a constitutive promoter, an inducible promoter and a tissue specific promoter.

41. A nucleic acid vector comprising the isolated polynucleotide of claim 37.

42. The nucleic acid vector of claim 41 selected from the group consisting of a plasmid, an expression vector and a viral vector.

43. An isolated cell comprising the nucleic acid vector of claim 41.

* * * * *